(12) United States Patent
Tomasetta et al.

(10) Patent No.: US 11,783,629 B2
(45) Date of Patent: Oct. 10, 2023

(54) HANDHELD ELECTRONIC DEVICE

(71) Applicant: Apple Inc., Cupertino, CA (US)

(72) Inventors: Christopher S. Tomasetta, Sunnyvale, CA (US); Jason B. Neevel, Santa Clara, CA (US); Sara E. Salmon, Cupertino, CA (US); Richard H. Koch, Cupertino, CA (US); Jonathan M. Lee, Fremont, CA (US); Nicholas Merz, San Francisco, CA (US); Daniel Jarvis, Sunnyvale, CA (US); Jared P. Ostdiek, San Francisco, CA (US); Michael B. Wittenberg, Sunnyvale, CA (US); Rasamy Phouthavong, San Jose, CA (US); David A. Pakula, San Francisco, CA (US); Ian A. Spraggs, San Francisco, CA (US); Marwan Rammah, San Francisco, CA (US)

(73) Assignee: Apple Inc., Cupertino, CA (US)

(*) Notice: Subject to any disclaimer, the term of this patent is extended or adjusted under 35 U.S.C. 154(b) by 0 days.

(21) Appl. No.: 17/471,693

(22) Filed: Sep. 10, 2021

(65) Prior Publication Data
US 2022/0284214 A1 Sep. 8, 2022

Related U.S. Application Data

(60) Provisional application No. 63/208,477, filed on Jun. 8, 2021, provisional application No. 63/170,327, filed
(Continued)

(51) Int. Cl.
G06V 40/16 (2022.01)
G06T 7/521 (2017.01)
(Continued)

(52) U.S. Cl.
CPC ............ *G06V 40/166* (2022.01); *G06T 7/521* (2017.01); *G06V 10/145* (2022.01); *H04M 1/0266* (2013.01); *G06T 2207/30201* (2013.01)

(58) Field of Classification Search
CPC .... G06V 40/166; G06V 10/145; G06T 7/521; G06T 2207/30201; H04M 1/0272
See application file for complete search history.

(56) References Cited

U.S. PATENT DOCUMENTS 6,834,181 B2    12/2004   Kaikuranta et al.
6,853,336 B2     2/2005   Asano et al.
(Continued)

FOREIGN PATENT DOCUMENTS

CN     206977392     2/2018
CN     108200238     6/2018
(Continued)

OTHER PUBLICATIONS

Borghi et al., "Driver Face Verification with Depth Maps," *Sensors*, 2019, vol. 19, No. 3361, pp. 1-16.
(Continued)

*Primary Examiner* — Michael Robert Cammarata
(74) *Attorney, Agent, or Firm* — Brownstein Hyatt Farber Schreck, LLP

(57) ABSTRACT

A portable electronic device may include a housing, a display at least partially within the housing, a front cover coupled to the housing and positioned over the display, and a biometric sensor module configured to illuminate an object and capture an image of the object through the front cover. The biometric sensor module may include a first lens positioned below the front cover, a first light source positioned below the first lens and configured to project, through the first lens, a dot pattern on the object, a second light source positioned below the first lens and configured to
(Continued)

illuminate, through the first lens, the object with a flood of light, a second lens positioned below the front cover, and a light sensor positioned below the second lens and configured to capture an image of the object.

20 Claims, 76 Drawing Sheets

Related U.S. Application Data on Apr. 2, 2021, provisional application No. 63/155,693, filed on Mar. 2, 2021.

(51) Int. Cl.
*G06V 10/145* (2022.01)
*H04M 1/02* (2006.01)

(56) References Cited

U.S. PATENT DOCUMENTS

| | | | |
|---|---|---|---|
| 7,142,827 B2 | 11/2006 | Dufosse et al. | |
| 7,452,077 B2 | 11/2008 | Meyer et al. | |
| 7,463,756 B2 | 12/2008 | Benkley et al. | |
| 7,474,799 B2 | 1/2009 | Bassi et al. | |
| 7,620,175 B2 | 11/2009 | Black et al. | |
| 8,207,897 B2 | 6/2012 | Alvey et al. | |
| 8,553,874 B2 | 10/2013 | Holmes et al. | |
| 9,030,440 B2 | 5/2015 | Pope et al. | |
| 9,501,685 B2 | 11/2016 | Bernstein et al. | |
| 9,524,413 B2 | 12/2016 | Kim | |
| 9,651,513 B2 | 5/2017 | Dunlap et al. | |
| 9,697,409 B2 | 7/2017 | Myers | |
| 9,767,971 B2 | 9/2017 | Hisano | |
| 9,811,713 B2 | 11/2017 | Pi et al. | |
| 9,876,273 B2 | 1/2018 | Lui et al. | |
| 9,922,229 B2 | 3/2018 | Cao et al. | |
| 9,924,004 B2 | 3/2018 | Park | |
| 9,959,444 B2 | 5/2018 | Young et al. | |
| 10,007,343 B2 | 6/2018 | Kim | |
| 10,049,251 B2 | 8/2018 | Cao et al. | |
| 10,128,907 B2 | 11/2018 | He | |
| 10,146,304 B2 | 12/2018 | Werblin et al. | |
| 10,146,982 B2 | 12/2018 | Hsu | |
| 10,198,131 B2 | 2/2019 | Yang et al. | |
| 10,201,273 B2 | 2/2019 | Choukroun et al. | |
| 10,356,500 B2 | 7/2019 | Kim | |
| 10,361,851 B2 | 7/2019 | Wu | |
| 10,425,561 B2 | 9/2019 | Jarvis et al. | |
| 10,430,630 B2 | 10/2019 | Zhang | |
| 10,564,521 B1* | 2/2020 | Zhu .......................... G01S 17/89 | |
| 10,606,218 B1 | 3/2020 | Ely et al. | |
| 10,656,596 B2 | 5/2020 | Callagy et al. | |
| 10,699,094 B2 | 6/2020 | Shim et al. | |
| 10,721,348 B2 | 7/2020 | Choi et al. | |
| 10,824,203 B2 | 11/2020 | Wong et al. | |
| 10,839,194 B2 | 11/2020 | Jung et al. | |
| 10,949,637 B2 | 3/2021 | Kang et al. | |
| 10,990,792 B2 | 4/2021 | Park et al. | |
| 11,132,055 B2 | 9/2021 | Jones et al. | |
| 11,189,248 B1 | 11/2021 | Lee et al. | |
| 11,209,146 B2* | 12/2021 | Chang ................... G02B 3/0056 | |
| 11,233,924 B2 | 1/2022 | Noh et al. | |
| 11,258,163 B2 | 2/2022 | Froese et al. | |
| 11,275,920 B1 | 3/2022 | Sargent et al. | |
| 11,310,400 B2 | 4/2022 | Choi et al. | |
| 11,330,351 B2 | 5/2022 | Su et al. | |
| 11,436,964 B1* | 9/2022 | Wang ..................... G02B 6/0006 | |
| 11,476,883 B2 | 10/2022 | Kumar et al. | |
| 2007/0049326 A1 | 3/2007 | Kim | |
| 2009/0066345 A1 | 3/2009 | Klauk et al. | |
| 2013/0313087 A1 | 11/2013 | Le | |
| 2014/0137054 A1 | 5/2014 | Gandhi et al. | |
| 2014/0282285 A1 | 9/2014 | Sadhvani et al. | |
| 2015/0302773 A1 | 10/2015 | Stone et al. | |
| 2015/0309316 A1 | 10/2015 | Osterhout et al. | |
| 2016/0178915 A1* | 6/2016 | Mor ................... G02B 27/4205 359/566 |
| 2016/0282977 A1 | 9/2016 | Moua et al. | |
| 2017/0372123 A1 | 12/2017 | Kim et al. | |
| 2018/0063390 A1* | 3/2018 | Trail ........................ G06T 7/50 | |
| 2018/0082102 A1 | 3/2018 | Lee et al. | |
| 2018/0196998 A1* | 7/2018 | Price .................... G06V 40/172 | |
| 2019/0041197 A1* | 2/2019 | Gernoth ................... G06T 7/514 | |
| 2019/0049097 A1* | 2/2019 | Rossi ..................... F21V 5/004 | |
| 2019/0264890 A1* | 8/2019 | Chang .................... G02B 3/08 | |
| 2019/0295271 A1* | 9/2019 | Xu ......................... G06V 40/169 | |
| 2019/0346687 A1* | 11/2019 | Zheng ................. G02B 27/425 | |
| 2020/0033710 A1* | 1/2020 | Ma ........................ G02B 5/1833 | |
| 2020/0126243 A1* | 4/2020 | Bleyer ..................... G06T 7/11 | |
| 2020/0174255 A1 | 6/2020 | Hollands et al. | |
| 2020/0174284 A1 | 6/2020 | Chan et al. | |
| 2021/0067619 A1* | 3/2021 | Wang ................. G03B 21/2033 | |
| 2021/0256244 A1 | 8/2021 | Bezot et al. | |
| 2021/0344675 A1 | 11/2021 | Cui et al. | |
| 2022/0012451 A1 | 1/2022 | Sargent et al. | |
| 2022/0059055 A1 | 2/2022 | Lee et al. | |
| 2022/0100833 A1 | 3/2022 | Koch et al. | |
| 2022/0142136 A1* | 5/2022 | Kubota ................... G01V 8/12 | |
| 2022/0252893 A1* | 8/2022 | Hsiao ................. G02B 27/0927 | |
| 2022/0283024 A1* | 9/2022 | Neevel ................. G01J 1/4204 | |
| 2022/0284214 A1* | 9/2022 | Tomasetta ............. H04M 1/026 | |
| 2022/0329678 A1* | 10/2022 | Zhang ................. H04M 1/0262 | |

FOREIGN PATENT DOCUMENTS

| | | | | |
|---|---|---|---|---|
| CN | 208673354 | | 3/2019 | |
| CN | 110196528 B | * | 12/2021 | .............. F21V 5/007 |
| EP | 3644337 | | 4/2020 | |
| JP | 2007114406 A | * | 5/2007 | ......... G03B 21/2053 |
| KR | 0100105004 | | 9/2010 | |
| KR | 20120013400 A | * | 2/2012 | |
| KR | 0190107490 | | 9/2019 | |
| KR | 0200015839 | | 2/2020 | |
| KR | 0200026000 | | 3/2020 | |

OTHER PUBLICATIONS

Huang et al., "Eyeglasses-free Display: Towards Correcting Visual Aberrations with Computational Light Field Displays," *ACM Transactions on Graphics*, vol. 33, No. 4, pp. 59:1-59:12, Jul. 2014.

Kakadiaris et al., "Multimodal Face Recognition: Combination of Geometry with Physiological Information," *IEEE Computer Society Conference on Computer Vision and Pattern Recognition*, Jun. 2005, VBPR '05, vol. 2, pp. 1022-1029.

Kim, "Apple iPhone 12 'notch' disappearing . . . New Face ID test," industry, retrieved from https://nocutnews.co.kr/news/5232116, Oct. 23, 2019, 5 pages.

Pamplona et al., "Tailored Displays to Compensate for Visual Aberrations," ACM Transactions on Graphics, vol. 31, No. 4, Article 81, Jul. 2012, pp. 81:1-81:12.

Sang et al., "Pose-Invariant Face Recognition via RGB-D Images," *Computational Intelligence and Neuroscience*, vol. 2016, Article ID 3563758, Oct. 2015, pp. 1-9.

White et al., "Quantitative Descriptors of Corneal Topography: A Clinical Study," Archives of Ophthalmology, vol. 109, No. 3, Mar. 1991, pp. 349-353.

Yong, "Analysis of Apple IA Chip," *UPI News*, retrieved from https://www.upinews.kr/newsView/upi201807150003, Jul. 15, 2018, including non-official translation, 22 pages.

\* cited by examiner

HANDHELD ELECTRONIC DEVICE

CROSS-REFERENCE TO RELATED APPLICATION(S)

This application is a nonprovisional patent application of and claims the benefit of U.S. Provisional Patent Application No. 63/155,693, filed Mar. 2, 2021 and titled "Handheld Electronic Device," U.S. Provisional Patent Application No. 63/170,327, filed Apr. 2, 2021 and titled "Handheld Electronic Device," and U.S. Provisional Patent Application No. 63/208,477, filed Jun. 8, 2021 and titled "Handheld Electronic Device," the disclosures of which are hereby incorporated herein by reference in their entireties.

FIELD

The subject matter of this disclosure relates generally to handheld electronic devices, and more particularly, to mobile phones.

BACKGROUND

Modern consumer electronic devices take many shapes and forms, and have numerous uses and functions. Smartphones, for example, provide various ways for users to interact with other people that extend beyond telephone communications. Such devices may include numerous systems to facilitate such interactions. For example, a smartphone may include a touch-sensitive display for providing graphical outputs and for accepting touch inputs, wireless communications systems for connecting with other devices to send and receive voice and data content, cameras for capturing photographs and videos, and so forth. However, integrating these subsystems into a compact and reliable product that is able to withstand daily use presents a variety of technical challenges. The systems and techniques described herein may address many of these challenges while providing a device that offers a wide range of functionality.

SUMMARY

A portable electronic device may include a housing, a display at least partially within the housing, a front cover coupled to the housing and positioned over the display, and a biometric sensor module configured to illuminate an object and capture an image of the object through the front cover. The biometric sensor module may include a first lens positioned below the front cover, a first light source positioned below the first lens and configured to project, through the first lens, a dot pattern on the object, a second light source positioned below the first lens and configured to illuminate, through the first lens, the object with a flood of light, a second lens positioned below the front cover, and a light sensor positioned below the second lens and configured to capture an image of the object. The object may be a user's face, and the portable electronic device may be configured to determine a depth map of the user's face using the dot pattern projected onto the user's face and authenticate the user based at least in part on the depth map of the user's face.

The first light source may project infrared light, the flood of light may be infrared light, and the light sensor may be an infrared light sensor. The first light source may be positioned below a central region of the first lens and the second light source may be positioned below a peripheral region of the first lens. Light from the first light source passing through the central region of the first lens may be rendered in focus on the object, and light from the second light source passing through the peripheral region of the first lens may be rendered out of focus on the object.

The biometric sensor module may include a housing structure and the first lens, the first light source, the second lens, the second light source, and the light sensor may be positioned at least partially within the housing structure. The second light source may include a radial array of light-emitting elements.

A mobile phone may include a housing, a display at least partially within the housing, a front cover coupled to the housing and positioned over the display, and a light emitter below the front cover and configured to emit light through the front cover. The light emitter may include a first lens positioned below the front cover, a first light source positioned below a central region of the first lens, and a second light source positioned below a peripheral region of the first lens. The mobile phone may further include a light receiver below the front cover and including a second lens positioned below the front cover and configured to receive light through the front cover and a light sensor positioned below the second lens.

The first light source may be aligned with an optical axis of the first lens and the second light source may be offset from the optical axis of the first lens. The central region of the first lens may be configured to focus a pattern of light emitted by the first light source onto an object and the peripheral region of the first lens may be configured to blur light emitted by the second light source. The pattern of light may be a grid of discrete points of infrared light. The light emitted by the second light source may be configured to illuminate the object with a flood of infrared light. The light receiver may be configured to capture an infrared image of the object while the pattern of light is focused on the object. The light emitter and the light receiver may be positioned at least partially within a housing structure of a biometric sensor module.

A portable electronic device may include a housing, a display at least partially within the housing, a front cover coupled to the housing and positioned over the display, and a biometric sensor module configured to illuminate a face of a user and to capture an image of the face of the user through the front cover. The biometric sensor module may include a housing structure, a first lens at least partially within the housing structure, a light sensor positioned below the first lens, a second lens at least partially within the housing structure, a first light source positioned below the second lens and configured to project a first illumination pattern on the face of the user, and a second light source positioned below the second lens and configured to project a second illumination pattern of light that, when reflected off of the object and captured by the light sensor, produces an image of the object.

The first illumination pattern may be a set of discrete points of light. The first light source may be an infrared laser light source. The infrared laser light source may be a first infrared laser light source and the second light source may be a second infrared laser light source. The first infrared laser light source may be a first vertical-cavity surface-emitting laser and the second infrared laser light source may be a second vertical-cavity surface-emitting laser. The first light source may be positioned below a central region of the second lens, the second light source may be positioned below a peripheral region of the second lens, and the peripheral region of the second lens may be configured to blur light emitted by the second light source.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Mobile phones as described herein may include complex, sophisticated components and systems that facilitate a multitude of functions. For example, mobile phones according to the instant disclosure may include touch- and/or force-sensitive displays, numerous cameras (including both front- and rear-facing cameras), GPS systems, haptic actuators, wireless charging systems, and all requisite computing components and software to operate these (and other) systems and otherwise provide the functionality of the mobile phones.

Figure 1A:
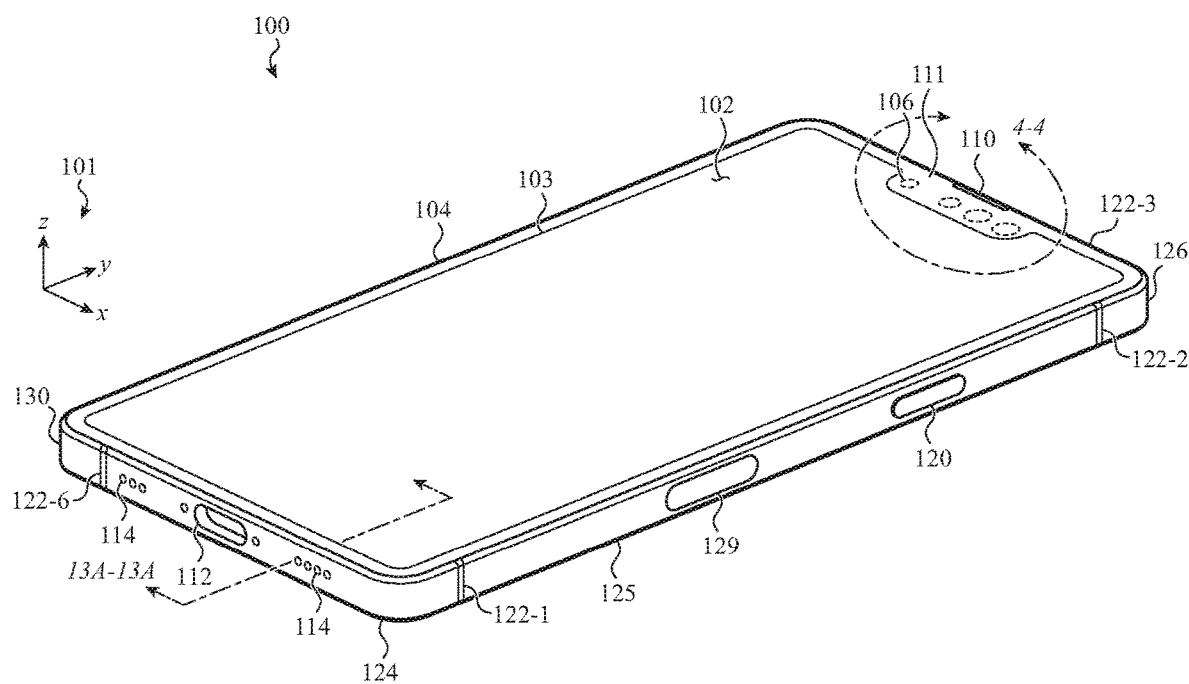
FIGS. 1A-1B depict an example electronic device.
Figure 1B:
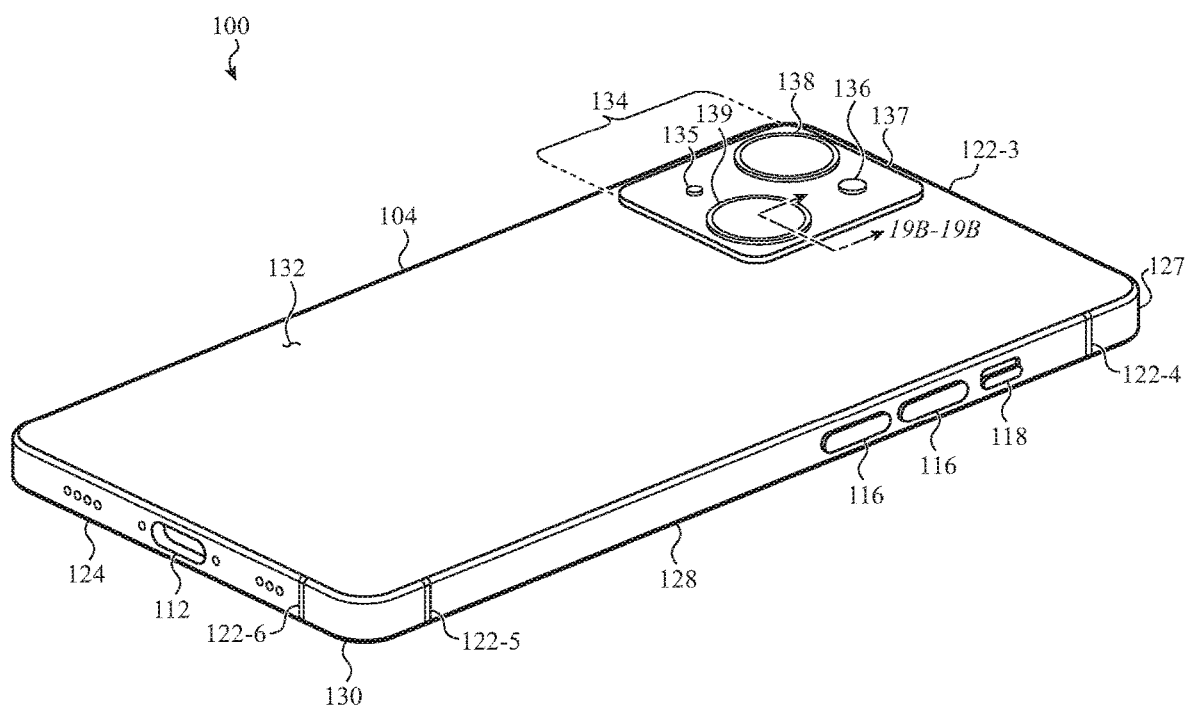

FIGS. 1A and 1B show an example electronic device 100 embodied as a mobile phone. FIG. 1A illustrates a front of the device 100, while FIG. 1B illustrates a back side of the device. While the device 100 is a mobile phone, the concepts presented herein may apply to any appropriate electronic devices, including portable electronic devices, wearable devices (e.g., watches), laptop computers, handheld gaming devices, tablet computers, computing peripherals (e.g., mice, touchpads, keyboards), or any other device. Accordingly, any reference to an "electronic device" encompasses any and all of the foregoing.

The electronic device 100 includes a cover 102 (e.g., a front cover), such as a glass, glass-ceramic, ceramic, plastic, sapphire, or other substantially transparent material, component, or assembly, attached to a housing 104 (which may include a housing structure defined by one or more housing members). The cover 102 may be positioned over a display 103. The cover 102 may be formed from glass (e.g., a chemically strengthened glass), sapphire, ceramic, glass-ceramic, plastic, or another suitable material. The cover 102 may be formed as a monolithic or unitary sheet. The cover 102 may also be formed as a composite of multiple layers of different materials, coatings, and other elements.

The display 103 may be at least partially positioned within the interior volume of the housing 104. The display 103 may be coupled to the cover 102, such as via an adhesive or other coupling scheme. The display 103 may include a liquid-crystal display (LCD), a light-emitting diode, an organic light-emitting diode (OLED) display, an active layer organic light emitting diode (AMOLED) display, an organic electroluminescent (EL) display, an electrophoretic ink display, or the like. The display 103 may be configured to display graphical outputs, such as graphical user interfaces, that the user may view and interact with. The device 100 may also include an ambient light sensor that can determine properties of the ambient light conditions surrounding the device 100. Example ambient light sensors are described herein with respect to FIGS. 11A-11C. The device 100 may use information from the ambient light sensor to change, modify, adjust, or otherwise control the display 103 (e.g., by changing a hue, brightness, saturation, or other optical aspect of the display based on information from the ambient light sensor).

The display 103 may include or be associated with one or more touch- and/or force-sensing systems. In some cases, components of the touch- and/or force-sensing systems are integrated with the display stack. For example, electrode layers of a touch and/or force sensor may be provided in a stack that includes display components (and is optionally attached to or at least viewable through the cover 102). The touch- and/or force-sensing systems may use any suitable type of sensing technology, including capacitive sensors, resistive sensors, surface acoustic wave sensors, piezoelectric sensors, strain gauges, or the like. The outer or exterior surface of the cover 102 may define an input surface (e.g., a touch- and/or force-sensitive input surface) of the device. While both touch- and force-sensing systems may be included, in some cases the device 100 includes a touch-sensing system and does not include a force-sensing system.

The device 100 may also include a front-facing camera 106. The front-facing camera 106 may be positioned below or otherwise covered and/or protected by the cover 102. The front-facing camera 106 may have any suitable operational parameters. For example, the front-facing camera 106 may include a 12 megapixel sensor (with 1 micron pixel size), and an 80-90° field of view. The front-facing camera 106 may have fixed focus optical elements with an aperture number of f/2.2. Other types of cameras may also be used for the front-facing camera 106, such as auto-focus cameras.

The front-facing camera 106 may be positioned in a front-facing sensor region 111. The front-facing sensor region 111 may be positioned in a notch-like area of the front of the device 100. In some cases, as described herein, the front-facing sensor region 111 may be positioned in or defined by a recessed area of the display 103 (e.g., an area that is not occupied by the display or by a visually active portion of the display). In some cases, the front-facing sensor region 111 includes a mask or other visually opaque component or treatment that defines openings for the sensors. In some cases, one or more of the sensors or other devices in the front-facing sensor region 111 (e.g., the front-facing camera 106) are aligned with a hole formed through one or more layers of the display 103 to provide optical access to the sensor. The front-facing sensor region 111 may include components such as a flood illuminator module, a proximity sensor module, an infrared light projector, an infrared image capture device, and the front-facing camera 106.

The device 100 may also include one or more buttons (e.g., button 120, and buttons 116 in FIG. 1B), switches (e.g., switch 118, FIG. 1B), and/or other physical input systems. Such input systems may be used to control power states (e.g., the button 120), change speaker volume (e.g., the buttons 116), switch between "ring" and "silent" modes, and the like (e.g., the switch 118).

The device 100 may also include a speaker port 110 to provide audio output to a user, such as to a user's ear during voice calls. The speaker port 110 may also be referred to as a receiver, receiver port, or an earpiece in the context of a mobile phone. The device 100 may also include a charging port 112 (e.g., for receiving a connector of a power cable for providing power to the device 100 and charging the battery of the device 100). The device 100 may also include audio openings 114. The audio openings 114 may allow sound output from an internal speaker system (e.g., the speaker system 224, FIG. 2) to exit the housing 104. The device 100 may also include one or more microphones. In some cases, a microphone within the housing 104 may be acoustically coupled to the surrounding environment through an audio opening 114.

The housing 104 may be a multi-piece housing. For example, the housing 104 may be formed from multiple housing members 124, 125, 126, 127, 128, and 130, which are structurally coupled together via one or more joint structures 122 (e.g., 122-1-122-6). Together, the housing members 124, 125, 126, 127, 128, and 130 and the joint structures 122 may define a band-like housing structure that defines four side walls (and thus four exterior side surfaces) of the device 100. Thus, both the housing members and the joint structures define portions of the exterior side surfaces of the device 100.

The housing members 124, 125, 126, 127, 128, and 130 may be formed of a conductive material (e.g., a metal such as aluminum, stainless steel, or the like), and the joint structures 122 may be formed of one or more polymer materials (e.g., glass-reinforced polymer). The joint structures 122 may include two or more molded elements, which may be formed of different materials. For example, an inner molded element may be formed of a first material (e.g., a polymer material), and an outer molded element may be formed of a second material that is different from the first (e.g., a different polymer material). The materials may have different properties, which may be selected based on the different functions of the inner and outer molded elements. For example, the inner molded element may be configured to make the main structural connection between housing members, and may have a higher mechanical strength and/or toughness than the outer molded element. On the other hand, the outer molded element may be configured to have a particular appearance, surface finish, chemical resistance, water-sealing function, or the like, and its composition may be selected to prioritize those functions over mechanical strength.

In some cases, one or more of the housing members 124, 125, 126, 127, 128, and 130 (or portions thereof) are configured to operate as antennas (e.g., members that are configured to transmit and/or receive electromagnetic waves to facilitate wireless communications with other computers and/or devices). To facilitate the use of the housing members as antennas, feed and ground lines may be conductively coupled to the housing members to couple the housing members to other antennas and/or communication circuitry. FIG. 11, described in more detail below, depicts example antenna feed and ground lines for an example device. Further, the joint structures 122 may be substantially nonconductive to provide suitable separation and/or electrical isolation between the housing members (which may be used to tune the radiating portions, reduce capacitive coupling between radiating portions and other structures, and the like). In addition to the housing members 124, 125, 126, 127, 128, and 130, the device 100 may also include various internal antenna elements that are configured to transmit and receive wireless communication signals through various regions of the housing 104. As shown in FIG. 1A, the device 100 may include an antenna window 129 that allows for the passage of radio-frequency communication signals through a corresponding region of the housing 104.

The joint structures 122 may be mechanically interlocked with the housing members to structurally couple the housing members and form a structural housing assembly. Further details about the joint structures 122 and their mechanical integration with the housing members are provided herein.

The exterior surfaces of the housing members 124, 125, 126, 127, 128, and 130 may have substantially a same color, surface texture, and overall appearance as the exterior surfaces of the joint structures 122. In some cases, the exterior surfaces of the housing members 124, 125, 126, 127, 128, and 130 and the exterior surfaces of the joint structures 122 are subjected to at least one common finishing procedure, such as abrasive-blasting, machining, polishing, grinding, or the like. Accordingly, the exterior surfaces of the housing members and the joint structures may have a same or similar surface finish (e.g., surface texture, roughness, pattern, etc.). In some cases, the exterior surfaces of the housing members and the joint structures may be subjected to a two-stage blasting process to produce the target surface finish.

FIG. 1A also includes an example coordinate system 101 that may define directions with reference to the device 100 (or other electronic devices described herein). The coordinate system 101 defines a positive x direction, a positive y direction, and a positive z direction. Unless stated otherwise, references herein to a positive x, positive y, or positive z direction will be understood to refer generally to the coordinate system 101 and its relationship to the device 100 in FIG. 1A. Negative x, y, and z directions will be understood to be opposite to the positive x, y, and z directions shown in the coordinate system in FIG. 1A.

FIG. 1B illustrates a back side of the device 100. The device 100 may include a back or rear cover 132 coupled to the housing 104 and defining at least a portion of the exterior rear surface of the device 100. The rear cover 132 may include a substrate formed of glass, though other suitable materials may alternatively be used (e.g., plastic, sapphire, ceramic, glass-ceramic, etc.). The rear cover 132 may include one or more decorative layers on the exterior or interior surface of the substrate. For example, one or more opaque layers may be applied to the interior surface of the substrate (or otherwise positioned along the interior surface of the substrate) to provide a particular appearance to the back side of the device 100. The opaque layer(s) may include a sheet, ink, dye, or combinations of these (or other) layers, materials, or the like. In some cases the opaque layer(s) have a color that substantially matches a color of the housing 104 (e.g., the exterior surfaces of the housing members and the joint structures). The device 100 may include a wireless charging system, whereby the device 100 can be powered and/or its battery recharged by an inductive (or other electromagnetic) coupling between a charger and a wireless charging system within the device 100. In such cases, the rear cover 132 may be formed of a material that allows and/or facilitates the wireless coupling between the charger and the wireless charging system (e.g., glass).

The device 100 may also include a sensor array 134, which may include various types of sensors, including one or more rear-facing cameras, depth sensing devices, flashes, microphones, and the like. The sensor array 134 may be at least partially defined by a protrusion 137 that extends from the rear of the device 100. The protrusion 137 may define a portion of the rear exterior surface of the device 100, and may at least partially define a raised sensor array region of the sensor array 134. In some cases, the protrusion 137 may be formed by attaching a piece of material (e.g., glass) to another piece of material (e.g., glass). In other cases, the rear cover 132 may include a monolithic structure, and the protrusion 137 may be part of the monolithic structure. For example, the rear cover 132 may include a monolithic glass structure (or glass ceramic structure) that defines the protrusion 137 as well as the surrounding area. In such cases, the protrusion 137 may be an area of increased thickness of the monolithic structure, or it may be molded into a substantially uniform thickness monolithic structure (e.g., and may correspond to a recessed region along an interior side of the monolithic structure).

The device may also include, as part of the sensor array, one or more rear-facing devices, which may include an ambient-light sensor (ALS), a microphone, and/or a depth sensing device that is configured to estimate a distance between the device 100 and a separate object or target. The sensor array 134 may also include multiple cameras, such as a first camera 138 and a second camera 139. The first camera 138 may include a super-wide camera having a 12 megapixel sensor and a wide field of view (e.g., 120° FOV) optical stack with an aperture number of f/2.4; the second camera 139 may include a wide view camera having a 12 megapixel sensor and an aperture number of f/1.6. In some cases, the sensor array 134 may include a telephoto lens having a 12 megapixel sensor with a 3× optical zoom optical stack having an aperture number ranging from f/2.0 to f/2.8 (e.g., in addition to the first and second cameras 138, 139, or in place of one of the first or second cameras). One or more of the cameras (e.g., cameras 138, 139) of the sensor array 134 may also include optical image stabilization, whereby the lens is dynamically moved relative to a fixed structure within the device 100 to reduce the effects of "camera shake" on images captured by the camera. The camera(s) may also perform optical image stabilization by moving the image sensor relative to a fixed lens or optical assembly. One or more of the cameras may include autofocus functionality, in which one or more lens elements (and/or sensors) are movable to focus an image on a sensor.

As shown in FIG. 1B, the cameras of the sensor array 134 may be positioned diagonally with respect to the protrusion 137 (e.g., the raised sensor array). For example, a first hole may extend through the rear cover 132 at a location proximate a first corner region of the senor array 134, and the first camera 138 may be positioned at least partially in the first hole, and a second hole may extend through the rear cover 132 at a location proximate a second corner region diagonal from the first corner region of the sensor array 134, and the second camera 139 may be positioned at least partially in the second hole. Thus, the first and second holes, and therefore the first and second cameras, may be positioned along a diagonal path from the first corner to the second corner of the sensor array 134.

The second camera 139 may have an image sensor with a pixel size between about 1.5 microns and about 2.0 microns, and the first camera 138 may have an image sensor with a pixel size between about 0.8 microns and about 1.4 microns. If a camera with a telephoto lens is provided, it may have an image sensor with a pixel size between about 0.8 microns and about 1.4 microns.

The sensor array 134, along with associated processors and software, may provide several image-capture features. For example, the sensor array 134 may be configured to capture full-resolution video clips of a certain duration each time a user captures a still image. As used herein, capturing full-resolution images (e.g., video images or still images) may refer to capturing images using all or substantially all of the pixels of an image sensor, or otherwise capturing images using the maximum resolution of the camera (regardless of whether the maximum resolution is limited by the hardware or software).

The captured video clips may be associated with the still image. In some cases, users may be able to select individual frames from the video clip as the representative still image associated with the video clip. In this way, when the user takes a snapshot of a scene, the camera will actually record a short video clip (e.g., 1 second, 2 seconds, or the like), and the user can select the exact frame from the video to use as the captured still image (in addition to simply viewing the video clip as a video).

The cameras of the sensor array 134 may also have or provide a high-dynamic-range (HDR) mode, in which the camera captures images having a dynamic range of luminosity that is greater than what is captured when the camera is not in the HDR mode. In some cases, the sensor array 134 automatically determines whether to capture images in an HDR or non-HDR mode. Such determination may be based on various factors, such as the ambient light of the scene, detected ranges of luminosity, tone, or other optical parameters in the scene, or the like. HDR images may be produced by capturing multiple images, each using different exposure or other image-capture parameters, and producing a composite image from the multiple captured images.

The sensor array 134 may also include or be configured to operate in an object detection mode, in which a user can select (and/or the device 100 can automatically identify) objects within a scene to facilitate those objects being processed, displayed, or captured differently than other parts of the scene. For example, a user may select (or the device 100 may automatically identify) a person's face in a scene, and the device 100 may focus on the person's face while selectively blurring the portions of the scene other than the person's face. Notably, features such as the HDR mode and the object detection mode may be provided with a single camera (e.g., a single lens and sensor).

The sensor array may include a flash 136 that is configured to illuminate a scene to facilitate capturing images with the sensor array 134. The flash 136 may include one or more light sources, such as one or more light emitting diodes (e.g., 1, 2, 3, 4, or more LEDs). The flash 136, in conjunction with the sensor array 134 or other systems of the device 100, may adjust the color temperature of the light emitted by the light sources in order to match or otherwise adapt to a color temperature within a scene being captured. The device 100 may also be configured to operate the flash 136 and the shutter of the sensor array 134 (e.g., the shutter of one or more of the cameras 138, 139) to avoid consequences of flash "flicker." For example, the device 100 may avoid capturing exposures during moments where the flash 136 is at a period of no or low illumination (e.g., which may be caused by discontinuous or pulsed operation of the LEDs).

The sensor array 134 may also include a microphone 135. The microphone 135 may be acoustically coupled to the exterior environment through a hole defined in the rear cover of the device 100 (e.g., through the portion of the rear cover that defines the protrusion 137).

Figure 1C:
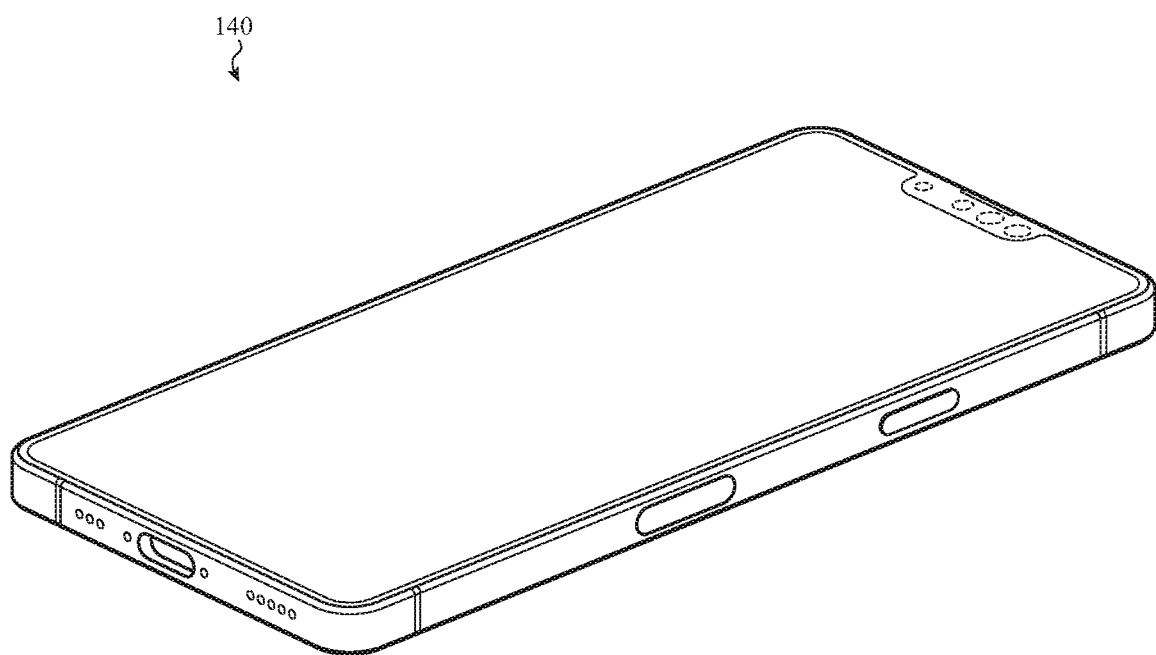
FIGS. 1C-1D depict another example electronic device.
Figure 1D:
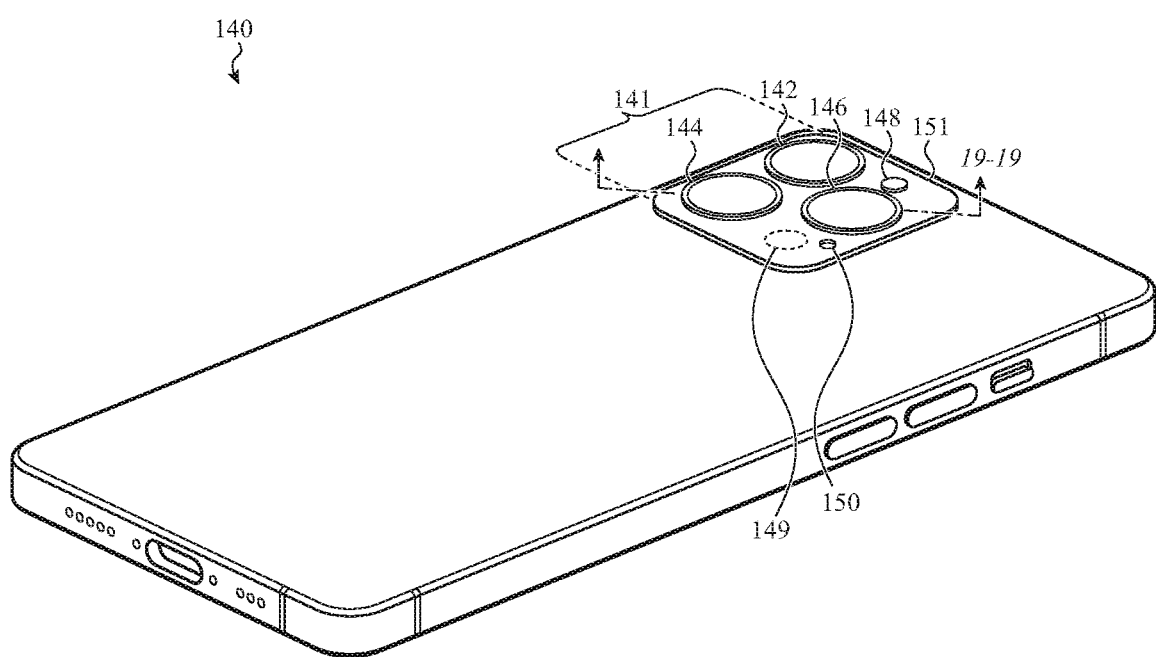

FIGS. 1C and 1D show another example electronic device 140 embodied as a mobile phone. The electronic device 140 may have many of the same or similar outward-facing components as the electronic device 100. Accordingly, descriptions and details of such components from FIGS. 1A-1B (e.g., displays, buttons, switches, housings, covers, charging ports, joint structures, etc.) apply equally to the corresponding components shown in FIGS. 1C and 1D.

Figure 3:
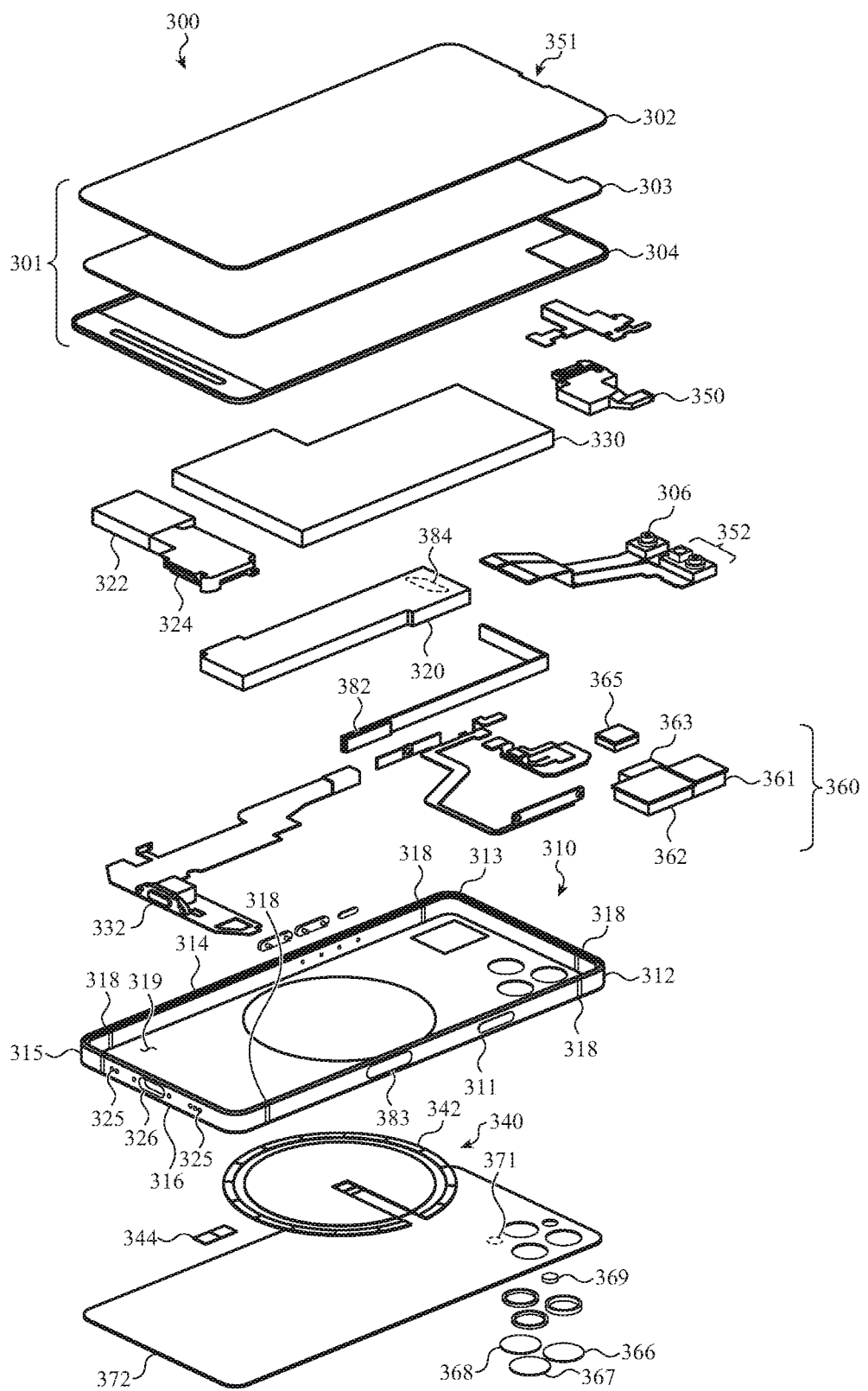
FIG. 3 depicts an exploded view of an example electronic device.

While the device 100 in FIG. 1B is shown as including a sensor array 134 with two cameras, the device 140 as shown in FIG. 1D includes a sensor array 141 that includes three cameras (as shown, for example, in FIG. 3, described herein). The sensor array 141 may be in a sensor array region that is defined by a protrusion 151 in a rear cover of the device 140. The protrusion 151 may have the same or similar construction as the protrusion 137 in FIG. 1B.

A first camera 142 may include a 12 megapixel sensor and a telephoto lens with a 3× optical zoom and an aperture number of f/2.8; a second camera 144 may include a 12 megapixel sensor and a wide angle lens having an aperture number of f/1.5; and a third camera 146 may include a 12 megapixel sensor and a super-wide camera with a wide field of view (e.g., 120° FOV) and an aperture number of f/1.8. One or more of the cameras of the sensor array 141 may also include optical image stabilization, whereby the lens is dynamically moved relative to a fixed structure within the device 100 to reduce the effects of "camera shake" on images captured by the camera. The camera(s) may also perform optical image stabilization by moving the image sensor relative to a fixed lens or optical assembly.

The first camera 142 may include an image sensor with a pixel size between about 0.8 microns and about 1.4 microns. The second camera 144 may include an image sensor with a pixel size between about 1.6 microns and about 2.3 microns. The third camera 146 may include an image sensor with a pixel size between about 0.8 microns and about 1.4 microns.

For example, a wide view camera having a 12 megapixel sensor and an aperture number of f/1.6 may have an image sensor with a pixel size between about 1.5 microns and about 2.0 microns; a super-wide camera having a 12 megapixel sensor and a wide field of view (e.g., 120° FOV) optical stack with an aperture number of f/2.4 may have an image sensor with a pixel size between about 0.8 microns and about 1.4 microns; and a telephoto lens having a 12 megapixel sensor with a 3× optical zoom optical stack having an aperture number ranging from f/2.0 to f/2.8 may have an image sensor with a pixel size between about 0.8 microns and about 1.4 microns. One or more of the cameras may include autofocus functionality, in which one or more lens elements (and/or sensors) are movable to focus an image on a sensor.

The sensor array 141 may also include a depth sensing device 149 that is configured to estimate a distance between the device and a separate object or target. The depth sensing device 149 may estimate a distance between the device and a separate object or target using lasers and time-of-flight calculations, or using other types of depth sensing components or techniques.

The device 140 may also include a flash 148 that is configured to illuminate a scene to facilitate capturing images with the cameras of the sensor array 141. The flash 148 is configured to illuminate a scene to facilitate capturing images with the sensor array 141. The flash 148 may include one or more light sources, such as one or more light emitting diodes (e.g., 1, 2, 3, 4, or more LEDs).

The sensor array 141 may also include a microphone 150. The microphone 150 may be acoustically coupled to the exterior environment through a hole defined in the rear cover of the device 140 (e.g., through the portion of the rear cover that defines the protrusion 151).

Other details about the sensor array, the individual cameras of the sensor array, and/or the flash described with respect to the device 100 may be applicable to the sensor array, the individual cameras, and/or the flash of the device 140, and such details will not be repeated here to avoid redundancy.

Figure 2:
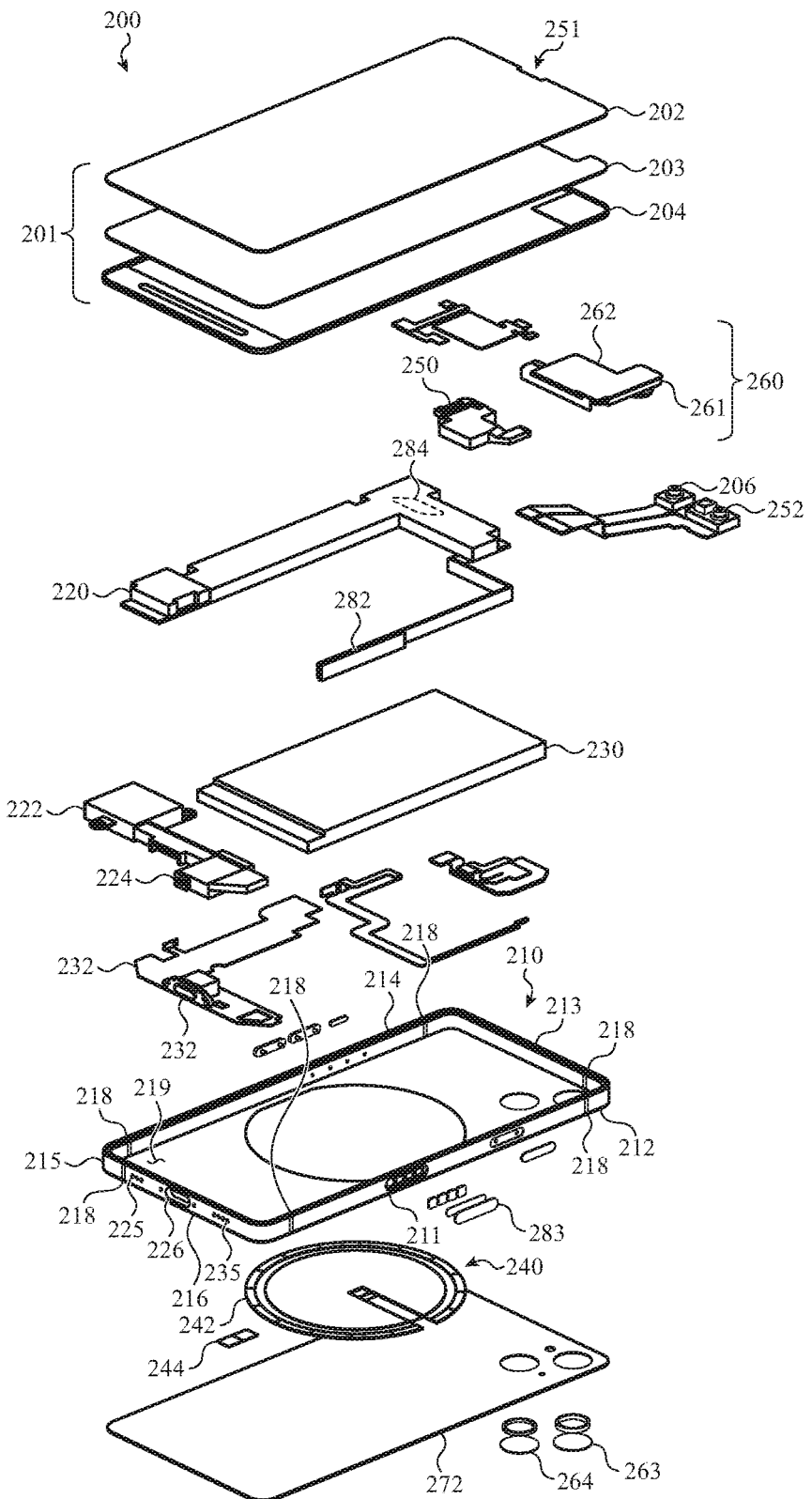
FIG. 2 depicts an exploded view of an example electronic device.

FIG. 2 depicts an exploded view of an example electronic device. In particular, FIG. 2 depicts an exploded view of a device 200, showing various components of the device 200 and example arrangements and configurations of the components. The description of the various components and elements of device 100 of FIGS. 1A and 1B may also be applicable to the device 200 depicted in FIG. 2. A redundant description of some of the components is not repeated herein for clarity.

As shown in FIG. 2, the device 200 includes a cover 202 (e.g., a front cover), which may be formed of glass, ceramic, or other transparent substrate. In this example, the cover 202 may be formed from a glass or glass-ceramic material. A glass-ceramic material may include both amorphous and crystalline or non-amorphous phases of one or more materials and may be formulated to improve strength or other properties of the cover 202. In some cases, the cover 202 may include a sheet of chemically strengthened glass or glass-ceramic having one or more coatings including an anti-reflective (AR) coating, an oleophobic coating, or other type of coating or optical treatment. In some cases, the cover 202 includes a sheet of material that is less than 1 mm thick. In some cases, the sheet of material is less than 0.80 mm. In some cases, the sheet of material is approximately 0.60 mm or less. The cover 202 may be chemically strengthened using an ion exchange process to form a compressive stress layer along exterior surfaces of the cover 202.

The cover 202 extends over a substantial entirety of the front surface of the device and may be positioned within an opening defined by the housing 210. As described in more detail below, the edges or sides of the cover 202 may be surrounded by a protective flange or lip of the housing 210 without an interstitial component between the edges of the cover 202 and the respective flanges of the housing 210. This configuration may allow an impact or force applied to the housing 210 to be transferred to the cover 202 without directly transferring shear stress through the display 203 or frame 204.

As shown in FIG. 2, the display 203 is attached to an internal surface of the cover 202. The display 203 may include an edge-to-edge organic light emitting diode (OLED) display that measures 13.7 cm (5.4 inches) corner-to-corner. The perimeter or non-active area of the display 203 may be reduced to allow for very thin device borders around the active area of the display 203. In some cases, the display 203 allows for border regions of 1.5 mm or less. In some cases, the display 203 allows for border regions of 1 mm or less. In one example implementation, the border region is approximately 0.9 mm. The display 203 may have a relatively high pixel density of approximately 450 pixels per inch (PPI) or greater. In some cases, the display 203 has a pixel density of approximately 475 PPI. The display 203 may have an integrated (on-cell) touch-sensing system. For example, an array of electrodes that are integrated into the OLED display may be time and/or frequency multiplexed in order to provide both display and touch-sensing functionality. The electrodes may be configured to detect a location of a touch, a gesture input, multi-touch input, or other types of touch input along the external surface of the cover 202. In some cases, the display 203 includes another type of display element, such as a liquid-crystal display (LCD) without an integrated touch-sensing system. That is, the device 200 may include one or more touch- and/or force-sensing layers that are positioned between the display 203 and the cover 202.

The display 203, also referred to as a display stack, may include always-on-display (AOD) functionality. For example, the display 203 may be configurable to allow designated regions or subsets of pixels to be displayed when the device 200 is powered on such that graphical content is visible to the user even when the device 200 is in a low-power or sleep mode. This may allow the time, date, battery status, recent notifications, and other graphical content to be displayed in a lower-power or sleep mode. This graphical content may be referred to as persistent or always-on graphical output. While some battery power may be consumed when displaying persistent or always-on graphical output, the power consumption is typically less than during normal or full-power operation of the display 203. This functionality may be enabled by only operating a subset of the display pixels and/or at a reduced resolution in order to reduce power consumption by the display 203.

As shown in FIG. 2, the device 200 may also include a frame member 204, also referred to simply as a frame 204, that is positioned below the cover 202 and that extends around at least an outer periphery of the display 203. A perimeter of the frame 204 may be attached to a lower or inner surface of the cover 202. A portion of the frame 204 may extend below the display 203 and may attach the cover 202 to the housing 210. Because the display 203 is attached to a lower or inner surface of the cover 202, the frame 204 may also be described as attaching both the display 203 and the cover 202 to the housing 210. The frame 204 may be formed of a polymer material, metal material, or combination of polymer and metal materials. The frame 204 may support elements of the display stack, provide anchor points for flexible circuits, and/or be used to mount other components and device elements. In some cases, the frame 204 includes one or more metal or conductive elements that provide shielding between device components, such as between the display stack (including display components and touch sensor components) and other components like the haptic actuator 222, the speaker system 224, and the like.

The cover 202, display stack 203, and frame member 204 may be part of a top module 201 of the device 200. The top module 201 may be assembled as a subassembly, which may then be attached to a housing member. For example, as described herein, the display 203 may be attached to the cover 202 (e.g., via a transparent adhesive), and the frame member 204 may be attached (e.g., via adhesive) to the cover around a periphery of the display stack 203. The top module 201 may then be attached to a housing member of the device 200 by mounting and adhering the frame member 204 to a ledge defined by the housing member.

The device 200 also includes a speaker module 250 that is configured to output sound via a speaker port. The speaker port may be positioned in and/or at least partially defined by a recess 251 of the cover 202. As described herein, a trim piece may be positioned at least partially in the recess 251 to facilitate the output of sound while also inhibiting the ingress of debris, liquid, or other materials or contaminants into the device 200. Output from the speaker module 250 may pass through an acoustic path defined at least in part by the speaker module 250 itself, and the trim piece. In some cases, part of the acoustic path (e.g., between the speaker module 250 and the trim piece) is defined by the housing 210 and/or a molded material that is coupled to the housing 210. For example, a molded material (e.g., a fiber-reinforced polymer) may be molded against a metal portion of the housing 210 (e.g., the housing member 213, described herein). The molded material may also form one or more joint structures that also structurally join housing members together (e.g., the joint structures 218). A passage (e.g., a tube-like tunnel) may be defined through the molded material to acoustically couple the speaker module 250 to the trim piece and/or the recess 251 more generally, thereby directing sound from the speaker module 250 to the exterior of the device 200. In some cases, a portion of the passage that extends through the molded material is defined by a housing member itself, as described herein with reference to FIGS. 6A-6B.

As shown in FIG. 2, the device 200 also includes one or more cameras, light emitters, and/or sensing elements that are configured to transmit signals, receive signals, or otherwise operate along the front surface of the device. In this example, the device 200 includes a front camera 206 that includes a high-resolution camera sensor. The front camera 206 may have a 12 megapixel resolution sensor with optical elements that provide a fixed focus and an 85° field of view. The device 200 also includes a facial recognition sensor 252 that includes an infrared light projector and infrared light sensor that are configured to sense an array of depth points or regions along the face of the user. The array of depth points may be characterized as a unique signature or bio-identifier, which may be used to identify the user and unlock the device 200 or authorize functionality on the device 200 like the purchase of software apps or the use of payment functionality provided by the device 200.

The device 200 may also include one or more other sensors or components. For example, the device 200 may include a front light illuminator element for providing a flash or illumination for the front camera 206. The device 200 may also include an ambient light sensor (ALS) that is used to detect ambient light conditions for setting exposure aspects of the front camera 206 and/or for controlling the operation of the display.

FIG. 2 also illustrates one or more cameras, light emitters, and/or sensing elements that are configured to transmit signals, receive signals, or otherwise operate along the rear surface of the device. As depicted in FIG. 2, these elements may be part of a sensor array 260. In this example, the sensor array 260 includes a first camera 261 having a 12 megapixel image sensor and a wide angle lens with an aperture number of f/1.6. The first camera 261 also includes a dual photodiode sensor having an APS+ sensor format. The sensor array 260 also includes a second camera 262 having a 12 megapixel image sensor and a super-wide angle lens (120° FOV) with an aperture number of f/2.4. The sensor array 260 also includes a light illuminator that may be used as a flash for photography or as an auxiliary light source (e.g., a flashlight). The sensor array 260 also features an integrated chassis design that minimizes space while providing the precision alignment required for multiple high-resolution cameras. In some cases, the sensor array 260 also includes a microphone, an ambient light sensor, a depth sensor, and/or other sensors that are adapted to sense along the rear surface of the device 200.

As shown in FIG. 2, the cameras 261 and 262 may be aligned with camera covers 263 and 264, respectively. The covers 263, 264 may be formed from a glass, glass-ceramic, or sapphire material and may provide a clear window through which the cameras 261, 262 are able to capture a photographic image. In other cases, the covers 263, 264 are optical lenses that filter, magnify, or otherwise condition light received by the respective camera 261, 262. The other sensing or transmitting elements of the sensor array 260 may transmit and/or receive signals through a region of the rear cover 272 or through a separate cover that is coupled to the rear cover 272. As shown in FIG. 2, the covers 263, 264 may extend beyond the exterior surface of the cover 272, and may define a recess along the interior side of the cover 272, such that the lens or other element of the cameras 261 and 262 can extend into the respective recesses. In this way, the device 200 may accommodate a larger lens or other elements of the cameras 261 and 262 than would be possible if the recess were not provided.

The device 200 also includes a battery 230. The battery 230 provides electrical power to the device 200 and its various systems and components. The battery 230 may include a 4.45 V lithium ion battery that is encased in a foil or other enclosing element (e.g., a pouch). The battery 230 may be attached to the device 200 (e.g., to the chassis 219) with one or more adhesives and/or other attachment techniques. In one example, the battery 230 may be attached to the chassis 219, or another structure of the device 200, with a two-layer adhesive, where a first adhesive is adhered to the battery 230 and to a second adhesive, and the second adhesive is bonded to the first adhesive and to the chassis 219 (or other structure of the device 200). The first and second adhesives may have different properties, such as different stiffness (e.g., Young's modulus), different adhesive properties, or the like. For example, in some cases, the first adhesive is configured to adhere to the material of the battery 230 (e.g., with a bond strength above a threshold value), while the second adhesive is configured to adhere to the chassis 219 or other structure of the device (e.g., with a bond strength above the threshold value). In such cases, the first adhesive may not form a sufficiently strong bond with the chassis 219, and the second adhesive may not form a sufficiently strong bond with the battery 230, though the first and second adhesives may form a sufficiently strong bond with one another. Accordingly, by using the two different adhesives (e.g., in the layered configuration described) to ultimately secure the battery 230 to the chassis 219, the overall strength and/or security of the attachment may be greater than if a single adhesive were used.

The battery 230 may be recharged via the charging port 232 (e.g., from a power cable plugged into the charging port 232 through a charging access opening 226), and/or via a wireless charging system 240. The battery 230 may be coupled to the charging port 232 and/or the wireless charging system 240 via battery control circuitry that controls the power provided to the battery and the power provided by the battery to the device 200. The battery 230 may include one or more lithium ion battery cells or any other suitable type of rechargeable battery element.

The charging system 240 may include a coil that inductively couples to an output or transmitting coil of a wireless charger. The coil may provide current to the device 200 to charge the battery 230 and/or power the device. In this example, the charging system 240 includes a coil assembly 242 that includes multiple wraps of a conductive wire or other conduit that is configured to produce a (charging) current in response to being placed in an inductive charging electromagnetic field produced by a separate wireless charging device or accessory. The coil assembly 242 also includes or is associated with an array of magnetic elements that are arranged in a circular or radial pattern. The magnetic elements may help to locate the device 200 with respect to a separate wireless charging device or other accessory. In some implementations, the array of magnets also help to radially locate, orient, or "clock" the device 200 with respect to the separate wireless charging device or other accessory. For example, the array of magnets may include multiple magnetic elements having alternating magnetic polarity that are arranged in a radial pattern. The magnetic elements may be arranged to provide a magnetic coupling to the separate charging device in a particular orientation or set of discrete orientations to help locate the device 200 with respect to the separate charging device or other accessory. This functionality may be described as self-aligning or self-locating wireless charging. As shown in FIG. 2, the device 200 also includes a magnetic fiducial 244 for helping to locate the separate wireless charging device or accessory. In one example, the magnetic fiducial 244 is adapted to magnetically couple to a cable or power cord of the separate wireless charging device or other accessory. By coupling to the cable or power cord, the rotational alignment of the device 200 and the separate wireless charging device or other accessory may be maintained with respect to an absolute or single position. Also, by magnetically coupling the cable or cord to the rear surface of the device 200, the charging device or other accessory may be more securely coupled to the device 200.

In some implementations, the wireless charging system 240 includes an antenna or other element that detects the presence of a charging device or other accessory. In some cases, the charging system includes a near-field communications (NFC) antenna that is adapted to receive and/or send wireless communications between the device 200 and the wireless charger or other accessory. In some cases, the device 200 is adapted to perform wireless communications to detect or sense the presence of the wireless charger or other accessory without using a dedicated NFC antenna. The communications may also include information regarding the status of the device, the amount of charge held by the battery 230, and/or control signals to increase charging, decrease charging, start charging and/or stop charging for a wireless charging operation.

The device 200 may also include a speaker system 224. The speaker system 224 may be positioned in the device 200 so that a respective port 235 is aligned with or otherwise proximate an audio output of the speaker system 224. Accordingly, sound that is output by the speaker system 224 exits the housing 210 via the respective port 235. The speaker system 224 may include a speaker positioned in a housing that defines a speaker volume (e.g., an empty space in front of or behind a speaker diaphragm). The speaker volume may be used to tune the audio output from the speaker and optionally mitigate destructive interference of the sound produced by the speaker. The speaker system 224 may include left and right speakers that are aligned with left and right ports 225, 235, respectively, in order to produce stereo sound.

The device 200 may also include a haptic actuator 222. The haptic actuator 222 may include a movable mass and an actuation system that is configured to move the mass to produce a haptic output. The actuation system may include one or more coils and one or more magnets (e.g., permanent and/or electromagnets) that interact to produce motion. The magnets may be or may include recycled magnetic material. As described herein, the haptic actuator 222 may have a profile or enclosure shape that facilitates physical integration with the battery 230 and other components of the device 200 in order to minimize space and/or maximize the size of the battery.

When the coil(s) are energized, the coil(s) may cause the mass to move, which results in a force being imparted on the device 200. The motion of the mass may be configured to cause a vibration, pulse, tap, or other tactile output detectable via an exterior surface of the device 200. The haptic actuator 222 may be configured to move the mass linearly, though other movements (e.g., rotational) are also contemplated. Other types of haptic actuators may be used instead of or in addition to the haptic actuator 222.

The device 200 also includes a logic board 220 (also referred to herein as a circuit board assembly). The logic board 220 may include a substrate, and processors, memory, and other circuit elements coupled to the substrate. The logic board 220 may include multiple circuit substrates that are stacked and coupled together in order to maximize the area available for electronic components and circuitry in a compact form factor. The logic board 220 may include provisions for a subscriber identity module (SIM). The logic board 220 may include electrical contacts and/or a SIM tray assembly for receiving a physical SIM card and/or the logic board 220 may include provisions for an electronic SIM. The logic board 220 may be wholly or partially encapsulated to reduce the chance of damage due to ingress of water or other fluid.

The logic board 220 may also include wireless communications circuitry, which may be coupled to and/or otherwise use the housing members 211, 212, 213, 214, 215, or 216 (or portions thereof) as radiating members to provide wireless communications. The logic board 220 may also include components such as accelerometers, gyroscopes, near-field communications circuitry and/or antennas, compasses, and the like. In some implementations, the logic board 220 may include a magnetometer that is adapted to detect and/or locate an accessory. For example, the magnetometer may be adapted to detect a magnetic (or non-magnetic) signal produced by an accessory of the device 200 or other device. The output of the magnetometer may include a direction output that may be used to display a directional indicia or other navigational guidance on the display 203 in order to guide the user toward a location of the accessory or other device.

The device 200 may also include one or more pressure transducers that may be operable to detect changes in external pressure in order to determine changes in altitude or height. The pressure sensors may be externally ported and/or positioned within a water-sealed internal volume of the housing 210. The output of the pressure sensors may be used to track flights of stairs climbed, a location (e.g., a floor) of a multi-story structure, movement performed during an activity in order to estimate physical effort or calories burned, or other relative movement of the device 200.

The logic board 220 may also include global position system (GPS) electronics that may be used to determine the location of the device 200 with respect to one or more satellites (e.g., a Global Navigation Satellite System (GNSS)) in order to estimate an absolution location of the device 200. In some implementations, the GPS electronics are operable to utilize dual frequency bands. For example, the GPS electronics may use L1 (L1C), L2 (L2C), L5, L1+L5, and other GPS signal bands in order to estimate the location of the device 200.

The housing 210 may also include a chassis 219, which may be attached to the housing 210. The chassis 219 may be formed of metal, and may act as a structural mounting point for components of the device 200. The chassis 219 may define an opening that corresponds to the size of the coil assembly 242 of the wireless charging system 240, such that the chassis 219 does not shield the wireless coil assembly 242 or otherwise negatively affect the inductive coupling between the coil of the charging system 240 and an external wireless charger or accessory.

As shown in FIG. 2, the housing may include a cover 272 (e.g., rear or back cover) that may define a substantial entirety of the rear surface of the device 200. The cover 272 may be formed from a glass (or glass-ceramic) substrate having portions that are less than 1 mm thick. In some cases, the sheet substrate has portions that are less than 0.80 mm. In some cases, the glass substrate has portions that are approximately 0.60 mm or less. The cover 272 may have a uniform thickness or, in some cases, may have a thickened or raised portion that surrounds the camera covers 263, 264. The cover 272 may be machined (e.g., ground) into a final shape before being polished and/or textured to provide the desired surface finish. The texture may be specially configured to provide a matte appearance while also being resistant to collecting a buildup of skin, lint, or other debris. A series of cosmetic layers may be formed along the inner surface of the cover 272 to provide a desired optical effect and final color of the device 200.

Similar to as described above with respect to cover 202, the cover 272 may be positioned at least partially within an opening defined in the housing 210. Also similar to as described above with respect to cover 202, the edges or sides of the cover 272 may be surrounded by a protective flange or lip of the housing 210 without an interstitial component between the edges of the cover 272 and the respective flanges of the housing 210. The cover 272 is typically chemically strengthened using an ion exchange process to form a compressive stress layer along exterior surfaces of the cover 272.

As described above, the housing 210 may include housing members 211, 212, 213, 214, 215, and 216 structurally joined together via joint structures 218. The joint structures 218 (e.g., the material of the joint structures) may extend over inner surfaces of the housing members. More particularly, a portion of the joint structures 218 may contact, cover, encapsulate, and/or engage with retention features of the housing members that extend from the inner surfaces of the housing members.

Housing members 211, 212, 213, 214, 215, and 216 may also be referred to herein as housing segments and may be formed from aluminum, stainless steel, or other metal or metal alloy material. As described herein, the housing members 211, 212, 213, 214, 215, and 216 may provide a robust and impact resistant sidewall for the device 200. In the present example, the housing members 211, 212, 213, 214, 215, and 216 define a flat sidewall that extends around the perimeter of the device 200. The flat sidewall may include rounded or chamfered edges that define the upper and lower edges of the sidewall of the housing 210. The housing members 211, 212, 213, 214, 215, and 216 may each have a flange portion or lip that extends around and at least partially covers a respective side of the front and rear covers 202, 272. There may be no interstitial material or elements between the flange portion or lip and the respective side surface of the front and rear covers 202, 272. This may allow forces or impacts that are applied to the housing 210 to be transferred to the front and rear covers 202, 272 without affecting the display or other internal structural elements, which may improve the drop performance of the device 200.

As shown in FIG. 2, the device 200 includes multiple antennas that may be adapted to conduct wireless communication using a 5G communication protocol. In particular, the device 200 may include a (side-fired) antenna array 282 that is configured to transmit and receive wireless communication signals through an antenna window 283 or waveguide formed along or otherwise integrated with the sidewall of the housing 210. The side-fired antenna array 282 may be coupled to the logic board 220 via a flexible circuit element or other conductive connection, as described herein. The device 200 may also include a rear antenna module 284 that may include one or more (rear-fired) antenna arrays that may be configured to transmit and receive wireless communication signals through the cover 272. The antenna module 284 may be attached to a back or bottom surface of the logic board 220.

The antenna module 284 may include multiple antenna arrays. For example, the antenna module 284 may include one or more millimeter-wave antenna arrays. In the case where the antenna module 284 includes multiple millimeter-wave antenna arrays (each of which may include one or more radiating elements), the multiple millimeter-wave antenna arrays may be configured to operate according to a diversity scheme (e.g., spatial diversity, pattern diversity, polarization diversity, or the like). The antenna module 284 may also include one or more ultra-wideband antennas.

Each of the antenna arrays (e.g., the antenna array 284 and the millimeter-wave arrays of the antenna module 282) may be adapted to conduct millimeter wave 5G communications and may be adapted to use or be used with beam-forming or other techniques to adapt signal reception depending on the use case. The device 200 may also include multiple antennas for conducting multiple-in multiple-out (MIMO) wireless communications schemes, including 4G, 4G LTE, and/or 5G MIMO communication protocols. As described herein, one or more of the housing members 211, 212, 213, 214, 215, and 216 may be adapted to operate as antennas for a MIMO wireless communication scheme (or other wireless communication scheme).

FIG. 3 depicts an exploded view of an example electronic device. In particular, FIG. 3 depicts an exploded view of a device 300, showing various components of the device 300 and example arrangements and configurations of the components. The description of the various components and elements of device 100 of FIGS. 1A and 1B may also be applicable to the device 300 depicted in FIG. 3. A redundant description of some of the components is not repeated herein for clarity.

As shown in FIG. 3, the device 300 includes a cover 302 (e.g., a front cover), which may be formed of glass, ceramic, or other transparent substrate. In this example, the cover 302 may be formed from a glass or glass-ceramic material. A glass-ceramic material may include both amorphous and crystalline or non-amorphous phases of one or more materials and may be formulated to improve strength or other properties of the cover 302. In some cases, the cover 302 may include a sheet of chemically strengthened material having one or more coatings including an anti-reflective (AR) coating, an oleophobic coating, or other type of coating or optical treatment. In some cases, the cover 302 includes a sheet of material that is less than 1 mm thick. In some cases, the sheet of material is less than 0.80 mm. In some cases, the sheet of material is approximately 0.60 mm or less. The cover 302 may be chemically strengthened using an ion exchange process to form a compressive stress layer along exterior surfaces of the cover 302.

The cover 302 extends over a substantial entirety of the front surface of the device and may be positioned within an opening defined by the housing 310. As described in more detail below, the edges or sides of the cover 302 may be surrounded by a protective flange or lip of the housing 310 without an interstitial component between the edges of the cover 302 and the respective flanges of the housing 310. This configuration may allow an impact or force applied to the housing 310 to be transferred to the cover 302 without directly transferring shear stress through the display 303 or frame 304.

As shown in FIG. 3, the display 303 is coupled to an internal surface of the cover 302. The display 303 may include an edge-to-edge organic light emitting diode (OLED) display that measures 16.97 cm (6.68 inches) corner-to-corner. The perimeter or non-active area of the display 303 may be reduced to allow for very thin device borders around the active area of the display 303. In some cases, the display 303 allows for border regions of 1.5 mm or less. In some cases, the display 303 allows for border regions of 1 mm or less. In one example implementation, the border region is approximately 0.9 mm. The display 303 may have a relatively high pixel density of approximately 450 pixels per inch (PPI) or greater. In some cases, the display 303 has a pixel density of approximately 458 PPI. The display 303 may have an integrated (on-cell) touch-sensing system. For example, an array of electrodes that are integrated into the OLED display may be time and/or frequency multiplexed in order to provide both display and touch-sensing functionality. The electrodes may be configured to detect a location of a touch, a gesture input, multi-touch input, or other types of touch input along the external surface of the cover 302. In some cases, the display 303 includes another type of display element, such as a liquid-crystal display (LCD) without an integrated touch-sensing system. That is, the device 300 may include one or more touch- and/or force-sensing layers that are positioned between the display 303 and the cover 302.

The display 303 may include always-on-display (AOD) functionality. For example, the display 303 may be configurable to allow designated regions or subsets of pixels to be displayed when the device 300 is powered on such that graphical content is visible to the user even when the device 300 is in a low-power or sleep mode. This may allow the time, date, battery status, recent notifications, and other graphical content to be displayed in a lower-power or sleep mode. This graphical content may be referred to as persistent or always-on graphical output. While some battery power may be consumed when displaying persistent or always-on graphical output, the power consumption is typically less than during normal or full-power operation of the display 303. This functionality may be enabled by only operating a subset of the display pixels and/or at a reduced resolution in order to reduce power consumption by the display 303.

As shown in FIG. 3, the device 300 may also include a frame 304 that is positioned below the cover 302 and that extends around an outer periphery of the display 303. A perimeter of the frame 304 may be attached to a lower or inner surface of the cover 302. A portion of the frame 304 may extend below the display 303 and may attach the cover 302 to the housing 310. Because the display 303 is attached to a lower or inner surface of the cover 302, the frame 304 may also be described as attaching both the display 303 and the cover 302 to the housing 310. The frame 304 may be formed of a polymer material, a metal material, or a combination of polymer and metal materials. The frame 304 may support elements of the display stack, provide anchor points for flexible circuits, and/or be used to mount other components and device elements. In some cases, the frame 304 includes one or more metal or conductive elements that provide shielding between device components, such as between the display stack (including display components and touch sensor components) and other components like the haptic actuator 322, the speaker system 324, and the like.

The cover 302, display or display stack 303, and frame member 304 may be part of a top module 301 of the device 300. The top module 301 may be assembled as a subassembly, which may then be attached to a housing member. For example, as described herein, the display 303 may be attached to the cover 302 (e.g., via a transparent adhesive), and the frame member 304 may be attached (e.g., via adhesive) to the cover around a periphery of the display stack 303. The top module 301 may then be attached to a housing member of the device 300 by mounting and adhering the frame member 304 to a ledge defined by the housing member.

The device 300 also includes a speaker module 350 that is configured to output sound via a speaker port. The speaker port may be positioned in and/or at least partially defined by a recess 351 of the cover 302. As described herein, a trim piece may be positioned at least partially in the recess 351 to facilitate the output of sound while also inhibiting the ingress of debris, liquid, or other materials or contaminants into the device 300. Output from the speaker module 350 may pass through an acoustic path defined at least in part by the speaker module 350 itself and the trim piece. In some cases, part of the acoustic path (e.g., between the speaker module 350 and the trim piece) is defined by the housing 310 and/or a molded material that is coupled to the housing 310. For example, a molded material (e.g., a fiber-reinforced polymer) may be molded against a metal portion of the housing 310 (e.g., the housing member 313, described herein). The molded material may also form one or more joint structures that also structurally join housing members together (e.g., the joint structures 318). A port may be defined through the molded material to acoustically couple the speaker module 350 to the trim piece and/or the recess 351 more generally, thereby directing sound from the speaker module 350 to the exterior of the device 300. In some cases, a portion of the port that extends through the molded material is defined by a housing member itself, as described herein with reference to FIGS. 6A-6B.

As shown in FIG. 3, the device 300 also includes one or more cameras, light emitters, and/or sensing elements that are configured to transmit signals, receive signals, or otherwise operate along the front surface of the device. In this example, the device 300 includes a front camera 306 that includes a high-resolution camera sensor. The front camera 306 may have a 12 megapixel resolution sensor with optical elements that provide a fixed focus and an 85° field of view. The front camera 306 may have an aperture number of f/2.2. The device 300 also includes a facial recognition sensor 352 that includes an infrared light projector and infrared light sensor that are configured to sense an array of depth points or regions along the face of the user. The array of depth points may be characterized as a unique signature or bio-identifier, which may be used to identify the user and unlock the device 300 or authorize functionality on the device 300 like the purchase of software apps or the use of payment functionality provided by the device 300.

The device 300 may also include one or more other sensors or components. For example, the device 300 may include a front light illuminator element for providing a flash or illumination for the front camera 306. The device 300 may also include an ambient light sensor (ALS) that is used to detect ambient light conditions for setting exposure aspects of the front camera 306 and/or for controlling the operation of the display.

FIG. 3 also illustrates one or more cameras, light emitters, and/or sensing elements that are configured to transmit signals, receive signals, or otherwise operate along the rear surface of the device. As depicted in FIG. 3, these elements may be integrated in a sensor array 360. In this example, the sensor array 360 includes a first camera 361 having a 12 megapixel image sensor and a wide angle lens with an aperture number of f/1.6. The first camera 361 may also include a sensor-shifting mechanism that allows for image stabilization and/or optical focusing. In some cases, the image sensor is moved with respect to one or more fixed elements of the optical lens assembly. The sensor array 360 also includes a second camera 362 having a 12 megapixel image sensor and a super-wide angle lens (120° FOV) with an aperture number of f/2.2. The sensor array 360 may also include a third camera 363 having a 12 megapixel image sensor and a telephoto optical lens assembly that enables 2.5× optical zoom. The third camera 363 may also have an aperture number of f/2.4.

The sensor array 360 also includes a light illuminator that may be used as a flash for photography or as an auxiliary light source (e.g., a flashlight). The sensor array 360 also features an integrated chassis design that minimizes space while providing the precision alignment required for multiple high-resolution cameras. In some cases, the sensor array 360 also includes a microphone, an ambient light sensor, and other sensors that are adapted to sense along the rear surface of the device 300.

The sensor array 360 may also include a depth sensor 365 that is able to estimate a distance to objects positioned behind the device 300. The depth sensor 365 may include an optical sensor that uses time-of-flight or other optical effect to measure a distance between the device 300 and an external object. The depth sensor 365 may include one or more optical emitters that are adapted to emit one or more beams of light, which may be used to estimate the distance. In some cases, the one or more beams of light are coherent light beams having a substantially uniform wavelength/frequency. A coherent light source may facilitate depth measurements using a time of flight, phase shift, or other optical effect. In some cases, the depth sensor 365 uses a sonic output, radio output, or other type of output that may be used to measure the distance between the device 300 and one or more external objects. The depth sensor 365 may be positioned proximate a window 371 (e.g., a region of the rear cover 372 or other component that covers the components of the sensor array 360) through which the depth sensor 365 may send and/or receive signals (e.g., laser light, infrared light, visible light, etc.).

As shown in FIG. 3, the cameras 361, 362, 363 may be aligned with camera covers 366, 367, 368, respectively. The covers 366, 367, 368 may be formed from a glass or sapphire material and may provide a clear window through which the cameras 361, 362, 363 are able to capture a photographic image. In other cases, the covers 366, 367, 368 are optical lenses that filter, magnify, or otherwise condition light received by the respective camera 361, 362, 363. The other sensing or transmitting elements of the sensor array 360 may transmit and/or receive signals through a region of the rear cover 372 or through a separate cover (e.g., 369) that is coupled to the rear cover 372. As shown in FIG. 3, the covers 366, 367, 368 may extend beyond the exterior surface of the cover 372, and may define a recess along the interior side of the cover 372, such that the lens or other element of the cameras 361, 362, 363 can extend into the respective recesses. In this way, the device 300 may accommodate a larger lens or other elements of the cameras 361, 362, 363 than would be possible if the recess were not provided.

The device 300 also includes a battery 330. The battery 330 provides electrical power to the device 300 and its various systems and components. The battery 330 may include a 4.40 V lithium ion battery that is encased in a foil or other enclosing element. The battery 330 may include a rolled electrode configuration, sometimes referred to as "jelly roll" or folded electrode configuration. The battery 330 may be recharged via the charging port 332 (e.g., from a power cable plugged into the charging port 332 through a charging access opening 326), and/or via a wireless charging system 340. The battery 330 may be coupled to the charging port 332 and/or the wireless charging system 340 via battery control circuitry that controls the power provided to the battery and the power provided by the battery to the device 300. The battery 330 may include one or more lithium ion battery cells or any other suitable type of rechargeable battery element.

The wireless charging system 340 may include a coil that inductively couples to an output or transmitting coil of a wireless charger. The coil may provide current to the device 300 to charge the battery 330 and/or power the device. In this example, the wireless charging system 340 includes a coil assembly 342 that includes multiple wraps of a conductive wire or other conduit that is configured to produce a (charging) current in response to being placed in an inductive charging electromagnetic field produced by a separate wireless charging device or accessory. The coil assembly 342 also includes an array of magnetic elements that are arranged in a circular or radial pattern. The magnetic elements may help to locate the device 300 with respect to a separate wireless charging device or other accessory. In some implementations, the array of magnets also help to radially locate, orient, or "clock" the device 300 with respect to the separate wireless charging device or other accessory. For example, the array of magnets may include multiple magnetic elements having alternating magnetic polarity that are arranged in a radial pattern. The magnetic elements may be arranged to provide a magnetic coupling to the separate charging device in a particular orientation or set of discrete orientations to help locate the device 300 with respect to the separate charging device or other accessory. This functionality may be described as self-aligning or self-locating wireless charging. As shown in FIG. 3, the device 300 also includes a magnetic fiducial 344 for helping to locate the separate wireless charging device or accessory. In one example, the magnetic fiducial 344 is adapted to magnetically couple to a cable or power cord of the separate wireless charging device or other accessory. By coupling to the cable or power cord, the rotational alignment of the device 300 and the separate wireless charging device or other accessory may be maintained with respect to an absolute or single position. Also, by magnetically coupling the cable or cord to the rear surface of the device 300, the charging device or other accessory may be more securely coupled to the device 300.

In some implementations, the wireless charging system 340 includes an antenna or other element that detects the presence of a charging device or other accessory. In some cases, the charging system includes a near-field communications (NFC) antenna that is adapted to receive and/or send wireless communications between the device 300 and the wireless charger or other accessory. In some cases, the device 300 is adapted to perform wireless communications to detect or sense the presence of the wireless charger or other accessory without using a dedicated NFC antenna. The communications may also include information regarding the status of the device, the amount of charge held by the battery 330, and/or control signals to increase charging, decrease charging, start charging and/or stop charging for a wireless charging operation.

The device 300 may also include a speaker system 324. The speaker system 324 may be positioned in the device 300 so that a respective port 325 is aligned with or otherwise proximate an audio output of the speaker system 324. Accordingly, sound that is output by the speaker system 324 exits the housing 310 via the respective port 325. The speaker system 324 may include a speaker positioned in a housing that defines a speaker volume (e.g., an empty space in front of or behind a speaker diaphragm). The speaker volume may be used to tune the audio output from the speaker and optionally mitigate destructive interference of the sound produced by the speaker. The speaker system 324 may include left and right speakers that are aligned with left and right ports 325, respectively, in order to produce stereo sound.

The device 300 may also include a haptic actuator 322. The haptic actuator 322 may include a movable mass and an actuation system that is configured to move the mass to produce a haptic output. The actuation system may include one or more coils and one or more magnets (e.g., permanent and/or electromagnets) that interact to produce motion. The magnets may be or may include recycled magnetic material. As described herein, the haptic actuator 322 may have a profile or enclosure shape that facilitates physical integration with the battery 330 and other components of the device 300 in order to minimize space and/or maximize the size of the battery.

When the coil(s) are energized, the coil(s) may cause the mass to move, which results in a force being imparted on the device 300. The motion of the mass may be configured to cause a vibration, pulse, tap, or other tactile output detectable via an exterior surface of the device 300. The haptic actuator 322 may be configured to move the mass linearly, though other movements (e.g., rotational) are also contemplated. Other types of haptic actuators may be used instead of or in addition to the haptic actuator 322.

The device 300 also includes a logic board 320 (also referred to herein as a circuit board assembly). The logic board 320 may include a substrate, and processors, memory, and other circuit elements coupled to the substrate. The logic board 320 may include multiple circuit substrates that are stacked and coupled together in order to maximize the area available for electronic components and circuitry in a compact form factor. The logic board 320 may include provisions for a subscriber identity module (SIM). The logic board 320 may include electrical contacts and/or a SIM tray assembly for receiving a physical SIM card and/or the logic board 320 may include provisions for an electronic SIM. The logic board 320 may be wholly or partially encapsulated to reduce the chance of damage due to ingress of water or other fluid.

The logic board 320 may also include wireless communications circuitry, which may be coupled to and/or otherwise use the housing members 311, 312, 313, 314, 315, or 316 (or portions thereof) as radiating members or structures to provide wireless communications. The logic board 320 may also include components such as accelerometers, gyroscopes, near-field communications circuitry and/or antennas, compasses, and the like. In some implementations, the logic board 320 may include a magnetometer that is adapted to detect and/or locate an accessory. For example, the magnetometer may be adapted to detect a magnetic (or non-magnetic) signal produced by an accessory of the device 300 or other device. The output of the magnetometer may include a direction output that may be used to display a directional indicia or other navigational guidance on the display 303 in order to guide the user toward a location of the accessory or other device.

The device 300 may also include one or more pressure transducers that may be operable to detect changes in external pressure in order to determine changes in altitude or height. The pressure sensors may be externally ported and/or positioned within a water-sealed internal volume of the housing 310. The output of the pressure sensors may be used to track flights of stairs climbed, a location (e.g., a floor) of a multi-story structure, movement performed during an activity in order to estimate physical effort or calories burned, or other relative movement of the device 300.

The logic board 320 may also include global position system (GPS) electronics that may be used to determine the location of the device 300 with respect to one or more satellites (e.g., a Global Navigation Satellite System (GNSS)) in order to estimate an absolution location of the device 300. In some implementations, the GPS electronics are operable to utilize dual frequency bands. For example, the GPS electronics may use L1 (L1C), L2 (L2C), L5, L1+L5, and other GPS signal bands in order to estimate the location of the device 300.

The housing 310 may also include a chassis 319, which may be attached to the housing 310. The chassis 319 may be formed of metal, and may act as a structural mounting point for components of the device 300. The chassis 319 may define an opening that corresponds to size of the coil assembly 342 of the wireless charging system 340, such that the chassis 319 does not shield the wireless coil assembly 342 or otherwise negatively affect the inductive coupling between the coil of the wireless charging system 340 and an external wireless charger or accessory.

As shown in FIG. 3, the housing may include a cover 372 (e.g., rear or back cover) that may define a substantial entirety of the rear surface of the device 300. The cover 372 may be formed from a glass, glass-ceramic, or other material having portions that are less than 1 mm thick. In some cases, the substrate has portions that are less than 0.80 mm. In some cases, the substrate has portions that are approximately 0.60 mm or less. The cover 372 may have a uniform thickness or, in some cases, may have a thickened or raised portion that surrounds the camera covers 366, 367, 368. The cover 372 may be machined (e.g., ground) into a final shape before being polished and/or textured to provide the desired surface finish. The texture may be specially configured to provide a matte appearance while also being resistant to collecting a buildup of skin, lint, or other debris. A series of cosmetic layers may be formed along the inner surface of the cover 372 to provide a desired optical effect and final color of the device 300.

Similar to as described above with respect to cover 302, the cover 372 may be positioned at least partially within an opening defined in the housing 310. Also similar to as described above with respect to cover 302, the edges or sides of the cover 372 may be surrounded by a protective flange or lip of the housing 310 without an interstitial component between the edges of the cover 372 and the respective flanges of the housing 310. The cover 372 may be chemically strengthened using an ion exchange process to form a compressive stress layer along exterior surfaces of the cover 372. In some cases, the (rear) cover 372 is formed from the same or a similar material as (front) cover 302.

As described above, the housing 310 may include housing members 311, 312, 313, 314, 315, and 316 structurally joined together via joint structures 318. The joint structures 318 (e.g., the material of the joint structures) may extend over inner surfaces of the housing members. More particularly, a portion of the joint structures 318 may contact, cover, encapsulate, and/or engage with retention features of the housing members that extend from the inner surfaces of the housing members.

Housing members 311, 312, 313, 314, 315, and 316 may also be referred to herein as housing segments and may be formed from aluminum, stainless steel, or other metal or metal alloy material. As described herein, the housing members 311, 312, 313, 314, 315, and 316 may provide a robust and impact resistant sidewall for the device 300. In the present example, the housing members 311, 312, 313, 314, 315, and 316 define a flat sidewall that extends around the perimeter of the device 300. The flat sidewall may include rounded or chamfered edges that define the upper and lower edges of the sidewall of the housing 310. The housing members 311, 312, 313, 314, 315, and 316 may each have a flange portion or lip that extends around and at least partially covers a respective side of the front and rear covers 302, 372. There may be no interstitial material or elements between the flange portion or lip and the respective side surface of the front and rear covers 302, 372. This may allow forces or impacts that are applied to the housing 310 to be transferred to the front and rear covers 302, 372 without affecting the display or other internal structural elements, which may improve the drop performance of the device 300.

As shown in FIG. 3, the device 300 includes multiple antennas that may be adapted to conduct wireless communication using a 5G communication protocol. In particular, the device 300 may include a (side-fired) antenna array 382 that is configured to transmit and receive wireless communication signals through an antenna window 383 or waveguide formed along or otherwise integrated with the side wall of the housing 310. The side-fired antenna array 382 may be coupled to the logic board 320 via a flexible circuit element or other conductive connection, as described herein. The device 300 may also include a rear antenna module 384 that may include one or more (rear-fired) antenna arrays that may be configured to transmit and receive wireless communication signals through the cover 372. The antenna module 384 may be attached to a back or bottom surface of the logic board 320.

The antenna module 384 may include multiple antenna arrays. For example, the antenna module 384 may include one or more millimeter-wave antenna arrays. In the case where the antenna module 384 includes multiple millimeter-wave antenna arrays (each of which may include one or more radiating elements), the multiple millimeter-wave antenna arrays may be configured to operate according to a diversity scheme (e.g., spatial diversity, pattern diversity, polarization diversity, or the like). The antenna module 384 may also include one or more ultra-wideband antennas.

Each of the antenna arrays (e.g., the antenna array 384 and the millimeter-wave arrays of the antenna module 382) may be adapted to conduct millimeter wave 5G communications and may be adapted to use or be used with beam-forming or other techniques to adapt signal reception depending on the use case. The device 300 may also include multiple antennas for conducting multiple-in multiple-out (MIMO) wireless communications schemes, including 4G, 4G LTE, and/or 5G MIMO communication protocols. As described herein, one or more of the housing members 311, 312, 313, 314, 315, and 316 may be adapted to operate as antennas for a MIMO wireless communication scheme (or other wireless communication scheme).

Figure 4A:
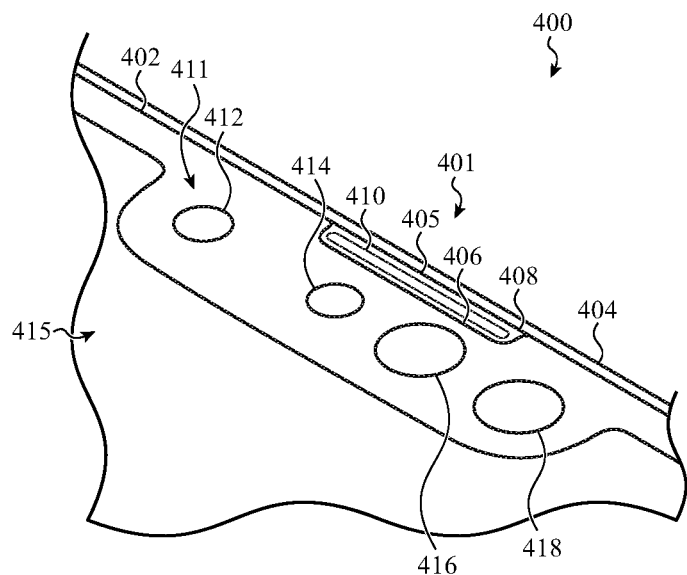
FIGS. 4A-4B depict a portion of an example electronic device.
Figure 4B:
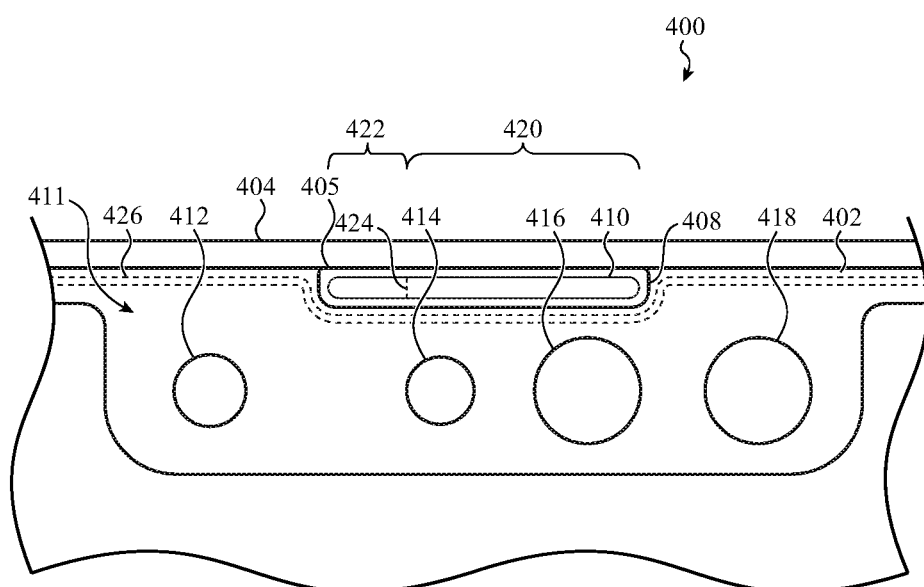

FIGS. 4A-4B depict a partial view of an example electronic device 400. The portion illustrated in FIGS. 4A-4B may correspond to an area 4-4 in FIG. 1A, though the same or a similar area may be found on other example devices described herein. The electronic device 400 may correspond to or be an embodiment of the electronic devices 100, 200, or 300, or any other device described herein. FIGS. 4A-4B illustrates an example configuration of a speaker port 401 as well as a front-facing sensor region.

Figure 4C:
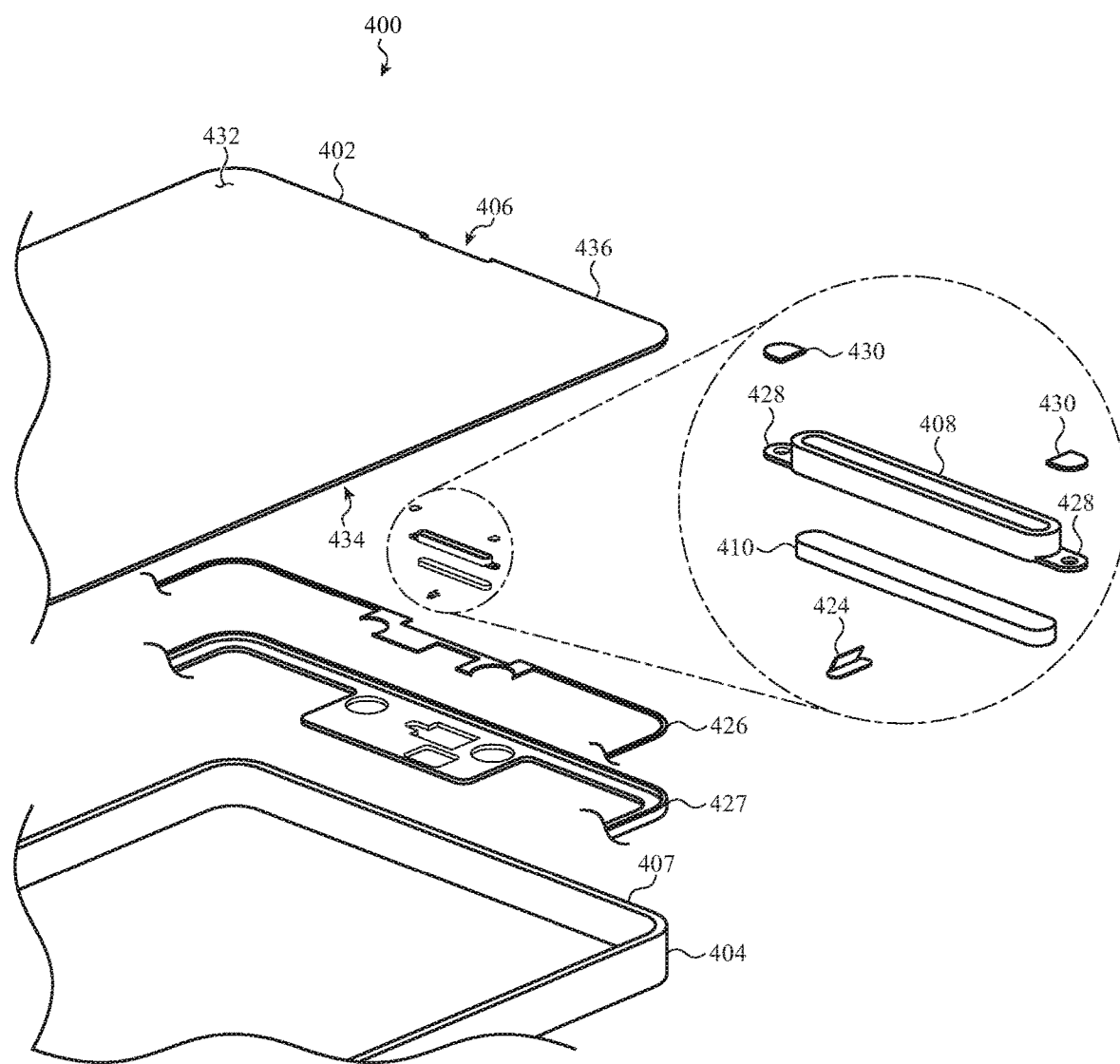
FIG. 4C depicts a partial exploded view of an example electronic device.

The device 400 includes a cover 402, which may correspond to or be an embodiment of other covers described herein, such as the covers 102, 202, 302, and a housing member 404, which may correspond to or be an embodiment of other housing members described herein, such as the housing members 127, 213, 313, and which may define at least a portion of four side surfaces of the device. As shown in FIG. 4C, the cover 402 may define a front surface 432, a rear surface 434, and a peripheral side surface 436 extending from the front surface 432 to the rear surface 434. The peripheral side surface 436 is at least partially surrounded by a wall 407 of the housing 404 (FIG. 4C).

The cover 402 defines a notch 406 along an edge of the cover 402. The notch 406 (also referred to as a recess or cutout) may be along a top edge of the cover 402 to define a space between the edge of the cover 402 and housing member 404 that defines a top side of the device 400. The space between the edge of the cover 402 and the housing member 404 may be referred to as a speaker port opening. A first side of the speaker port opening may be defined by the wall 407 of the housing member, and a second side of the speaker port opening may be defined by the notch 406 of the front cover 402. The notch 406 may define at least three sides of the speaker port opening, including third and fourth sides of the speaker port opening, as shown in FIGS. 4A-4C.

The notch 406 may at least partially define an acoustic path of the device. For example, sound from a speaker positioned within the device may pass through the space defined by the notch (e.g., between a peripheral side surface of the cover 402 and the wall of the housing 404). Because the speaker port 401 is proximate the top of the device, the speaker port 401 is ultimately provided at an area of the device 400 that may be held against a user's ear during telephone calls or other uses.

The device 400 may include a speaker port cover structure 405 (also referred to as an acoustic port cover). The speaker port cover structure 405 may be positioned at least partially in the recess 406, and between the edge portion of the cover 402 (into which the recess 406 is defined) and the housing member 404. The speaker port cover structure 405 may include a trim piece 408 and a mesh member 410. The trim piece 408 may be adjacent an edge of the cover 402 and adjacent the housing member 404. The front surface of the trim piece 408 may be flush with the front exterior surface 432 of the cover 402. In some cases, there is no interstitial component or material between the trim piece 408 and the cover 402, or between the trim piece 408 and the housing member 404. As described herein, the speaker port cover structure 405 provides a cover over a portion of an acoustic path in the device 400 that directs sound from a speaker module to the speaker port 401. In some cases, the speaker port cover structure 405 also covers an acoustic path that couples to a microphone within the device, as described in greater detail herein.

The mesh member 410 may be configured to allow sound to pass through, while inhibiting ingress of dust, liquids, or other contaminants into the device 400. The mesh member 410 may be a metal mesh, a polymer mesh, or the like. The mesh member 410 may be a unitary structure with holes or gaps formed therethrough (e.g. a perforated or molded polymer sheet), or it may be formed of multiple separate members (e.g., a woven fabric or metal mesh). In some cases, between about 30% and about 40% of the area of the mesh member 410 may be open (e.g., the openings or perforations defined by the mesh may make up between about 30% and about 40% of the area of the mesh member 410). In this way, sound may pass through the mesh member 410 without undue attenuation or other acoustic impact.

FIGS. 4A-4B also illustrate an example arrangement of components in a front-facing sensor array 411, which may be at least partially surrounded by an active region 415 of the display. The front-facing sensor array 411 includes a front-facing camera 412, a proximity sensor 414, a combination flood illuminator and dot projector 416 (e.g., for projecting flood illumination and a pattern of dots onto an object, such as a user's face), and an infrared light sensor 418 (e.g., for capturing images of objects illuminated by the flood illuminator and dot projector). Each of the components in the front-facing sensor array 411 may be positioned below the cover 402 and may emit and/or receive light through the cover 402. In some cases, a region of the cover 402 over a particular component of the front-facing sensor array 411 has a masking that is visually opaque, but transparent to the particular wavelengths of light that are utilized by an underlying sensor. For example, in some implementations, the combination flood illuminator and dot projector 416 and the infrared light sensor 418 are covered with a visually opaque, infrared transparent coating or material.

The front-facing sensor array 411 may be located in a portion of the front side of the device that is not an active display area. For example, the line shown enclosing the front-facing camera 412, proximity sensor 414, combination flood illuminator and dot projector 416, and infrared light sensor 418 may indicate a boundary between an active region 415 of the display, and an area that does not include the display or that is not configured to produce graphical outputs. The front-facing sensor array 411 may include a mask, ink, coating, or other material, which may be visually opaque.

FIG. 4B depicts another view of the device 400, showing additional details of the front-facing sensor array 411 and the speaker port 401. In some cases, the speaker port 401, and more particularly the trim piece 408 and mesh member 410, may be positioned outside of a glue line 426. The glue line 426 may adhere the cover 402 (and/or the top module) of the device to an underlying structure (e.g., the housing member 404), and may define a seal that inhibits ingress of dust, liquids, or other contaminants or debris into the device. Because the speaker port 401 is outside of the glue line 426, other seals and sealing techniques may be used to inhibit ingress of dust, liquids, or other contaminants or debris into the device via the speaker port 401.

As noted above, the speaker port cover structure 405 may provide acoustic access for both a speaker module and a microphone. In some cases, a separator 424 may be positioned in the speaker port cover structure 405 (as shown in greater detail with respect to FIG. 4C) to increase the acoustic separation and/or isolation between the acoustic path to the microphone and to the speaker. As shown in FIG. 4B, the region 422 of the speaker port cover structure 405 may correspond to an acoustic path for a microphone (e.g., an acoustic input path), and the region 420 of the speaker port cover structure 405 may correspond to an acoustic path for the speaker (e.g., an acoustic output path). The separator 424 may be a piece of metal, plastic, or any other suitable material.

FIG. 4C depicts a partial exploded view of the device 400, illustrating additional detail of the integration of the speaker port cover structure 405 with the cover 402, the housing member 404, and other device components. FIG. 4C illustrates the mesh member 410 separated from the trim piece 408. The mesh member 410 may be coupled to the trim piece 408 via adhesives, welds, brackets, fasteners, interference fit, latching structures, or the like. A separator 424 may be secured in a cavity of the trim piece 408 as well (e.g., below the mesh member 410). The separator 424 may be secured to the trim piece 408 via welding, adhesives, fasteners, interference fit, latching structures, or the like. The separator 424 may provide a barrier between the acoustic path to a microphone and the acoustic path to a speaker.

After the trim piece 408 is assembled with the mesh member 410 and optionally the separator 424, the trim piece 408 may be attached to the cover 402 via adhesive members 430. The adhesive members 430 (e.g., liquid adhesive, adhesive foam, pressure-sensitive adhesive ("PSA"), heat-sensitive adhesive ("HSA"), etc.) may adhere to the top sides of the flanges 428 of the trim piece and to an underside of the cover 402. After the trim piece 408 is adhered to the cover 402 via the adhesive member 430, the cover 402, along with other top module components such as a display, may be attached to a frame member 427 via an adhesive 426. The trim piece 408, and in particular the flanges 428, may be captured between the underside of the cover 402 and the frame member 427. Further, the adhesive 426 may contact and/or at least partially surround the bottom sides of the flanges 428, as well as other surfaces of the trim piece 408, thereby contributing to the strength and stability of the trim piece 408 in the device.

Figure 5:
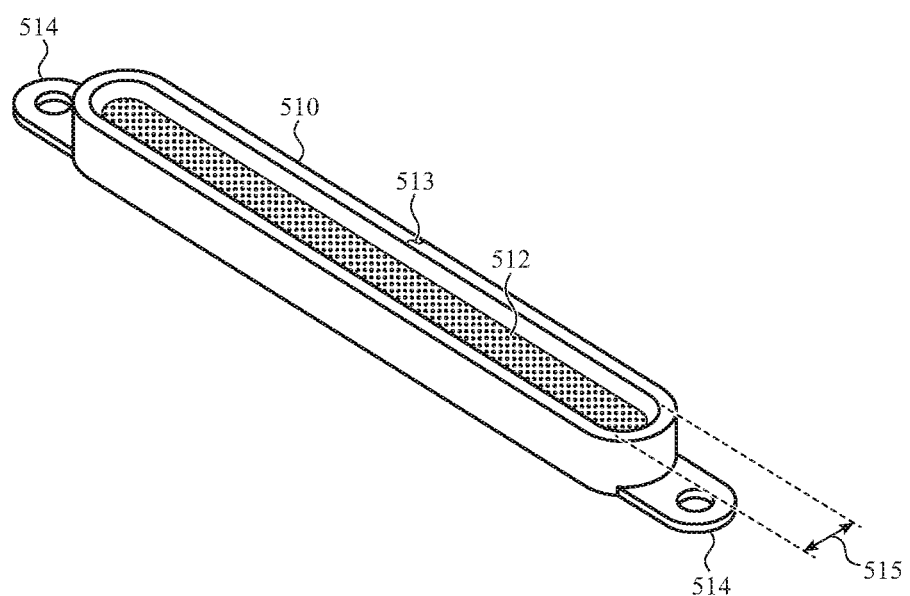
FIG. 5 depicts an example cover structure for a speaker port of an example electronic device.

FIG. 5 depicts an example cover structure 510 for use in a speaker port, as described herein. The cover structure 510 defines flanges 514, as well as a recessed region 512. The recessed region 512 may include holes, which may be defined by a mesh member, such as the mesh member 410, or defined through the material of the cover structure 510 itself (e.g., by laser-forming, drilling, or otherwise forming holes through a wall structure of the cover structure 510). The recessed region may be recessed relative to a frame region 513 that surrounds the recessed region. In some cases, the recessed region corresponds to a thinned region of the cover structure 510. For example, the thickness between the top (exterior) surface of the recessed region and the bottom (interior) surface of the recessed region may be less than the thickness between the top (exterior) surface of the frame region 513 and the bottom (interior) surface of the frame region 513. Where the recessed region is part of the cover structure 510 itself, the recessed region may have a minimum thickness between about 20 microns and about 40 microns (e.g., 25 microns, 30 microns, 35 microns, etc.). The recessed region 512 may have a width dimension (e.g., the dimension 515). The dimension 515 may be about 0.4 mm, about 0.5 mm, about 0.6 mm, about 0.7 mm, or any other suitable dimension. The recessed region may be surrounded by the frame region 513, as noted above. The frame region 513 may be between about 0.3 mm and about 0.6 mm thick. The holes in the mesh and/or defined through the cover structure 510 may have a diameter (or other opening size) between about 90 microns and about 110 microns (e.g., about 90 microns, about 100 microns, about 105 microns, about 110 microns, etc.). The web that defines the holes (e.g., the material of the cover structure that is between the holes) may have a minimum thickness between about 20 microns and about 40 microns (e.g., 25 microns, 30 microns, 35 microns, etc.).

FIG. 5 illustrates one example pattern of holes. In other examples, a monolithic cover structure may have a different pattern of holes and/or holes of a different size or shape (e.g., square-shaped holes, pentagon-shaped holes, etc.). For example, a first corner (e.g., proximate a top side of a device) of the perforated region may have a first minimum (e.g., smallest) radius of curvature, while a second corner (e.g., towards a bottom side of the device) has a second minimum radius of curvature that is different from the first minimum radius of curvature. The same radii of curvature may be mirrored on the opposite side of the perforated region. In this way, the perforated region exhibits an asymmetry about a horizontal axis (e.g., left-to-right in FIG. 4B). In some cases, the frame region of a cover structure also exhibits a similar asymmetry about a horizontal axis, as defined by the top corners of the frame region having a minimum radius of curvature that is smaller than the bottom corners of the frame region. A minimum (e.g., smallest) thickness of the frame region (e.g., distance between the perforated region and the outer periphery of the cover structure) may be between about 0.2 mm and about 0.3 mm. In some cases, a minimum thickness of the frame region (e.g., distance between the perforated region and the outer periphery of the cover structure) may be between about 0.05 mm and about 0.2 mm.

In some cases, a perforated region may have corners with a substantially equal radius of curvature. For example, a first corner (e.g., proximate a top side of a device) of the perforated region may have a first minimum radius of curvature, and a second corner (e.g., towards a bottom side of the device) has a second minimum radius of curvature that is the same as the first minimum radius of curvature. The same radii of curvature may be mirrored on the opposite side of the perforated region. In this way, the perforated region is symmetrical about a horizontal axis (e.g., left-to-right in FIG. 4B). In some cases, the frame region exhibits an asymmetry about a horizontal axis, or it may be substantially symmetrical (e.g., having four corners with substantially the same radius of curvature).

The corners of the perforated regions as described above, as well as the frame regions, may have a constant radius of curvature (e.g., they may define a portion of a circle), or a variable radius of curvature (e.g., they may define a non-circular spline).

Figure 6A:
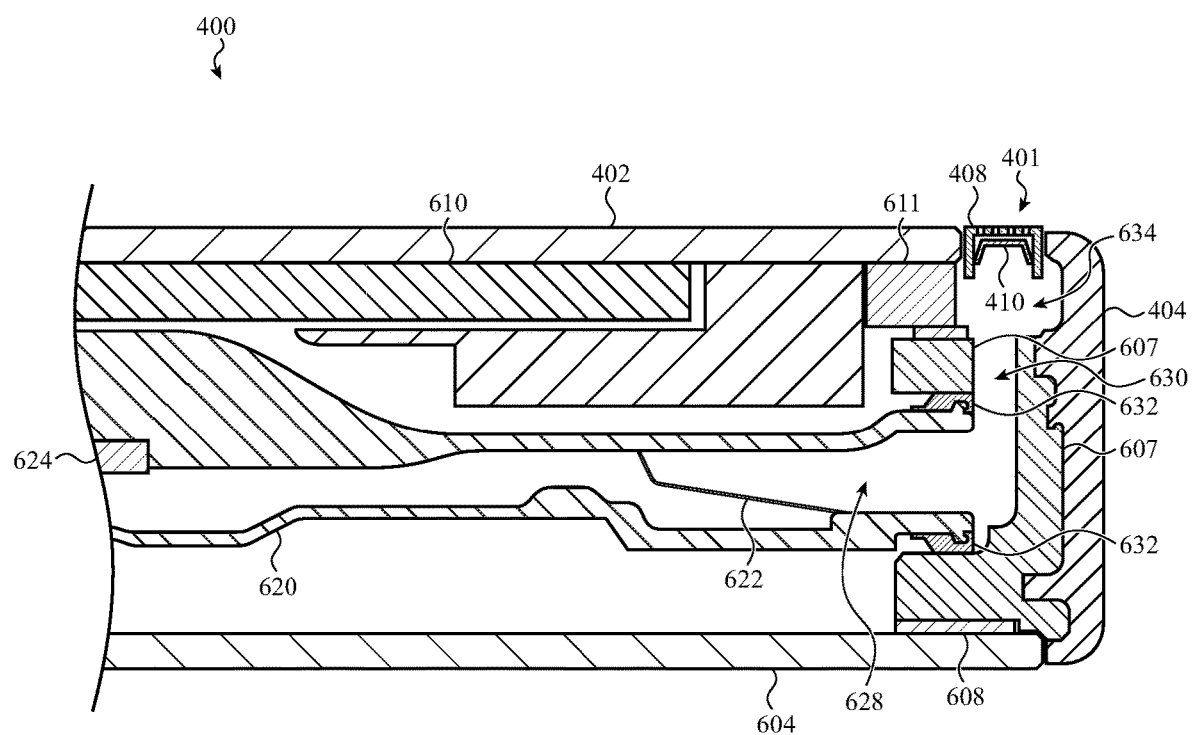
FIGS. 6A-6B depict partial cross-sectional views of a speaker configuration for an example electronic device.

FIG. 6A depicts a partial cross-sectional view of the device 400, illustrating an acoustic path through the device and to (and through) the speaker port 401. The device 400 includes a speaker module 620, which may correspond to or be an embodiment of the speaker module 250, 350, or any other speaker module described herein. The device 400 also includes a cover 402, a display 610, a frame member 611 coupled to an interior surface of the front cover 402, and a back cover 604. The speaker module 620 may be positioned below an active region of the display 610 (e.g., a region of the display 610 that is configured to display graphical output to a user).

The back cover 604 is attached to a housing structure via an adhesive 608. The housing structure may be formed from or include the housing member 404 and a molded member 607. The molded member 607 may be a polymer material (e.g., a fiber-reinforced polymer) that is molded against the housing member 404 and/or other housing members and/or components of the device 400. In some cases, the molded member 607 is unitary with one or more joint structures and/or joining elements of the device 400 (e.g., joint structures 122, 218, 318, joining elements 1416, 1418, 1420, 1422, 1424, and 1426, or any other joint structure/joining element described herein). Thus, the molded member 607 may define at least a portion of an exterior surface of the housing structure, as well as defining part of an acoustic path, as described herein.

The speaker module 620 may be coupled to the molded member 607. For example, a portion of the speaker module 620 may be inserted into a hole defined by the molded member 607. FIG. 6A shows a portion of the speaker module 620 positioned in the hole of the molded member 607, with a sealing member 632 (attached to the speaker module 620) forming a seal between the speaker module 620 and a surface of the hole. The sealing member 632 may form a seal between the acoustic path (defined by path portions 628, 630, and 634, for example) and other areas inside the device 400. In particular, in some cases, water, liquids, or contaminants are not prevented from entering into the acoustic path through the speaker port 401. Accordingly, the seal between the speaker module 620 and the molded member 607 may help prevent any water, liquids, or other contaminants that have entered the acoustic path from escaping into other areas of the device 400, and may also help prevent acoustic losses as sound passes through the acoustic path. A barrier 622 (e.g., a mesh or other material that allows sound to pass through) may be positioned in the speaker module 620 and between a speaker driver 624 and the speaker port 401. The barrier 622 may help inhibit liquids or contaminants from contacting or collecting on the speaker driver 624. The speaker driver 624 may be or may include a speaker diaphragm, and may produce sound that is directed through the acoustic path to the speaker port 401. More particularly, sound from the speaker driver 624 may pass through a first path portion 628, a second path portion 630, and a third path portion 634, and ultimately through the speaker port 401 (e.g., through the mesh member 410 or other holes or openings provided in the speaker port 401).

As noted above, the acoustic path may be defined by path portions 628, 630, and 634. The first path portion 628 may be defined by the speaker module 620, may extend from the speaker driver 624 to the second path portion, and may be configured to direct sound from the speaker driver 624 to the speaker port opening. At least a portion of the first path portion 628 may extend under an active region of the display 610. At least a portion of the first path portion 628 may extend under the front-facing sensor array 411 (FIGS. 4A-4B). The second path portion 630 may be defined by the molded member 607. In some cases, the second path portion 630 is formed as a result of the molding process of the molded member 607, while in some cases it is formed subsequently to the molding process (e.g., it is drilled or otherwise machined after the molded member 607 is molded against the housing member 404 and cured). A third path portion 634 may be defined by the housing member 404. More particularly, at least one side or surface of the third path portion 634 may be defined by the housing member 404. In some cases, another side or surface of the third path portion 634 (e.g., an opposite side or surface of the third path portion 634) may be defined by another component or structure of the device 400, such as the frame member 611 of a top module (e.g., a frame member that is attached to the cover 402 and is used to couple the cover 402 to the molded member 607 and/or other device components or structures).

Figure 6B:
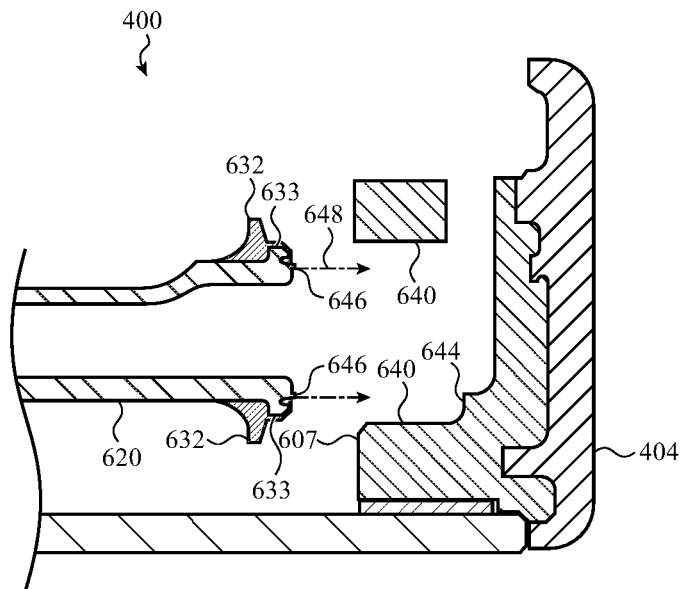

FIG. 6B depicts a partial cross-sectional view of the device 400, showing the speaker module 620 decoupled from the molded member 607, and illustrating a manner in which the speaker module 620 may be coupled to and sealed against the molded member 607.

The speaker module 620 may be coupled to the molded member 607 via a translation indicate by arrows 648. The translation may be substantially horizontal (as depicted in the figure), which may correspond to a lateral translation of the speaker module 620 in a positive y direction (e.g., towards the housing member 404, which may correspond to the housing member 213 in FIG. 2, for example).

When the speaker module 620 is inserted into the hole defined in the molded member 607, an end surface 646 of the speaker module may contact a surface 644 of the molded member 607. The contact between the end surface 646 and the surface 644 may serve as a datum to define the y-position of the speaker module 620 in the device. Even if the end surface 646 does not contact the surface 644, the end surface 646 and the surface 644 may together define a maximum y-position of the speaker module 620 in the device, and may help inhibit free movement of the speaker module 620.

Similarly, the molded member 607 may define a hole having a sealing surface 640, which the sealing member 632 contacts to seal the acoustic path. The sealing member 632, which may be a polymer material such as a rubber, silicone (e.g., a molded liquid silicone rubber), foam, or the like, may be deformed against the sealing surface 640 to define the seal. The speaker module 620 may also define a flange portion 633 that acts as a hard-stop between the speaker module 620 and the molded member 607. The flange portion 633 may define a maximum z-position of the speaker module 620 within the system and/or inhibit motion of the speaker module 620 in the z-direction. The vertical position or vertical direction in FIG. 6B may be referred to as a z-position or z-direction (e.g., a direction extending generally perpendicularly from a rear cover to a front cover of a device). In some cases, the flange portion 633 may prevent the sealing member 632 from causing the speaker module 620 to be forced too far downward or upward (e.g., in the positive or negative z-direction) due to the forces produced by the deflection and/or deformation of the sealing member 632. The flange portion 633 may extend above the interface between the sealing member 632 and the speaker module 620, such that the flange portion 633 acts as a hard-stop in the z-direction before the sealing member 632 reaches maximum deformation or deflection. For example, a force that would tend to move or misalign the speaker module 620 in the z-direction would result in the flange portion 633 interfering with the molded member 607 or other structure, thereby inhibiting further movement of the speaker module 620 and defining the limits of its position in the z-direction (e.g., rather than allowing the force to continue to deform the sealing member 632 and produce more misalignment).

Figure 6C:
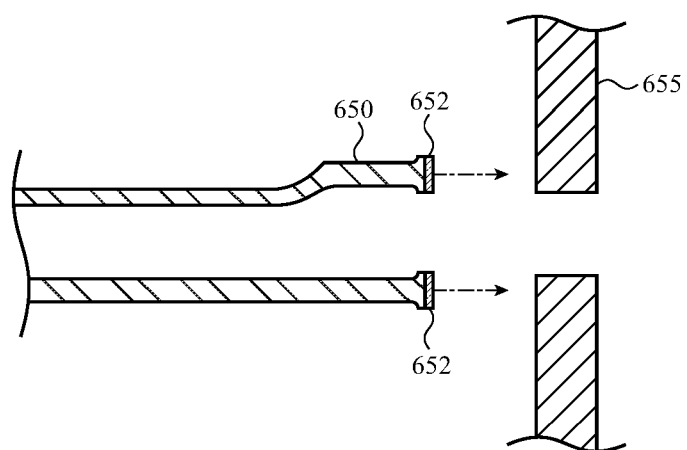
FIG. 6C depicts a partial cross-sectional view of another example speaker configuration for an example electronic device.

FIG. 6C depicts another example speaker module 650 and molded member 655 that may be used in a device as described herein. As shown in FIG. 6C, an end face of the speaker module 650 may be coupled to a corresponding face of the molded member 655 such that an outlet of the speaker module 650 communicates with a hole in the molded member 655 to direct sound through the acoustic path defined by the molded member 655. A sealing member 652 may be positioned between the end face of the speaker module 650 and the corresponding face of the molded member 655 to provide an acoustic and/or environmental (e.g., liquid, debris) seal. The sealing member 652 may be a compliant material (e.g., a foam, an elastomer gasket). In some cases, the sealing member 652 is or includes an adhesive, such as an adhesive film, a PSA, HSA, or the like. The speaker module 650 may be secured to the device with fasteners, brackets, or the like and, in the case where the sealing member 652 is or includes adhesives, the speaker module 650 may be secured at least in part by the adhesive.

Figure 7A:
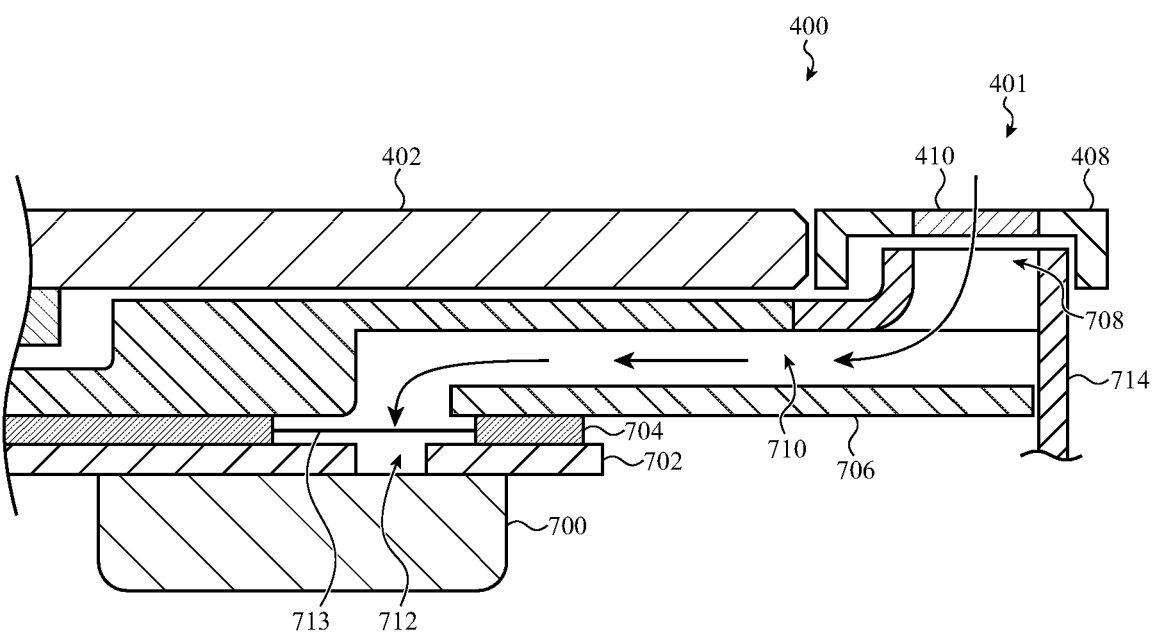
FIG. 7A depicts a partial cross-sectional view of a microphone configuration for an example electronic device.

As noted above, the speaker port 401 may provide acoustic access to both an internal speaker and an internal microphone. In some cases, the device may include one or more structures configured to provide acoustic separation between the acoustic paths for the speaker and microphone. One example structure is the separator 424 that is positioned in the speaker port cover structure (FIGS. 4B, 4C). FIG. 7A depicts a partial cross-sectional view of the device 400, illustrating an acoustic path through the speaker port 401 to a microphone module 700. FIG. 7A illustrates an example boot member 714 (or simply boot 714) that may define part of an acoustic path from the speaker port 401 to the microphone module 700.

In particular, a microphone module 700 may be coupled to an underside of a cover 402 and/or a top module. In some cases, as shown, the microphone module 700 is coupled to a substrate 702, which is in turn coupled to a portion of a frame member 706 or other component of the top module (e.g., via an adhesive 704). The substrate 702 may define a hole 712 that allows the microphone module 700 to acoustically couple to the acoustic path defined through the frame member 706. A membrane 713 may be positioned over the hole 712 (e.g., covering the hole) to inhibit the passage of water and/or other contaminants, while allowing the passage of sound. One or more additional membranes may be incorporated into the microphone module 700 as well. The membranes, including the membrane 713, may be meshes, screens, foams, or the like, and may be formed of any suitable material, such as polymer, metal, or the like.

The frame member 706 may define a first path portion 710 of the acoustic path to direct sound from the speaker port 401 to the microphone module 700. The frame member 706 may correspond to or be an embodiment of the frame member 204, 304, 611, or any other frame member described. In other cases, the frame member 706 is a separate component that is coupled to the cover 402 and/or a separate frame or structural component of the device.

The boot 714 may be positioned at an end of the first path portion 710 and may define a second path portion 708 of the acoustic path. The boot 714 may be formed from a compliant material, such as an elastomer, and may seal against the frame member 706 (e.g., be in intimate contact with the frame member 706) to help define the acoustic path and inhibit acoustic interference between the acoustic path and other areas of the device. Stated another way, the boot 714 may seal against the frame member 706 to provide acoustic isolation to the acoustic path and the microphone module 700 more generally.

The boot 714 may define a corner or turn portion of the acoustic path to the microphone, and a portion of the boot 714 may extend at least partially into a cavity defined at least in part by the trim piece 408. For example, in implementations that include a separator, such as the separator 424, a cavity in the trim piece 408 may be defined on three sides by the trim piece 408, and on a fourth side by the separator. A portion of the boot 714 (e.g., the top-most portion of the boot as shown in FIG. 7A) may extend into the cavity so that sound entering through the mesh member 410 is directed along the acoustic path to the microphone, and so that sound from other sources (e.g., a speaker module) is inhibited from entering the acoustic path. Generally, the separator 424 may define two separated cavities or volumes along the underside of the speaker port cover structure, and the boot 714 may extend into one of those cavities or volumes, while the speaker module acoustically communicates to the other cavity or volume. This may provide a measure of acoustic isolation between the speaker and the microphone.

Figure 7B:
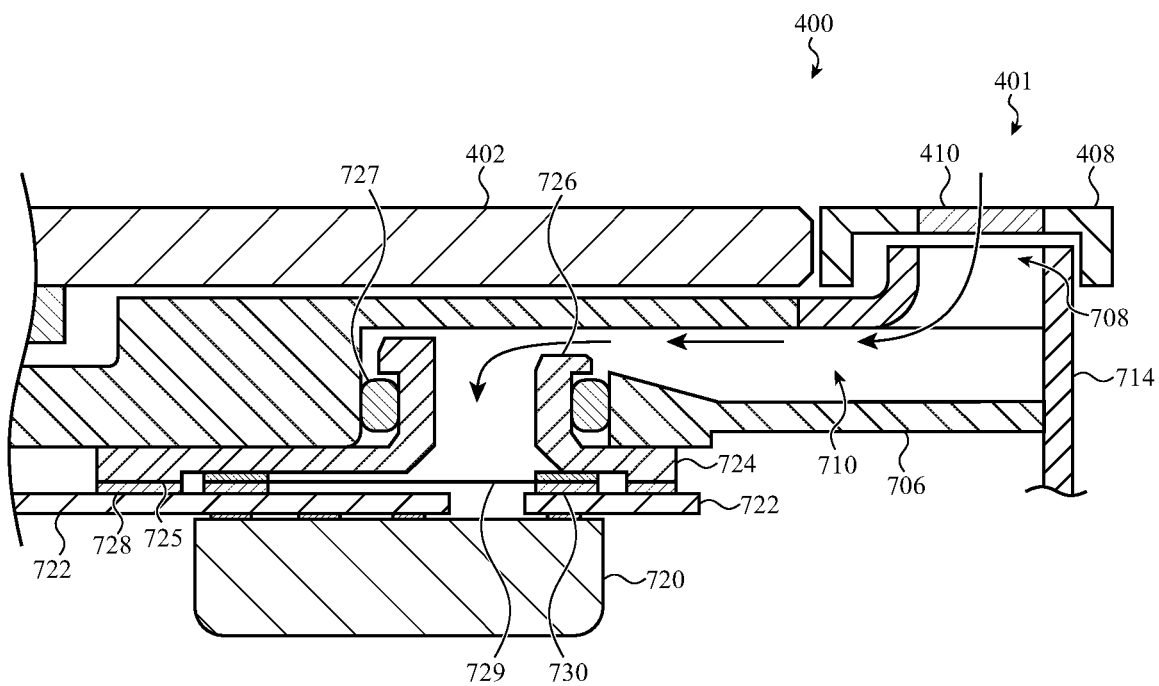
FIG. 7B depicts a partial cross-sectional view of another microphone configuration for an example electronic device.

FIG. 7B depicts a partial cross-sectional view of the device 400, illustrating an acoustic path through the speaker port 401 to another example microphone module 720. As shown in FIG. 7B, and similar to FIG. 7A, the microphone module 720 may be coupled to an underside of a cover 402 and/or a top module. In some cases, as shown, the microphone module 720 is coupled to a substrate 722, which is in turn coupled to a mounting plate 724. The mounting plate 724 defines a base portion 725 and a waveguide 726 that extends from the base portion 725. The waveguide 726 extends into a hole formed in the frame member 706 (or other component of the top module) and defines a portion of the acoustic path that is defined from the speaker port 401 to the microphone module 720. More particularly, the acoustic path may be defined, at least in part, by the boot 714, the channel defined through the frame member 706, and the waveguide 726.

A sealing member 727, such as an O-ring, may define a seal between the waveguide 726 and the frame member 706 (or whatever other component(s) the waveguide 726 extends into). The interface between the waveguide 726 and the hole helps align the microphone module 720 with the frame member 706. Further, the sealing member 727 helps form an acoustic and environmental seal between the acoustic path defined through the frame member 706 and to the microphone module 720. For example, the sealing member 727 may inhibit water or other contaminants that may enter the acoustic path (e.g., through the speaker port 401) from escaping the acoustic path and entering other internal areas of a device. The sealing member 727 may also provide a retention force due to the friction between the sealing member 727 and the surfaces of the hole in the frame member 706 (optionally aided by the compression of the sealing member 727 between the frame member 706 and the waveguide 726). The sealing member 727 may be retained by a lip, channel, and/or groove defined by the waveguide 726, as shown in FIG. 7B.

In some cases, the mounting plate 724 is adhered to the frame member 706. Where an adhesive is used, it may be positioned between and adhered to the base portion 725 and the frame member 706. Alternatively or additionally, the mounting plate 724 (and thus the microphone module 720 and substrate 722) may be secured to the frame member 706 using brackets, cowlings, fasteners, or the like. In some cases, the friction from the sealing member 727 is sufficient to retain the mounting plate 724 to the frame member 706.

The substrate 722, to which the microphone module 720 may be soldered, adhered, or otherwise secured, may be secured to the mounting plate 724 via an adhesive 728 (e.g., a PSA, HSA, adhesive foam, or the like). The substrate 722 may be a circuit board (e.g., a rigid or flexible circuit board), and may include conductive traces that interconnect the microphone module 720 with other circuitry of the device.

A membrane 729 may be positioned over a hole in the substrate 722 (e.g., covering the hole) to inhibit the passage of water and/or other contaminants into the microphone module 720, while allowing the passage of sound. The membrane 729 may be a mesh, screen, foam, or the like, and may be formed of any suitable material, such as polymer, metal, or the like. The membrane 729 may be positioned in place using a compliant stack 730, which may include one or more layers of adhesive, foam, and/or other materials. The compliant stack 730 may adhere or be adhered to both the base portion 725 of the mounting plate 724 and the substrate 722.

Figure 7C:
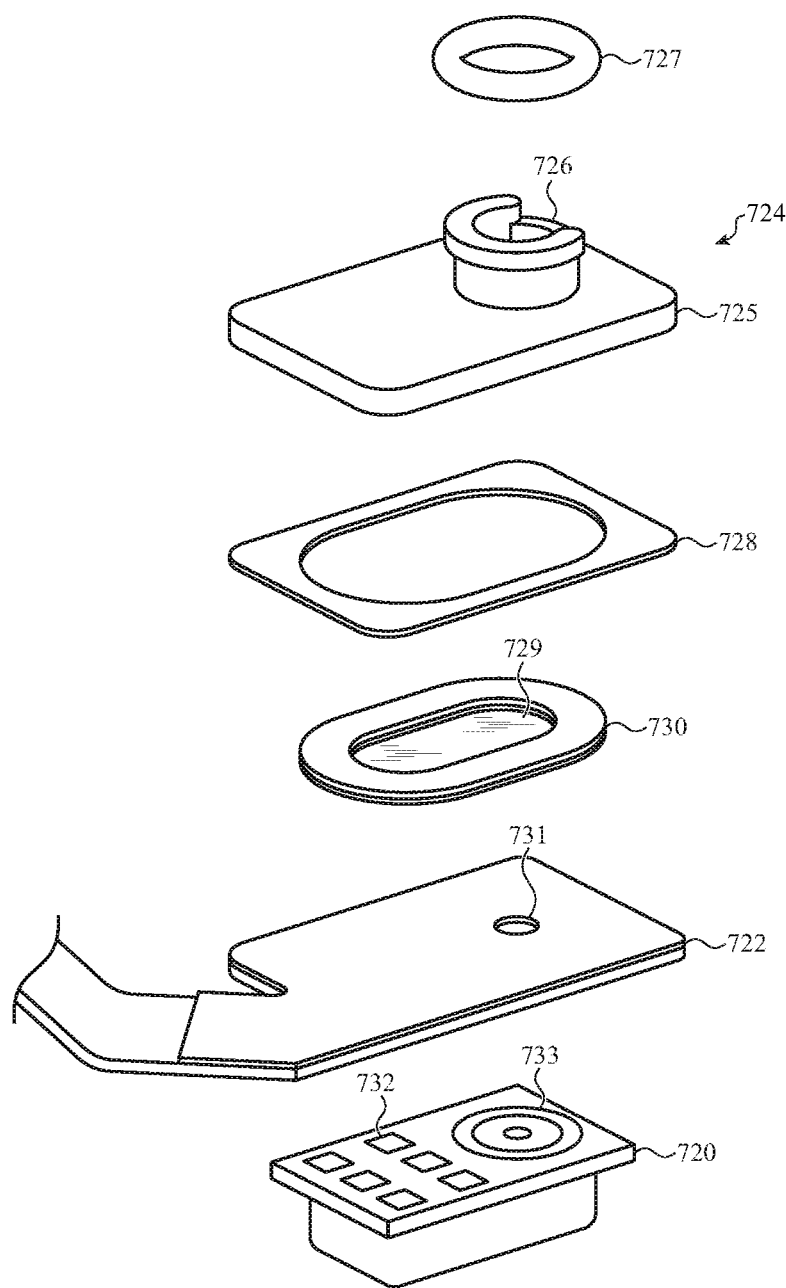
FIG. 7C depicts an exploded view of the microphone configuration of FIG. 7B.

FIG. 7C depicts an exploded view of the microphone subassembly shown in FIG. 7B, illustrating additional details of the components of the microphone subassembly. As shown in FIG. 7B, the sealing member 727 may be positioned around the waveguide 726, which defines a lip (as shown), groove, slot, or other retention feature that retains the sealing member 727 in place on the waveguide 726. The base portion 725 of the mounting plate 724 is secured to the substrate 722 (e.g., a circuit board and/or circuit board assembly) via an adhesive 728 (e.g., an HSA, PSA, adhesive foam, etc.). The adhesive 728 may define a hole in which the membrane 729 and compliant stack 730 may be positioned. As described above, the membrane 729 may be positioned over a hole 731 that extends through the substrate 722 and provides acoustic access to the microphone module 720. In some cases, the surface(s) that define the hole 731 are considered part of the acoustic path that extends from the speaker port 401 to the microphone module 720.

The microphone module 720 may include conductive pads 732 that are conductively coupled (e.g., soldered) to corresponding conductive pads on the substrate 722 to facilitate communicative coupling between the microphone module 720 and other circuitry. The microphone module 720 also includes a microphone sensor element 733. As shown in FIG. 7C, the microphone sensor element 733 is positioned proximate the hole 731, though in other cases it may be positioned elsewhere in the microphone module 720.

Figure 8A:
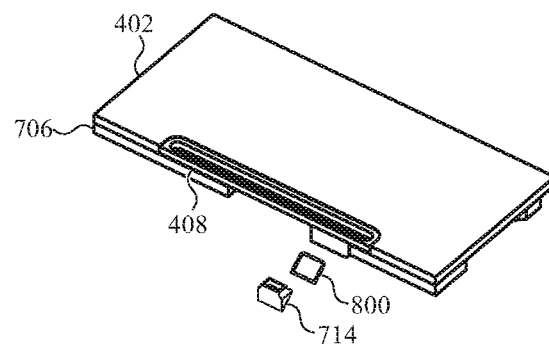
FIGS. 8A-8C depict partial views of example electronic devices, illustrating example speaker port configurations.

FIG. 8A depicts another view of the boot 714 of FIG. 7A, showing how the boot 714 may be integrated with the cover 402 and the frame 706. In particular, the boot 714 may be positioned below the trim piece 408 and against the frame member 706 in the area where the first path portion through the frame member 706 ends. As shown, an adhesive 800 (e.g., a PSA, HSA, adhesive foam, etc.) may adhere the boot 714 to the frame member 706.

Figure 8B:
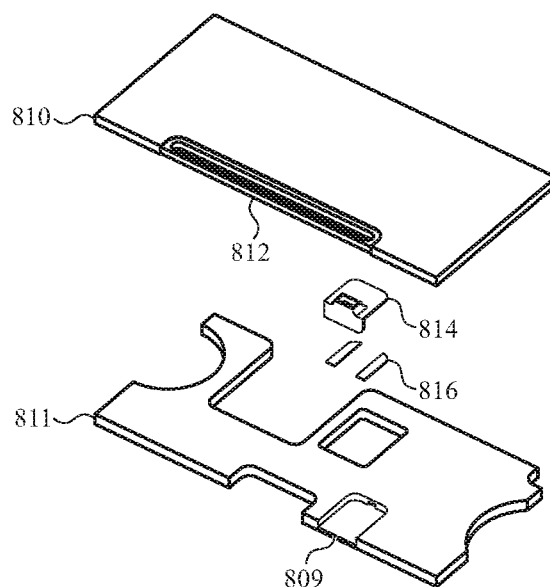
Figure 8C:
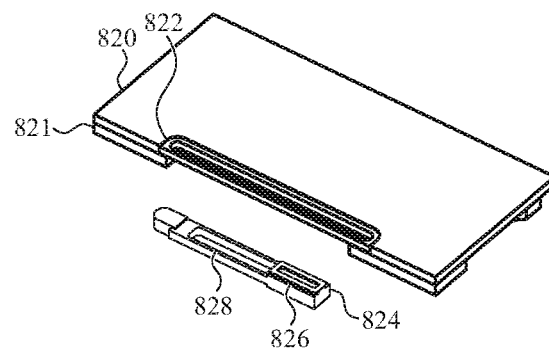

FIGS. 8B-8C depict other example configurations of boots and/or acoustic separators that may be used to acoustically isolate a speaker from a microphone. FIG. 8B shows a cover 810 separated from a frame member 811. The frame member 811 (which may be an embodiment of the frame member 706) defines an output port 809 at an end of an acoustic path portion defined by the frame member 811. A microphone may be coupled to the frame member 811 along a bottom surface of the frame member (as shown in FIG. 7A), optionally before the frame member 811 is attached to the cover 810. A boot 814 may be attached to the frame member 811 with adhesive 816. The boot 814 may define a snout-portion that extends into the recess defined under the trim piece 812, in a manner similar to the boot 714 in FIG. 7A. The boot 814 may be attached to the frame member 811 prior to the frame member 811 being coupled to the cover 810.

FIG. 8C depicts an acoustic isolation structure 824 that may be positioned below the trim piece 822. The acoustic isolation structure 824 may include a first passage 826 for porting sound to a microphone module, and a second passage 828 for porting sound to a speaker module. The first and second passages 826, 828 may define portions of the acoustic paths to the microphone and speaker modules, respectively. The acoustic isolation structure may be adhered or otherwise attached to the cover 820 and/or the frame member 821, and may be attached after the frame member 821 is coupled to the cover 820.

Figure 9A:
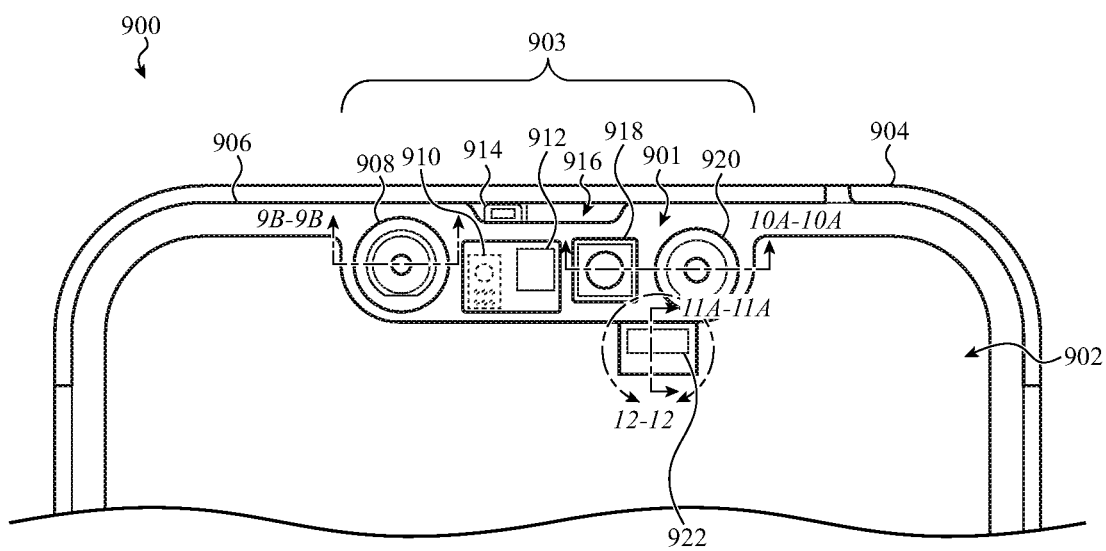
FIG. 9A depicts a partial view of an example front-facing sensor region of an example electronic device.

FIG. 9A depicts a portion of a device 900. The device 900 may correspond to or be an embodiment of the device 100, 140, 200, 300, or any other device described herein. The device 900 is shown without a cover and/or display, such that internal components of the device 900 are visible. FIG. 9A shows a housing 904, as well as a frame member 906 of a top module (or a representation of where a frame member would be).

FIG. 9A generally illustrates a front-facing sensor region 901. With the exception of an ambient light sensor 922, the components of the front-facing sensor region 901 may be outside of an active area of the display. The front-facing sensor region 901 (which may also be referred to as a notch, due to the manner in which it extends downward into the display region) may have a width 903 that is less than about 60%, less than about 50%, or less than about 40% of the width of the display area 902. In some cases, one or more of the components in the front-facing sensor region 901 provide multiple functions, thereby allowing the width of the front-facing sensor region 901 to be minimized or reduced. In some cases, the width 903 of the front-facing sensor region 901 is about 30 millimeters or less.

The device 900 includes, in the front-facing sensor region 901, a front-facing camera 908, a proximity sensor 912, a combination flood illuminator and dot projector 918 (e.g., a biometric sensor module), and an infrared light sensor (or camera) 920. The device 900 also includes an ambient light sensor 922 positioned within an active display region 902 of the device 900. FIG. 9A also illustrates an example positioning of a microphone module 910, which may be attached to an underside of the frame member 906. As described herein, the microphone module 910 may communicate with an acoustic boot 914 in the speaker port of the device 900.

The combination flood illuminator and dot projector 918 (which may correspond to or be an embodiment of the combination flood illuminator and dot projector 416) may be or may include a biometric sensor module. The combination flood illuminator and dot projector 918 may project both an infrared flood illumination of an object, as well as a pattern of infrared dots or points of light. The infrared light sensor (or camera 920) may capture an image of an object (e.g., a user's face) using the projected flood illumination and dot pattern. The images captured by the sensor 920 may be used to authenticate a user, as described above. Further, by combining the flood illuminator and dot projector into a single module, valuable space may be saved in the front-facing sensor region 901, thereby allowing for a greater amount of active display area to be provided.

Figure 9B:
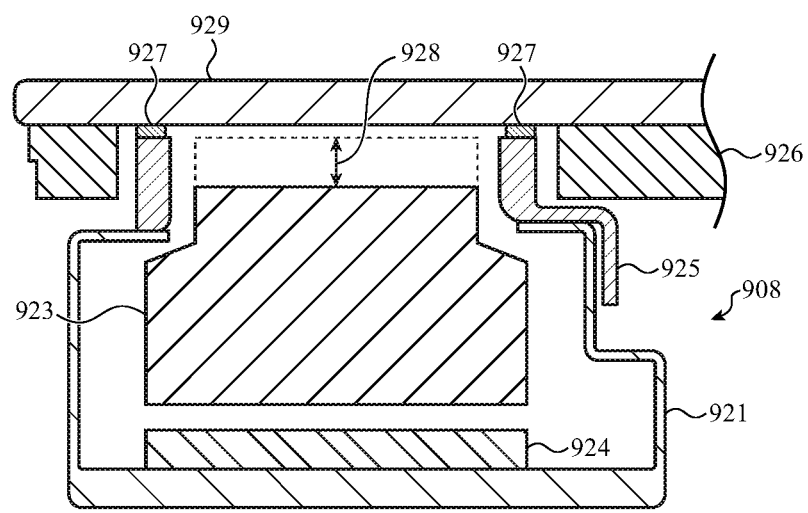
FIG. 9B depicts a partial cross-sectional view of an example device, illustrating a portion of a front-facing sensor region of the example electronic device.

FIG. 9B depicts a partial cross-sectional view of the device 900, viewed along line 9B-9B in FIG. 9A, depicting an example configuration of the front-facing camera 908. The front-facing camera 908 may include a lens assembly 923 and an image sensor 924, both contained in a housing 921. The camera 908 may be an auto-focus camera in which the lens assembly 923 is configured to extend, contract, or otherwise change length or position within the housing 921 to focus an image on the image sensor 924. In such cases, a front surface of the lens assembly 923 may be configured to move vertically as indicated by arrow 928.

In cases where the front surface of the lens assembly 923 moves towards and/or away from the cover 929 (e.g., the front cover of the device 900), it may not be feasible to mount the lens assembly 923 directly to the interior surface of the cover 929. Accordingly, FIG. 9B illustrates an example configuration for mounting an auto-focus camera to the interior side of a cover 929. For example, the housing 921 may be coupled to a mounting bracket 925 (e.g., via adhesive, welding, soldering, brazing, fasteners, or the like). The mounting bracket 925 may be attached to the interior surface of the cover 929, such as via adhesive 927, fasteners, or the like. The mounting bracket 925 may have a height that provides sufficient clearance between the lens assembly 923 and the interior surface of the cover 929 to facilitate the necessary movement of the front of the lens assembly 923 (indicated by arrow 928).

The mounting bracket 925 and the adhesive 927 may extend completely around the periphery of the lens assembly. In this way, the mounting bracket 925 and the adhesive 927 inhibit ingress of dust or other contaminants into the housing 921 and prevent light from the display 926 (or other light sources) from entering the lens assembly 923 and potentially negatively affecting images captured by the camera or otherwise interfering with the operation of the camera.

While FIG. 9B illustrates an auto-focus camera, the same or similar construction may be used for fixed focus cameras as well. In such cases, the lens assembly may not be configured to move vertically, but instead may remain in a fixed length and/or position within the housing.

Figure 9C:
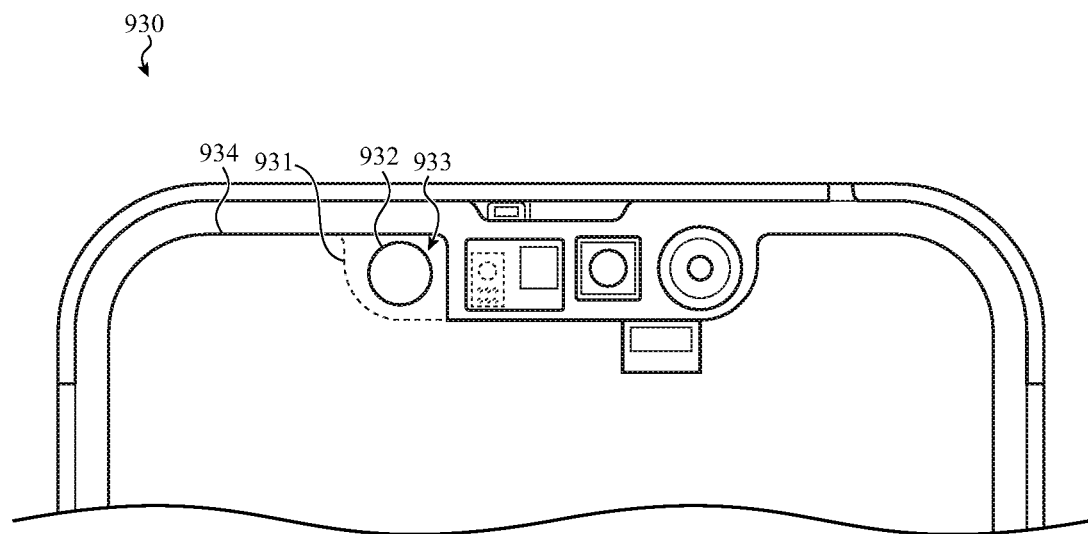
FIG. 9C depicts a partial view of an example front-facing sensor region of another example electronic device.
Figure 9D:
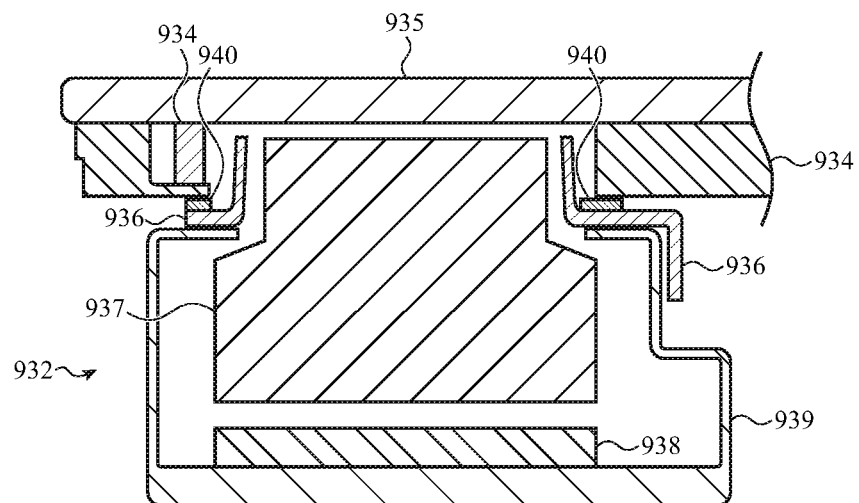
FIGS. 9D-9F depict partial cross-sectional views of front-facing sensor regions of example electronic devices.

FIG. 9A depicts an example device 900 in which components of a front-facing sensor region are positioned outside of an active region of the display, in a "notch" region. In such cases, the display may define a notch-like recess or shape to accommodate the front-facing sensor region, such that the display stack is not positioned between the sensors and the cover (e.g., the sensors are not covered by the display). In other example devices, the display defines one or more additional holes, openings, or discontinuities, in addition to or instead of the "notch," to accommodate one or more components of the front-facing sensor region. For example, FIGS. 9C and 9D illustrate an example electronic device 930 in which a front-facing camera 932 is positioned below a hole formed through a display stack 934. The display stack 934 may also define a cut-away region, or notch, in which other components of the front-facing sensor region may be positioned (e.g., a microphone module, a flood and dot projector, an infrared light sensor, or the like).

In some cases, the region 933 of the display stack 934 that extends around (or partially around) the front-facing camera 932 is an active portion of the display. For example, the region 933 may produce graphical outputs. In other cases, the region 933 is an inactive region of the display stack 934 (e.g., that region of the display stack may be incapable of producing graphical outputs, or it may be capable of producing graphical outputs but configured to remain inactive). In cases where the region 933 is an inactive region of the display, a paint, ink, dye, mask, layer, or the like may be positioned on top of the display in that region such that the region 933 has a matching visual appearance to the other areas of the front-facing sensor region.

A border 931 may extend around the camera 932 to visually indicate that the camera 932 is within the front-facing sensor region, and to provide vertical symmetry to the front-facing sensor region. In such cases, the border shown above and to the right of the camera 932 in FIG. 9C may not be present. The border 931 may be a paint, ink, dye, or other structure or material.

FIG. 9D depicts a partial cross-sectional view of the device 930 of FIG. 9C, illustrating an example configuration of the camera 932 and the display stack 934. The camera 932, which may be an autofocus or fixed focus camera, may include a lens assembly 937 and an image sensor 938, both contained in a housing 939. The camera 932 may also include a shroud 936 that is attached to the housing 939 and to the display stack 934 (e.g., with adhesive 940). The shroud 936 and the adhesive 940 may extend completely around the periphery of the lens assembly. In this way, the shroud 936 and the adhesive 940 inhibit ingress of dust or other contaminants into the housing 939. Further, the shroud 936 extends almost completely to (and optionally contacts) the interior surface of the cover 935 (which may be an embodiment of the cover 102, or any other front covers described herein), thereby shielding the lens assembly 937 from light emitted from the sides of the display 934, which may otherwise enter the lens assembly 937 and potentially negatively affecting images captured by the camera or otherwise interfering with the operation of the camera.

FIG. 9D depicts the camera 932 positioned in a hole in the display stack 934, such that the display stack surrounds the wall portion of the shroud 936 (as illustrated by the display stack 934 having portions both on the left and right side of the shroud 936). The same or similar shroud construction may also be used in implementations where the camera 932 is not positioned in a hole in a display stack 934. In such implementations, the portion of the display stack 934 that is shown on the left side of FIG. 9D may not be present and/or it may be replaced by a different structural component.

Figure 9E:
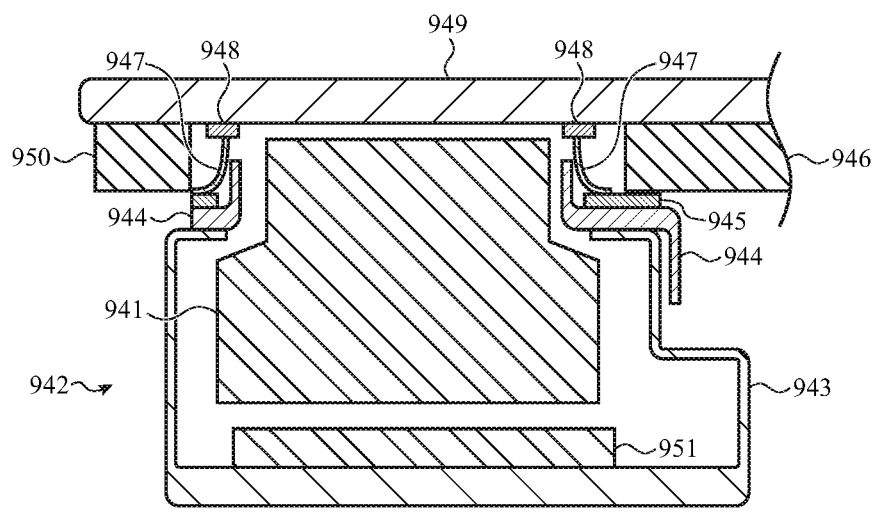

FIG. 9E depicts a partial cross-sectional view of another example configuration of a front-facing camera. The camera 942, which may be an autofocus or fixed focus camera, may include a lens assembly 941 and an image sensor 951, both contained in a housing 943. The camera 942 may also include a shroud 944 that is attached to the housing 943 and optionally to the display stack 946 (e.g., with adhesive 945) and optionally to a frame or other component of the top module of a device. In some cases, the shroud 944 is not attached to the display stack 946. The camera 942 also includes a ring member 947 that is attached to the shroud 944 (e.g., via adhesive 945) and to the interior surface of the cover 949 (which may be an embodiment of the cover 102, or any other front covers described herein). The ring member 947 may extend completely around the periphery of the lens assembly, and may be adhered to the interior surface of the cover 949 via adhesive 948 (e.g., PSA, HSA, adhesive foam, or the like). In this way, the ring member 947 and the adhesive 948 inhibit ingress of dust or other contaminants into the housing 943. Further, because the ring member 947 is adhered to or otherwise contacts the interior surface of the cover 949, the ring member 947 shields the lens assembly 941 from light emitted from the side of the display 946, which may otherwise enter the lens assembly 941 and potentially negatively affecting images captured by the camera or otherwise interfering with the operation of the camera. The configuration of the camera in FIG. 9E may be implemented in a device with a hole through its display stack to accommodate the camera (as shown in FIG. 9C), or in a device where the camera is positioned outside the outer periphery of the display (as shown in FIG. 9A). In the former case, component 950 may represent part of the display stack 946, while in the latter case, component 950 may represent a frame or other component of the top module of a device.

Figure 9F:
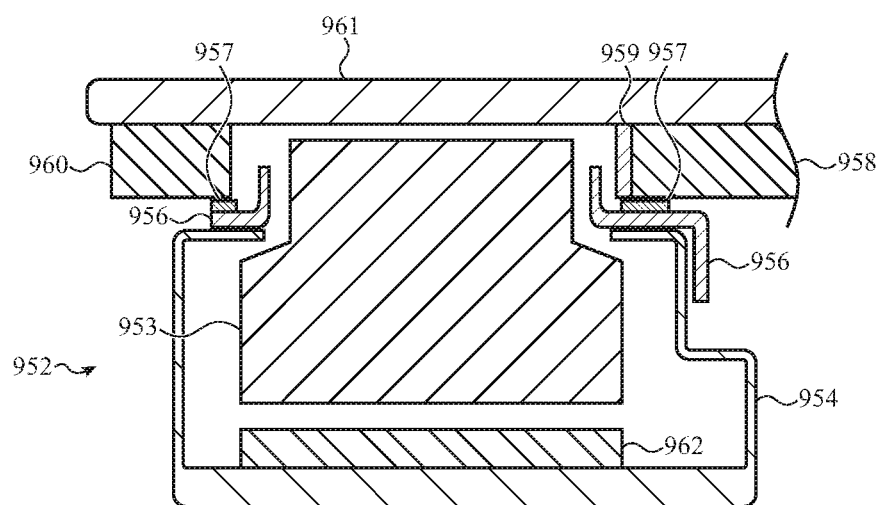

FIG. 9F depicts a partial cross-sectional view of another example configuration of a front-facing camera 952. The camera 952, which may be an autofocus or fixed focus camera, may include a lens assembly 953 and an image sensor 962, both contained in a housing 954. The camera 952 may also include a shroud 956 that is attached to the housing 954 and optionally to the display stack 958 (e.g., with adhesive 957) and optionally to a frame or other component of the top module of a device. In some cases, the shroud 956 is not attached to the display stack 958.

As shown in FIG. 9F, the shroud 956 does not contact or otherwise extend sufficiently towards the cover 961 to shield the lens assembly 953 from light that may leak from the edge of the display stack 958. Accordingly, a shield 959 may be applied to an edge of the display stack 958. The shield 959 may be a paint, ink, dye, film, or other material or component that is opaque or otherwise blocks or reduces light from leaving the display stack 958 through the edge. In some cases, any edge of the display stack 958 that is proximate an optical device, such as a lens assembly, image sensor, light sensor, etc., may include a shield similar to the shield 959 along that edge.

The configuration of the camera in FIG. 9F may be implemented in a device with a hole through its display stack to accommodate the camera (as shown in FIG. 9C), or in a device where the camera is positioned outside the outer periphery of the display (as shown in FIG. 9A). In the former case, component 960 may represent part of the display stack 958, while in the latter case, component 960 may represent a frame or other component of the top module of a device. Where the component 960 represents part of the display stack 958, the edge of that portion of the display stack that is exposed to the camera 952 may include a shield similar to the shield 959. In such cases, the shield 959 may be a single unitary component, such as a film, paint, ink, dye, or the like, that extends along a continuous edge of the display stack.

FIGS. 9B and 9D-9F illustrate example lens configurations that include mitigations to prevent or limit the effects of light contaminants (e.g., dust) on the operation of the camera. For example, FIG. 9B describes a mounting bracket that attaches to an interior surface of a cover to seal the camera; FIG. 9D describes a shroud that extends around the periphery of a lens assembly to block light; FIG. 9E describes a ring member 947 that attaches to an interior surface of a cover to seal the camera; and FIG. 9F describes a paint or other coating that is applied to the edge of a display stack to reduce or prevent light leakage.

Figure 9G:
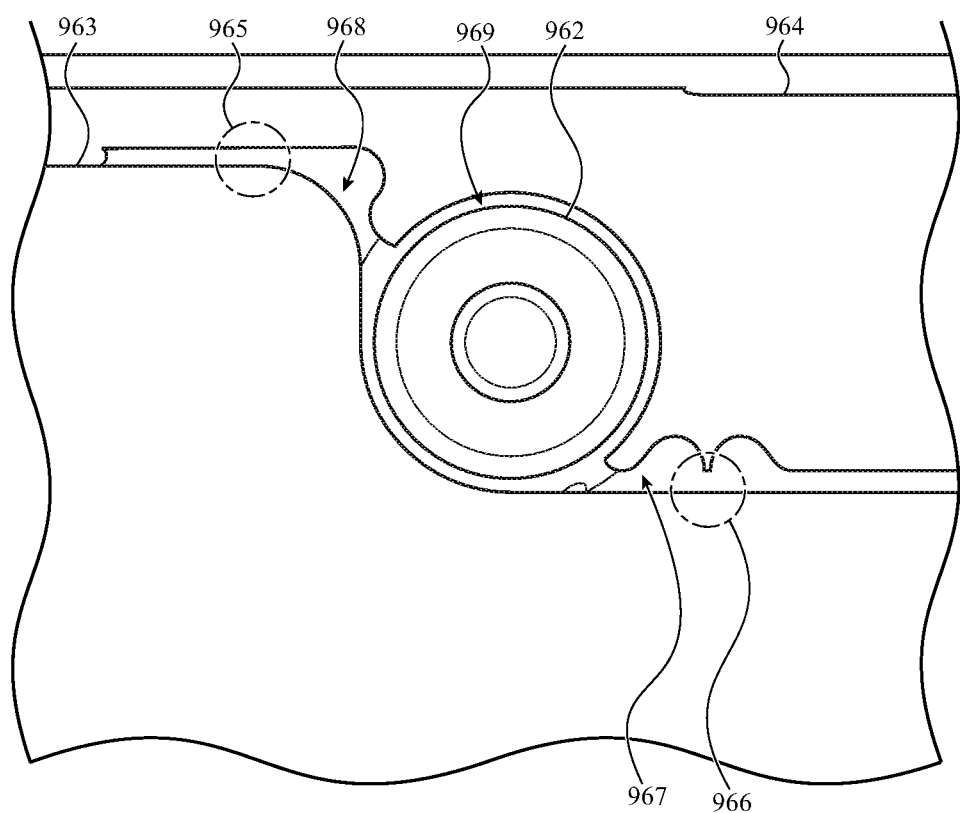
FIG. 9G depicts an example front-facing camera of an example electronic device.

Cameras may also or alternatively be at least partially encapsulated by a curable material to help prevent or limit light leakage and other contamination. FIG. 9G illustrates a portion of a device with a front-facing camera, illustrating how a camera, such as any of the cameras shown or described in FIGS. 9A-9F, may be at least partially encapsulated. In particular, a front-facing camera 962 (which may be an embodiment of the cameras 908, 932, 942, 952, or any other front-facing camera described herein) may be positioned in a front-facing sensor region of a device. The camera 962 may be positioned in a gap or space that is between a frame member 964 (which may be a polymer, metal, laminate stack, or other member or assembly of a top module) and a display stack 963. The frame member 964 and/or the display stack 963 may define curves or contours to at least partially surround or frame the camera 962. A gap 969 may be defined between the camera 962 and the frame member 964 and the display stack 963.

The camera 962 may be attached to or otherwise positioned proximate the interior surface of a cover. FIG. 9G shows a device with the cover removed for ease of illustration, but it will be understood that a cover may be positioned over the camera 962, the display stack 963, and the frame member 964 (e.g., as if the cover is placed directly on the page).

In order to at least partially encapsulate the camera 962, a curable material may be introduced into the spaces between the display stack 963 and the frame member 964 (e.g., spaces 968 and 967) and into the gap 969. The curable material may be introduced through one or more holes (e.g., holes 965, 966) formed through a back component of the top module, such as a plate (e.g., the metal plate 1314, FIG. 13A). The curable material may flow along the interior surface of the cover, through the spaces 967 and 968, and into the gap 969. In some cases, one of the holes 965, 966 is used as an injection port, and the other is used as a vent (or vacuum) port to help draw the curable material into the desired locations. The curable material may at least partially surround the camera and may abut (and optionally adhere to) a housing, shroud, ring member, or other component of the camera, as well as contacting (and optionally adhering to) the interior surface of the cover and any other components that it comes into contact with. The curable material may then be allowed to cure to form a seal around the camera 962. As noted above, the cured material may help seal the camera 962 against light and contaminants. The curable material may be an epoxy, glue, thermoset polymer, or the like.

Figure 9H:
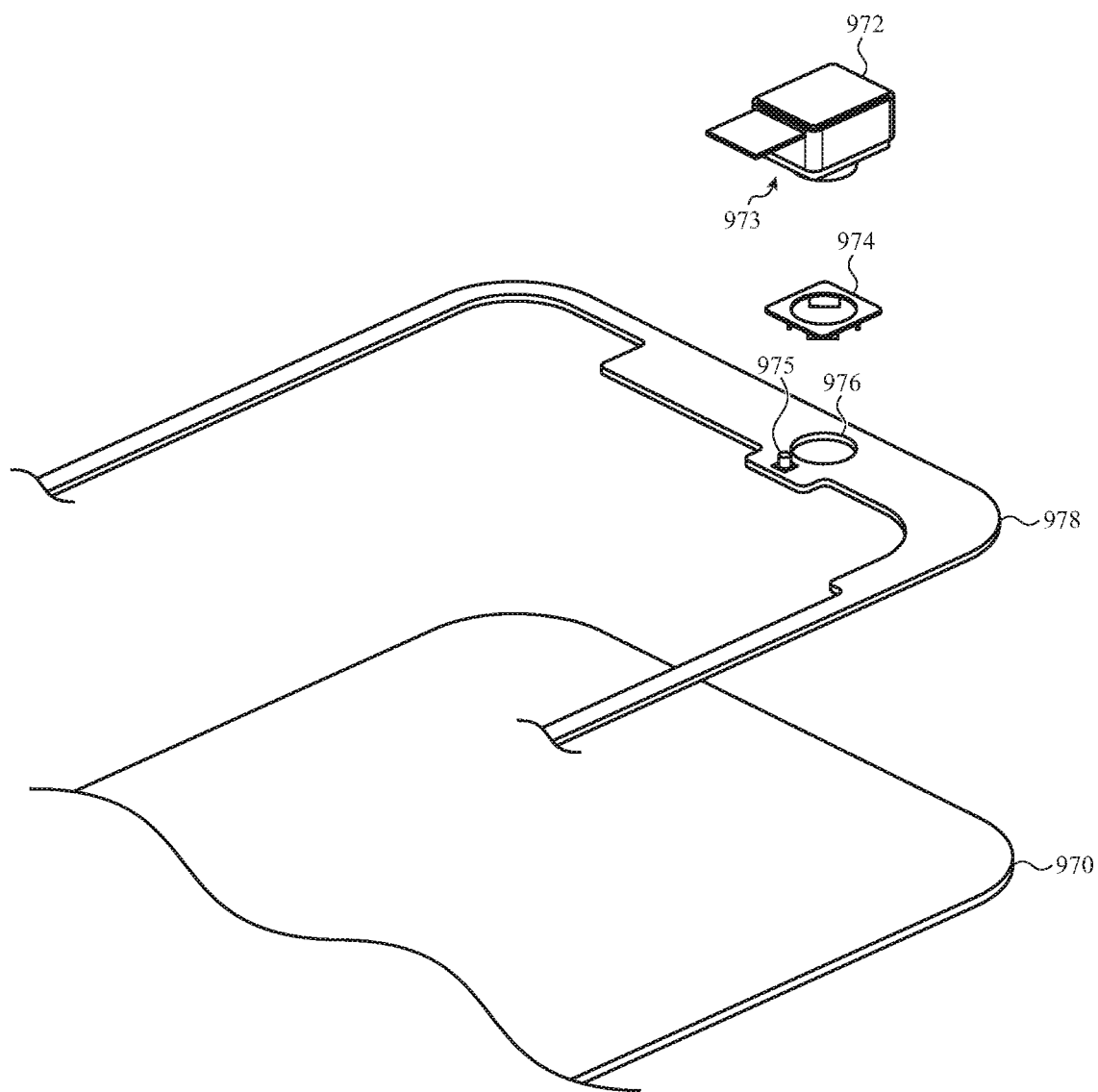
FIG. 9H depicts an exploded view of a portion of a front-facing sensor region of an example electronic device.

FIG. 9H depicts a partial exploded view of a device, showing example techniques for aligning and/or securing a front-facing camera 972 to the top module. FIG. 9H illustrates a cover 970 and a frame member 978 defining a camera hole 976. The frame member 978 may be an assembly comprising multiple components or materials, and may be configured to be attached to the cover 970 and to provide structural rigidity to the top module and attach the top module to other components of a device. The frame member 978 may include other holes, openings, features, or the like, to accommodate or attach to other top module components (including, for example, components of a front-facing sensor array), though for simplicity only the camera hole 976 is shown in FIG. 9H.

The camera 972 may be attached to the frame member 978 via adhesives, fasteners, brackets, or any other suitable technique. A lens assembly, shroud, or other portion of the camera 972 may extend through the hole 976 in the frame member 978, and may attach to or otherwise be proximate the interior surface of the cover 970, as shown and described with respect to FIGS. 9B and 9D-9F. The frame member 978 may include either or both of an alignment ring 974 or an alignment pin 975. The alignment ring 974 may be affixed to the frame member 978 so that a hole through the alignment ring 974 is properly positioned relative to the hole 976. The camera 972 may be attached to or otherwise secured against the alignment ring 974. The alignment ring 974 may be configured to contact the camera 972 and position the camera 972 in a fixed position relative to the alignment ring 974, thereby establishing and fixing the position of the camera 972 in the device. For example, a shroud or other cylindrical component of the camera 972 may contact the inner surface of the hole through the alignment ring 974 to establish and fix the relative positions of the camera 972 and the frame member 978 (at least within a plane parallel to the cover 970). Alternatively or additionally, the frame member 978 may include an alignment pin 975 protruding from the frame member 978. The camera 972 may define an alignment pin receptacle 973 (e.g., a blind hole formed into the camera 972) into which the alignment pin 975 extends. When the camera 972 is assembled onto the frame member 978, the interface between the alignment pin 975 and the alignment pin receptacle 973 establishes and fixes the relative position of the camera 972 and the frame member 978 (at least within a plane parallel to the cover 970).

Figure 10A:
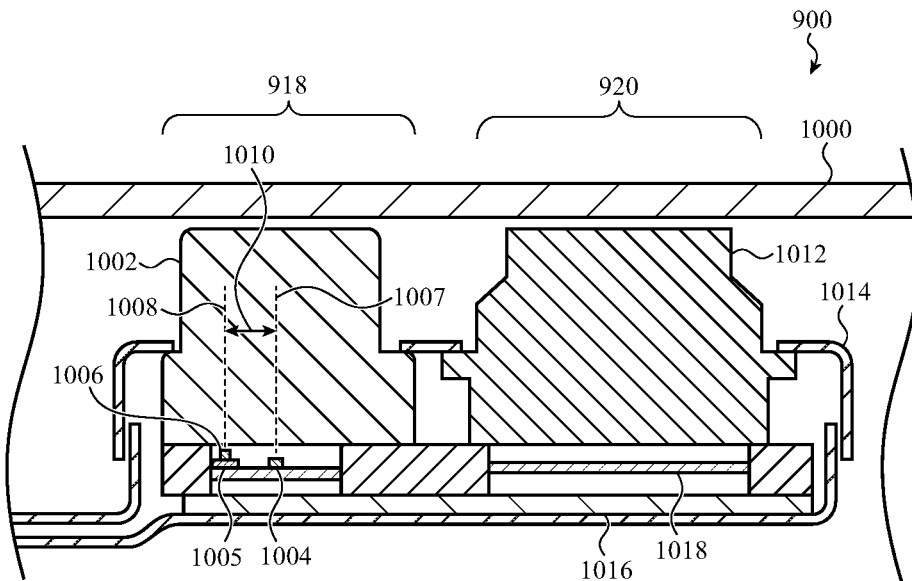
FIGS. 10A-10C depict partial cross-sectional views of an example electronic device, illustrating an example combination flood illuminator and dot projector configuration.

FIG. 10A depicts a partial cross-sectional view of the device 900 viewed along line 10A-10A in FIG. 9A. FIG. 10A illustrates an example arrangement of the combination flood illuminator and dot projector 918 and the infrared light sensor 920, shown below a cover 1000 (e.g., corresponding to the cover 102 or any other cover described herein).

The infrared light sensor 920 may include a lens assembly 1012 (also referred to as a second lens) and a light receiver, such as a sensor element 1018. The lens assembly 1012 may include one or more lens elements and may focus an image onto the light receiver (e.g., the sensor element 1018) to capture an object that is illuminated by the flood and/or dot pattern projected by the combination flood illuminator and dot projector 918. In some cases, the infrared light sensor 920 produces a depth map of a user's face (or other object) based on the way in which the user's face reflects the dot pattern. The sensor element 1018 may be coupled to a substrate 1016 and the lens assembly 1012, the sensor element 1018, and the substrate 1016 may be contained in a housing 1014. The housing 1014 may also contain components of the combination flood illuminator and dot projector 918.

The combination flood illuminator and dot projector 918 includes a lens assembly 1002 (also referred to as a first lens), a dot pattern light source 1004 (also referred to as a first light source and/or light emitter), and a flood illumination light source 1006 (also referred to as a second light source and/or light emitter). The lens assembly 1002 may include one or more lens elements. The dot pattern light source 1004 may produce and/or emit a pattern of light (e.g., a pattern of dots or points of infrared light), which may be projected, through the lens assembly 1002, onto an object. The dot pattern may be a grid of discrete points of light, or a set of discrete points of light in another arrangement.

The dot pattern light source 1004 may be positioned relative to the optical axis 1007 of the lens assembly 1002 such that the dots are substantially in focus and/or the dot pattern maintains a pattern of discrete dots or points of infrared light. In some cases, the dot pattern light source 1004 is aligned with an optical axis 1007 of the lens assembly 1002 or otherwise positioned below a central region of the lens assembly 1002, as shown in FIG. 10A. In some cases, the dot pattern light source 1004 includes multiple discrete light-producing elements. In other cases, a pattern or mask is provided over one or more light-producing elements to produce the pattern of dots.

Figure 10B:
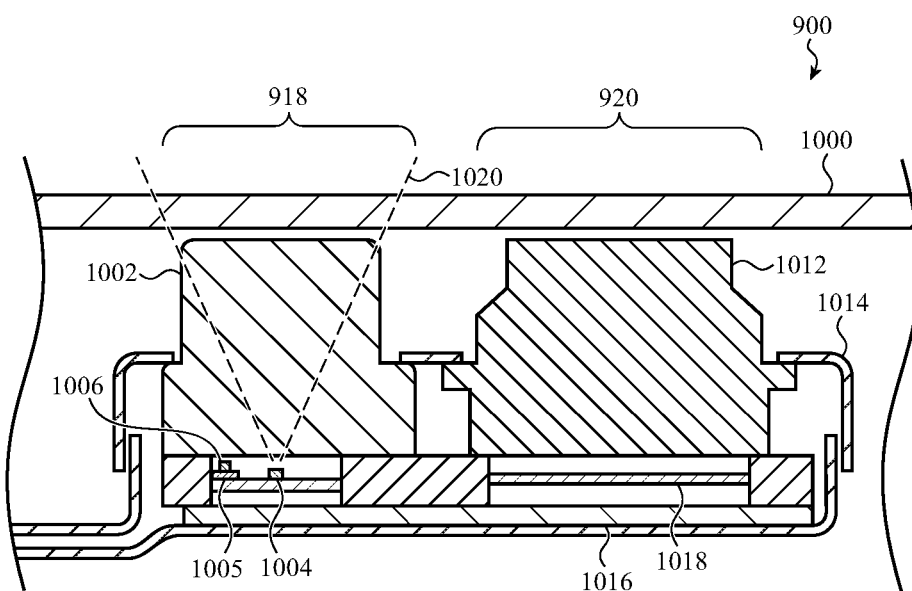
Figure 10C:
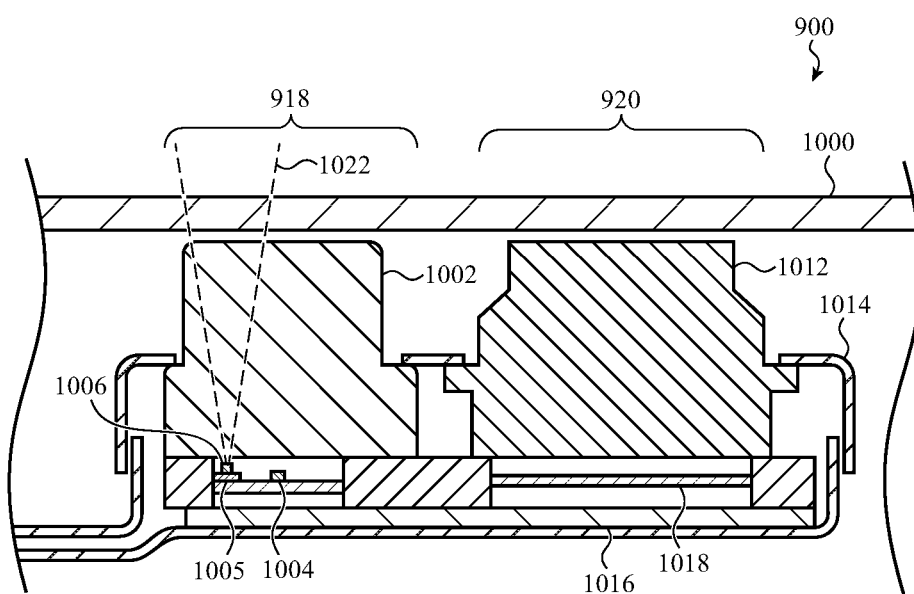

The flood illumination light source 1006 may be configured to produce a more uniform flood of light (as compared to the dot pattern of the dot pattern light source 1004). In order to produce the flood of light, the flood illumination light source 1006 may be offset from the optical axis 1007 of the lens assembly 1002, such that it is positioned below a peripheral region of the lens assembly 1002 (e.g., a region about a periphery of the lens assembly 1002 and around the central region of the lens assembly 1002). For example, as shown in FIG. 10A, the flood illumination light source 1006 may be offset from the optical axis 1007 by a distance 1010. In some cases, the flood illumination light source 1006 may also be positioned at a different height, relative to the lens assembly 1002, than the dot pattern light source 1004. For example, as shown in FIGS. 10A-10C, the flood illumination light source 1006 may be closer to the lens assembly 1002 (e.g., it may be mounted on a spacer 1005 or otherwise positioned nearer to the lens assembly 1002). In other cases it may be positioned lower than the dot pattern light source 1004 (e.g., further from the lens assembly 1002). The positioning of the dot pattern light source 1004 and the flood illumination light source 1006 may be related to a focal plane of the lens assembly 1002. For example, in some cases, the dot pattern light source 1004 is positioned at or in the focal plane of the lens assembly 1002, and the flood illumination light source 1006 is offset from (e.g., not in) the focal plane of the lens assembly 1002. In other cases, the dot pattern light source 1004 and the flood illumination light source 1006 are offset by different distances from the focal plane of the lens assembly 1002.

By positioning the flood illumination light source 1006 away from the optical axis 1007 (and optionally closer to or further from the lens assembly 1002 than the dot pattern light source 1004), the light emitted by the flood illumination light source 1006 may be blurred or otherwise projected in a diffuse pattern, even if the light emitted by the flood illumination light source 1006 is one or multiple point sources of light. More particularly, light passing through the lens assembly 1002 at a distance from the optical axis (e.g., near an outer periphery of the lens elements in the lens assembly 1002) may not be rendered in focus, and instead may be blurry and/or diffuse, thereby producing a flood-like illumination pattern. In some cases, the illumination pattern produced by the flood illumination light source 1006, as projected by the lens assembly 1002, may substantially uniformly illuminate a user's face with a flood of infrared light when the device is held within a particular distance from the user's face (e.g., between about 6 inches and about 4 feet, or any other suitable distance range). In this way, the infrared light sensor 920 can capture an image (e.g., an infrared image) of the user's face for purposes of authentication or the like. More particularly, the flood of infrared light is reflected by the user's face to produce an image of the user's face via the light sensor 920 (and more particularly the sensor element 1018).

FIG. 10B illustrates the dot pattern illumination light source 1004 projecting a pattern of dots through the lens assembly 1002, as illustrated by the illumination pattern 1020. For example, the central region of the lens assembly 1002 may focus the pattern of light emitted by the dot pattern illumination light source 1004 onto an object.

FIG. 10C illustrates the flood illumination light source 1006 projecting a diffuse, flood-like pattern of illumination along an off-axis path through the lens assembly 1002, as illustrated by the illumination pattern 1022. While FIGS. 10B and 10C each illustrate only one illumination pattern, it will be understood that both illumination patterns may be produced at the same time. In some cases, the illumination patterns are produced in an alternating pattern, such that each illumination pattern is incident on an object for a period of time in which the other is not incident on the object.

In some cases, the flood illumination light source 1006 includes multiple light emitting elements, such as an array of light emitting elements positioned in a radial array, with each light emitting element offset from the optical axis 1007.

Both the flood illumination light source 1006 and the dot pattern illumination light source 1004 may be or may include one or more infrared laser light sources, such as vertical-cavity surface-emitting laser ("VCSEL") modules, or any other suitable light-producing elements. As described above, the VCSEL modules may produce light in an infrared spectrum. In some cases, the light produced by the flood illumination light source 1006 and the dot pattern illumination light source 1004 is not generally visible to the unaided human eye.

Figure 11A:
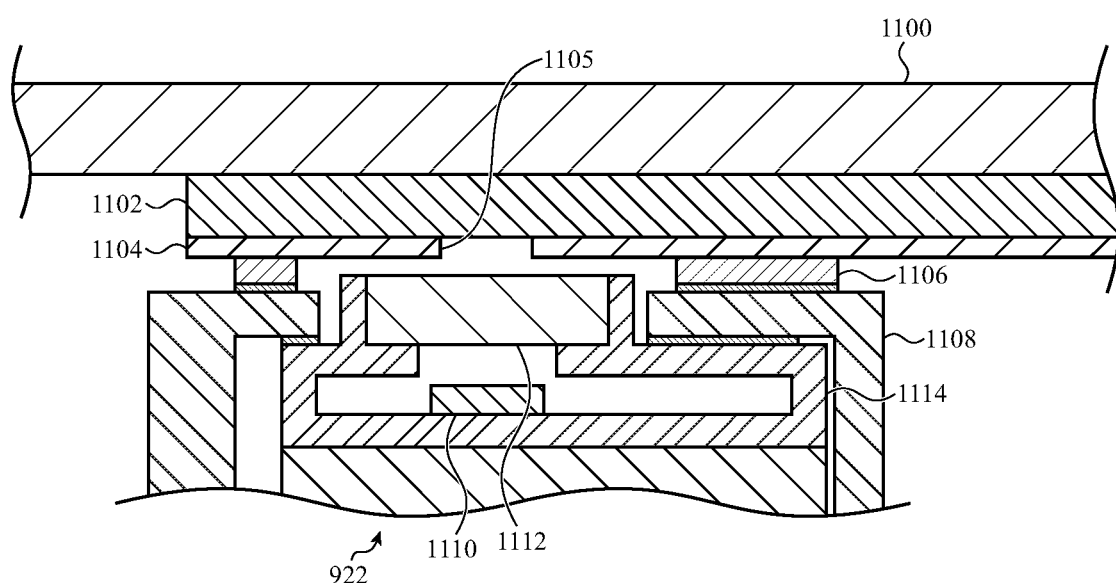
FIG. 11A depicts a partial cross-sectional view of an example electronic device, illustrating an example ambient light sensor.

FIG. 11A depicts a partial cross-sectional view of the device 900, viewed along line 11A-11A in FIG. 9A, and illustrating an example configuration of the ambient light sensor 922. The ambient light sensor 922 may include a light sensor module with a light sensing element 1110 and a light-transmissive cover element 1112 (e.g., a glass, polymer, sapphire, or other light-transmissive material(s)) in a housing 1114. The light-transmissive cover element 1112 (e.g., diffuser) may be configured to diffuse light to produce a more uniform illumination on the light sensing element 1110. The light sensing element 1110 may be a photosensitive system or component, and may detect various characteristics of light, including intensity, color, color temperature, or the like.

The housing 1114 may be attached to a bracket 1108, which may in turn be attached to a layer 1104 below display components 1102 (e.g., display layers). The bracket 1108 may be attached to the layer 1104 via adhesive, for example. The layer 1104 may be part of a display stack that includes both the layer 1104 and the display components 1102, or it may be a separate component. The display components 1102 may include one or more display layers that produce graphical outputs visible through a cover 1100, as well as one or more electrode layers that provide touch and/or force-sensing functionality. As described in greater detail with respect to FIGS. 11B-11C and 12A-12B, the ambient light sensor 922 may be configured to detect an ambient light (e.g., light outside of the device) through the display 1102 and the cover 1100.

The layer 1104 may be an opaque masking layer that defines a hole 1105. The hole 1105 may define the smallest aperture in the optical system that includes the ambient light sensor 922, and thus may be the limiting factor in the amount and angle of light that can enter the ambient light sensor 922. The area of the hole 1105 may be smaller than the area of the light sensing element 1110.

The layer 1104 may be formed from any suitable material, such as a metal (e.g., a metal plate or metal foil), polymer, ink, or the like. In some cases, the location of the hole 1105 is tightly controlled with respect to the display components 1102, such that the hole 1105 is aligned with a known set of pixels defined by the display components 1102. Thus, as described below, the device can compensate for the light being produced by the pixels above and/or nearby the hole 1105 with specificity. By forming the hole in a layer 1104 that is part of the display stack, a high degree of accuracy can be achieved between the location of the hole 1105 and the intended pixels. By contrast, if the light-limiting aperture of the system were positioned in the ambient light sensor 922, the accuracy of the alignment between the ambient light sensor 922 and the hole 1105 would be dependent on the accuracy of the assembly of the ambient light sensor 922 to the display stack, which may be lower than can be achieved by forming the hole in a layer of the display stack itself. Further, because the layer 1104 is part of the display stack, it may be securely retained to the other layers of the display stack, such as via adhesive (e.g., an adhesive that extends along the entire or substantially the entire area of the display stack between the layer 1104 and an adjacent layer of the display stack). This coupling between the layer 1104 and the adjacent layer of the display stack provides a stable, durable alignment between the hole 1105 and the pixels above and/or nearby the hole 1105. Further, by forming the smallest aperture (e.g., the hole 1105) in a layer of the display stack, rather than a separate component that may be knocked loose or otherwise more likely to shift relative to the display stack, the alignment between the hole 1105 may remain stable through extensive use.

In some cases, the ambient light sensor 922 is positioned proximate an edge or boundary of the active area of the display stack in order to reduce the amount of light from the display that can enter the ambient light sensor. For example, the ambient light sensor 922 (and more particularly the hole 1105) may be positioned about 0.5 mm, 1.0 mm, 1.5 mm, 2.0 mm, or any other suitable distance (e.g., left-to-right in FIG. 11A) from the edge of the active area of the display. The hole 1105 may have dimensions of between about 0.25 and about 0.75 mm in the y-direction of the device (left-to-right in FIG. 11A), and between about 5.0 and about 7.0 mm in the x-direction of the device (into the page in FIG. 11A).

Figure 11B:
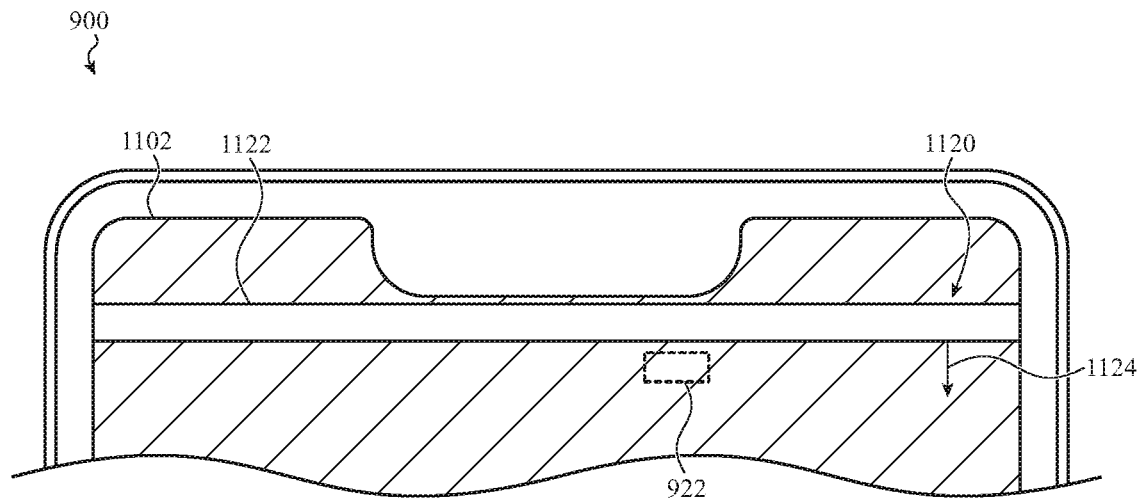
FIGS. 11B-11C depict a portion of an example electronic device, illustrating an operation of the example ambient light sensor.
Figure 11C:
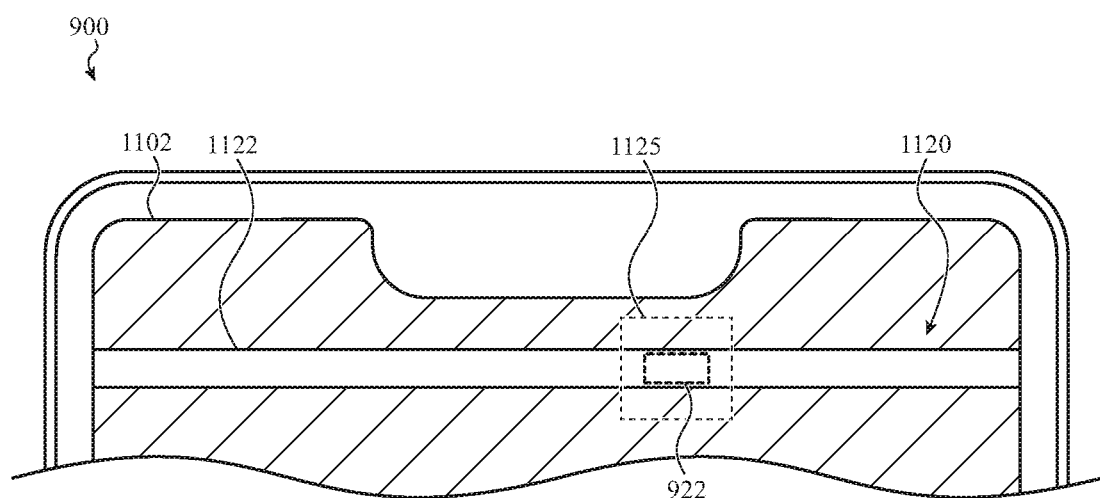

FIGS. 11B-11C depict a partial front view of the device 900, illustrating an example operation of the ambient light sensor 922. As noted above, the ambient light sensor 922 detects and/or senses ambient light (e.g., a color, color temperature, intensity, or other property of the light in the environment external to the device 900) through a display stack as well as through one or more electrode layers on or integrated with the display stack. However, the display stack emits light in order to produce graphical outputs. Because the ambient light sensor 922 detects light conditions through the display, the light from the display may interfere with or prevent accurate readings of the ambient light conditions. Accordingly, the ambient light sensor 922 may be configured to capture measurements during a time when the pixels over the ambient light sensor 922 are not illuminated. In particular, when producing graphical outputs, the display may produce a vertical blanking interval 1122, which is a horizontal region of the display in which the pixels are not illuminated or producing light. The vertical blanking interval 1122 scrolls vertically along the display area (e.g., from a top of the display to a bottom of the display). Accordingly, the ambient light sensor 922 may be configured to capture measurements or samples over a duration that includes a time when the vertical blanking interval 1122 is positioned over the ambient light sensor 922. While the instant discussion refers to a vertical blanking interval 1122 by way of example, other types of blanking intervals may also be used, including regions of inactive pixels that are included in the frames of the graphical output solely for the purpose of providing an inactive area for ambient light sensing.

FIG. 11B illustrates the device 900 with the display 1102 producing a graphical output 1120 and the vertical blanking interval 1122 moving downward as indicated by arrow 1124. At this point in time, the vertical blanking interval 1122 is not positioned above the ambient light sensor 922. Rather, the display pixels above the ambient light sensor 922 are active and/or producing light (e.g., to output the graphical output 1120). Accordingly, the ambient light sensor 922 may be in an inactive state or otherwise not capturing or using ambient light measurements during this time.

FIG. 11C illustrates the device 900 at a time when the vertical blanking interval 1122 is positioned directly over the ambient light sensor 922. The ambient light sensor 922 may capture measurements during this time when the vertical blanking interval 1122 is positioned over the ambient light sensor 922 (or otherwise activate or use readings captured during this time). In some cases, the sensing window of the ambient light sensor 922 (e.g., the time that the ambient light sensor 922 is actively measuring or using measurements of light through the display) is greater than the vertical blanking interval 1122. For example, the sensing window may begin and/or end while at least some of the pixels above the ambient light sensor 922 are active. In some cases, the time that the vertical blanking interval 1122 is above the ambient light sensor 922 is more than about 70% of the sensing window of the ambient light sensor 922 (or more than about 80%, more than about 85%, or any other suitable value). The device 900 may synchronize the operation of the ambient light sensor to the timing and/or position of the vertical blanking interval 1122 to allow the ambient light measurements to be captured at an appropriate time. The operation of the ambient light sensor 922 may be intermittent, such that it is only actively capturing measurements during the sensing window, and is inactive at other times. In other cases, the operation of the ambient light sensor 922 is capturing measurements more continuously, but the device 900 and/or the ambient light sensor 922 only uses values captured during the sensing window.

In some cases, the device 900 also compensates for the light emitted by the display in the area around the ambient light sensor 922. For example, even when capturing measurements through the vertical blanking interval 1122, light from nearby active pixels (e.g., a subset of the pixels of the display) may be incident on or otherwise detectable by the ambient light sensor 922, thereby giving inaccurate measurements of the ambient light conditions. Accordingly, for ambient light measurements captured during a particular sensing window, the device 900 and/or ambient light sensor 922 may subtract or otherwise modify the light measurements based at least in part on the light being emitted by the pixels in an area 1125 surrounding the ambient light sensor 922. The area 1125 may correspond to an n×m grid of pixels, and may be positioned above the ambient light sensor 922 (optionally centered above the ambient light sensor 922). In some cases, the grid of pixels is 256×256 pixels centered about the center of the hole 1105, though other sizes and alignments are also possible depending on, for example, the size of the ambient light sensor, the size of the pixels, the location of the ambient light sensor relative to the active area of the display, the extent to which the light from nearby pixels is detectable by the ambient light sensor, and the like. The size of the area 1125 may be larger than the hole 1105. Thus, the area 1125 includes a first subset of pixels that are positioned over the hole 1105, and a second subset of pixels that are positioned remote from the hole 1105.

Using the foregoing techniques, the ambient light sensor 922 receives light passing through the front cover 1100 and through the display 1102 (e.g., the display layers of the display 1102), and, while the blanking interval is positioned over the ambient light sensor 922, produces an output corresponding to the received ambient light. The device may then determine an ambient light value based at least in part on the output. The device may change a display parameter of the display stack based at least in part on the ambient light value. For example, the device may change a brightness, a color temperature, or the like, or determine whether to activate or deactivate the entire display (e.g., turn the display on or off).

Figure 12A:
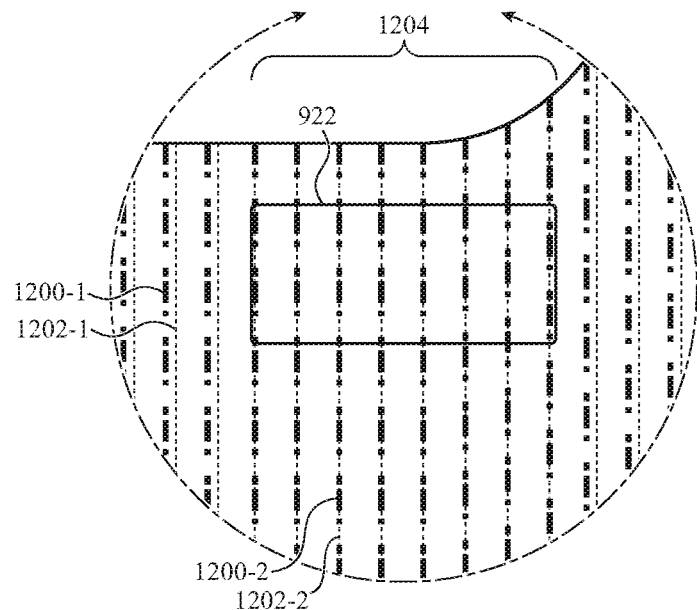
FIGS. 12A-12B depict example electrode patterns on example electronic devices.
Figure 12B:
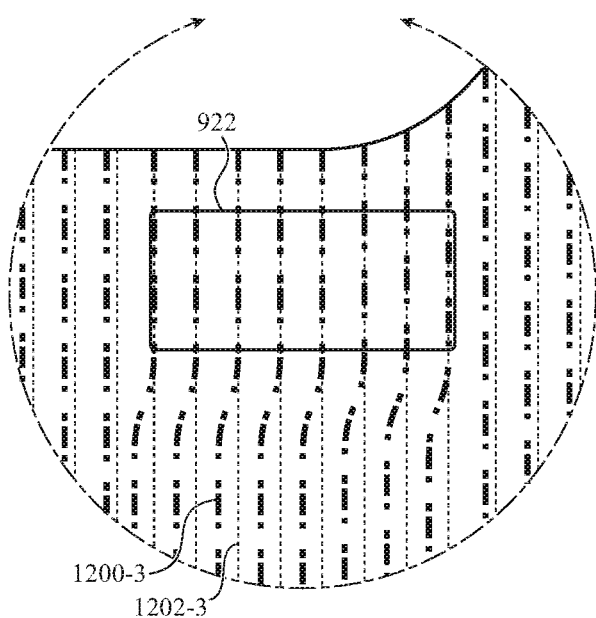

As noted above, the ambient light sensor 922 may also be capturing ambient light measurements through one or more electrode layers that are on or integrated with the display stack. The electrode layers may be used for any of various purposes, such as touch sensing, force sensing, display functionality, or the like. While the electrodes may appear transparent to the unaided eye, they may interfere with the light sensing functionality of the ambient light sensor 922 (e.g., by blocking, occluding, attenuating, or otherwise interfering with the ambient light that is detected by the ambient light sensor 922). FIGS. 12A-12B depict example arrangements of electrodes on electrode layers to reduce or eliminate the impact of the electrodes on the ambient light sensing functionality.

FIG. 12A, corresponding to area 12-12 in FIG. 9A, shows an example electrode pattern over the ambient light sensor 922. In particular, FIG. 12A illustrates how electrodes may be co-located in an area above the ambient light sensor 922. For example, electrodes in areas outside of the ambient light sensor 922, such as electrodes 1200-1 and 1202-1 may be set apart from one another, and electrodes along a portion 1204 of the display that corresponds to or includes the ambient light sensor 922, such as electrodes 1200-2 and 1202-2, are co-located (e.g., layered on or over one another). As shown in FIG. 12A, the electrodes in the portion 1204 of the display are co-located along an entire length of the display (e.g., from the top of the display to the bottom of the display). In implementations where electrodes are instead or also positioned horizontally or along a different direction, the electrodes extending over the ambient light sensor 922 may also be co-located along the entire display. In some cases, all of the electrodes in the display are co-located in the manner shown in the portion 1204.

FIG. 12B illustrates an example in which electrodes that are positioned over the ambient light sensor 922 are co-located with one another where they are over the ambient light sensor 922, but are set apart from one another in other areas of the display. For example, where electrodes 1200-3 and 1202-3 are positioned over the ambient light sensor 922, they are co-located, but they jog apart in an area outside of the ambient light sensor 922 such that they are set apart.

The electrodes 1200-*n* and 1202-*n* may be positioned on different substrates or the same substrate. In some cases, the electrodes 1200-*n* are positioned on a top surface of a substrate, and the electrodes 1202-*n* are positioned on a bottom surface of the same substrate. In some cases, the electrodes 1200-*n* and 1202-*n* are on the same surface of the same substrate. In some cases, the electrodes 1200-*n* and 1202-*n* are each on different substrates.

While FIGS. 12A-12B illustrate two sets of electrodes, there may be more sets of electrodes than shown. Further, the electrodes 1200-*n* and 1202-*n* are shown as different electrodes for the purpose of illustration, but in an implementation they may be different electrodes of a single set of otherwise identical electrodes. As noted above, the electrodes may provide various different types of functionality, including touch and/or force sensing (e.g., capacitive sensing, resistive sensing, etc.), display functionality, or the like. The electrodes may be formed from any suitable material, such as indium tin oxide (ITO), transparent conductive oxides (TCO), conductive polymers, nanowire layers (e.g., silver nanowire), or the like.

Figure 13A:
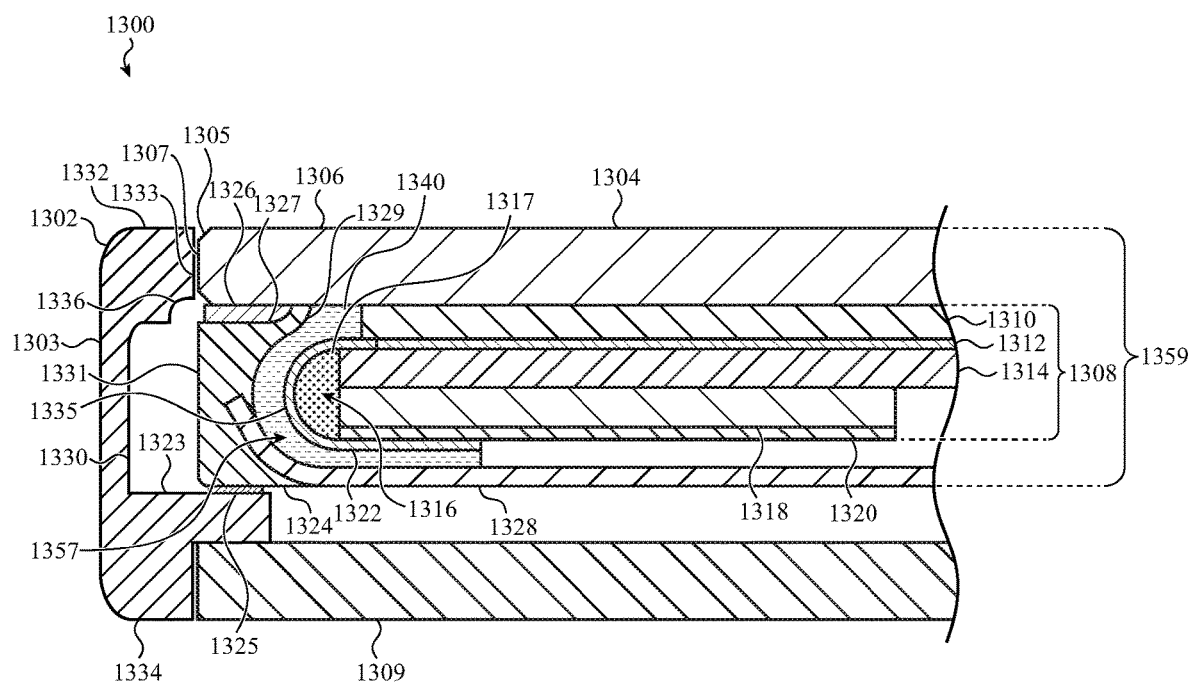
FIGS. 13A-13C depict partial cross-sectional views of example electronic devices, illustrating example display potting configurations.

FIG. 13A depicts a partial cross-sectional view of an example electronic device 1300, viewed along line 13A-13A in FIG. 1A. The electronic device 1300 may correspond to or be an embodiment of the electronic devices 100, 140, 200, 300, or any other device described herein.

The device 1300 may include a housing member 1302, which may correspond to or be an embodiment of the housing member 130. The housing member 1302 may also represent other housing members of the devices described herein, such as the housing members 124, 125, 126, 127, and 128. The housing member 1302 may define an exterior side surface 1303 of the device 1300. The device 1300 may also include a cover 1304, which may correspond to or be an embodiment of the cover 102 of FIGS. 1A-1B (or any other cover described herein). The cover 1304 may define a front exterior surface 1306 of the device 1300, which may be planar. In some cases, the cover 1304 defines a chamfer 1305 that extends around the periphery of the planar front exterior surface 1306 and extends between an edge of the front exterior surface 1306 and an edge of a side surface 1307 of the cover 1304. The device 1300 may also include a rear cover 1309, which may correspond to or be an embodiment of the rear cover 132 (or any other rear cover described herein).

The cover 1304 may be positioned over a display stack 1308, which may correspond to or be an embodiment of the display 103 of FIG. 1A (or any other display described herein). The display stack 1308 may be coupled to the cover 1304 along an interior surface of the cover 1304 via an adhesive 1310, which may be a transparent adhesive. The adhesive 1310 may have a thickness, such as about 100 microns, 200 microns, about 300 microns, about 400 microns, or the like.

The display stack 1308 may include a display element 1312, which may be configured to produce graphical outputs. The display element 1312 may be an OLED display, and may include multiple layers and/or other components that facilitate the production of graphical outputs, including, for example, substrates, an anode, a cathode, one or more organic layers, an emissive layer, adhesives, and the like. In some cases, the display element 1312 may include an integrated (on-cell) touch-sensing system, as described above. For example, an array of electrodes that are integrated into the OLED display may be time and/or frequency multiplexed in order to provide both display and touch-sensing functionality. In other cases, separate touch- and/or force-sensing systems may be included above or below the display element 1312 (each of which may include, for example, capacitive electrode layers, compliant layers, and the like). While an OLED display is described, the display element may be any suitable type of display, such as an LCD display, an active layer organic light emitting diode (AMO-LED) display, an organic electroluminescent (EL) display, an electrophoretic ink display, or the like.

The display stack 1308 may include various electrically active layers and components that need to be electrically interconnected to other electrical components, processors, circuit elements, and the like. Because such layers (e.g., anode and cathode layers of an OLED display) may be sandwiched between other layers of the display stack 1308, a flexible circuit element 1322 (e.g., a flexible circuit board) may wrap around a side of the display stack 1308 (forming a loop) to electrically couple the electrically active layers of the display stack 1308 to a more accessible circuit element 1320 of the display stack 1308. More particularly, the flexible circuit element 1322 may include conductive traces that interconnect electrical components within the display element 1312 (e.g., cathode and anode layers, electrode layers of touch and/or force sensors, on-cell touch-sensing layers, etc.) to other electrical traces, connectors, processors, or other electrical components that are mounted on the circuit element 1320. The circuit element 1320 may be a rigid or flexible circuit board. In some cases, a first encapsulating structure (e.g., an epoxy, foam, or other material or component) may be provided in the loop area 1316 between the side of the display stack 1308 and the flexible circuit element 1322 to help provide structure to the flexible circuit element 1322 and to help prevent deformation of the flexible circuit element 1322 due to impacts or other damage. For example, a first encapsulating structure 1317 (also referred to as a potting material) may be provided in the inside of the loop area 1316 to help provide structure to the flexible circuit element 1322 at the loop area 1316 and to help prevent deformation of the flexible circuit element 1322 due to drops, impacts, or the like. For example, if the device 1300 is dropped on the housing member 1302, the housing member 1302 could force a frame member 1324 against the loop area 1316 of the flexible circuit element 1322. The first encapsulating structure 1317 may help prevent such impacts from breaking, pinching, bending, deforming, or otherwise damaging the flexible circuit element 1322 at the loop area 1316.

In some cases, in addition to or instead of providing the first encapsulating structure 1317 in the loop area 1316, a second encapsulating structure 1340 may be provided in a region 1357 between the frame member 1324 and a loop 1335 of the flexible circuit element 1322. The loop 1335 may define a convex outer surface and a concave inner surface, as shown in FIG. 13A. The second encapsulating structure 1340 may be an epoxy, foam, or other material or component, and may be unitary with the first encapsulating structure 1317 (e.g., they may both be formed during a single injection process of a single curable material), or it may be distinct from the first encapsulating structure 1317 (e.g., the first and second encapsulating structures may be introduced separately, such as in two subsequent injection operations).

The second encapsulating structure 1340 may provide several benefits. For example, the second encapsulating structure 1340 may reinforce the loop 1335 of the flexible circuit element 1322. More particularly, the second encapsulating structure 1340 may reduce the likelihood that the flexible circuit element 1322 will be deformed or otherwise damaged due to an impact or other type of shock event. The second encapsulating structure 1340 may also improve the strength of the bond between the cover 1304, the display stack 1308, and the frame member 1324. For example, the second encapsulating structure 1340 may have an adhesive property such that the second encapsulating structure 1340 adheres to the flexible circuit element 1322, the cover 1304, and the frame member 1324, thereby bonding these components together via an adhesive bond. The physical shapes of the frame member 1324 and the loop 1335 of the flexible circuit element 1322 may also provide a mechanical interlock that retains the frame member 1324 and the display stack 1308 to the cover 1304. For example, the frame member 1324 defines a flange portion 1329 which forms an undercut region that the second encapsulating structure 1340 fills and/or engages. Similarly, the second encapsulating structure 1340 wraps under the loop 1335 to engage the flexible circuit element, and the display stack 1308 more generally. Due to the way in which the second encapsulating structure 1340 engages these components, the adhesion between the second encapsulating structure 1340 and the cover 1304 helps retain the frame member 1324 and display stack 1308 to the cover 1304.

In some cases, the additional attachment security provided by the second encapsulating structure 1340 may facilitate the use of less adhesive 1326 to attach the frame member 1324 to the cover 1304, and thereby allow a thinner adhesive layer 1310, which ultimately reduces the overall thickness of the display stack and can provide more room inside the device for other components (e.g., a battery), and/or allow the device to be made thinner. More particularly, the increased attachment strength provided by the second encapsulating structure 1340 may facilitate the use of a smaller glue region for the adhesive 1326, and thus the flange portion 1329 can extend a smaller distance towards the display (e.g., it is shorter in a left-to-right direction, as shown in FIG. 13A). By making the flange portion 1329 smaller in this direction, the display stack can be placed closer to the cover 1304 without the loop 1335 contacting or being too close to the flange portion 1329, thereby allowing a thinner layer of adhesive 1310 between the display element 1312 and the cover 1304.

The encapsulating structures may also provide an environmental seal that supplements the seal provided by the adhesive 1326. For example, if an impact or other damage were to compromise the adhesion between the adhesive 1326 and the cover 1304 and/or the frame member 1324, the first and second encapsulating structures may continue to inhibit or prevent liquids or other contaminants from reaching and damaging the display stack or other sensitive components of the device.

The display stack 1308 may include other components in addition to the display element 1312 and touch- and/or force-sensing components, such as support and shielding layers, and adhesive layers to hold the various components of the display stack 1308 together. For example, the display stack 1308 may include a first metal plate 1314 that supports the display element 1312 and imparts structural support, rigidity, and flatness to the display element 1312. The first metal plate 1314 may have the same or substantially the same front-facing area as the display element 1312 (e.g., the first metal plate 1314 may have a front-facing area that is greater than 90% of the display element 1312). The display stack may also include a second metal plate 1318 that supports the circuit element 1320. The second metal plate 1318 may have a smaller frontal area than the first metal plate 1314, and may have a size that is similar to the circuit element 1320. Both the circuit element 1320 and the second metal plate 1318 may have a front-facing area that is less than 50% of the front-facing area of the display element 1312, and optionally less than 30% of the front-facing area of the display element 1312.

The display stack 1308 may include other layers and components, as well. For example, the display stack 1308 may include adhesives between various layers and elements in the display stack 1308. More specifically, the display stack 1308 may include an adhesive between the display element 1312 and the first metal plate 1314, an adhesive between the first metal plate 1314 and the second metal plate 1318, and an adhesive between the second metal plate 1318 and the circuit element 1320. Of course, other layers, sheets, substrates, adhesives, and/or other components may also be included in the display stack 1308.

The cover 1304 may be attached to a frame member 1324. The frame member 1324 may be formed from or include a polymer material, and may extend around all or substantially all of a perimeter of the cover 1304. The frame member 1324 may at least partially encapsulate and/or otherwise be coupled to a back plate 1328. The back plate 1328 may be formed of or include metal, plastic, or any other suitable material. The back plate 1328 may provide shielding and structural support to the device, and may protect the display stack 1308 by forming an at least partially enclosed area in which the display stack 1308 is positioned. The back plate 1328 may be at least partially encapsulated in the frame member 1324, or it may be attached to the frame member 1324 in any other suitable manner.

The frame member 1324 may be attached to the housing member 1302. For example, the frame member 1324 may be attached to a ledge 1323 or other feature defined by the housing member, as depicted in FIG. 13A. The ledge 1323 may extend from an interior side of the housing member 1302. The ledge 1323 may be part of a monolithic structure of the housing member 1302 (e.g., the housing member may be molded, machined, or otherwise formed from a single piece of material to define the ledge 1323 as well as the other features and/or surfaces of the housing member 1302). The frame member 1324 may be attached to the housing member 1302 via an adhesive 1325, which may be between and in contact with the ledge 1323 and the frame member 1324. The adhesive 1325 may be any suitable adhesive, such as a pressure sensitive adhesive (PSA), heat sensitive adhesive (HSA), adhesive film, epoxy, or the like. In some cases, the ledge or other feature to which the frame member 1324 is attached acts as a datum surface for the frame member 1324. Thus, the alignment (e.g., flushness) of the front exterior surface 1306 of the cover 1304 and the upper portion 1332 (e.g., the front exterior surface) of the housing member 1302 may be defined or established by the location of the ledge (relative to the upper portion 1332), as well as the location of the bottom surface of the frame member 1324 (relative to the front exterior surface 1306 of the cover 1304).

The cover 1304 may be attached to the frame member 1324 via an adhesive 1326. The frame member 1324 may define a recessed region 1327 (which defines a bonding surface), and the adhesive 1326 may be placed in the recessed region 1327. The recessed region 1327 may provide a trough-like volume for the adhesive 1326, while also allowing a flange portion 1329 of the frame member 1324 to contact the underside of the cover 1304. The direct contact between the flange portion 1329 of the frame member 1324 and the cover 1304 may provide a rigid connection between the cover 1304 and the frame member 1324 and may ensure that forces applied to the cover 1304 are transferred to the structural frame member 1324. While the recessed region 1327 is defined by a single flange portion 1329 (e.g., on the right side of the recessed region 1327), other configurations are also possible, such as a recessed region defined by two flange portions or other sidewall-like features (e.g., a channel defined by two walls).

The housing member 1302 may be specifically configured to allow a close coupling between it and the assembly that includes the cover 1304, the display stack 1308, and the frame member 1324. In particular, the housing member 1302 may define a recessed region 1330 (also referred to simply as a recess) along an interior surface of the housing member 1302 that is adjacent or proximate the frame member 1324. The recessed region 1330 may be formed into the housing member 1302 in any suitable way. For example, the recessed region 1330 may be machined into the housing member 1302, or the housing member 1302 may be molded or cast and the recessed region 1330 may be formed as part of the casting or molding process.

The recessed region 1330 may correspond to a portion of the housing member 1302 that is thinner than other portions of the housing member 1302. For example, the housing member 1302 may define an upper portion 1332 and a lower portion 1334 that have a greater thickness (in the left-to-right direction as depicted in FIG. 13A) than the portion of the housing member 1302 that defines the recessed region 1330.

The recessed region 1330 may be configured so that the interior surface of the housing member 1302 that is directly opposite the frame member 1324 is set apart from the frame member 1324 by a target distance. The target distance may be selected so that deformations or deflections of the housing member 1302 along the side wall (e.g., due to the device 1300 being dropped or otherwise subjected to predictable misuse or damage) do not contact the frame member 1324 and/or the display stack 1308. More particularly, the recessed region 1330 allows the device 1300 to accommodate a certain amount of deformation of the side wall of the housing member 1302 without the housing member 1302 contacting the frame member 1324. For example, the inner surface of the recessed region 1330 may be spaced apart from the outer peripheral surface 1331 of the frame member 1324 by about 0.3 mm, 0.5 mm, 0.7 mm, 1.0 mm, or any other suitable distance. In some cases, the distance between the inner surface of the recessed region 1330 and the outer surface of the frame member 1324 is greater than a housing deformation that is produced as a result of a standard test, such as a side impact test (e.g., in which the device 1300 is dropped from a certain height (e.g., 1 m, 2 m, or 3 m) onto a certain surface (e.g., an edge of a triangular prism).

In some cases, the height (e.g., the vertical direction as depicted in FIG. 13A) of the recessed region 1330 (and optionally the height of the recessed region 1330 and the additional recessed region 1336 combined) is equal to or greater than a height of the frame member 1324. In this way, the recessed region 1330 (optionally with the additional recessed region 1336) is large enough so that the frame member 1324 could extend at least partially into the recessed region 1330 in the event of an impact or drop (e.g., causing the housing member 1302 to deform or deflect), without the frame member 1324 contacting the housing member 1302. This may help prevent damage to the frame-cover interface and help prevent separation of the cover 1304 from the frame member 1324 (e.g., by preventing or reducing the magnitude of forces applied to the frame member 1324 by the housing member 1302 in the event of an impact, drop, or the like). In some cases, the height of the recessed region 1330 (and optionally the recessed region 1330 combined with the additional recessed region 1336) extends from the ledge 1323 to a height or location that is at or above the bottom surface of the cover 1304.

In some cases, the distance between the inner surface of the recessed region 1330 and the outer surface of the frame member 1324 is greater than a distance between a side surface 1307 of the cover 1304 and an inner side surface 1333. Thus, for example, a deformation or deflection of the housing member 1302 towards the cover 1304 and the frame member 1324 may result in the side surface 1307 of the cover 1304 contacting the inner side surface 1333 of the frame member 1324 before the housing member 1302 (and in particular the inner surface of the recessed region 1330) contacts the frame member 1324. Thus, by forming a recessed region 1330 that establishes a greater distance between the housing member 1302 and the frame member 1324 than the distance between the housing member 1302 and the cover 1304, the risk of contact between the housing member 1302 and the frame member 1324 during deformation or deflection of the housing member 1302 may be reduced.

The side surface 1307 of the cover 1304 may abut an inner side surface 1333 of the housing member 1302 (or be adjacent the inner side surface 1333 without interstitial components, as described herein). In some cases, there is no interstitial component or other material between the side surface 1307 of the cover 1304 and the inner side surface 1333 of the housing member 1302. This construction provides several structural and cosmetic advantages. For example, the lack of a bezel or other interstitial component or material between these surfaces provides a clean, frameless appearance to the front of the device 1300. In particular, the front-facing surfaces of the device 1300 may be defined only by the upper portion 1332 of the housing member 1302 and the front exterior surface 1306 of the cover 1304. While the side surface 1307 of the cover 1304 may abut an inner side surface 1333 of the housing member 1302, in some cases an air gap may exist between these surfaces. In some cases, an adhesive or sealing material may be positioned between the side surface 1307 of the cover 1304 and the inner side surface 1333 of the housing member 1302. In such cases, the adhesive or sealing material may be the only material between these surfaces, may be in contact with both surfaces, and may have a thickness less than about 0.5 mm, 0.3 mm, 0.1 mm, 0.05 mm, or any other suitable thickness.

The proximity between the side surface 1307 of the cover 1304 and the inner side surface 1333 of the housing member 1302 may define a load path through the upper portion 1332 of the housing member 1302 and into the cover 1304. For example, forces applied to the exterior side surface 1303 of the housing member 1302 may be directed into the cover 1304 at the interface between the side surface 1307 of the cover 1304 and the inner side surface 1333 of the housing member 1302. (In cases where the inner side surface 1333 abuts the side surface 1307 of the cover 1304, loads may be directly transferred or directed into the cover 1304, while in cases where there is an air gap between the inner side surface 1333 and the side surface 1307 of the cover 1304, the forces may initially cause the gap to close such that the inner side surface 1333 comes into contact with the side surface 1307.) The rigidity and structural integrity of the cover 1304 may help prevent or reduce deformation of the housing member 1302 in the event of a drop or other impact on the exterior side surface 1303, thereby protecting internal components of the device 1300 from damage due to the housing member 1302 contacting them. By defining the load path through the cover 1304 and by configuring the housing member 1302 to include the recessed region 1330, the device 1300 may be designed to omit the frame member 1324 from the load path during many impact events (e.g., the device 1300 being dropped). For example, as shown in FIG. 6A, the recessed region 1330 ensures that the frame member 1324 is set apart from the housing member 1302 by a suitable distance. Also, no portion of the frame member 1324 is between the housing member 1302 and the cover 1304. Accordingly, the frame member 1324 may be positioned so that it is not contacted or impacted by the housing member 1302, even if the housing member 1302 is subjected to an impact, deformed, deflected, or otherwise damaged (up to a certain amount of deformation or deflection).

In some cases, the rear cover 1309 interfaces with the lower portion 1334 of the housing member 1302, in that the lower portion 1334 may contact a side surface of the rear cover 1309, thereby defining a load path through the lower portion 1334 and into the rear cover 1309.

In some cases, the housing member 1302 may include an additional recessed region 1336. The additional recessed region 1336 may be configured so that the housing member 1302 in that region is set a distance away from components in the display stack 1308, touch- and/or force-sensing components, antennas, or other electrical components of the device 1300. In particular, as the housing member 1302 may be formed of metal, the metal may capacitively couple to other electronic components. By increasing the distance between the metal of the housing member 1302 and the electrical components, the capacitive coupling may be reduced to an acceptable level. Accordingly, the additional recessed region 1336 may be configured so that the distance between the additional recessed region 1336 and another electrical component is greater than about 0.5 mm, 1.0 mm, 1.5 mm, 2.0 mm, or any other suitable distance. In some cases, the recessed region 1330 may be recessed further (and thus correspond to a thinner portion of the housing member 1302) than the additional recessed region 1336.

Figure 13B:
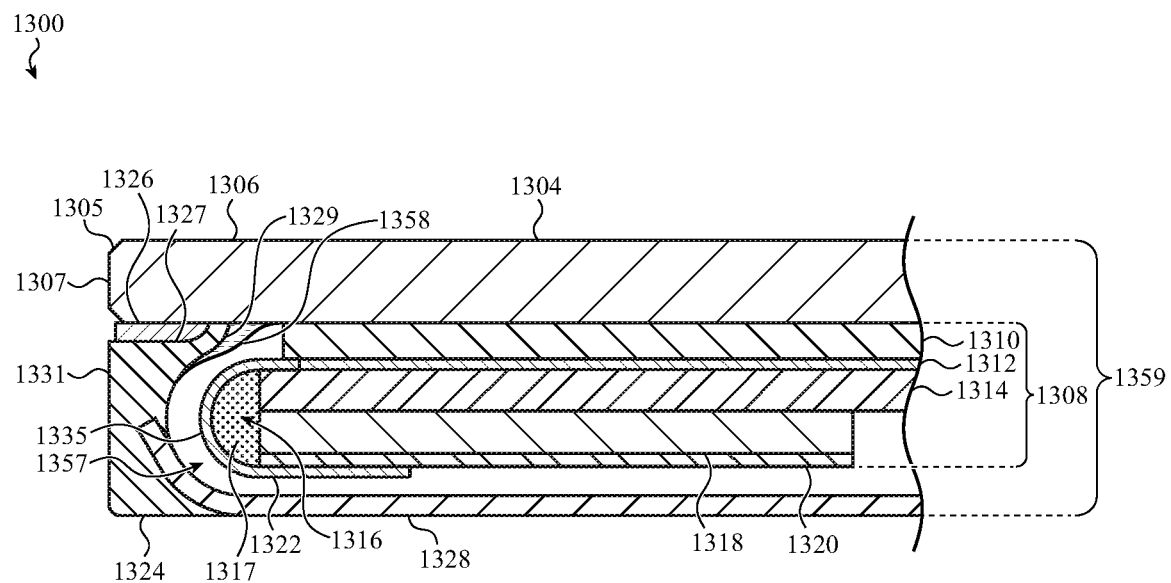

FIG. 13B depicts another example embodiment of the device 1300, showing another configuration for the second encapsulating structure. FIG. 13B omits the housing member 1302 and rear cover 1309 for simplicity. As shown in FIG. 13B, the second encapsulating structure 1358 does not fill the entire region 1357. Rather, the second encapsulating structure 1358 is positioned in a corner region where the flange portion 1329 of the frame member 1324 meets the cover 1304. The second encapsulating structure 1358 thus contacts and adheres to both the frame member 1324 and the cover 1304, thereby contributing to the bond strength between those components. This implementation also provides an air gap between the loop 1335 and the frame member 1324.

Figure 13C:
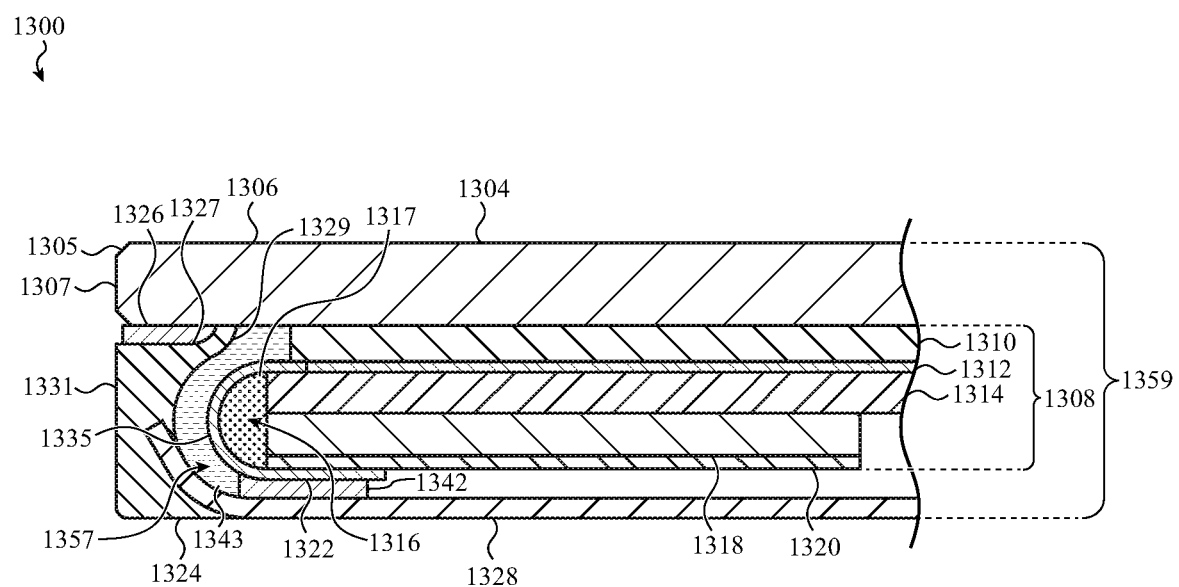

FIG. 13C depicts another example embodiment of the device 1300, showing another configuration for the second encapsulating structure. FIG. 13C omits the housing member 1302 and rear cover 1309 for simplicity. As shown in FIG. 13C, the second encapsulating structure 1343 extends around a portion of the loop 1335, and compliant member 1342 is positioned between the flexible circuit element 1322 (or other component of the display stack 1308) and the back plate 1328. The compliant member 1342 may be less rigid (e.g., more flexible and/or compressible) than the second encapsulating structure 1343. The compliant member 1342 may absorb energy from impacts, pinches, or other force events that may tend to force the flexible circuit element 1322 and the back plate 1328 together, thereby reducing the amount or intensity of the force that ultimately contacts the flexible circuit element 1322. The compliant member 1342 may be a compliant polymer, foam, elastomer, silicone, or any other suitable material. In some cases, the compliant member 1342 is adhesive and adheres to the flexible circuit element 1322 and/or the back plate 1328. In some cases, the compliant member 1342 is adhered to the flexible circuit element 1322 and/or the back plate 1328 with a separate adhesive (e.g., a PSA, HSA, an adhesive film, a liquid adhesive, etc.).

Figure 13D:
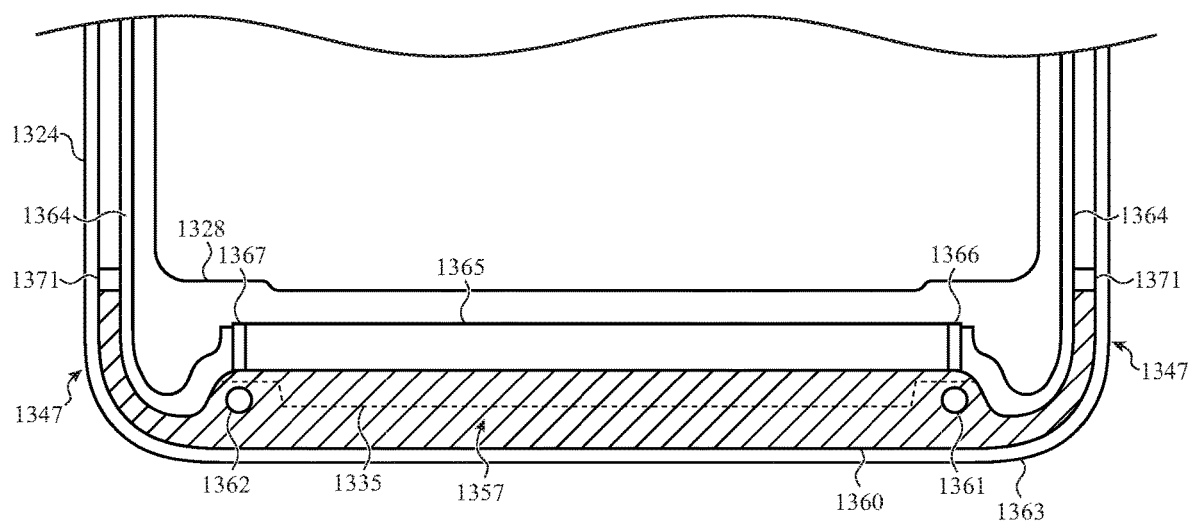
FIG. 13D depicts a partial view of an example electronic device, illustrating an example display potting configuration.

FIG. 13D depicts a portion of the electronic device shown in FIGS. 13A-13C, illustrating another view of the location of the encapsulating structures, and how potting material may be introduced into the area around the loop 1335 of the flexible circuit element 1322 to form encapsulating structures. FIG. 13D generally illustrates the frame member 1324 and the back plate 1328, with the cover 1304 and display stack 1308 removed. The dashed line illustrates an example location of the loop 1335 of the display if the display stack 1308 and cover 1304 were attached. Further, while FIG. 13D shows the cover and display removed, in some implementations the potting material is introduced with those components attached to the frame member 1324.

In some cases, potting material 1360 (which may correspond to or produce the first encapsulating structure and/or the second encapsulating structure described with respect to FIGS. 13A-13C) may be introduced into the region 1357 via an injection port 1362. The potting material may be understood as being introduced into the injection port 1362 in a direction out of the page, by an injection device that is behind the frame member 1324. Stated differently, the frame member 1324 as shown in FIG. 13D would be flipped over during the injection process.

The potting material 1360 may be a curable polymer, such as an epoxy, that can be introduced as a liquid or other flowable state, and then allowed to cure. A vent port 1361 may allow air to escape from the region 1357 (FIG. 13A) while the potting material is being introduced. In some cases, a vacuum or negative pressure is applied to the vent port 1361 to aid the flow of the potting material 1360 into the desired locations. As the loop 1335 of the flexible circuit element 1322 may be open on its ends, the potting material may flow into the loop area 1316 (FIG. 13A) while the potting material 1360 is introduced through the injection port 1362.

Barrier structures 1363, 1364, 1365, 1366, and 1367 may define walls of the volume in which the potting material 1360 is positioned. The barrier structures may be positioned between (and may contact and/or be sandwiched by) the display stack and a back plate 1328, or the cover 1304 and the back plate 1328, or any other suitable components or structures. The barrier structures may include adhesives, foams, glues, structural portions of the frame member, or the like, and may have other functionalities in addition to acting as barriers to the potting material 1360. For example, the barrier structure 1363 may correspond to the frame member 1324 and adhesive 1326, and the barrier structures 1364 and 1356 may correspond to an adhesive structure (e.g., an adhesive foam) that is used to couple the frame member 1324 and/or back plate 1328 to the cover and/or display stack. The barrier structures 1366 and 1367 may correspond to an adhesive that bridges gaps between the barrier structures 1364 and 1365 and/or between other components of the device.

In some implementations, barrier structures, such as the barrier structures 1363 and 1364 define channel segments extending along corner regions 1347 of the frame member 1324. During an injection process, the potting material 1360 may travel, within the channel segments, along the corner regions 1347, and extending at least partially along a side of the frame member 1324 (e.g., along the long sides of the device and/or display). In some cases, a portion of either the barrier structure 1363 and/or 1364 (or a different component or material) may define an optional barrier 1371 that blocks the channel segment or otherwise defines a blind end of the channel segment, thereby limiting the flow path of the potting material 1360 during its introduction, ultimately assisting in defining the shape of the structure that is produced when the potting material 1360 hardens or cures.

Figure 13E:
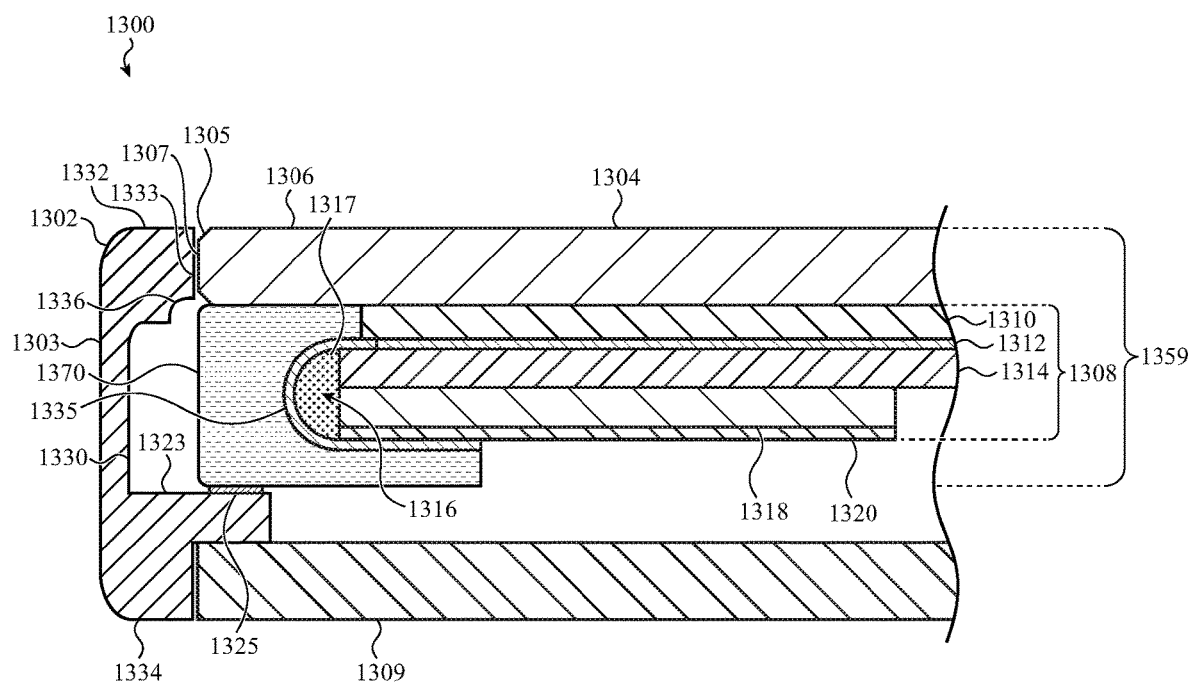
FIG. 13E depicts a partial cross-sectional view of an example electronic device, illustrating an example display potting configuration.

FIGS. 13A-C illustrate example device configurations that include a frame member 1324 that is attached to a cover (and optionally coupled to a back plate 1328), and which is attached to a housing member (e.g., via an adhesive 1325) to secure the top module to the housing and/or other component(s) of the device. The frame member 1324 may be formed of or include plastic, metal, and/or other materials, and may be formed separately from the other components of the top module (e.g., the cover, the display stack, etc.), and then assembled with those components to form the top module. FIG. 13E illustrates an example embodiment of the device 1300 in which a molded frame member 1370 is used instead of the frame member 1324. More particularly, the molded frame member 1370 may be formed, after the display stack 1308 is attached to the cover 1304, by molding a moldable material in place, and allowing the material to cure or otherwise harden to define the molded frame member 1370. For example, the display stack 1308 may be attached to the cover 1304 to form a subassembly. That subassembly may then be placed in a mold that defines at least part of the shape of the molded frame member 1370, and a moldable material (e.g. a polymer, reinforced polymer, thermoplastic polymer, thermoset polymer, epoxy, or the like) may be introduced into the mold. The material flows against the cover 1304 and the display stack 1308 (including against and around the loop 1335), and may adhere or bond to those components via mechanical or chemical bonds (or both). The material is allowed to cure or otherwise harden to form the molded frame member 1370, and the subassembly with the molded frame member 1370 is removed from the mold. Optionally, a back plate is incorporated into the mold as well, and is at least partially encapsulated in the molded frame member 1370. The top module may then be attached to the housing member 1302 by affixing the molded frame member 1370 to the housing member 1302 with adhesive 1325 (or via any other attachment technique).

FIG. 13E also illustrates the loop area 1316 having been filled with a potting material 1317. In some cases, the potting material 1317 is part of the molded frame member 1370. For example, when the moldable material for the molded frame member 1370 is introduced into a mold, the material may also flow into the loop area 1316, thereby defining a unitary (monolithic) structure that acts as the molded frame member and the potting in the loop area 1316. In some cases, the potting material 1317 is a separate material than that of the molded frame member 1370, and is introduced into the loop area 1316 separately from the material that forms the molded frame member 1370 (e.g., before or after the molded frame member 1370 is molded in place).

The molded frame member 1370 can provide numerous advantages and benefits by combining the functions of a frame member and a potting material into a single component that can be manufactured in a single operation. For example, the molded frame member 1370 can perform the structural functions of a separate frame member, including providing structural rigidity to the top module and providing a structural attachment member to secure the cover 1304 to the housing member 1302 (or any other suitable structural component of the device. Further, the molded frame member 1370 can self-adhere to the cover 1304 during the molding operation, thereby reducing assembly operations and time as compared to separately manufacturing a frame member that then has to be attached to the cover 1304. Additionally, the molded frame member 1370 can perform the same stabilizing function to the loop 1335 as the potting material 1340 (FIG. 13A) or 1343 (FIG. 13C), without requiring an additional potting operation (as is the case with potting materials introduced after a frame member is formed and attached).

While FIG. 13E shows only a portion of the molded frame member 1370 that is positioned proximate the loop 1335 of the display, the molded frame member 1370 may extend around the entire periphery of the top module, effectively defining a frame along all four sides of the interior surface of the cover 1304, and optionally at least partially encapsulating the display stack along multiple sides of the display stack. In some cases, the molded frame member 1370 extends around less than the entire periphery of the top module.

Other components, features, or other details of the device 1300 shown in FIG. 13E are the same as or similar to those shown and described with respect to FIGS. 13A-13C, and those descriptions apply equally to those components, features, or other details shown in FIG. 13E.

Figure 13F:
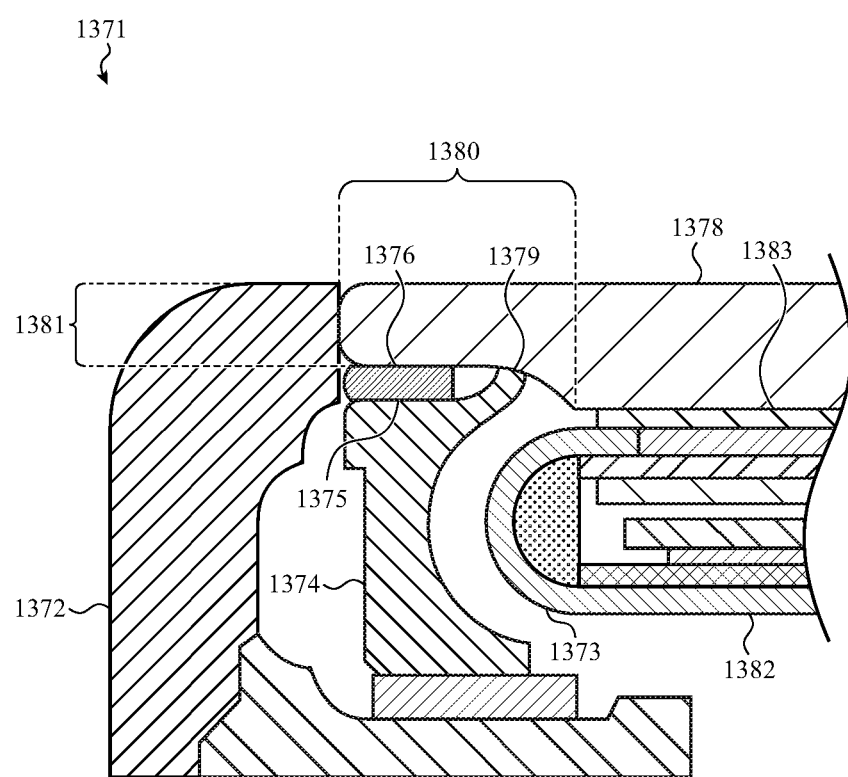
FIG. 13F depicts a partial cross-sectional view of an example electronic device, illustrating an example cover configuration.

FIG. 13F illustrates another example configuration of a device that may enable the use of a thinner adhesive to attach a display stack to a cover. For example, FIG. 13F illustrates a partial cross-sectional view of a device with a cover 1378 with a thinned outer region 1380. Except for the thinned outer region 1380, the cover 1378 may be the same as or similar to the cover 1304, and for brevity those details are not repeated here. The cover 1378 may be attached to a frame member 1374 via an adhesive 1376 that is positioned in a recessed region 1375 (which defines a bonding surface) of the frame member 1374. The frame member 1374, adhesive 1376, and recessed region 1375 may be the same as or similar to the frame member 1324, adhesive 1326, and recessed region 1327, and for brevity those details are not repeated here.

The thinned outer region 1380 may extend along one or more edges of the cover 1378. For example, the thinned outer region 1380 may extend along one edge of the cover 1378, and in particular, an edge of the cover 1378 that is proximate a flexible circuit element 1373 of the display stack 1382. In some cases, the thinned outer region 1380 may extend along two, three, or four sides of the cover 1378. For example, in the case of a substantially rectangular cover, the thinned outer region 1380 may extend around the entire outer periphery of the cover 1378 (e.g., the thinned outer region 1380 may extend around a display region of the cover 1378, where the display region corresponds to a central region of the cover 1378 through which the display is visible and/or produces graphical outputs). The display stack 1382 and the flexible circuit element 1373 may be the same as or similar to the display stack 1308 and the flexible circuit element 1322, and for brevity those details are not repeated here.

The thinned outer region 1380 may facilitate the use of a thinner layer of adhesive 1383 (e.g., optically clear or transparent adhesive) to attach the display stack 1382 to the cover 1378. More particularly, the thinned outer region 1380 may allow a flange portion 1379 (similar to the flange portion 1329, FIG. 13A) to be positioned further towards the exterior surface of the cover 1378 (e.g., higher in a vertical direction, as depicted in FIG. 13F), such that the display stack 1382, and thus the flexible circuit element 1373, may likewise be positioned further towards the exterior surface of the cover 1378 without causing the flexible circuit element 1373 to contact or otherwise interfere with the flange portion 1379. Accordingly, the thickness of the adhesive 1383 may be made thinner (e.g., relative to the adhesive 1310), resulting in an overall height of the display stack 1382 and cover 1378 that is less than a height of a device that does not include a cover with a thinned outer region (e.g., the overall height may be less than the overall height 1359 in FIG. 13A). In some cases, the adhesive 1383 has a thickness of about 150 microns, about 125 microns, about 100 microns, or about 75 microns.

The thinned outer region 1380 of the cover 1378 may have a thickness 1381 of about 400 microns, and the main portion of the cover 1378 (e.g., the portion to which the display stack 1382 is attached and that includes the graphically active area of the device) may have a thickness of about 600 microns. In some cases, the thinned outer region 1380 is about 100 microns, about 200 microns, or about 300 microns thinner than the main portion of the cover 1378. The thickness 1381 may be between about 375 microns to about 425 microns, and the thickness of the main portion may be between about 575 microns to about 625 microns.

The cover 1378 may define a transition region that extends from the thinned outer region 1380 to the main portion of the cover 1378. For example, as shown in FIG. 13F, the transition region defines a curved portion of the bottom surface of the cover 1378 that extends from the thinned outer region 1380 to the main portion of the cover 1378. The transition region (e.g., the surface of the transition region) may have a continuous curve (as shown), or it may have another shape or configuration. For example, the transition surface may be fully or partially planar, and may resemble a chamfered surface. FIGS. 13G-13L illustrate other example shapes for a thinned outer region of a cover.

Figure 13G:
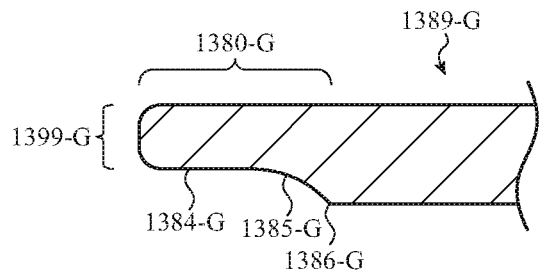
FIGS. 13G-13L depict partial cross-sectional views of example covers for electronic devices.

FIGS. 13G-13L illustrate example configurations of a thinned outer region for a cover. For example, FIG. 13G illustrates a cover with a thinned outer region 1380-G, similar to the thinned outer region shown in FIG. 13F. In this example, the thinned outer region 1380-G includes or is defined by a flat region 1384-G at the outer portion of the thinned outer region 1380-G, and a curved region 1385-G that extends from the flat region 1384-G to a corner or edge 1386-G. The corner or edge 1386-G may represent an edge where the main portion 1389-G of the cover (e.g., the planar surface to which a display stack is attached) meets the curved region, and may appear as a discontinuity or distinct apex. The curved region 1385-G may define a concave surface shape, while the corner or edge 1386-G may define a pointed convex feature. In cases where a cover that includes the thinned outer region 1380-G is attached to a frame member, as shown in FIG. 13F, adhesive may be positioned on the flat region 1384-G alone, the curved region 1385-G alone, or on at least a portion of both the flat and curved regions. Further, a frame member (or other component) may contact the cover on the flat region 1384-G and/or the curved region 1385-G.

Figure 13H:
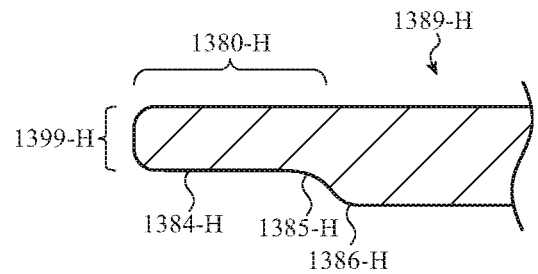

FIG. 13H illustrates a cover with a thinned outer region 1380-H. In this example, the thinned outer region 1380-H includes or is defined by a flat region 1384-H at the outer portion of the thinned outer region 1380-H, and a first curved region 1385-H that extends from the flat region 1384-H to a second curved region 1386-H. In contrast to the corner 1386-G, which may appear as a sharp to distinct apex or edge, the second curved region 1386-H defines a curved profile. The first curved region 1385-H may define a curved concave surface shape, and the second curved 1386-H may define a curved convex surface shape. In some cases, the absolute values of the radii of curvature of the first and second curved regions are the same, while in other cases they are different from one another. The two curved regions defining the transition between the main portion 1389-H and the thinned outer region of a cover may help eliminate sharp features (or other features) that can act as stress concentrating features, thereby increasing providing a strong cover that resists breaking or other damage. In cases where a cover that includes the thinned outer region 1380-H is attached to a frame member, as shown in FIG. 13F, adhesive may be positioned on the surface(s) of the flat region 1384-H, and/or either (or both) of the curved regions 1385-H, 1386-H. Further, a frame member (or other component) may contact the cover on the surface(s) of the flat region 1384-H and/or either (or both) of the curved regions 1385-H, 1386-H.

Figure 13I:
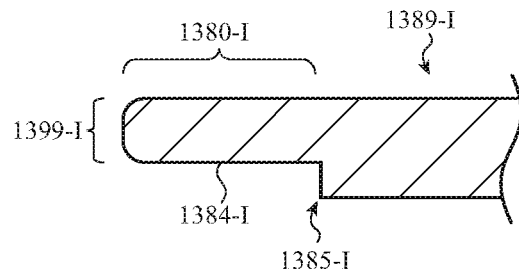

FIG. 13I illustrates a cover with a thinned outer region 1380-I. In this example, the thinned outer region 1380-I includes or is defined by a flat region 1384-I at the outer portion of the thinned outer region 1380-I, and a step region 1385-I defining a discontinuous transition from the thinned outer region 1380-I to the main portion 1389-I of the cover. The step region 1385-I may define two substantially 90 degree corners, thus resulting in a step surface that is substantially perpendicular to the surface of the flat region 1384-I and the main portion 1389-I of the cover (as well as to an exterior surface of the cover), as shown in FIG. 13I. In other examples, the corners, and thus the step surface, may have different angles. For example, a corner between the flat region 1384-I and the step surface may be about 80 degrees, and the corner between the step surface and the main portion 1389-I of the cover may be about 100 degrees, resulting in a step surface that is about 80 degrees relative to the flat region 1384-I (and the exterior surface of the cover). In cases where a cover that includes the thinned outer region 1380-I is attached to a frame member, as shown in FIG. 13F, adhesive may be positioned on the surface(s) of the flat region 1384-I, and/or the step surface of the step region 1385-I. Further, a frame member (or other component) may contact the cover on the surface(s) of the flat region 1384-I, and/or the step surface of the step region 1385-I.

Figure 13J:
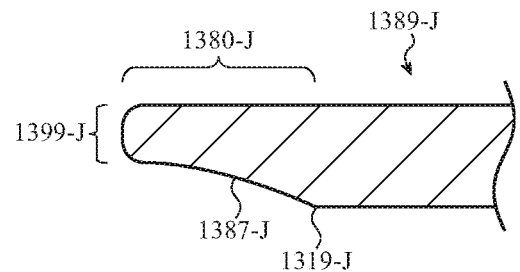

FIG. 13J illustrates a cover with a thinned outer region 1380-J. In this example, the thinned outer region 1380-J includes or is defined by a curved transition region 1387-J extending from the main portion 1389-J of the cover to the outer peripheral edge of the thinned outer region 1380-J. The curved transition region 1387-J may define a continuous concave curved profile, which may meet the main portion 1389-J of the cover at a corner or edge 1319-J. More particularly, the corner or edge 1319-J may represent an edge where the main portion 1389-J of the cover (e.g., the planar surface to which a display stack is attached) meets the curved transition region 1387-J, and may appear as a discontinuity or distinct apex. The curved transition region 1387-J may have a constant radius of curvature (e.g., it defines a portion of a circle), or a variable radius of curvature (e.g., it may define a non-circular spline). In cases where a cover that includes the thinned outer region 1380-J is attached to a frame member, as shown in FIG. 13F, adhesive may be positioned on the surface(s) of the curved transition region 1387-J. Further, a frame member (or other component) may contact the cover on the surface(s) of the curved transition region 1387-J.

Figure 13K:
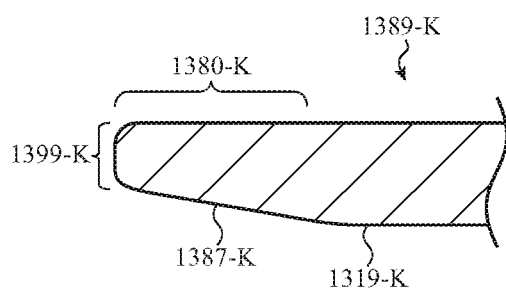

FIG. 13K illustrates a cover with a thinned outer region 1380-K. In this example, the thinned outer region 1380-K includes or is defined by a flat transition region 1387-K extending from the main portion 1389-K of the cover to the outer peripheral edge of the thinned outer region 1380-K. The flat transition region 1387-K may define a substantially planar surface, which may meet the main portion 1389-K of the cover at a corner or edge 1319-K. More particularly, the corner or edge 1319-K may represent an edge where the main portion 1389-K of the cover (e.g., the planar surface to which a display stack is attached) meets the flat transition region 1387-K, and may appear as a discontinuity or distinct apex. In cases where a cover that includes the thinned outer region 1380-K is attached to a frame member, as shown in FIG. 13F, adhesive may be positioned on the surface(s) of the flat transition region 1387-K. Further, a frame member (or other component) may contact the cover on the surface(s) of the flat transition region 1387-K.

Figure 13L:
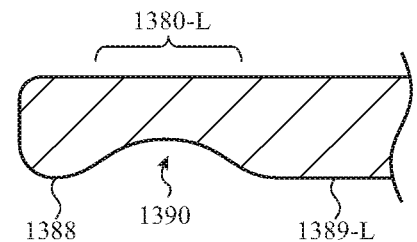

FIG. 13L illustrates a cover with a thinned outer region 1380-L, where the thinned outer region is inset from the outer peripheral edge of the cover. More particularly, the thinned outer region 1380-L includes or is defined by a recess 1390 formed between a main portion 1389-L of the cover, and a peripheral ridge 1388. The thickness of the cover at the main portion 1389-L and at the peripheral ridge 1388 (e.g., the thickness corresponding to the thickest dimension in these locations) may be equal, or they may be different. In cases where a cover that includes the thinned outer region 1380-L is attached to a frame member, as shown in FIG. 13F, adhesive may be positioned on the surface(s) of the peripheral ridge 1388 and/or the recess 1390. Further, a frame member (or other component) may contact the cover on the surface(s) of the peripheral ridge 1388 and/or the recess 1390.

As noted above, the reduced thickness regions of the covers shown in FIGS. 13F-13L may allow a display stack to be positioned closer to the interior surface of a cover, such as by allowing the use of thinner adhesives or other layers between the display stack and the cover. In some cases, the particular thicknesses of the thinned region and the main region of a cover may depend at least in part on a target thickness for an adhesive layer between the display stack and the cover, or other dimensions and/or other shapes or configurations of the display stack. In each of the covers shown in FIGS. 13F-13L, the thickness 1399 of the thinned outer region may be about 400 microns, and the thickness of the main portion of the cover (e.g., the portion to which the display stack is attached and that includes the graphically active area of the device) may have a thickness of about 600 microns. In some cases, the thickness 1399 of the thinned outer region may be about 100 microns, about 200 microns, or about 300 microns thinner than the main portion of the cover. The thickness 1399 may be between about 375 microns to about 425 microns, and the thickness of the main portion may be between about 575 microns to about 625 microns. In some cases, the thickness 1399 may be about 10%, about 20%, about 30%, about 40%, or about 50% thinner than the thickness of the main portion of the cover. The thicknesses 1399 may correspond to a thickness dimension of the cover as measured between the thinnest portion of a thinned outer region, as illustrated in FIGS. 13G-13L.

The covers shown in FIGS. 13F-13L may be formed in various ways. For example, the covers, including the thinned outer regions 1380, may be formed by molding (e.g., heating glass or another transparent material and applying a mold or press to produce the desired shape), machining (e.g., grinding, lapping, or otherwise removing material from a sheet to form the desired shape), and/or by additive manufacturing (e.g., adhering, bonding, or otherwise attaching a first glass sheet to a second glass sheet to form the desired shape). Combinations of these processes may also be used to form the covers and produce the thinned outer regions.

Figure 13M:
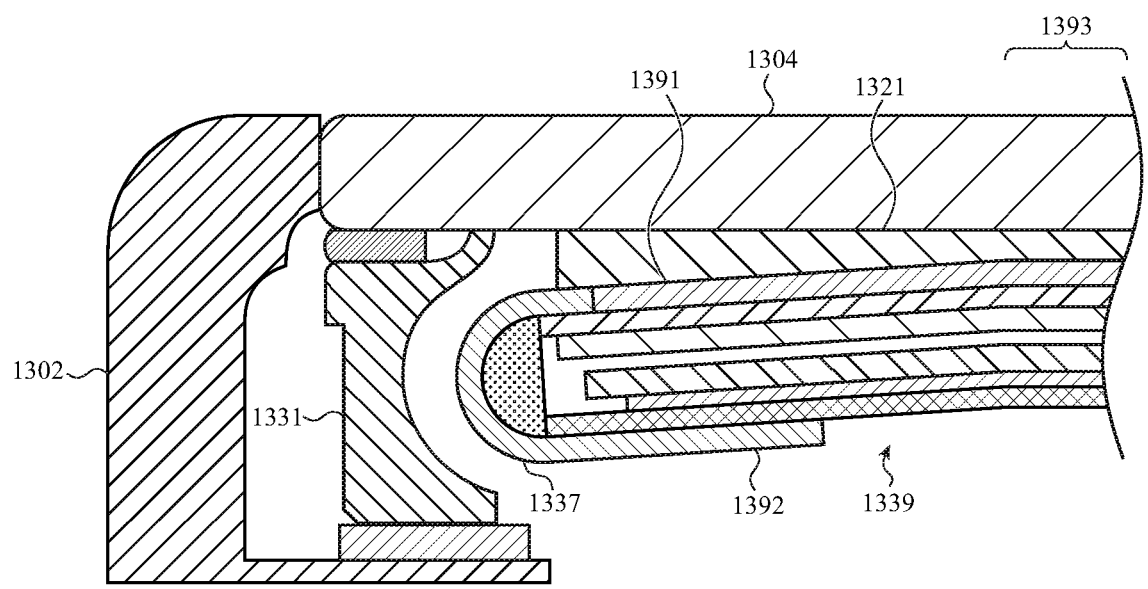
FIG. 13M depicts a partial cross-sectional view of an example electronic device, illustrating an example adhesive for attaching a display to a cover.

FIG. 13M illustrates an example cover and frame member configuration in which an adhesive 1321 that attaches a display stack 1392 to a bottom or interior surface of a cover 1304 defines an angled ramp surface 1391 that deflects a portion of the display stack 1392 downwards (e.g., away from the front cover) to help prevent or reduce the risk of contact between the display stack and the frame member 1324. The angled ramp surface 1391 may be configured to deflect the loop 1337 of the flexible circuit element of the display stack, as well as a portion of the layered region 1339 of the display stack 1392 (optionally including an active region of the display that is configured to produce graphical outputs). The angled ramp surface 1391 may be unitary with the rest of the adhesive layer that attaches the display stack 1392 to the cover 1304 (e.g., the angled ramp surface 1391 may be a thickened region of the adhesive 1321). In some cases, the adhesive 1321 is a liquid optically clear adhesive (LOCA) that is dispensed on the cover 1304 and/or the display stack 1392 to define a substantially uniform-thickness portion (e.g., region 1393) that is positioned over an active area of the display, and the angled ramp surface 1391.

The angled ramp surface 1391 is configured to deflect the loop 1337 and a portion of the layered region 1339 of the display stack 1392 away from the cover 1304 (e.g., downward as shown in FIG. 13M). The angled ramp surface 1391 may have a curved or flat surface (e.g., the surface that contacts the display stack 1392) and may have a maximum thickness of between about 100 microns and about 200 microns.

Figure 13N:
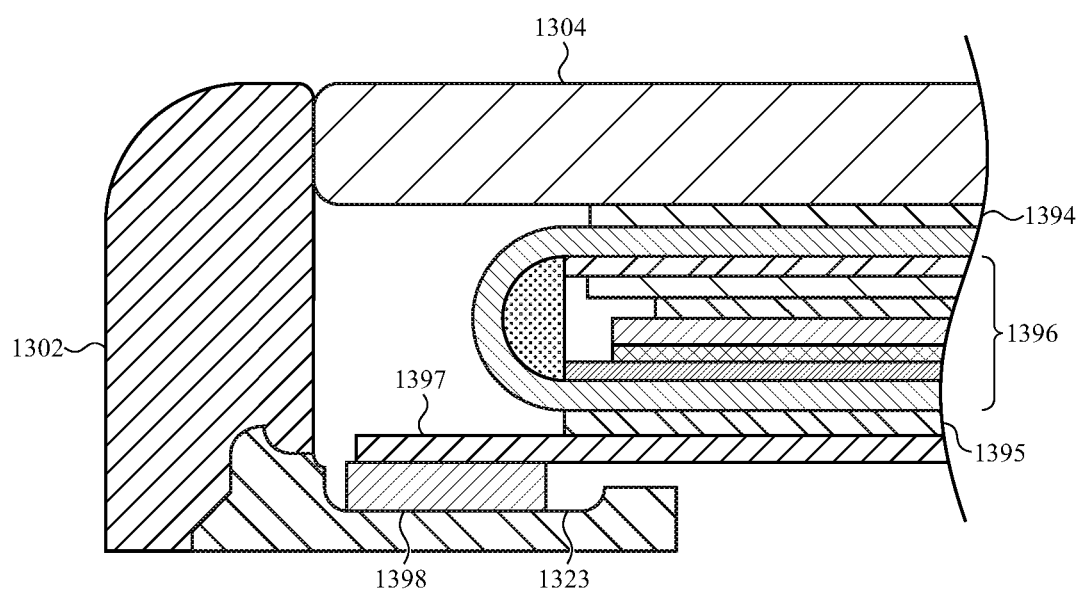
FIG. 13N depicts a partial cross-sectional view of an example electronic device, illustrating an example configuration for mounting a top module to a housing.

FIG. 13N depicts another example configuration for attaching a cover and display stack to the housing member 1302. In the example shown in FIG. 13N, a display stack 1396 is attached to an interior surface of a cover 1304 via an adhesive 1394 (e.g., an optically clear adhesive). A mounting plate 1397 is attached to the display stack 1396 via adhesive 1395 and/or other attachment techniques (e.g., fasteners, brackets, etc.). The mounting plate 1397 is attached to a housing member 1302 to secure the cover 1304 and display stack 1396 (also referred to as a top module) to the housing member 1302. More particularly, the mounting plate 1397 may be attached to a ledge 1323 of the housing member 1302 via an adhesive 1398 (e.g., an HSA, TSA, adhesive foam, epoxy, etc.). In some cases, the attachment between the mounting plate 1397 and the ledge 1323 with the adhesive 1398 may be the only attachment between the top module and the housing member 1302. In other cases, the top module is further secured to the housing member 1302 in other ways as well, such as with fasteners (e.g., screws, bolts, rivets), interlocking features, latching features, brackets, or the like.

The ledge 1323 may be part of a single unitary structure that also defines the side wall of the housing member 1302. For example, the housing member 1302 may be formed of metal, plastic, or the like, and may define a side wall of the housing as well as the ledge 1323. In other cases, the ledge 1323 may be a different component that is attached to or otherwise integrated with a portion of the housing member 1302 that defines the side wall. For example, the ledge 1323 may be part of a polymer material (e.g., fiber-reinforced polymer) that is molded against a metal housing structure. Other configurations and constructions for the ledge 1323 are also contemplated.

The configuration shown in FIG. 13N, in which the mounting plate 1397 is used to attach the top module to the housing member 1302, allows the top module to be attached to the housing member 1302 without a frame member (e.g., without the frame member 1324 shown in FIGS. 13A-13C, 13F, and 13M). The lack of the frame member may provide greater clearance between the display loop and/or other portions of the display stack 1396 and other components of the device (e.g., the housing member 1302). Alternatively, the display loop may be positioned closer to the housing member 1302, thereby facilitating a larger active area of the display screen, a smaller device, or both. Further, by omitting the frame member, the display stack 1396 may be positioned closer to the interior surface of the cover 1304, as there is no portion of the frame member (e.g., no flange) that interferes with or otherwise limits the vertical positioning of the display stack 1396 relative to the cover 1304. More broadly, removing the frame member as shown in FIG. 13N may produce a more space-efficient device in the x, y, and/or z directions.

While FIG. 13N shows only a portion of the mounting plate 1397 and housing member 1302 proximate the loop of the display stack 1396, the same or similar configuration of the housing 1302 (including the ledge 1323), the mounting plate 1397, and the adhesive 1398 may extend around the entire periphery of the top module, effectively defining an adhesive mounting area along all four sides of the device. In some cases, the mounting plate 1397 and adhesive 1398 extend around less than the entire periphery of the top module.

Figure 14A:
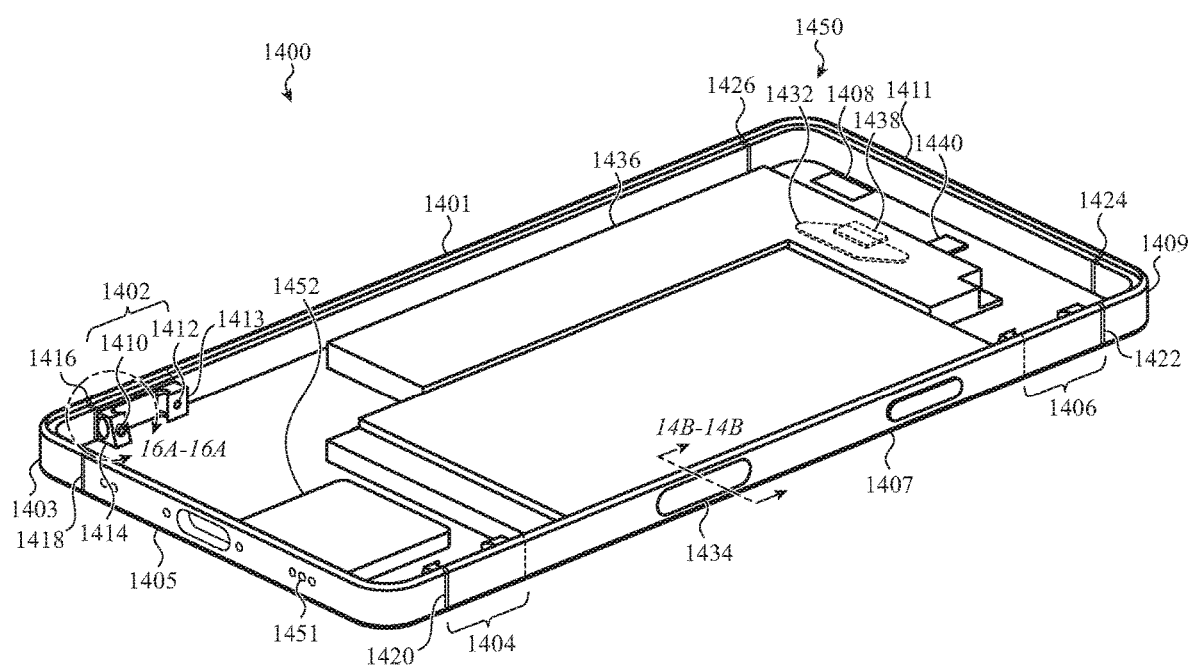
FIG. 14A depicts a partial view of an example electronic device.

As noted above, devices as described herein may include one or more groups of antennas that include elements that are configured to communicate via a 5G wireless protocol (including millimeter wave and/or 6 GHz communication signals). FIG. 14A depicts a portion of an electronic device 1400, with components removed to better illustrate example antenna groups for 5G wireless communications. 5G communications may be achieved using various different communications protocols. For example, 5G communications may use a communications protocol that uses a frequency band below 6 GHz (also referred to as the sub-6 GHz spectrum). As another example, 5G communications may use a communications protocol that uses a frequency band above 24 GHz (also referred to as the millimeter-wave spectrum). Further, the particular frequency band of any given 5G implementation may differ from others. For example, different wireless communications providers may use different frequency bands in the millimeter-wave spectrum (e.g., one provider may implement a 5G communications network using frequencies around 28 GHz, while another may use frequencies around 39 GHz). The particular antenna group(s) implemented in a device as described herein may be configured to allow communications via one or multiple of the frequency bands that implement 5G communications.

The device 1400 in FIG. 14A includes at least two groups of antennas, each configured to operate to provide 5G communications using a different communications protocol. For example, the first antenna group includes multiple antennas to communicate via the sub-6 GHz spectrum, and the second antenna group includes multiple antennas to communicate via the millimeter-wave spectrum.

As noted above, the housing members of a device, such as a mobile phone, may be adapted for use as antennas. In the device 1400, for example, the housing 1450 may include housing members 1401, 1403, 1405, 1407, 1409, and 1411. These housing members may be formed from metal or another conductive material, and may be electrically coupled to communications circuitry (as described in greater detail herein) in order to cause portions of the housing members to send and/or receive wireless communications. The housing members 1401, 1403, 1405, 1407, 1409, and 1411 may be coupled together with joining elements 1416, 1418, 1420, 1422, 1424, and 1426 to form the housing members into a single structural housing component. For simplicity, the joining elements 1416, 1418, 1420, 1422, 1424, and 1426 are shown as being separate components, though some of the joining elements may be contiguous (e.g., the joining elements 1416 and 1418 may be parts of a contiguous molded polymer structure).

The joining elements may both mechanically and/or structurally couple the housing members together, and provide electrical isolation between adjacent housing members to facilitate the use of the housing members as radiating antennas. More particularly, with respect to the mechanical coupling, a joining element may securely attach to adjacent housing members (e.g., via mechanical interlocks between the joining element and the housing members and/or via adhesive or chemical bonds between the joining element and the housing members). With respect to the electrical isolation functions, a joining element may provide a requisite electrical isolation between an antenna and another conductive component (e.g., another conductive housing member, whether acting as an antenna or a non-radiating structural member) to reduce attenuation of the antenna performance (e.g., due to capacitive coupling between the antenna and the other conductive component). The joining elements may be formed from or include a nonconductive and/or dielectric material, such as a polymer, fiber-reinforced nylon, epoxy, or the like. Thus, the joining elements may be referred to herein as nonconductive joining elements.

The joining elements may be formed by a molding process. For example, the housing members may be placed into a mold or otherwise maintained in a fixed position relative to one another such that gaps are defined between adjacent housing members. One or more polymer materials may then be injected into the gaps (and optionally into engagement with retention structures and/or interlock features defined in the housing members), such that the polymer materials at least partially fill the gaps, and allowed to cure or otherwise harden to form the joining elements. In some cases, joining elements may be formed from multiple different materials. For example, an inner portion of the joining element may be formed of a first material (e.g., a polymer material), and an outer portion of the joining element (e.g., that defines part of the exterior surface of the housing) may be formed of a second material that is different from the first (e.g., a different polymer material). The materials may have different properties, which may be selected based on the different functions of the inner and outer portions of the joining elements. For example, the inner material may be configured to make the main structural connection between housing members, and may have a higher mechanical strength and/or toughness than the outer material. On the other hand, the outer material may be configured to have a particular appearance, surface finish, chemical resistance, water-sealing function, or the like, and its composition may be selected to prioritize those functions over mechanical strength. The joining elements may be formed from fiber-reinforced polymer, epoxy, or any other suitable material(s).

In the device 1400, at least three segments of the housing are adapted for use as antennas for communicating via the sub-6 GHz spectrum. More particularly, the housing members may be adapted for use as antennas by conductively coupling ground lines and feed lines to particular locations on the housing members (which are conductive and may be formed of or include metal). The particular location of the ground and feed lines on a housing member may in part define the particular wavelengths for which the antennas are tuned.

The device 1400 includes one example configuration of a first group of antennas for communicating via the sub-6 GHz spectrum. The first group of antennas includes a first sub-6 GHz antenna 1402, a second sub-6 GHz antenna 1404, a third sub-6 GHz antenna 1406, and a fourth sub-6 GHz antenna 1408. In this example configuration, the first, second, and third sub-6 GHz antennas 1402, 1404, 1406 are defined by segments of housing members, while the fourth sub-6 GHz antenna 1408 is a conductive trace (e.g., on a circuit board) or other radiating element that is positioned within the device. The four antennas of the first group of antennas may be configured to operate according to a 4×4 MIMO (multiple input, multiple output) scheme.

The antennas that are defined by segments of the housing members may be similar to one another in structure and function. Accordingly, to avoid redundancy, only the first sub-6 GHz antenna 1402 will be described in detail. However, it will be understood that the description applies equally to the second sub-6 GHz antenna 1404 and the third sub-6 GHz antenna 1406 as well.

The first sub-6 GHz antenna 1402 may be defined by a portion of the housing member 1401, and more particularly, a portion of the housing member 1401 that is proximate the joining element 1416. In order to send and receive electromagnetic signals from the first sub-6 GHz antenna 1402, ground and feed lines may be conductively coupled to the housing member 1401. For example, a ground line may be conductively coupled to location 1412 and a feed line may be conductively coupled to location 1410.

The portion of the housing member 1401 that acts as the first sub-6 GHz antenna 1402 may define structural features 1413 and 1414. These features may extend from the interior side of the housing member 1401 and towards the interior volume of the device 1400. The features 1413, 1414 may have several functions, including defining physical mounting locations for the ground and feed lines, and defining interlock features with which the material of the joining elements engage and/or encapsulate to form the structural coupling between the housing members. While the features 1413, 1414 are shown in FIG. 14A without being encapsulated by or otherwise engaged with the material of the joining element 1416, it will be understood that in some cases the material of the joining element 1416 contacts, engages, and/or at least partially encapsulates the features 1413 and/or the features 1414. Further, while such features are only shown on the housing members 1401 and 1407, the other housing members may include similar features proximate the joining elements.

As noted above, the second sub-6 GHz antenna 1404 and the third sub-6 GHz antenna 1406 may have the same or similar structures as the first sub-6 GHz antenna 1402. In some cases, first, second, and third sub-6 GHz antennas are each configured to communicate via a different frequency band. Accordingly, the exact shape, length, or other physical characteristic of each of these antennas may differ from one another.

As noted above, the fourth sub-6 GHz antenna 1408, which is part of the first group of antennas that operates according to a 4×4 MIMO scheme, is a conductive trace or other radiating element that is positioned within the device. In some cases, however, a portion of the first housing member 1401 that is proximate the joining element 1426 may be configured to act as the fourth sub-6 GHz antenna. In such case the first housing member 1401 may include structural features similar to those of the first sub-6 GHz antenna 1402 (e.g., the features 1413, 1414), and ground and feed lines may be similarly coupled to that region of the first housing member 1401 to facilitate transmitting and receiving electromagnetic signals.

While the sub-6 GHz antennas 1402, 1404, 1406, and 1408 may be used to communicate via the sub-6 GHz spectrum, the device 1400 may also (or instead) include antennas for communicating via the millimeter-wave spectrum. The device 1400 may include, for example, a first millimeter-wave antenna 1432 and a second millimeter-wave antenna 1434. Millimeter-wave antennas may be more directional and more susceptible to attenuation from occlusion than antennas for other spectra. For example, with respect to attenuation, if a user places his or her hand over a millimeter-wave antenna, communications via that antenna may suffer or be completely ceased. With respect to directionality, if the millimeter-wave antenna is pointed more than a certain angle away from a cell tower, the antenna may cease being able to effectively communicate with that cell tower. In order to mitigate these effects, the device may include multiple millimeter-wave antennas strategically positioned to enable wireless communications in a number of different positions, locations, orientations, or the like. For example, in the device 1400, the first millimeter-wave antenna 1432 may be configured as a rear-fired antenna (e.g., sending and receiving electromagnetic signals primarily along a direction that is perpendicular to the rear surface of the device). The second millimeter-wave antenna 1434 may be configured as a side-fired antenna (e.g., sending and receiving electromagnetic signals primarily along a direction that is perpendicular to a side surface of the device). It will be understood that the directional millimeter-wave antennas need not be oriented directly at another antenna in order to communicate, but may tolerate slight misalignments (e.g., +/−15 degrees, +/−30 degrees, or another value).

Returning to FIG. 14A, the first (rear-fired) millimeter-wave antenna 1432 may be coupled to a logic board 1436 (which may be an embodiment of the logic boards 220, 320, or any other logic board described herein). In some cases, the first millimeter-wave antenna 1432 (which may be or may include a passive antenna board) is surface mounted directly to the logic board 1436. The first millimeter-wave antenna 1432 may include antenna arrays for two different frequencies (e.g., 28 GHz and 39 GHz, though other frequencies are also possible). Each antenna array may include four antenna elements, and each antenna element may have two different polarizations. By including two (or more, such as four) different antenna arrays, rather than using the same antenna elements for two different bands, the first millimeter-wave antenna 1432 may have a greater overall bandwidth than an antenna that uses the same antenna elements to communicate over two (or more) frequency bands. The greater bandwidth of the first millimeter-wave antenna 1432 may allow for greater tolerances in the positioning of the antenna 1432 in the device 1400 while still providing adequate antenna performance. Further, the multiple millimeter-wave antenna arrays of the first millimeter-wave antenna 1432 may be used in a diversity configuration to improve wireless communications functionality and reliability.

The device 1400 may also include antenna circuitry in a system-in-package (SiP) component 1438. The SiP component 1438, referred to herein as the SiP 1438, may include components such as one or more processors, memory, analog-to-digital converters, filters, amplifiers, power control circuitry, or the like. The SiP 1438 may be coupled to the logic board 1436, and may be positioned above the first millimeter-wave antenna 1432. The antenna elements in the first millimeter-wave antenna 1432 may be conductively coupled to the SiP 1438 so that the SiP 1438 can process signals received via the first millimeter-wave antenna 1432 and cause the first millimeter-wave antenna 1432 to send signals.

Figure 14B:
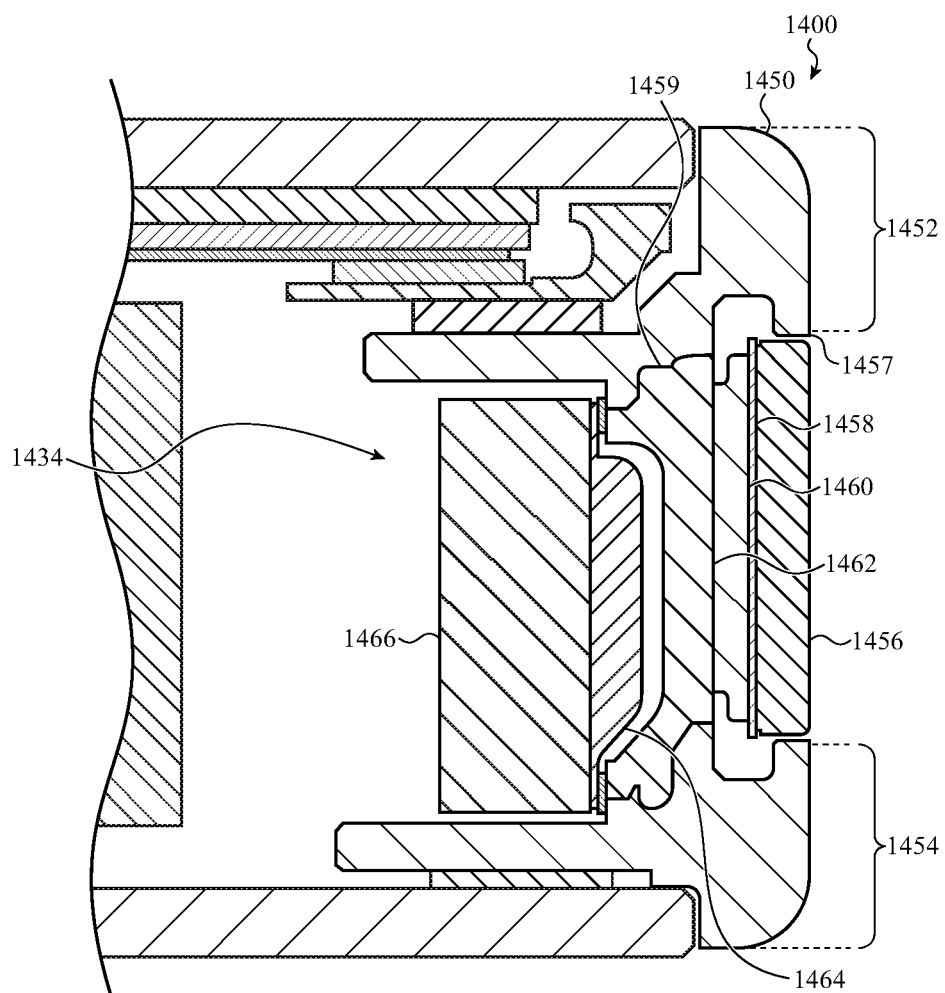
FIGS. 14B-14D depict an example side-fired antenna for an electronic device.

FIG. 14B is a partial cross-sectional view of the device 1400, viewed along line 14B-14B in FIG. 14A. The cross-sectional view illustrates example details of the second (side-fired) millimeter-wave antenna 1434 of the device 1400. The side-fired antenna 1434 (also referred to as an antenna module) is secured to an interior of the housing 1450 (FIG. 14A) of the device 1400 (e.g., to the housing member 1407), and is configured to transmit and receive electromagnetic signals through one or more openings 1457 in the side wall of the housing member 1409. The openings 1457 may extend through the side wall of the housing member 1409 and may at least partially define an antenna window for the side-fired antenna 1434.

The side-fired antenna 1434 includes an antenna array 1466, which includes a plurality of directional antenna elements. The antenna array 1466 may include antenna elements for two different frequencies (e.g., 28 GHz and 39 GHz, though other frequencies are also possible). For example, two antenna elements may be provided for each frequency, and each antenna element may have two different polarizations. Of course, other configurations of antenna elements are also possible. For example, the antenna array 1466 may include four antenna elements for each frequency.

The antenna array 1466 may include or be coupled to antenna circuitry in a SiP component. The SiP component may include components such as one or more processors, memory, analog-to-digital converters, filters, amplifiers, power control circuitry, or the like. The SiP may be conductively coupled to the logic board 1436 (e.g., via a flexible circuit element). The antenna elements in the antenna array 1466 may be conductively coupled to the SiP so that the SiP can process signals received via the antenna array 1466 and cause the antenna array 1466 to send signals.

The side wall of the housing member 1409 may be configured to function as a waveguide for guiding electromagnetic signals to and from the antenna array 1466. The waveguide may be defined by a passage or hole 1459 through the side wall of the housing member 1409. The passage 1459 may be defined in part by walls that extend from an exterior side surface of the side wall of the housing member 1409 to an interior surface of the housing member 1409. As shown, the walls are angled such that the opening 1459 on the exterior side surface is offset from the opening on the interior surface of the housing. More particularly, the center of the opening in the exterior side surface of the side wall may be vertically offset from the center of the opening in the interior side of the housing member 1409.

The vertical offset of the openings defines a generally non-horizontally aligned passage (relative to the orientation shown in FIG. 14B), which allows the internal components of the side-fired antenna 1434 to be offset from a central axis of the device 1400 while also allowing the opening 1457 in the exterior side surface to be vertically centered in the exterior side surface. For example, the height 1452 of the housing member 1409 above the opening 1457 may be the same as the height 1454 of the housing member 1409 below the opening 1457. By aligning the opening 1457 with the middle of the side surface (e.g., the middle along the vertical direction), the structural integrity (e.g., stiffness, strength, etc.) of the housing member 1409 may be higher than if the opening 1457 were offset vertically from the center of the side surface (e.g., because the amount of housing material above the opening 1457 would be different from the amount below, leading to one side being weaker than the other). Further, the central alignment of the opening 1457 provides an overall symmetrical and balanced appearance to the device 1400.

The side-fired antenna 1434 may include a cover element 1462 (also referred to as an insert) within part of the passage 1459. The insert 1462 may be a plastic, glass, or other material (e.g., a nonconductive material) insert, and may be adhered to the antenna array 1466 via an adhesive. The insert 1462 may be placed into the passage 1459, or it may be formed in place by, for example, injecting a polymer material into the passage 1459 and allowing the polymer material to cure or otherwise harden.

The device 1400 may also include a cover element 1456 positioned in the passage 1459 and defining part of the exterior side surface of the device 1400 (e.g., in conjunction with the exterior side surface of the housing member 1409). The cover element 1456 may be formed of glass, sapphire, glass-ceramic, plastic, or any other suitable material (e.g., nonconductive material). The thickness of the cover element 1456 may be determined at least in part on the material being used and the effect of the material (and the dimensions) on the electromagnetic signals passing through the passage 1459. For example, in order to achieve the same or similar electromagnetic performance, the thickness of the cover element 1456 may be greater if it is formed of glass than if it is formed from sapphire. If the cover element 1456 is formed of sapphire, a spacer layer (e.g., a plastic, epoxy, or other suitable material) may be included between the cover element 1456 and an adhesive (e.g., the adhesive 1460) that secures the cover to the device 1400.

The cover element 1456 may include a mask layer 1458, which may be applied to the back or front surface of the cover element 1456. As shown, the mask layer 1458 is applied to the back surface of the cover element 1456. The mask layer 1458 may be an ink, dye, film, paint, coating, or other material, and may be visible through the cover element 1456. The mask layer 1458 may be opaque. The mask layer 1458 may also be a single layer, or it may include multiple sub-layers. The cover element 1456 may be secured to the housing member 1409 via an adhesive 1460. The adhesive 1460 may also adhere the cover element 1456 to the insert 1462. An outer surface of the cover element 1456 may be substantially flush with the adjacent surfaces of the housing member 1409 (e.g., the surfaces defining the heights 1452, 1454).

The side-fired antenna 1434 may also include a dielectric cap 1464. The dielectric cap 1464 may be positioned on and optionally conductively coupled to the antenna array 1466. In some cases, the dielectric cap 1464 may be considered part of the antenna array 1466. The shape and material (e.g., the dielectric properties of the material) of the dielectric cap 1464 may contribute to the bandwidth of the side-fired antenna 1434. For example, the bandwidth of the side-fired antenna 1434 with the dielectric cap 1464 may be greater than one without the dielectric cap 1464.

Figure 14C:
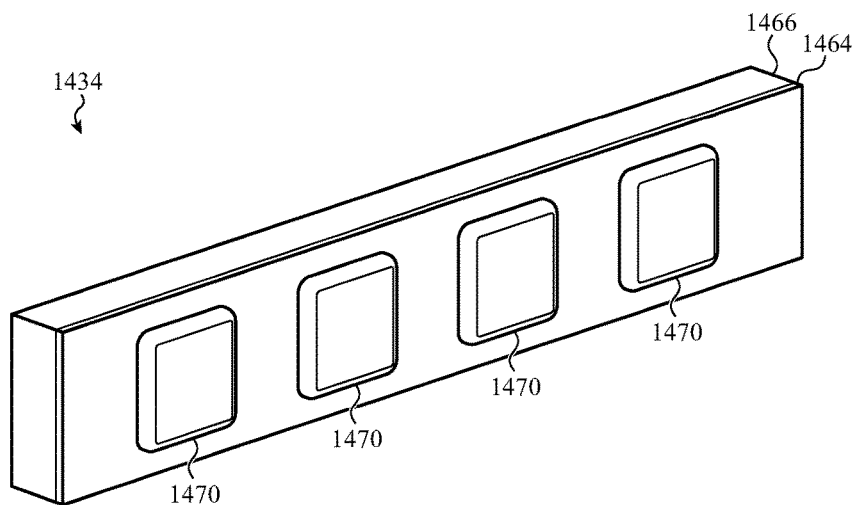
Figure 14D:
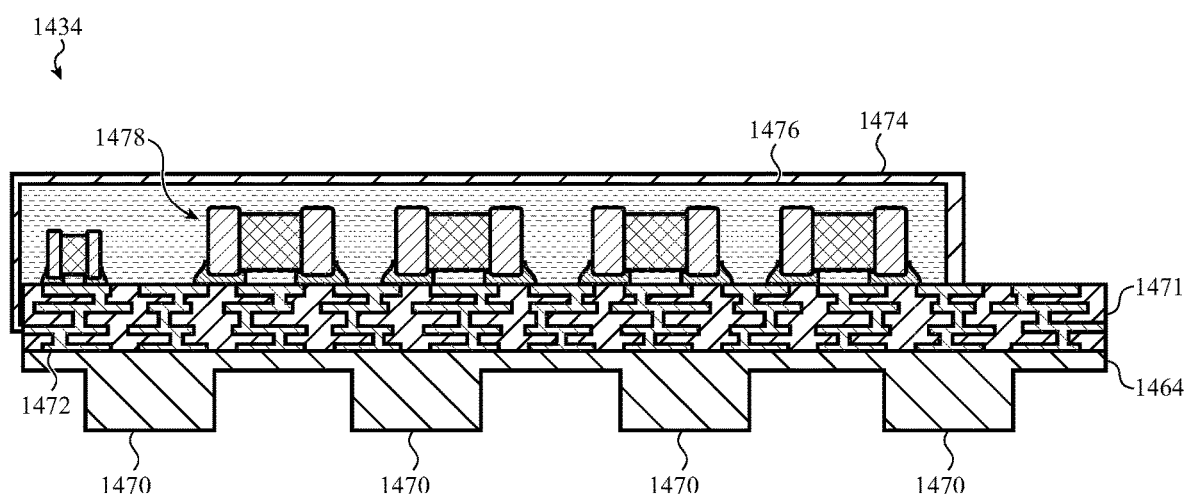

FIG. 14C depicts a portion of the side-fired antenna 1434 separate from the device 1400, and FIG. 14D depicts a partial cross-sectional view of the portion of the side-fired antenna 1434 shown in FIG. 14C. As shown in FIGS. 14C and 14D, the dielectric cap 1464 may include loading block features 1470. The loading block features 1470 may be conductively coupled to antenna elements 1478 in the side-fired antenna 1434, as shown in FIG. 14D. For example, vias or other conductive conduits 1472 in a circuit board 1471 or other substrate may conductively couple the loading block features 1470 to the antenna elements 1478. The loading block features 1470 may at least partially define a radiation pattern of the respective antenna elements 1478 to which they are coupled.

The dielectric cap 1464 and the integral loading block features 1470 may be formed from an epoxy or other suitable moldable material. For example, the dielectric cap 1464 may be formed by molding the epoxy against the antenna array 1466. The epoxy that is used to form the dielectric cap 1464 may have a dielectric constant between about 4 and about 6.

The side-fired antenna 1434 may also include a cap member 1474 at least partially enclosing the antenna elements 1478, and a potting material 1476 in the antenna array 1466 and at least partially encapsulating the antenna elements 1478.

Figure 15:
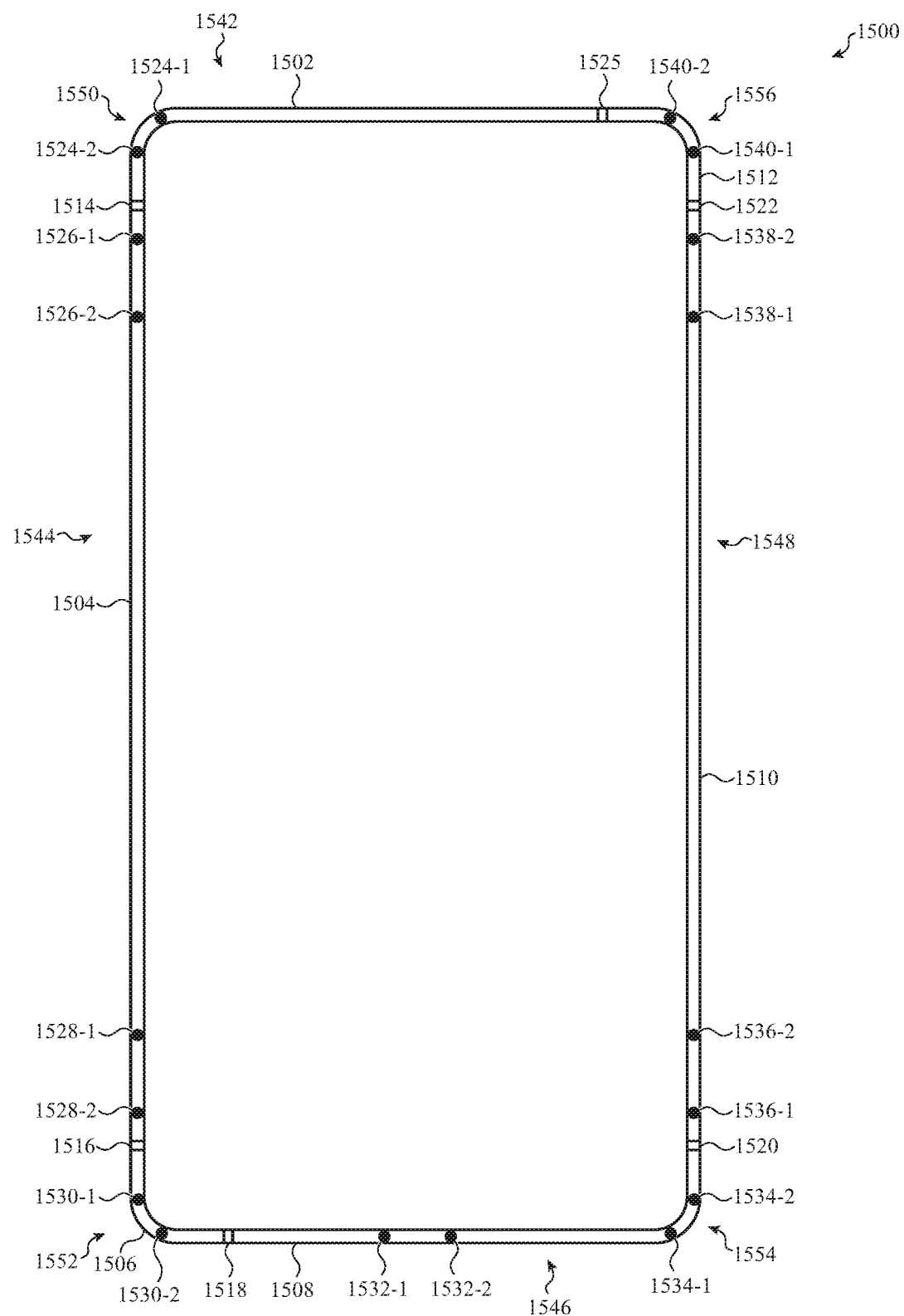
FIG. 15 depicts example antenna feed and ground points for an electronic device.

As noted above, portions of a metal or conductive housing of a device may be used as antenna elements to send and receive wireless signals. More particularly, the portions of the metal or conductive housing may act as the radiating elements of antennas. FIG. 14A, for example, shows an example device 1400 that uses metal housing members to define antenna elements for the sub-6 GHz spectrum. Metal housing members may be used to define antenna elements for other frequencies and/or protocols in addition to the sub-6 GHz antennas described with respect to FIG. 14A. FIG. 15 is a schematic representation of a portion of a housing 1500 formed of multiple conductive housing members joined together with joining elements. FIG. 15 also schematically represents example connection points on the housing members where feed and/or ground lines may be conductively coupled to the housing members to carry electromagnetic signals from the housing member to other antenna circuitry (and from the antenna circuitry to the housing member).

As shown in FIG. 15, the housing 1500 may include a first housing member 1502 that defines a portion of a first side surface 1542 as well as a first corner surface 1550 and part of a second side surface 1544. The first housing member 1502 is structurally coupled to a second housing member 1504 via a first joining element 1514. As noted above, joining elements, such as the joining element 1514, may be formed from a polymer material (e.g., a fiber-reinforced polymer) that can structurally join housing members while also providing sufficient electrical isolation between the housing members to allow them to act as antenna elements.

The housing 1500 also includes a second housing member 1504 that defines a portion of the second side surface 1544 and is structurally coupled to a third housing member 1506 via a second joining element 1516. The third housing member 1506 defines part of the second side surface 1544 as well as a second corner surface 1552.

The third housing member 1506 also defines part of a third side surface 1546 of the housing and is structurally connected to a fourth housing member 1508 via a third joining element 1518. The fourth housing member 1508 also defines a portion of the third side surface 1546, a third corner surface 1554, and part of the fourth side surface 1548.

The fourth housing member 1508 is coupled to a fifth housing member 1510 via a fourth joining element 1520. The fifth housing member 1510 defines a portion of the fourth side surface 1548 and is coupled to a sixth housing member 1512 via a fifth joining element 1522. The sixth housing member 1512 defines a portion of the fourth side surface 1548, a fourth corner surface 1556, and a portion of the first side surface 1542. The sixth housing member 1512 is structurally connected to the first housing member 1502 via a sixth joining element 1525.

Each of the joining elements of the housing 1500 may define a portion of an exterior surface of the housing 1500. Thus, the exterior side surfaces of the housing 1500 may be defined entirely or substantially entirely by the housing members and the joining elements.

In order to operate as antenna elements, the housing members of the housing 1500 may be conductively coupled to antenna circuitry, electrical ground planes, and the like. The particular locations of the connection points on the housing members, as well as the sizes and shapes of the housing members, may at least partially define parameters of the antenna elements. Example antenna parameters may include resonant frequency, range, radiation pattern, efficiency, bandwidth, directivity, gain, or the like.

FIG. 15 illustrates example positions for the connection points of feed and ground lines to the housing members. For example, feed and ground lines may be conductively coupled to the first housing member 1502 at connection points 1524-1, 1524-2, thereby facilitating wireless communication via the first housing member 1502.

Feed and ground lines may be conductively coupled to the second housing member 1504 at connection points 1528-1, 1528-2 and optionally at connection points 1526-1, 1526-2. The portion of the second housing member 1504 between or proximate the connection points 1526-1, 1526-2 may act as one antenna element, while the portion of the second housing member 1504 between or proximate the connection points 1528-1, 1528-2 may act as another, independent antenna element (e.g., it may send and receive electromagnetic signals independently of the antenna element between the connection points 1526-1, 1526-2, despite being defined by the same housing member 1502). While FIG. 15 illustrates connection points 1526-1, 1526-2, these may be omitted in some implementations, such as in the device 1400 of FIG. 14A, which uses a conductive element on a circuit board as an antenna element in that corner of the device instead of using a housing member.

Feed and ground lines may be conductively coupled to the third housing member 1506 at connection points 1530-1, 1530-2, and to the fourth housing member 1508 at connection points 1532-1, 1532-2 and connection points 1534-1, 1534-2. The fourth housing member 1508 may define different antenna element configurations depending on which feed and ground lines are used at a given time. For example, in a first mode, the connection points 1532-1, 1532-2 are used, such that the fourth housing member 1508 is configured to communicate via a first communications protocol (or frequency), and in a second mode, the connection points 1534-1, 1534-2 are used, such that the fourth housing member 1508 is configured to communicate via a second communications protocol (of frequency) that differs from the first.

Feed and ground lines may be conductively coupled to the fifth housing member 1510 at connection points 1536-1, 1536-2, and at connection points 1538-1, 1538-2. Similar to the configuration of the second housing member 1504, the portion of the fifth housing member 1510 between or proximate the connection points 1536-1, 1536-2 may act as one antenna element, while the portion of the fifth housing member 1510 between or proximate the connection points 1538-1, 1538-2 may act as another, independent antenna element (e.g., it may send and receive electromagnetic signals independently of the antenna element between the connection points 1536-1, 1536-2, despite being defined by the same housing member 1510). Feed and ground lines may also be conductively coupled to the sixth housing member 1512 at connection points 1540-1, 1540-2.

As noted above, the housing members of the herein described device housings may be used to form multiple groups or sets of antennas, with each group or set communicating via a different communication protocol or frequency band. For example, the housing may define multiple antennas of a first MIMO antenna array or group (e.g., for a 4G communication protocol) as well as multiple antennas of a second MIMO antenna array (e.g., for a 5G communication protocol). In one non-limiting example configuration, the antenna elements defined by the connection points 1524, 1530, 1532, 1534, and 1540 may be configured to operate as part of a first MIMO antenna array (e.g., for a 4G communication protocol), while the antenna elements defined by the connection points 1526 (if provided), 1528, 1536, and 1538 may be configured to operate as part of a second MIMO antenna array (e.g., for a 5G communication protocol). For any given antenna group, the antenna elements of that group do not all need to be housing members. For example, the second MIMO antenna array or group may use an internal antenna (e.g., the antenna 1408, FIG. 14A) as one of the antennas in a 4×4 MIMO array.

As described above, conductive housing members, which may act as a radiating structure of an antenna or antenna system, may be structurally coupled together via joining elements. The joining elements may be formed from a polymer material or other dielectric material that can provide sufficient electrical isolation between housing members to facilitate the use of the housing members as radiating structures for antennas. In some cases, the joining elements include one, two, or more molded elements, which are molded into a gap between the housing members and into engagement with the housing members. Because the joining elements structurally retain housing members together, a strong engagement between the joining elements and the housing members may be preferred. Accordingly, the housing members may include or define structures and/or features that a joining element engages in order to retain the joining element to the housing members, and thereby retain the housing members together.

Figure 16A:
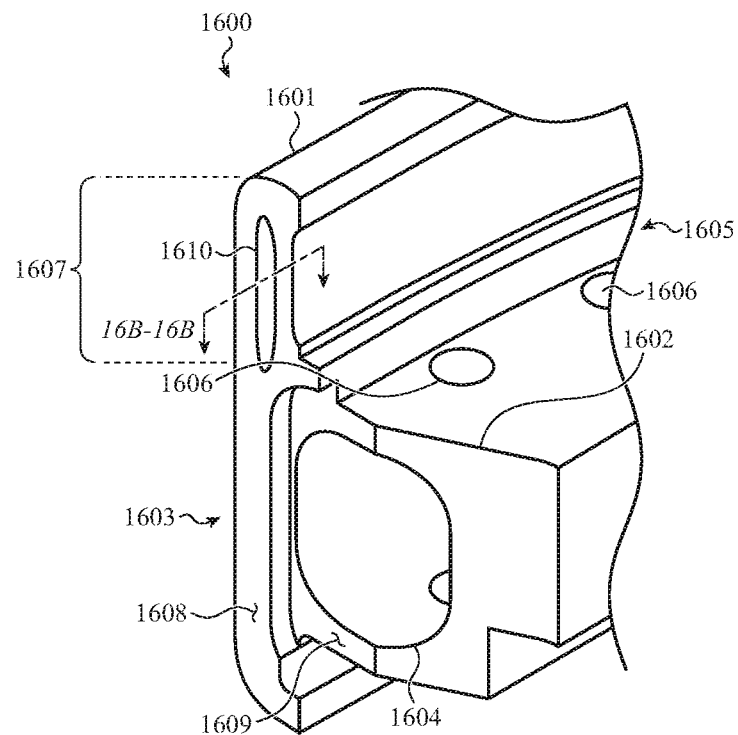
FIG. 16A depicts a partial view of a housing member for an electronic device.

FIG. 16A illustrates an example housing member 1600 that includes features with which a joining element may engage. The portion of the housing member shown in FIG. 16A may correspond generally to the area 16A-16A in FIG. 14A.

Figure 16B:
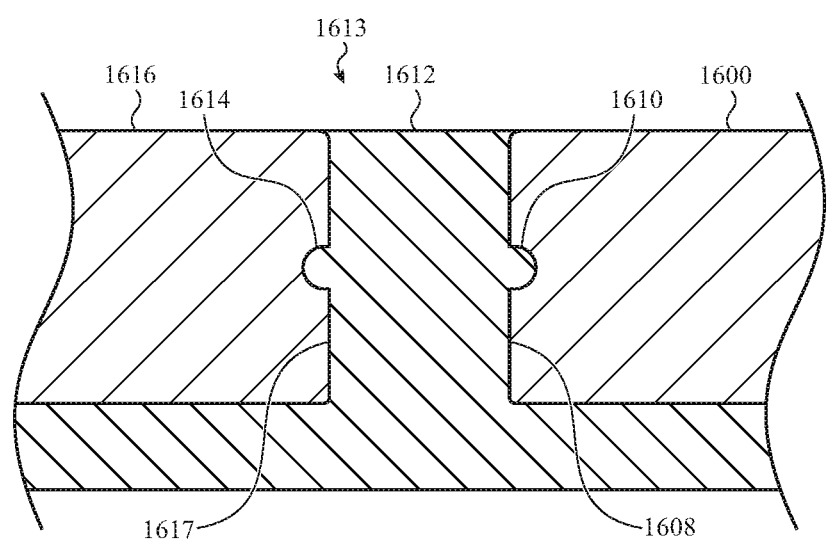
FIG. 16B depicts a partial cross-sectional view of a housing of an electronic device including the housing member of FIG. 16A.

The housing member 1600 may be formed from or include a conductive material, such as stainless steel, aluminum, a metal alloy or the like, and may be conductively coupled to an antenna circuit (e.g., via feed and/or ground lines, as described above) to act as a radiating structure for a device. The portion of the housing member 1600 shown in FIG. 16A may abut and/or engage with a joining element, as shown in FIG. 16B.

The housing member 1600 defines a first interlock feature 1602 that extends inwardly (e.g., towards an interior of the device) from a sidewall 1601 defined by the housing member 1600. The first interlock feature 1602 may extend from an interior side 1605 of the housing member 1600, where the interior side 1605 is opposite an exterior side 1603.

The sidewall 1601 may define an exterior surface of the device of which the housing member 1600 is a part. The first interlock feature 1602 may define a first hole 1604 and one or more second holes 1606. When a joining element is formed by injecting or otherwise molding a moldable material against the housing member 1600, the moldable material may at least partially surround and/or encapsulate the first interlock feature 1602, and may flow into and optionally through the first and second holes 1604, 1606. By at least partially encapsulating the interlock feature 1602 and flowing into and/or through the first and second holes 1604, 1606, the joining elements may be structurally interlocked with the housing member 1600, thereby securely retaining the joining element to the housing member 1600.

The housing member 1600 may also define a second interlock feature, such as a recess 1610, which may be an indentation, cavity, or other similar feature that is recessed relative to an end surface 1608 of the housing member 1600. The end surface 1608 of the housing member 1600 may be the portion of the housing member 1600 that extends closest to another housing member to which the housing member 1600 is coupled via a joining element. The end surface 1608 may be offset from an end surface 1609 defined by the first interlock feature 1602. More particularly, the end surface 1609 may be recessed relative to the end surface 1608 (e.g., along a direction that is perpendicular to the end surfaces 1608, 1609).

The recess 1610 may have a depth between about 100 microns and about 1000 microns, and may have a width (e.g., the left-to-right dimension as depicted in FIG. 16A) between about 100 microns and about 400 microns, and a length (e.g., the top-to-bottom dimension as depicted in FIG. 16A) between about 750 microns and about 3000 microns. In some cases, the housing member 1600 may also define pores along the end surface 1608 and/or the end surface 1609. The pores may be formed on the end surfaces 1608 and/or 1609, and may also be formed on the surface of the recess 1610. The pores may be a distinct structure than the recess 1610. For example, the recess 1610 may have a length dimension greater than about 1000 microns and a width dimension greater than about 100 microns, while the pores may have length and/or width dimensions less than about 10 microns. Similarly, the recess 1610 may have a depth greater than about 100 microns, while the pores may have a depth less than about 10 microns. In some cases, the pores are formed by chemical etching, abrasive blasting, laser or plasma etching, or the like. The material of the joining element may extend or flow into the pores during formation of the joining element and engage and/or interlock with the pores to secure the joining element to the housing member 1600. In some cases, the pores are formed after the recess 1610 is formed, such that the pores are present on the surface of the recess 1610. In other cases, the pores are formed prior to formation of the recess 1610, such that the surface of the recess 1610 lacks the pores, or has a different surface morphology and/or topography than the end surface on which the pores are formed (e.g., the end surface 1608 may have pores from a chemical etching, while the recess 1610 may have machine marks from a machining process). In some cases, the largest dimension (e.g., length, width, depth) of the pores is at least an order of magnitude smaller than the largest dimension (e.g., length, width, depth) of the recess 1610.

The housing member 1600 may define a flange portion 1607 that is adjacent to and/or extends along a peripheral side of a top module (which may include a cover member, a display, touch-sensing components, and the like). In some cases, the second interlock feature 1610 (e.g., the recess, as shown) is positioned in the flange portion 1607, thereby reinforcing the portion of the joint that is along the side of the top module. More particularly, the flange portion 1607 may define a cantilever that extends away from the first interlock feature 1602, and the second interlock feature 1610 may provide a supplemental interlocking engagement with a joining element to help prevent or limit separation or detachment of the flange portion 1607 from the joining element (e.g., the joining element 1612, FIG. 16B). The flange may extend along a direction (e.g., the vertical direction in FIG. 16A, which may be parallel to an exterior side surface defined by the housing member 1600 and/or perpendicular to the front surface defined by a cover member of the device), and the second interlock feature 1610 may be an elongate recess or channel with a longitudinal axis that extends parallel to the exterior side surface of the housing member (e.g., along the same direction that the flange extends from the first interlock feature 1602).

When a moldable material is flowed into place (e.g., between the housing member 1600 and another housing member) to form a joining element, the moldable material may flow into and at least partially fill the recess 1610, thereby forming a corresponding protrusion in the moldable material. When the moldable material is then cured or otherwise hardened, the protrusion of the joining element and the recess 1610 interlock with one another. The interlock between the recess 1610 and the protrusion may help prevent separation of the joining element and the housing member 1600. Further, the position of the recess 1610 relative to the exterior surface defined by the sidewall 1601 may help improve the structural rigidity of the joint and help maintain the alignment (and mechanical coupling) between the housing member 1600, the joining element, and the adjoining housing member in the event of a drop or other impact event. For example, while the first interlock feature 1602 may provide substantial structural strength to the interface between the joining element and the housing member 1600, its position is further inboard (e.g., relatively nearer the internal volume of a housing) than the recess 1610. By contrast, the further outboard position of the recess 1610 (e.g., relatively nearer the external surface of the housing member 1600) may improve the strength and stability of the alignment between the exterior surfaces of the housing members and the joining element.

FIG. 16B is a partial cross-sectional view of the housing member 1600 (joined to another housing member 1616 via a joining element 1612), viewed along line 16B-16B in FIG. 16A. (While FIG. 16A does not show the joining element and the housing member 1616, FIG. 16B represents the view along line 16B-16B if such components were present.) The joining element 1612 may be positioned between and in contact with the end surface 1608 of the housing member 1600 and a corresponding end surface 1617 of the housing member 1616. The joining element 1612 may also extend into and interlock with the recess 1610 of the housing member 1600, as well as a recess 1614 defined by the housing member 1616. In addition to the mechanical interlocking between the joining element 1612 and the recesses 1610, 1614 (and/or other retention structures and/or interlock features), the moldable material of the joining element 1612 may form a chemical or other adhesive bond with the material of the housing members 1600, 1616.

The exterior surfaces of the joining element 1612 and the housing members 1600, 1616 may define a smooth continuous exterior surface 1613 of the housing. For example, any gaps, seams, or other discontinuities between the joining element 1612 and the housing members 1600, 1616 along the exterior surface 1613 of the housing may be undetectable to the touch and/or to the unaided eye. For example, a fingernail sliding along the exterior surface 1613 may not catch on the seam between the joining element 1612 and the housing members 1600, 1616. In some cases, any gap, seam, or other discontinuity between the joining element 1612 and the housing members 1600, 1616 may be less than about 200 microns, less than about 100 microns, less than about 50 microns, less than about 20 microns, or less than about 10 microns (in depth, length, offset, and/or other dimension). The interlock between the joining element 1612 and the recesses 1610, 1614 may help prevent or inhibit relative motion between the housing members 1600, 1616 and the joining element 1612, such as relative motion of these components along a vertical direction (as oriented in FIG. 16B). Accordingly, the recesses 1610, 1614 may help maintain the substantially seamless texture and appearance between the joining element 1612 and the housing members 1600, 1616.

Figure 16C:
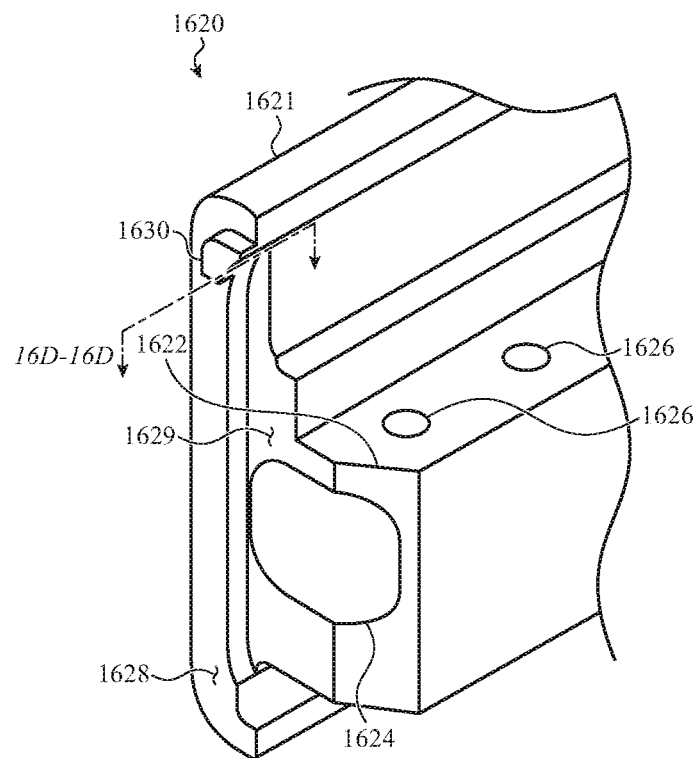
FIG. 16C depicts a partial view of a housing member for an electronic device.
Figure 16D:
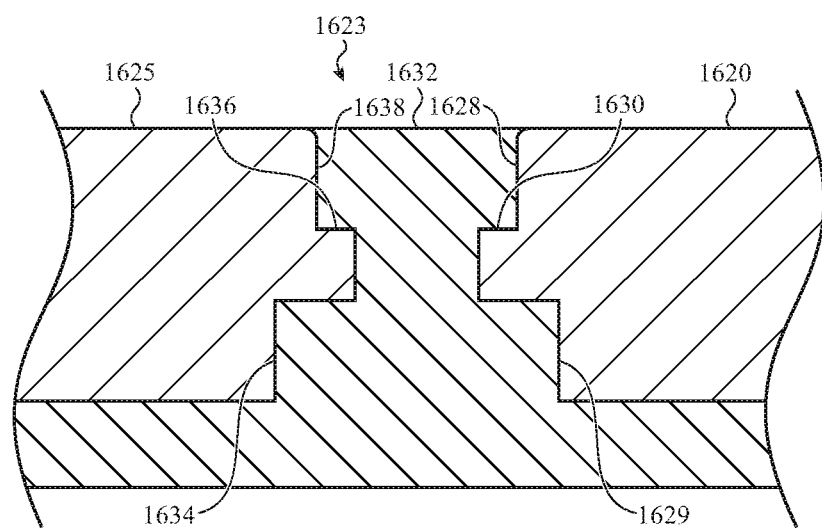
FIG. 16D depicts a partial cross-sectional view of a housing of an electronic device including the housing member of FIG. 16C.

FIG. 16C illustrates another example housing member 1620 that includes features with which a joining element may engage. The housing member 1620 may be formed from or include a conductive material, such as stainless steel, aluminum, a metal alloy or the like, and may be conductively coupled to an antenna circuit (e.g., via feed and/or ground lines, as described above) to act as a radiating structure for a device. The portion of the housing member 1620 shown in FIG. 16C may abut and/or engage with a joining element, as shown in FIG. 16D.

The housing member 1620 defines a first interlock feature 1622 that extends inwardly (e.g., towards an interior of the device) from a sidewall 1621 defined by the housing member 1620. The first interlock feature 1622 may extend from an interior side of the housing member 1620 (e.g., analogous to the interior side 1605, FIG. 16A), where the interior side is opposite an exterior side (e.g., analogous to the exterior side 1603, FIG. 16A).

The sidewall 1621 may define an exterior surface of the device of which the housing member 1620 is a part. The first interlock feature 1622 may define a first hole 1624 and one or more second holes 1626. When a joining element is formed by injecting or otherwise molding a moldable material against the housing member 1620, the moldable material may at least partially surround and/or encapsulate the first interlock feature 1622, and may flow into and optionally through the first and second holes 1624, 1626. By at least partially encapsulating the interlock feature 1622 and flowing into and/or through the first and second holes 1624, 1626, the joining elements may be structurally interlocked with the housing member 1620, thereby securely retaining the joining element to the housing member 1620.

The housing member 1620 may also define a protruding feature 1630, which may be a post, pin, or have any other suitable shape or configuration that protrudes or extends from an end surface 1628 of the housing member 1620. The end surface 1628 of the housing member 1620 may be the portion of the housing member 1620 that, with the exception of the protruding feature 1630, extends closest to another housing member to which the housing member 1620 is coupled via a joining element.

The protruding feature 1630 may operate in a similar manner as the recess 1610 in FIGS. 16A-16B. For example, when a moldable material is flowed into place (e.g., between the housing member 1620 and another housing member) to form a joining element, the moldable material may flow around the protruding feature 1630 to at least partially encapsulate the protruding feature 1630. When the moldable material is then cured or otherwise hardened, the protruding feature 1630 and the recess in the moldable material that is formed around the protruding feature 1630 interlock with one another. The interlock between the protruding feature 1630 and the moldable material may help prevent separation of the joining element and the housing member 1620. Further, the position of the protruding feature 1630 relative to the exterior surface defined by the sidewall 1621 may help improve the structural rigidity of the joint and help maintain the alignment (and mechanical coupling) between the housing member 1620, the joining element, and the adjoining housing member in the event of a drop or other impact event. For example, while the first interlock feature 1622 may provide substantial structural strength to the interface between the joining element and the housing member 1620, its position is further inboard (e.g., relatively nearer the internal volume of a housing) than the protruding feature 1630. By contrast, the further outboard position of the protruding feature 1630 (e.g., relatively nearer the external surface of the housing member 1620) may improve the strength and stability of the alignment between the exterior surfaces of the housing members and the joining element.

In some cases, the housing member 1620 may also define pores along the end surface 1628 and/or the end surface 1629. The pores may be formed on the end surfaces 1628 and/or 1629, and may also be formed on the surface of the protruding feature 1630. The pores may be a distinct structure than the protruding feature 1630. For example, the protruding feature 1630 protrudes by a distance greater than about 100 microns, and may have a length and width dimension greater than about 100 microns, while the pores may have depth, length, and/or width dimensions less than about 10 microns. In some cases, the pores are formed by chemical etching, abrasive blasting, laser or plasma etching, or the like. The material of the joining element may extend or flow into the pores during formation of the joining element and engage and/or interlock with the pores to secure the joining element to the housing member 1620. In some cases, the pores are formed after the protruding feature 1630 is formed, such that the pores are present on the surfaces of the protruding feature 1630. In other cases, the surfaces of the protruding feature 1630 lack the pores, or have a different surface morphology and/or topography than the end surface on which the pores are formed. In some cases, the largest dimension (e.g., length, width, depth) of the pores is at least an order of magnitude smaller than the largest dimension (e.g., length, width, depth) of the protruding feature 1630.

FIG. 16D is a partial cross-sectional view of the housing member 1620 (joined to another housing member 1625 via a joining element 1632), viewed along line 16D-16D in FIG. 16C. (While FIG. 16C does not show the joining element 1632 and the housing member 1625, FIG. 16D represents the view along line 16D-16D if such components were present.) The joining element 1632 may be positioned between and in contact with the housing members 1620, 1625. The joining element 1632 may also at least partially (and optionally fully) encapsulate the protruding feature 1630. As can be seen in FIG. 16D, the protruding feature 1630 may extend and/or be adjacent to two offset surfaces. For example, with respect to the housing member 1620, the two offset surfaces include the end surface 1628 and an additional end surface 1629. The protruding feature 1630 may extend a first distance from the end surface 1628, and a second (greater) distance from the additional end surface 1629. A similar structure may be used on the housing member 1625 (e.g., a protruding feature 1636 extending a first distance from an end surface 1638 and a second (greater) distance from an additional end surface 1634). Thus, as shown in FIG. 16D, the end surfaces 1628, 1638 may be closer together than the additional end surfaces 1629, 1634 (and the ends of the protruding features 1630, 1636 may be the portions of the housing members 1620, 1625 that are closest together). In addition to the mechanical interlocking between the joining element 1632 and the protruding features 1630, 1636 (and any other retention structures and/or interlock features), the moldable material of the joining element 1632 may form a chemical or other adhesive bond with the material of the housing members 1620, 1625.

The exterior surfaces of the joining element 1632 and the housing members 1620, 1625 may define a smooth continuous exterior surface 1623 of the housing. For example, any gaps, seams, or other discontinuities between the joining element 1632 and the housing members 1620, 1625 along the exterior surface 1623 of the housing may be undetectable to the touch and/or to the unaided eye. For example, a fingernail sliding along the exterior surface 1623 may not catch on the seam between the joining element 1632 and the housing members 1620, 1625. In some cases, any gap, seam, or other discontinuity between the joining element 1632 and the housing members 1620, 1625 may be less than about 200 microns, less than about 100 microns, less than about 50 microns, less than about 20 microns, or less than about 10 microns (in depth, length, offset, and/or other dimension). The interlock between the joining element 1632 and the housing members 1620, 1625 may help prevent or inhibit relative motion between the housing members 1620, 1625 and the joining element 1632, such as relative motion of these components along a vertical direction (as oriented in FIG. 16D). Accordingly, the protruding features 1630, 1636 may help maintain the substantially seamless texture and appearance between the joining element 1632 and the housing members 1620, 1625.

Figure 16E:
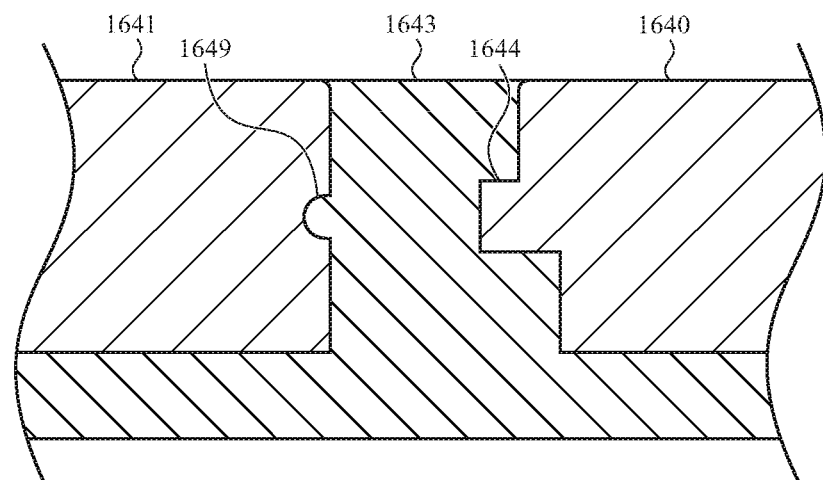
FIG. 16E depicts a partial cross-sectional view of a housing of an electronic device including the housing members of FIG. 16A and FIG. 16C.

In some cases, different types of structures may be used to reinforce or otherwise increase the strength and/or structural integrity of the coupling between housing members and joining elements. FIG. 16E, for example, illustrates an example cross-sectional view of a housing that includes a joining element 1643 and a first housing member 1640 that defines a protruding feature 1644 (as shown in FIGS. 16C-16D) and a second housing member 1641 that defines a recess 1649 (as shown in FIGS. 16A-16B). Using a protruding feature 1644 and a recess 1649 may help increase the average or overall distance between the nearest portions of the first and second housing members 1640, 1641. In particular, because one or both of the housing members 1640, 1641 may be used as a radiating component of an antenna system, it may be desirable to increase the distance between them to reduce capacitive coupling or other electromagnetic effects due to proximity of the two conductive components. By positioning a recess opposite a protrusion, the structural benefits of the protrusion (and the recess) may be achieved while also providing a greater distance between the closest surfaces of the housing members 1640, 1641 (as compared to a configuration with two protruding features, for example).

Figure 17A:
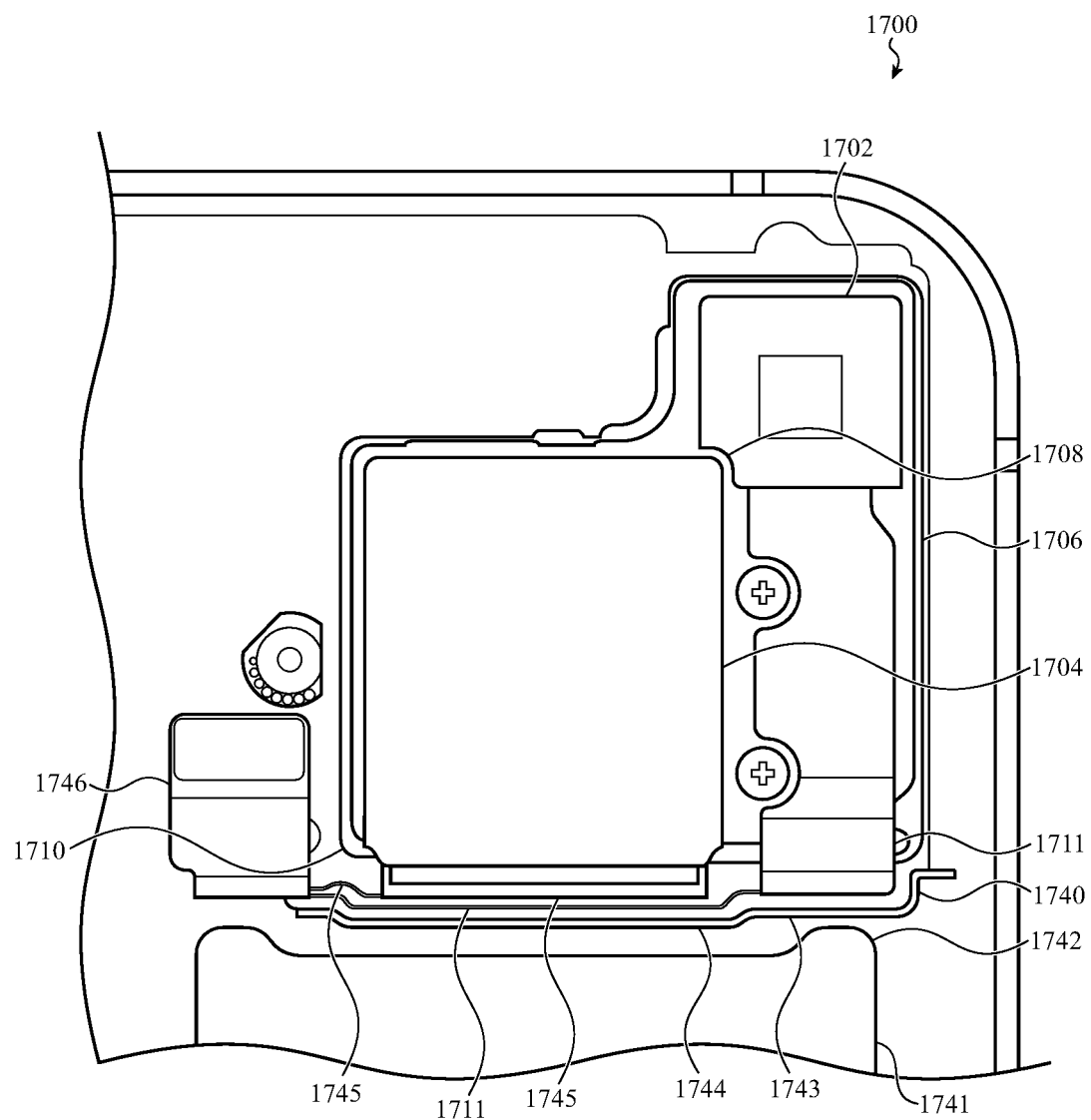
FIG. 17A depicts a portion of an electronic device illustrating an example arrangement of camera modules in an example electronic device.

FIG. 17A illustrates an example arrangement of cameras in a rear-facing sensor array of a device 1700. FIG. 17A may correspond to a corner of a device (e.g., the devices 100, 200), viewed with the cover and display (and optionally other components) removed to show the arrangement of the cameras. The device 1700 may include a first camera module 1702 (which may be an embodiment of or otherwise correspond to the first camera 138 in FIG. 1B, and/or the first camera 261 in FIG. 2) and a second camera module 1704 (which may be an embodiment of or otherwise correspond to the second camera 139 in FIG. 1B, and/or the second camera 262 in FIG. 2). The first and second camera modules 1702 and 1704 may include camera housings. Any of the cameras shown in FIG. 17A (or elsewhere herein) may include an image stabilization system that helps maintain a sharp image (e.g., reducing the effects of camera shake on the image) by sensing movement of the device and moving one or more components of the camera in a manner that at least partially compensates for (and/or counteracts) the movement of the device.

The device 1700 may also include a bracket member 1706 (also referred to herein as a camera bracket) to which the first and second camera modules 1702, 1704 may be coupled. The bracket member (or camera bracket) 1706 may define first and second respective camera portions 1780, 1781, or receptacles, to which the first and second respective camera modules may be coupled. The first and second camera portions 1780, 1781 may be positioned along the diagonal path defined from the first corner region to the second corner region of the rear-facing sensor array. Each camera portion may define an opening for the optical components (e.g., lenses) of its respective camera module. The camera portions (e.g., receptacles) may be defined by flanges or side walls that at least partially surround the camera modules. The bracket member 1706 may be configured to fix the relative positions of the camera modules.

In modern consumer electronic devices, such as mobile phones, internal space is at a premium, and space-saving arrangements of components can have a significant positive impact on various aspects of the device. For example, space-saving or compact arrangements of components can free up internal space that can be used to increase the size and capacity of a battery, or can be used to make the device smaller, thinner, and/or lighter. FIG. 17A shows one example configuration of the camera modules that reduces the overall footprint of the camera modules in the system. In particular, the first camera module 1702 (e.g., the camera housing of the first camera module) defines a recess 1708 at a corner of the module. For example, instead of a convex corner, one of the corners of the first camera module 1702 is a concave shape (e.g., a recess 1708). This configuration allows a corner of the second camera module 1704 (e.g., a corner of a housing of the second camera module) to extend into the recess 1708, thereby allowing the first and second camera modules 1702, 1704 to be positioned more closely together than would be possible if the first camera module 1702 had conventional convex corners.

In some cases the first camera module 1702 may have a generally quadrilateral shape with three convex corners and one concave corner. In some cases, the first camera module 1702 has a parallelogram shape with three convex corners and one concave corner.

FIG. 17A shows the first camera module 1702 defining the concave corner and a portion of the second camera module 1704 (e.g., a convex corner of the second camera module 1704) positioned in the concave corner of the first camera module 1702. In other implementations, the second camera module 1704 may define a concave corner, and a convex corner of the first camera module 1702 may be positioned in the concave corner of the first camera module. In some cases, portions of other components or structures of an electronic device are positioned in the concave corner of a camera module, such as a fastener, a mounting post, a battery, a housing member, a circuit board, or the like. The device 1700 may also include a frame member 1710 to which the bracket member 1706 may be attached. The frame member 1710 may define a wall structure 1731 (FIG. 17D), which in turn defines a container region 1723 (FIG. 17D). As described herein, one or more cameras (which may be mounted to the bracket member 1706) may be positioned in the container region 1723.

Figure 17B:
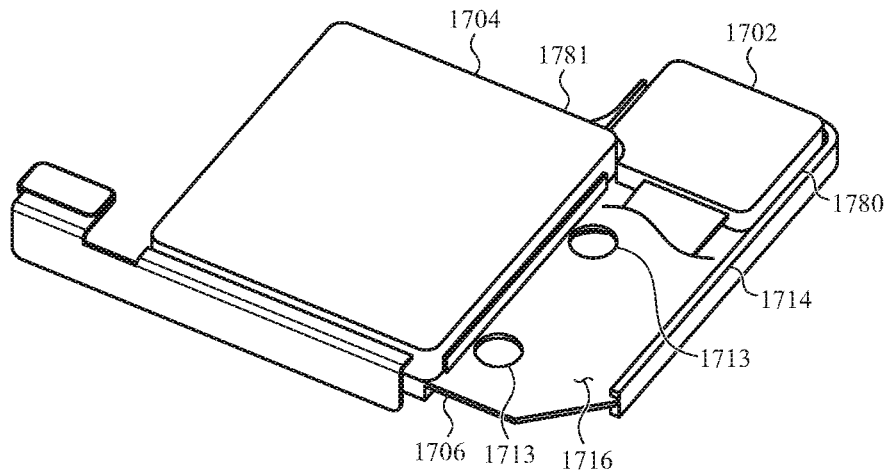
FIGS. 17B-17C depict the camera modules of FIG. 17A.
Figure 17C:
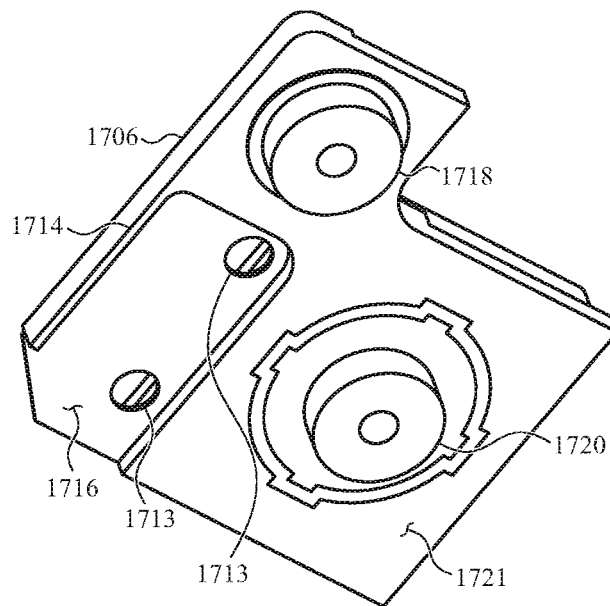
Figure 17D:
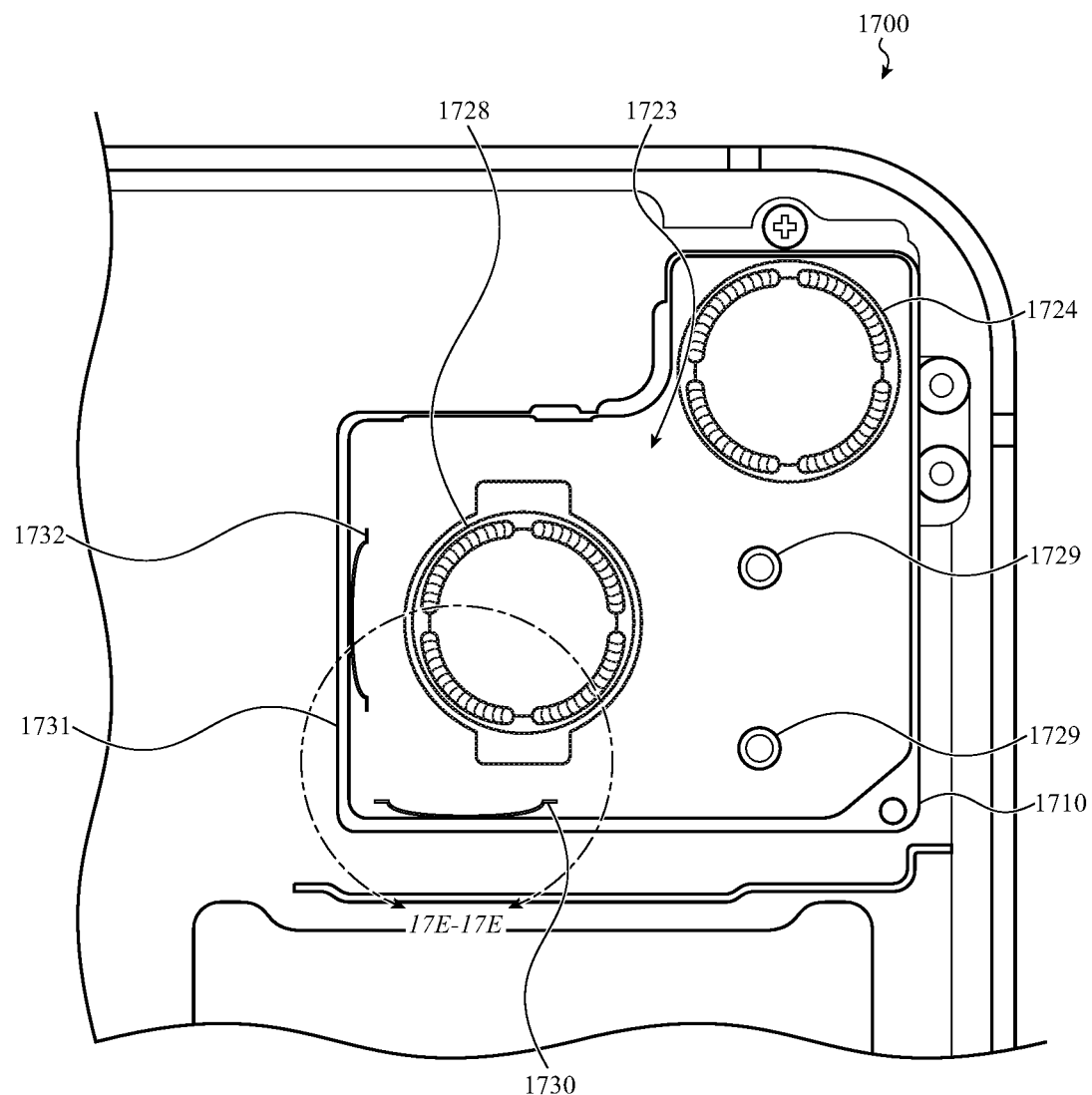
FIG. 17D depicts a portion of an example electronic device with camera modules removed.

FIG. 17B depicts the first and second camera modules 1702, 1704 and the bracket member 1706 removed from the device 1700. The bracket member 1706 may be a structural component that defines the positions of the first and second camera modules 1702, 1704 relative to each other. The bracket member 1706 may serve as a rigid structure to prevent or inhibit the first and second camera modules 1702, 1704 from moving, twisting, or shifting relative to one another during use or misuse of the device 1700. The bracket member 1706 may therefore have a structural configuration that contributes to the rigidity, stiffness, and/or strength of the bracket member 1706. For example, the bracket member 1706 may define, along one side of the first camera portion 1780 and along one side of the second camera portion 1781, a web portion 1716 (or web 1716) and an outer wall 1714, also referred to as a stiffening wall. As shown in FIG. 17C, the web 1716 resembles a plate having a thickness, and the stiffening wall 1714 extends from the web 1716 along at least one side of the web 1716. Accordingly, the stiffening wall 1714 defines a T-shaped flange extending from opposite sides of the web 1716. This configuration increases the area moment of inertia of the bracket member 1706, thereby increasing its resistance to twisting, bending, flexing, or other deflections or deformations. The web 1716 may also define holes 1713, through which mounting posts and/or fasteners may extend to secure components (including optionally the bracket member 1706 itself) to the frame member 1710 and/or the device more generally.

The web 1716 and stiffening wall 1714 may define a recessed area of the bracket member 1706. In some cases, one or more device components may be positioned in the recessed area defined by these features. For example, a flexible circuit element 1711 (FIG. 17A) that conductively couples the first camera module 1702 to another component (e.g., a logic board, processor, etc.) may be positioned in the recessed area. In such cases, the recessed area, and more particularly the stiffening wall 1714, may protect the flexible circuit element 1711.

FIG. 17C depicts an opposite side of the bracket member 1706 and the first and second camera modules 1702, 1704. As shown, a first lens 1718 of the first camera module 1702 and a second lens 1720 of the second camera module 1704 may extend through the bracket member 1706 and beyond a bottom surface 1721 of the bracket member 1706. The lenses 1718, 1720 may extend into corresponding openings in the frame member 1710 and may be positioned adjacent camera covers of the device 1700 (e.g., camera covers 263, 264, FIG. 2). The first lens 1718 may have a first field of view, and the second lens 1720 may have a second field of view that is different from the first field of view.

FIG. 17D depicts the frame member 1710 secured to the housing of the device 1700, with the bracket member 1706 and the first and second camera modules 1702, 1704 removed. The frame member 1710 may define openings 1724 and 1728 into which lenses of the first and second camera modules 1702, 1704 may extend. The openings 1724, 1728 may be aligned with camera covers, such as the covers 263, 264 in FIG. 2. The frame member 1710 may define mounting posts 1729. The mounting posts 1729 may extend through openings in the bracket member 1706, and may receive fasteners that secure one or more components to the frame member 1710 (e.g., a cowling or cover that extends over the camera modules, the bracket member 1706, etc.).

The frame member 1710 also defines a wall structure 1731 extending around all or at least a portion of an outer periphery of the frame member 1710 (and extending at least partially around a periphery of the bracket member 1706 when the bracket member 1706 is positioned in the container region 1723). Biasing springs 1730, 1732 may be coupled to the wall structure 1731 to provide biasing forces on the bracket member 1706 and to help maintain the bracket member 1706 (and thus the first and second camera modules 1702, 1704) in a target position. For example, the first biasing spring 1730 may impart a biasing force on the bracket member 1706 tending to push the bracket member 1706 in a positive y direction (e.g., towards a top of the device), while the second biasing spring 1732 may impart a biasing force tending to push the bracket member 1706 in a positive x direction (e.g., towards a lateral side of the device). These biasing forces may ultimately force the bracket member 1706 against the wall structure 1731 and help maintain the bracket member 1706 in that position during use (or misuse) of the device. Further, the biasing springs 1730, 1732 may provide compliance to the bracket member 1706, such that impacts or other forces acting on the device may cause the bracket member 1706 to be forced against the biasing springs 1730, 1732. Because the biasing springs 1730, 1732 are flexible and/or compliant, they can absorb some of the energy and allow the bracket member 1706 to move slightly, rather than the bracket member 1706 itself absorbing all of the impact and/or energy, which could damage the camera modules, cause misalignment of the camera modules and/or the bracket member 1706, or the like.

Figure 17E:
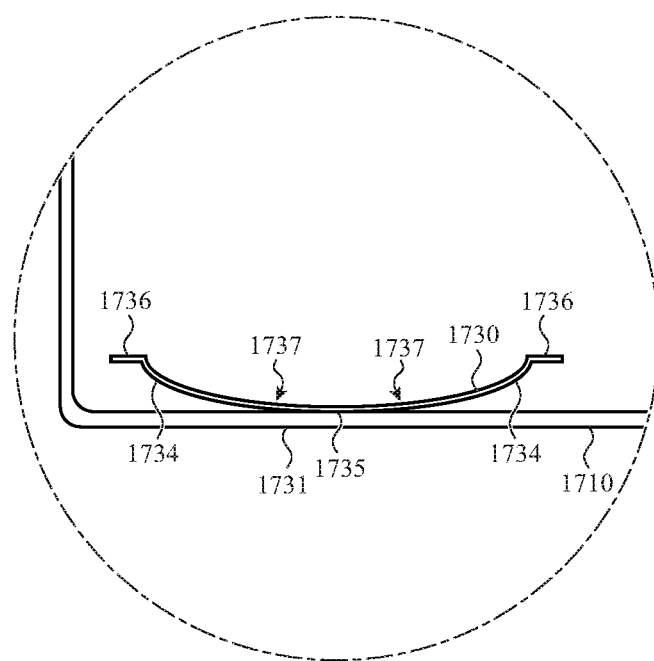
FIGS. 17E-17F depict a spring member for use with camera modules for an electronic device.
Figure 17F:
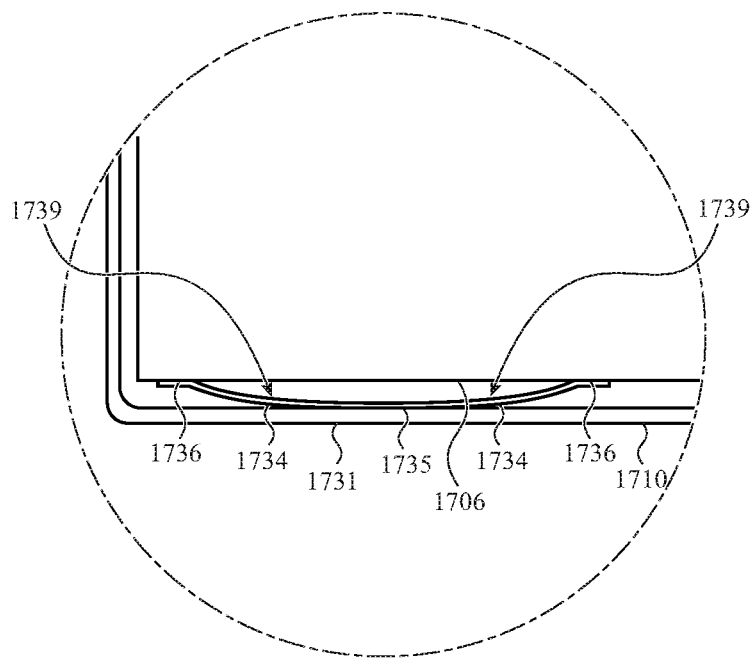

FIGS. 17E and 17F depict a detail view of the frame member 1710 and biasing spring 1730, corresponding to area 17E-17E in FIG. 17D. The biasing spring 1730 may include a beam member that defines an attachment region 1735 where the beam is attached to the wall structure 1731 (e.g., via welding, adhesive, fasteners, rivets, heat stakes, brazing, soldering, etc.). The beam may also define compliant portions 1734, which may be curved, extending from the attachment region 1735, and contact regions 1736 extending from the compliant portions 1734. The contact regions 1736 may contact the bracket member 1706 and may impart the biasing force produced by the biasing spring 1730 onto the bracket member 1706.

The compliant portions 1734 may deflect and/or deform (e.g., towards the wall structure 1731) when the bracket member 1706 is positioned in the frame member 1710. The compliant portions 1734 may have a curvature that is generally convex towards the wall structure 1731. The convex curvature of the compliant portions 1734 may provide a dynamic fulcrum location along the compliant portions 1734. For example, as shown in FIG. 17E, when the bracket member 1706 is not yet installed, the fulcrum location 1737 of the compliant portions 1734 (e.g., where the compliant portions 1734 contact and/or bend against the wall structure 1731) are proximate the attachment region 1735. As shown in FIG. 17F, when the bracket member is installed, the fulcrum location 1739 is further towards the distal ends (e.g., towards the contact regions 1736) of the biasing spring 1730. If the bracket member 1706 were to be forced towards the wall structure 1731 (e.g., due to the device being dropped onto a hard surface, for example), the compliant portions 1734 may deflect further towards the wall structure 1731, resulting in the fulcrum locations moving even further outboard towards the distal ends of the biasing spring 1730. The dynamic fulcrum locations may also correspond to differing or varying spring rates of the biasing spring 1730. For example, as the fulcrum location moves outboard, the spring rate of the biasing spring may increase or otherwise change in accordance with the deflection, resulting in a greater resistance to further deformation or deflection. In some cases, the spring rate may remain substantially constant despite movement of the fulcrum location. In some cases, the spring rate may vary in a nonlinear way as the fulcrum location moves outboard. The particular spring rate and/or spring rate changes (e.g., caused by the dynamic fulcrum location) may be selected to produce a desired force or movement profile of the bracket member 1706.

While FIGS. 17D-17F show the biasing springs as each having two compliant portions, other examples may have only a single compliant portion (e.g., the biasing springs may have one "wing" instead of two "wings" as shown). Further, while FIGS. 17E-17F describe the biasing spring 1730, the discussion applies equally to the biasing spring 1732. The biasing springs 1730, 1732 may be formed from any suitable material, such as metal (e.g. aluminum, steel, titanium), a polymer, a fiber-reinforced polymer (e.g., carbon fiber), and/or a composite material. The biasing springs 1730, 1732 may be a single, monolithic member (e.g., a unitary piece of metal), or they may be formed from multiple components.

Figure 17G:
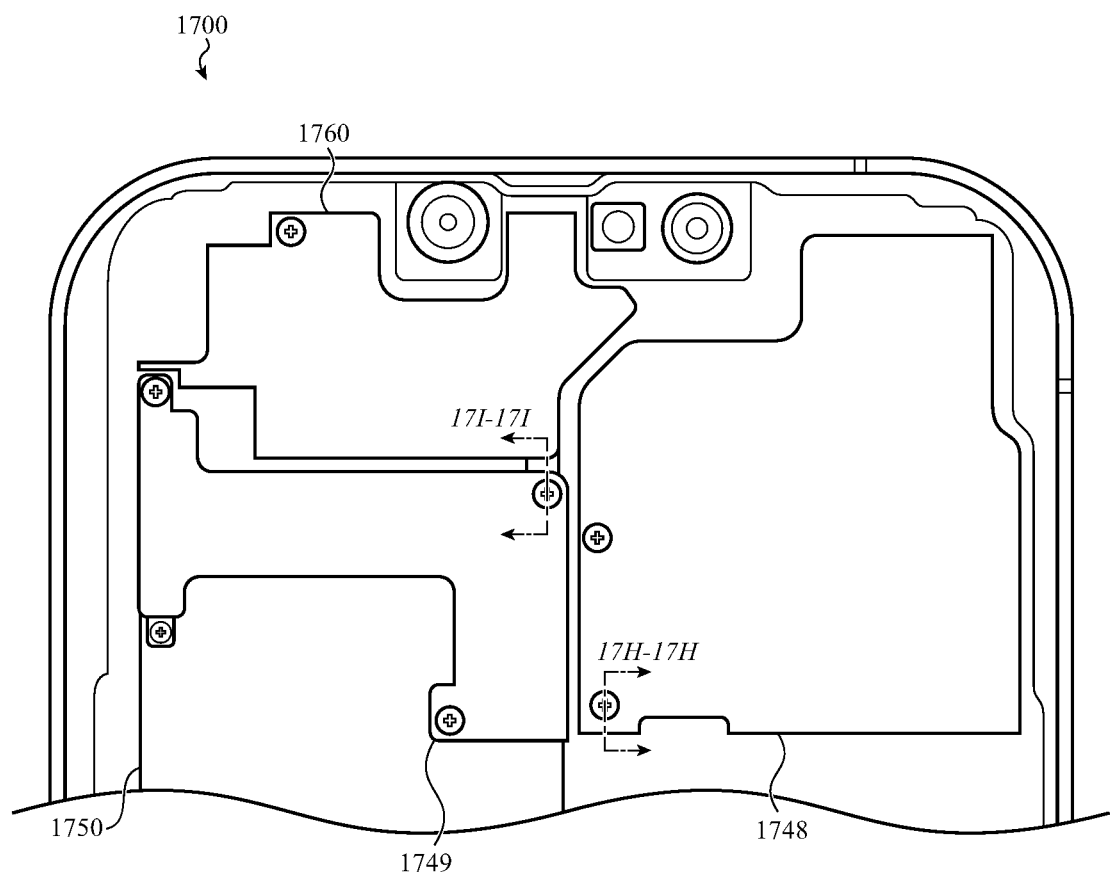
FIG. 17G depicts a portion of an electronic device, illustrating an example arrangement of components in the device.

FIG. 17G depicts an example arrangement of several components within the device 1700, including several shrouds that are positioned over components of the device 1700. For example, a camera shroud 1748 may be positioned over the first and second camera modules 1702, 1704 of the device 1700. In examples where a device includes more or fewer cameras, the same or a similar camera shroud 1748 may be used. FIG. 17G also depicts a logic board shroud 1749 positioned over at least a portion of a main logic board 1750. FIG. 17G also depicts a speaker module 1760, which may be an embodiment of the speaker modules 250, 350, or any other speaker modules described herein. The speaker module 1760 may include a shroud that at least partially covers the speaker module 1760.

The shrouds may be formed from metal, plastic, carbon fiber, or any other material(s). The shrouds may be configured to protect underlying components from physical damage due to contact with other components (e.g., a top module), as well as to provide electromagnetic shielding between components. The shrouds may be affixed to the device in various ways. In some cases, for example, the shrouds may be affixed to the device via fasteners such as screws or bolts.

Figure 17H:
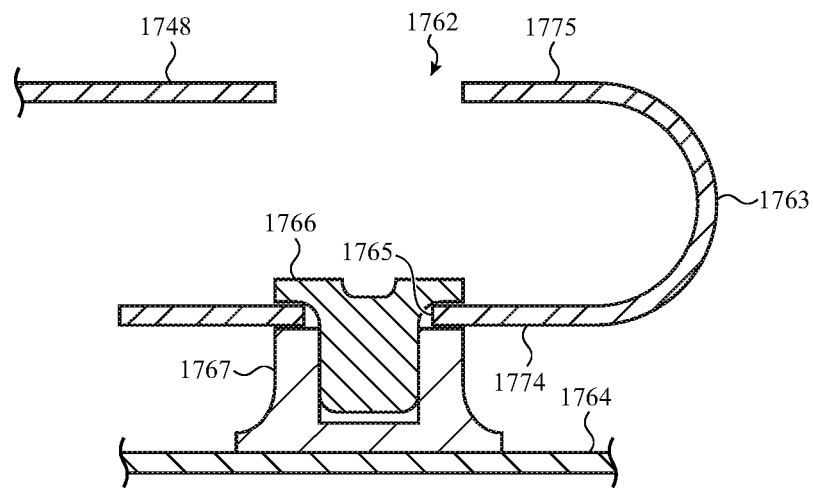
FIG. 17H depicts a partial cross-sectional view of an example mounting configuration for a shroud of an electronic device.

FIG. 17H depicts a partial cross-sectional view of the device 1700, viewed along line 17H-17H in FIG. 17G, illustrating an example configuration of the camera shroud 1748. As noted above, shrouds may act as a physical barrier between components of the device. The camera shroud 1748, for example, acts as a barrier between the camera module(s) and the top module, and can help prevent the camera(s) and the top module from contacting and potentially damaging each other during drops, impacts, or other forceful events. Some shrouds may be designed with physical compliance or flexibility to help dissipate or reduce the energy from an impact. FIG. 17H illustrates an example configuration for securing the camera shroud 1748 to the device while also providing physical compliance to the camera shroud 1748. The camera shroud 1748 may have a wrapped segment such that the camera shroud 1748 has two levels. More particularly, the camera shroud 1748 may define a top portion 1775, a loop portion 1763, and a lower portion 1774. The top portion 1775 may define a clearance hole 1762 to provide access for a fastener 1766 (e.g., a screw, bolt, etc.) to pass through to reach a fastening hole 1765 defined through the lower portion 1774. The fastener 1766 may capture a portion of the lower portion 1774 between a flange of the fastener 1766 and a top surface of a mounting post 1767 to secure the camera shroud 1748 to the device. The mounting post 1767 may be attached to a base 1764, which may be a frame, base, plate, or other structure of the device.

The multi-level configuration of the camera shroud 1748, and more particularly the loop portion 1763, may provide physical compliance to the camera shroud 1748. For example, the loop portion 1763 may act as a spring or other compliant structure that bends when a force is applied to the top portion 1775 (e.g., by a component of the top module), thus allowing the top portion 1775 to move relative to the lower portion 1774. The bending or flexing of the loop portion 1763 may absorb and/or dissipate energy associated with the impact, or otherwise reduce the magnitude of shock loading or other forces resulting from contact with the camera shroud 1748.

Parameters of the loop portion 1763, such as spring constant, stiffness, or the like, may be defined by the materials and/or dimensions of the loop portion 1763. For example, the thickness of the loop portion may be selective to provide a particular spring constant to the camera shroud 1748. The thickness of the loop portion 1763 may be constant, or it may vary along the length of the loop portion 1763. The thickness of the loop portion 1763 may be the same as or different from the thickness of the top and lower portions 1775, 1774.

Figure 17I:
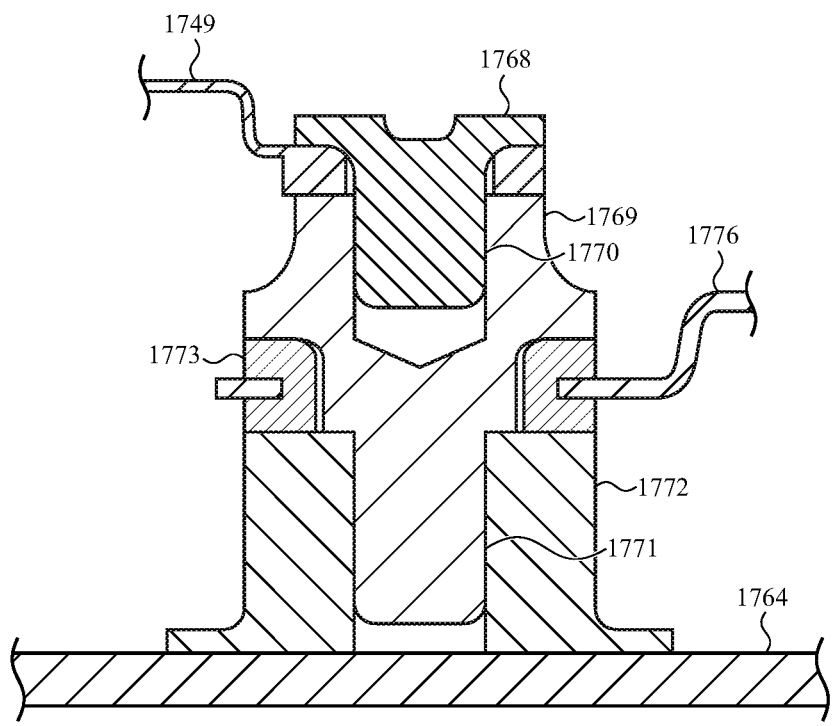
FIG. 17I depicts a partial cross-sectional view of an example mounting configuration for attaching components to an electronic device.

FIG. 17I depicts a partial cross-sectional view of the device 1700, viewed along line 17I-17I in FIG. 17G, illustrating an example configuration for mounting the logic board shroud 1749 and the speaker module 1760 (FIG. 17G) to a device. As shown in FIG. 17I, both the logic board shroud 1749 (or a mounting tab of the logic board itself, such as the tab portion 2108, FIG. 21B) and a mounting tab 1776 of the speaker module 1760 may be secured to the device via a single fastening assembly. In particular, the mounting tab 1776 may be captured between a mounting post 1772 and a main fastener 1769.

A compliant member 1773 may be attached to the mounting tab 1776. The compliant member 1773 may be formed of a polymer such as silicone, rubber, or the like, and may be compressed or otherwise captured between the mounting post 1772 and the main fastener 1769, thereby imparting a corresponding compression force on the mounting tab 1776 to secure and substantially immobilize the speaker module 1760. The compliant member 1773 may help inhibit the transmission of vibrations, oscillations, or other physical forces from the speaker module 1760 to other components of the device 1700 through the mounting post 1772. More particularly, the speaker module 1760 is configured to output sounds, such as music, notification sounds (e.g., ringtones), voice output for telephone calls, audio tracks for videos or movies, and the like. As such, the speaker module 1760 (and more particularly a diaphragm of the speaker module 1760) vibrates in order to produce the sounds. These vibrations may be detrimental to other components of the device. For example, vibrations may cause other components such as fasteners, electrical connectors, or the like, to loosen and potentially become detached. Vibrations may also contribute to the weakening of adhesive joints or cause unwanted rubbing or friction between components in a device. Accordingly, the compliant member 1773 may help reduce the effect (e.g., amount, amplitude, frequency, etc.) of vibrations from the speaker module 1760 on the mounting post 1772 and/or main fastener 1769, and thus reduce the transfer of vibrations to other components of the device 1700 (e.g., to the logic board via a tab portion 2108 or other mounting tab of the logic board). The particular properties of the compliant member, such as the durometer, vibration damping characteristics, and the like, may be selected based on the parameters of the expected vibrations from the speaker module 1760 (e.g., the amplitude and/or frequency of the expected vibrations).

As shown in FIG. 17I, both the speaker module 1760 and the logic board shroud 1749 may be secured to the device using a single fastening assembly. The main fastener 1769 may define a threaded post portion 1771 that threads into the mounting post 1772, as well as a threaded hole portion 1770 into which a threaded fastener 1768 (e.g., a screw, bolt, etc.) threads. The logic board shroud 1749 may be captured between the fastener 1768 and the main fastener 1769. As described above, the compliant member 1773 may help inhibit vibrations from the speaker module 1760 from being transferred to the logic board shroud 1749.

Returning to FIG. 17A, the device 1700 may include a barrier wall 1740 (or wall 1740) that is positioned between the battery 1741 of the device 1700 and the cameras (including the first and second camera modules 1702, 1704. The wall 1740 may be configured to prevent or inhibit any potential motion of the battery 1741 from damaging the cameras and/or the flexible circuit elements that connect the cameras to other circuitry of the device. The wall 1740 may be formed of metal, polymer, carbon fiber, or the like, and may be attached to a housing member or other component of the device 1700 (e.g., via adhesive, welding, fasteners, etc.). In some cases, portions of flexible circuit elements 1711 and 1745 are routed between the wall 1740 and the cameras. These portions of the flexible circuit elements 1711 and 1745 may be coupled to a joint connector 1746, which may physically and electrically couple to a corresponding connector on another component of the device 1700, such as a main logic board or the like. The joint connector may thereby conductively couple both the first and second camera modules 1702, 1704 to other circuitry of the device 1700.

In order for portions of the flexible circuit elements 1711 and 1745 to fit between the cameras and the wall 1740, those portions of the flexible circuit elements 1711 and 1745 may be oriented substantially vertically, while other portions of the flexible circuit elements 1711 and 1745 may be oriented substantially horizontally. In such cases, the portions of the flexible circuit elements 1711 and 1745 that are between the wall 1740 and the cameras may be substantially perpendicular to other portions of the flexible circuit elements 1711 and 1745 (e.g., the portion of the flexible circuit element 1711 that extends between the first camera module 1702 and the wall 1740, and the portion of the flexible circuit element 1745 that extends from the second camera module 1704 to the vertical portion of the flexible circuit element 1745 (e.g., the portion between the wall 1740 and the second camera module 1704 itself).

The wall 1740 may define one or more recesses or jogged regions to accommodate portions of the battery 1741. For example, the battery 1741 may include a flexible pouch that contains the battery cell therein. The flexible pouch may be formed by fusing or attaching two layers of a flexible material together around a periphery of the battery cell. The layers that are attached may be folded up against the side of the battery such that the sides or edges of the battery are irregular or otherwise not perfectly straight. For example, as shown in FIG. 17A, the battery 1741 defines a protruding portion 1742 at a corner of the battery 1741. The protruding portion 1742 may correspond to or be a result of folding a portion of the pouch against a side of the battery. In other cases, the protruding portion 1742 is an outwardly protruding portion that corresponds to an internal recess in the pouch that accommodates circuitry, additional battery cells, or the like. Regardless of the function of a protruding portion 1742, the wall 1740 may define one or more recesses into which the protruding portion 1742 extends. For example, the first segment 1743 of the wall 1740 may be offset relative to a second segment 1744 of the wall, such that the first segment 1743 defines a recess. The second segment 1744 of the wall may be at a position in the y direction of the device that would contact, interfere with, or otherwise be too close to the protruding portion 1742. Accordingly, the first segment 1743 of the wall is positioned further away from the battery 1741 (e.g., it defines a recess), such that the protruding portion 1742 does not contact or otherwise interfere with the wall 1740. In some cases, the minimum distance between the wall 1740 and the battery 1741 is less than about 1 mm. The minimum distance may be defined between the protruding portion 1742 of the battery and the first segment 1743 of the wall.

Figure 18A:
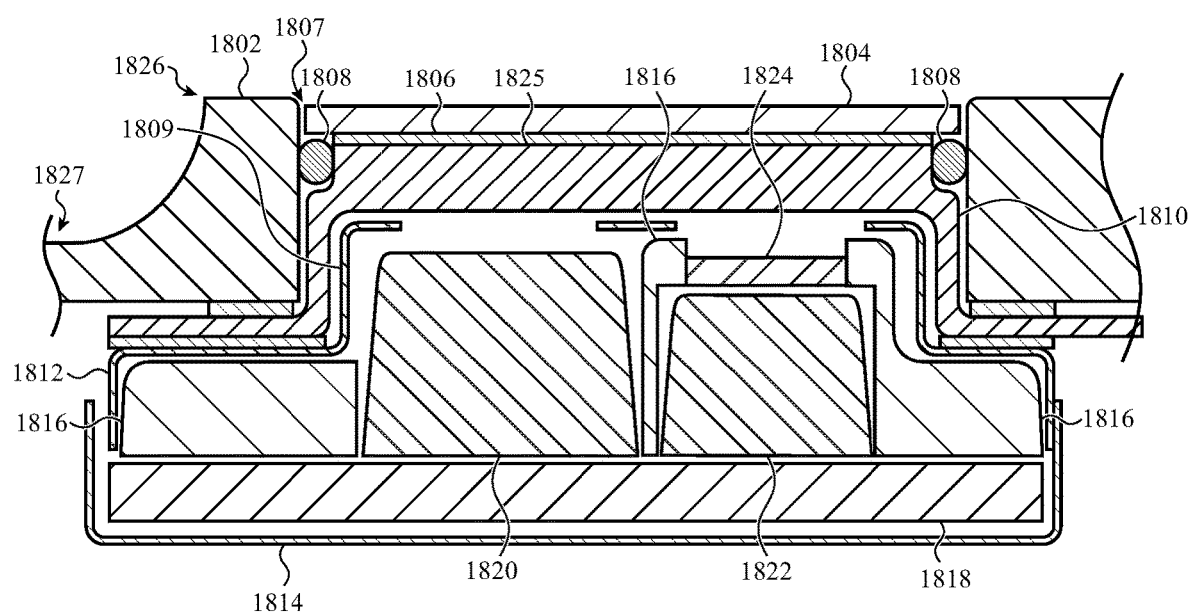
FIG. 18A depicts a partial cross-sectional view of an example electronic device, illustrating an example depth sensor configuration.

FIG. 18A depicts a cross-sectional view of a device through a portion of a rear-facing sensor array (e.g., the sensor array 141, FIG. 1D) that includes a depth sensor module. The depth sensor module may include an emitter assembly 1822 and a sensor assembly 1820. A cover lens 1824 may be positioned on or over the emitter assembly 1822. The emitter assembly 1822 and sensor assembly 1820 may include lens assemblies, light emitters, light sensors, and the like.

For example, the emitter assembly 1822 is adapted to emit one or more beams of light, such as coherent light beams having a substantially uniform wavelength/frequency (e.g., infrared laser light). The sensor assembly 1820 may detect beams of light that are emitted by the emitter assembly 1822 and reflected by an object external to the device. The depth sensor module may determine, based on time-of-flight measurements for example, a distance to an object based on the reflected light detected by the sensor assembly 1820.

The sensor assembly 1820 and emitter assembly 1822 may be coupled to a substrate 1818 (e.g., a circuit board), and may be held in place by a frame member 1816. The sensor assembly 1820, emitter assembly 1822, circuit board 1818, and frame member 1816 (and optionally other components) may be at least partially enclosed in an enclosure, which may include a first enclosure member 1812 and a second enclosure member 1814.

The depth sensor may generally define a snout portion 1809. The snout portion 1809 may have a height that is less than the depth of an opening 1807 in the rear cover 1802. More particularly, the depth sensor may be positioned in a thickened region 1826 of the rear cover 1802, where the thickened region 1826 corresponds to or defines the rear-facing sensor array (and is thicker than a main portion 1827 of the rear cover 1802). As such, the end of the snout portion 1809 may be recessed relative to the top surface of the rear cover 1802. However, an air gap between the emitter and sensor assemblies 1822, 1820 and the cover 1804 may be detrimental to performance of the depth sensor. Accordingly, a transparent interposer structure 1810 may be positioned between the snout portion 1809 of the depth sensor module and the underside of the cover 1804. The interposer structure 1810 may include a lens portion 1825 that is positioned between the cover 1804 and the snout portion 1809. The lens portion 1825 reduces the size of the air gap between the snout portion 1809 and the cover 1804, and may therefore reduce the extent to which the light emitted by the emitter assembly 1822 disperses (e.g., angles away from a centerline of the emitter assembly 1822) prior to the light exiting the device through the cover 1804.

The interposer may include flanges that are adhered to the first enclosure member 1812 and to the rear cover 1802. The lens portion 1825 may also be adhered to the cover 1804 via an optically clear adhesive 1806. In some cases, the cover 1804, the optically clear adhesive 1806, and the lens portion 1825 of the interposer may have the same or substantially similar index of refraction. For example, in some cases the indices of refraction of the cover 1804, the optically clear adhesive 1806, and the lens portion 1825 differ by less than about 5%. In some cases, the cover 1804, the optically clear adhesive 1806, and the lens portion 1825 each have a refractive index between about 1.7 and about 1.8.

A sealing member 1808 (e.g., an O-ring) may form an environmental and/or light seal between the interposer structure 1810 and the inner wall of the hole 1807 defined through the rear cover 1802. In some cases, an infrared-transparent, visually opaque coating may be applied to the cover 1804 (e.g., to an inner surface of the cover 1804 and adjacent the adhesive 1806). The interposer structure 1810 may be formed from a transparent material, such as glass, a polymer (e.g., polycarbonate), sapphire, or the like.

Figure 18B:
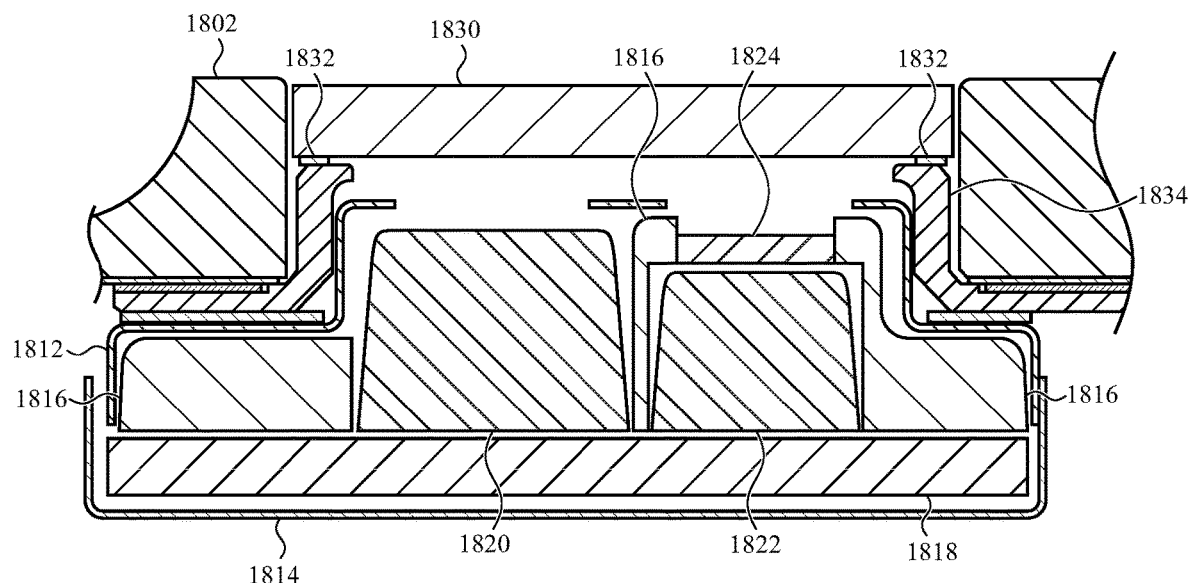
FIG. 18B depicts a partial cross-sectional view of an example electronic device, illustrating another example depth sensor configuration.

FIG. 18B depicts a cross-sectional view of a device through a portion of a rear-facing sensor array (e.g., the sensor array 141, FIG. 1D) that includes a depth sensor module. FIG. 18B depicts another example configuration for integrating the depth sensor module of FIG. 18A into a device. As noted with respect to FIG. 18A, the depth sensor may generally define a snout portion 1809 that has a height that is less than the depth of an opening 1807 in the rear cover 1802. More particularly, the depth sensor may be positioned in a thickened region 1826 of the rear cover 1802, where the thickened region 1826 corresponds to or defines the rear-facing sensor array (and is thicker than a main portion 1827 of the rear cover 1802). As such, the end of the snout portion 1809 may be recessed relative to the top surface of the rear cover 1802. While FIG. 18A illustrates an interposer structure 1810 that defines a lens portion 1825, the example in FIG. 18B includes a depth sensor mounting bracket 1834, and a separate cover member 1830 that is positioned in the opening 1807 of the rear cover 1802 and is coupled to (e.g., via adhesive 1832) the mounting bracket 1834. The mounting bracket 1834 may include flanges that are adhered to the first enclosure member 1812 and to the rear cover 1802. The mounting bracket 1834 may be formed from metal (e.g., aluminum, steel, etc.), a polymer, or any other suitable material.

The cover 1830 may have a thickness that is substantially equal to the combined thickness of cover 1804, adhesive 1806, and lens portion 1825 in FIG. 18A. Further, the thickness of the cover 1830 may be greater than the covers positioned over rear-facing cameras that are also part of the rear-facing sensor array. The thick cover 1830 may reduce or minimize any air gap between the snout portion 1809 and the cover 1830, and may therefore reduce the extent to which the light emitted by the emitter assembly 1822 disperses (e.g., angles away from a centerline of the emitter assembly 1822) prior to the light exiting the device through the cover 1830. The cover 1830 may be formed from sapphire, glass, plastic, or another suitable material. The cover 1830 may include one or more coatings, dyes, inks, layers, or other materials or treatments that render the cover 1830 visually opaque (e.g., opaque to at least some portions of light in the visible spectrum). While the cover 1830 may appear visually opaque, it may be at least partially transparent to light from the emitter assembly 1822 (e.g., to allow the depth sensor module to function, while also occluding the depth sensor module from visibility).

Figure 18C:
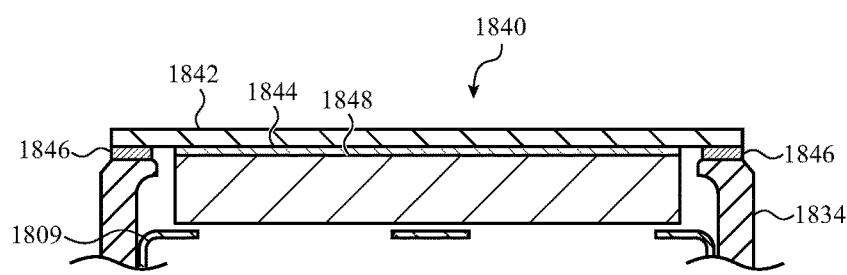
FIG. 18C depicts a partial cross-sectional view of an example electronic device, illustrating another example depth sensor configuration.

FIG. 18C illustrates another example cover assembly 1840 that may be used in place of the cover 1830 shown in FIG. 18B. In this case, instead of the monolithic cover 1830, a cover assembly 1840 may include an outer cover 1842 that defines the exterior surface of the cover assembly 1840, and an inner cover 1848, coupled to the outer cover 1842 via an adhesive 1844. The outer cover 1842 may be mounted to the mounting bracket 1834 via adhesive 1846, and the inner cover 1848 may be positioned in the hole that is defined by the mounting bracket 1834. In this example, the chimney-like structure of the mounting bracket 1834 to which the outer cover 1842 is coupled may be taller than the example shown in FIG. 18B to accommodate the thinner outer cover 1842 and to position the exterior surface of the outer cover 1842 substantially flush with the exterior surface of the rear cover 1802 (e.g., the surface of the rear-facing sensor array). Further, because the inner cover 1848 is within the chimney-like structure of the mounting bracket 1834, it may extend closer to the snout 1809 than the cover 1830 shown in FIG. 18B.

The inner cover 1848 may be adhered to the outer cover 1842 via an optically clear adhesive 1844. In some cases, the inner cover 1848, the optically clear adhesive 1844, and the outer cover 1842 may have the same or substantially similar index of refraction. For example, in some cases the indices of refraction of the inner cover 1848, the optically clear adhesive 1844, and the outer cover 1842 differ by less than about 5%. In some cases, the inner cover 1848, the optically clear adhesive 1844, and the outer cover 1842 each have a refractive index between about 1.7 and about 1.8. The inner cover 1848 and outer cover 1842 may be formed of the same or different materials. Example materials of the inner cover 1848 and the outer cover 1842 include sapphire, glass, polymers (e.g., polycarbonate, acrylic, etc.), or the like.

The cover assembly 1840 may include one or more coatings, dyes, inks, layers, or other materials or treatments that render the cover assembly 1840 visually opaque (e.g., opaque to at least some portions of light in the visible spectrum). While the cover assembly 1840 may appear visually opaque, it may be at least partially transparent to light from the emitter assembly 1822 (e.g., to allow the depth sensor module to function, while also occluding the depth sensor module from visibility).

Figure 19A:
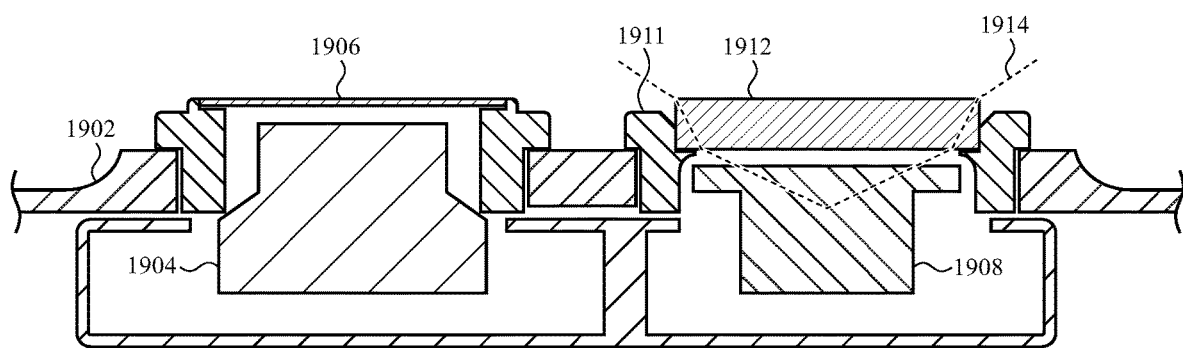
FIG. 19A depicts a partial cross-sectional view of an example electronic device, illustrating an example rear camera configuration.

FIG. 19A depicts a partial cross-sectional view of a device through a portion of a rear-facing sensor array (e.g., the sensor array 141, FIG. 1D), viewed along line 19-19 in FIG. 1D, for example. FIG. 19A illustrates a first lens assembly 1904 of a camera (e.g., the second camera 144, FIG. 1D) and a second lens assembly 1908 of another camera (e.g., the third camera 146, FIG. 1D).

As shown in FIG. 19A, the second lens assembly 1908 is shorter than that of the first lens assembly 1904. Accordingly, when positioned in the device (e.g., through the openings in the sensor region of the rear cover 1902), the first lens assembly 1904 extends a first distance into its hole, while the second lens assembly 1908 extends a second distance into its hole, the second distance less than the first distance. The terminal end of the second lens assembly 1908 is positioned further below the top surfaces of the cover windows 1906, 1912 (which may be substantially co-planar) than the first lens assembly 1908.

In some cases, the second lens assembly 1908 is a wide angle lens (e.g., having a 120° or greater field of view). As such, because the second lens assembly 1908 is shorter (and/or is positioned more distant from the top surfaces of the covers 1906, 1912), if a cover 1912 over the second lens assembly 1908 were to have the same thickness as the cover 1906, the second lens assembly 1908 may capture in its field of view a portion of the camera window trim 1911 that is attached to the rear cover 1902 and surrounds the opening of the second lens assembly 1908. This may produce undesirable artifacts in the images captured by the camera or limit the usable field of view of the second lens assembly 1908. Accordingly, the cover 1912 may be thicker than the cover 1906, despite having a top surface that is substantially co-planar or flush with the top surface of the cover 1906. The co-planarity of the two covers 1912 and 1906 may help to stabilize the device when the device is placed (face up) on a surface such as a table. In particular, if one of the covers were higher than another, the device may wobble or tip back and forth on a surface due to having only two points of contact between the device and the surface. By having both covers 1912, 1906 co-planar (e.g., protruding a same distance from the back cover of the device), the device may have three points of contact with the surface, thereby inhibiting tipping or wobbling on the surface.

The thickness of the cover 1912 may refract light entering the cover 1906, as shown by ray trace 1914, such that the full field of view of the second lens assembly 1908 may be used without capturing the window trim 1911 in the frame. In this way, the exterior surfaces of the cover windows 1906, 1912 may be substantially co-planar, while also accommodating the different heights (or positions) of the lens assemblies in the device, and also using the full field of view of the wide-angle lens.

In some cases, the positioning of the camera window trim 1911 helps reduce light interference from various sources. For example, the camera window trim 1911 may act as a lens hood to reduce flare from low-angle light sources, strobe or flash output, or the like.

The cover 1906 may have a thickness between about 0.2 mm and about 0.5 mm, while the cover 1912 may have a thickness between about 1.8 mm and about 2.5 mm. The covers 1906 and 1912 may be formed from the same material or different materials. The covers 1906 and 1912 may be formed from sapphire, glass, polycarbonate, acrylic, or any other suitable material.

Figure 19B:
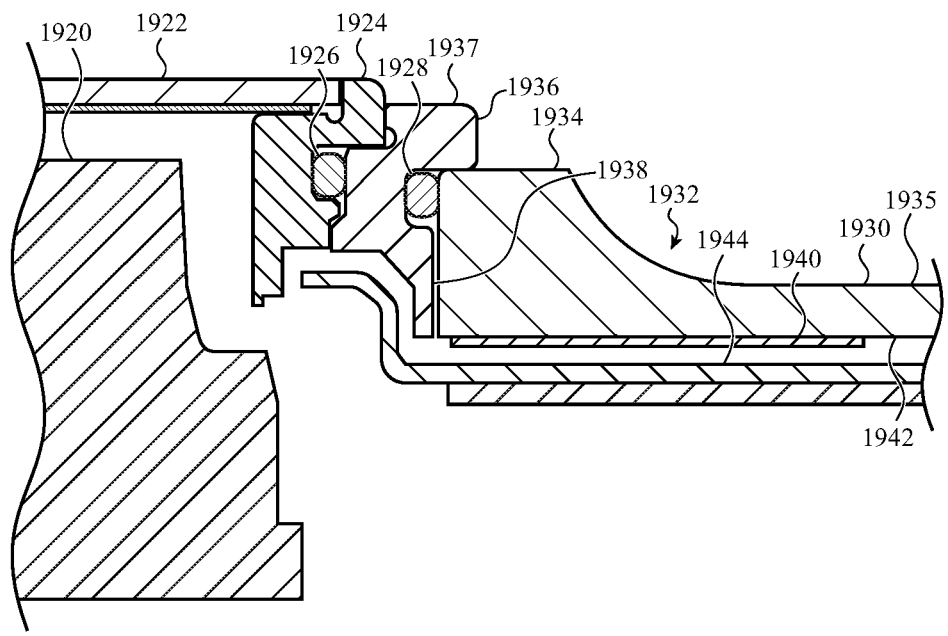
FIG. 19B depicts a partial cross-sectional view of an example electronic device, illustrating an example arrangement of a window trim in a rear cover of the electronic device.

Devices as described herein may include rear covers that are formed from a transparent material such as glass. Further, the rear covers may include a rear-facing sensor array region, in which rear-facing sensors such as cameras, depth sensors, microphones, or the like may be positioned. The rear-facing sensor array region of a rear cover may be a portion of the rear cover that has a greater thickness than a main portion of the rear cover. Further this region may define holes that receive and/or accommodate cameras, depth sensors, microphones, etc. Due to the transition in thickness and the transparency of the material of the rear cover, a direct line of sight may exist from a user to the sensors or other components of the rear sensor array. For example, FIG. 19B is a partial cross-sectional view of a device, through a portion that includes a rear cover 1935 and a camera. The components and features described with respect to FIG. 19B may be used in conjunction with any of the cameras described herein. The rear cover 1935 defines a main portion 1930 (defining a first surface), a sensor region portion 1934 having a greater thickness than the main portion 1930 (and defining a second surface), and a transition region 1932 extending from the main portion 1930 to the sensor region portion 1934. The transition region 1932 may define a curved surface (or alternatively a flat surface) that extends from and joins the first surface (of the main portion 1923) and the second surface (of the sensor region portion 1934). Because the rear cover 1935 is formed of a transparent material (e.g., glass, sapphire, etc.), the transition region 1932 and/or the sensor region portion 1934 may allow a line of sight into the device, and specifically towards the structural components of or nearby a camera assembly.

FIG. 19B depicts an example configuration in which the visual path through the transition region 1932 and/or the sensor region portion 1934 is blocked. In the example shown, a lens assembly 1920 of a camera is positioned below a cover 1922. The cover 1922 is attached to a first trim ring 1924, which may be coupled to a second trim ring 1936. In some cases, a first sealing member 1926 (e.g., an O-ring) may be positioned between the first and second trim rings 1924, 1936, and a second sealing member 1928 (e.g., an O-ring) may be positioned between the second trim ring 1936 and the rear cover 1935. The first and second sealing members 1926, 1928 may inhibit ingress of water, dust, or other contaminants into the device. Because the sealing member 1928 contacts the vertical wall of the rear cover 1935 (e.g., the wall that defines the hole for the camera assembly), the sealing member 1928 may be visible through the transition region 1932 and/or the sensor region portion 1934 of the rear cover 1935. Accordingly, the sealing member 1928 may have a color that is the same as or similar to the color of the second trim ring 1936. For example, the sealing member 1928 and the second trim ring 1936 may both be black. Other colors are also contemplated for both of these components (e.g., silver, white, grey, etc.).

In order to block the line of sight into the device, the device may include one or more blocking features. For example, as shown in FIG. 19B, the second trim ring 1936 may define an extended wall portion 1938 that extends from an exterior surface of the rear cover 1935 (e.g., the exterior surface of the raised sensor array region of the rear cover 1935) to the interior surface 1942 of the rear cover 1935 (e.g., an end surface of the extended wall 1938 is substantially flush with the interior surface 1942 of the rear cover 1935). The extended wall 1938 blocks the line of sight through the vertical wall (of the rear cover 1935) that defines the hole, thus occluding the visibility of internal components such as a frame structure 1944 (or, if the frame structure 1944 were omitted, the lens assembly 1920 and/or other internal components of the device). More particularly, the extended wall 1938 blocks light that passes through the hole surface. The second trim ring 1936 may also include a flange portion 1937 extending from the wall 1938 and contacting the exterior surface of the raised sensor array region. The flange portion 1937 also defines an opening, in which a cover window and optionally the first trim ring may be positioned.

An opaque mask 1940 may be included on at least a portion the interior surface 1942 of the rear cover 1935 to block the line of sight through the interior surface 1942. The opaque mask 1940 may be an ink, dye, film, paint, adhesive foam, or any other suitable material(s) that occlude the visibility of internal components through the interior surface 1942. In some cases, the opaque mask 1940 is only applied to a region of the interior surface 1942 that is proximate the camera hole (e.g., such that all or a substantial portion of the main portion 1930 of the rear cover 1935 does not include the opaque mask 1940.

Figure 19C:
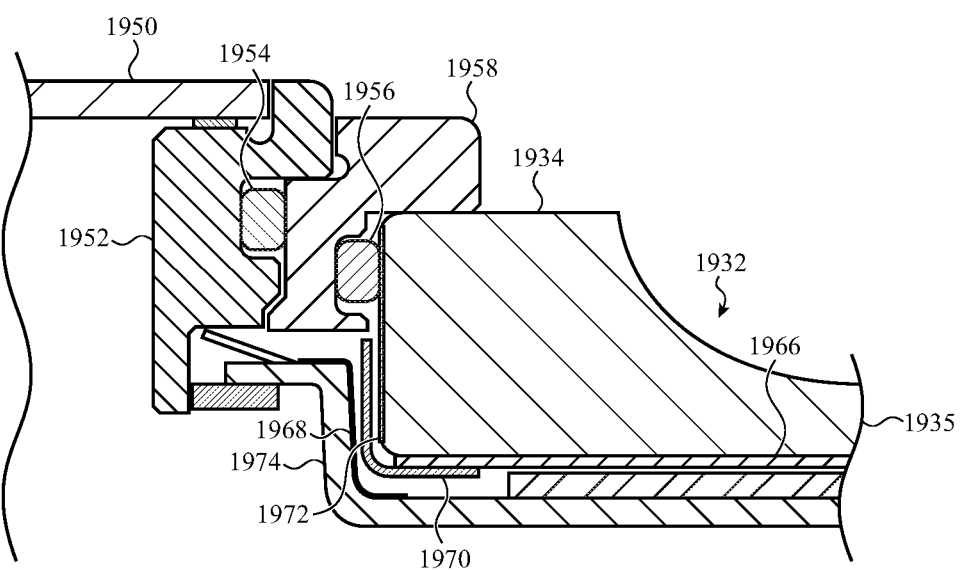
FIG. 19C depicts a partial cross-sectional view of an example electronic device, illustrating another example arrangement of a window trim in a rear cover of the electronic device.

FIG. 19C depicts another example configuration in which the visual path through the transition region 1932 and/or the sensor region portion 1934 is blocked. FIG. 19C includes numerous example techniques that may be used to reduce the visibility into the device through the rear cover, though not all of these example techniques are necessarily implemented in the same device. In the example shown in FIG. 19C, a lens assembly of a camera may be positioned below a cover 1950. The cover 1950 is attached to a first trim ring 1952, which may be coupled to a second trim ring 1958. In some cases, a first sealing member 1954 (e.g., an O-ring) may be positioned between the first and second trim rings 1952, 1958, and a second sealing member 1956 (e.g., an O-ring) may be positioned between the second trim ring 1958 and the rear cover 1935. The first and second sealing members 1954, 1956 may inhibit ingress of water, dust, or other contaminants into the device.

Whereas the second trim ring 1936 in FIG. 19B had an extended wall that blocked the line of sight through the vertical wall that defines the hole for the camera, the second trim ring 1958 in FIG. 19C does not extend fully to the interior surface. Accordingly, an opaque mask 1972 may be included on at least a portion of the vertical wall (e.g., the surface of the hole formed through the rear cover) to block the line of sight through the vertical wall. The opaque mask 1972 may be an ink, dye, film, paint, adhesive foam, or any other suitable material(s) that occlude the visibility of internal components through the vertical wall. In some cases, instead of or in addition to the opaque mask 1972, the vertical wall may have a surface treatment (e.g., a surface texture) that renders the vertical wall translucent. In some cases, a surface texture of the vertical wall is characterized by a surface roughness value ($R_a$) of between about 1.5 microns and about 10 microns.

In some cases, instead of or in addition to the opaque mask 1972, a bracket 1970 may be positioned along (and either contacting or set apart from) a portion of the vertical wall of the rear cover 1935 and at least a portion of the interior surface of the rear cover 1935. The bracket 1970 may block the line of sight through these portions of the rear cover 1935. The bracket 1970 may be formed from any suitable material (e.g., metal, polymer, etc.). The bracket 1970 may be opaque, and/or may have a color that reduces the noticeability of the bracket 1970 itself (e.g., a color that matches nearby components, a dark and/or matte color that absorbs light and hides or minimizes visible features, etc.). The bracket 1970 may include an ink, dye, film, paint, or the like, to provide the color. In some cases, the bracket 1970 is attached to one or both of the vertical wall or the interior surface of the rear cover via an adhesive.

In some cases, such as examples where the mask 1972 and/or the bracket 1970 are not included, a mask 1968 may be positioned on an internal component 1974 (e.g., a frame member) that may otherwise be visible through the rear cover 1935. The internal component 1974 may define a first portion extending along an interior surface of the rear cover, and a second portion extending at least partially into the hole in which the trim rings and camera components are at least partially positioned. In some cases, the second portion of the internal component 1974 may at least partially overlap the wall portion of a trim ring. The mask 1968 may be positioned along at least a portion of each of the first and second portions of the internal component 1974, and may be configured to reduce the visibility or noticeability of the component 1974 to which the mask 1968 is applied. The mask 1968 may be opaque, and/or may have a color that reduces the noticeability of the component (e.g., a color that matches nearby components, a dark and/or matte color that absorbs light and hides or minimizes visible features, etc.). The mask 1968 may be an ink, dye, film, paint, adhesive foam, or any other suitable material(s).

In some cases, an opaque mask 1966 may be included on at least a portion of the interior surface of the rear cover 1935 to block the line of sight through the interior surface. The opaque mask 1966 may be an ink, dye, film, paint, adhesive foam, or any other suitable material(s) that occlude the visibility of internal components through the interior surface. In some cases, the opaque mask 1966 is only applied to a region of the rear cover 1935 that is proximate the camera hole (e.g., such that all or a substantial portion of the main portion 1930 of the rear cover 1935 does not include the opaque mask 1966.

In some cases, instead of or in addition to the techniques described with respect to FIGS. 19B and 19C for occluding the line of sight into the device through the transition region 1932, the transition region 1932 (and/or other portions of the rear cover) may include a surface texture that renders the exterior surface of the transition region 1932 translucent.

The surface texture may be formed using laser etching, chemical etching, abrasive blasting, grinding, or any other suitable technique.

FIGS. 19B-19C illustrate an example camera configuration that includes two trim rings (e.g., first and second trim rings 1924, 1936 in FIG. 19B, and first and second trim rings 1952 and 1958 in FIG. 19C). While other example camera systems shown herein may include only one trim piece, it will be understood that the configurations shown in FIGS. 19B-19C may be applied to any devices and/or cameras shown or described herein.

As noted above, the devices described herein may include a flash (e.g., a light source) that is configured to illuminate a scene to facilitate capturing images with one or more cameras of the electronic device. The flash, also referred to as a flash module or more broadly a light source, may include one or more light emitting diodes (LEDs) that produce the light to illuminate the scene. The flash module may be part of or positioned proximate a sensor array to facilitate illumination of scenes for flash photography.

Figure 20A:
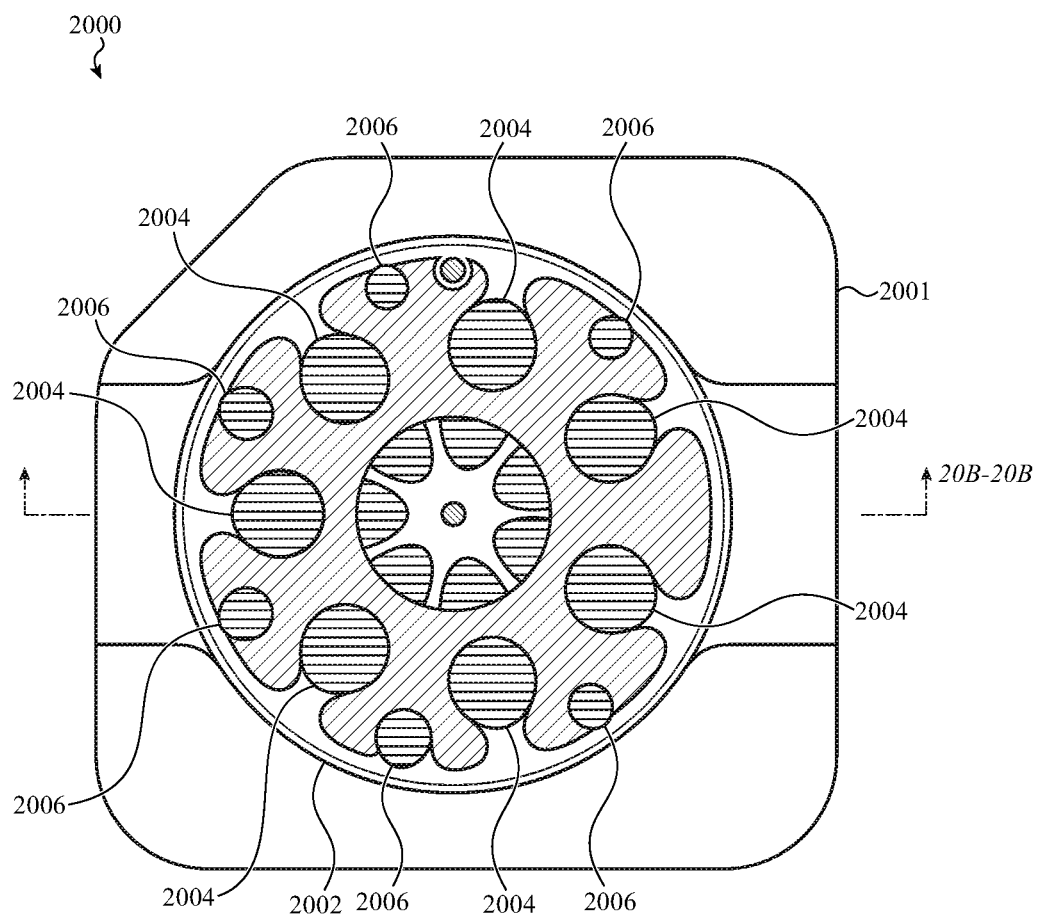
FIG. 20A depicts a flash module of an example electronic device.

FIG. 20A illustrates a back view of a flash module 2000 (e.g., the side of the flash module that faces the interior of the device) that may be used with the devices described herein. For example, the flash module may be part of the rear-facing sensor array of a device. The flash module 2000 may include a carrier 2001 and a circuit board 2002. The circuit board 2002 may be attached to the carrier 2001, and the carrier 2001 may be secured to the device (e.g., in an opening or proximate a window in a rear cover of the device).

The circuit board 2002 may include electrical contact pads 2004 and 2006 arranged in a generally circular arrangement. For example, the circuit board 2002 may include a set of first contact pads 2004 arranged in a first generally circular arrangement (e.g., along a circle having a first diameter), and a set of second contact pads 2006 arranged in a second generally circular arrangement (e.g., along a circle having a second diameter that is larger than the first diameter) and around the set of first contact pads 2004. The set of first contact pads 2004 and/or the set of second contact pads 2006 may be spaced evenly about their respective circles (e.g., having a same distance between any two adjacent contact pads).

The set of first contact pads 2004 may be used to conductively couple the LEDs (and/or other circuitry, processors, or other electrical components) of the flash module 2000 to other circuitry and/or components of a device. Thus, wires, traces, leads, or other conductive elements may be soldered, welded, or otherwise conductively coupled to the set of first contact pads 2004. The set of second contact pads 2006 may also be conductively coupled to the LEDs (and/or other circuitry, processors, or other electrical components) of the flash module 2000, and may be provided to facilitate testing of the flash module without having to make physical contact with the set of first contact pads 2004, thereby avoiding potential damage or contamination of the set of first contact pads 2004.

Figure 20B:
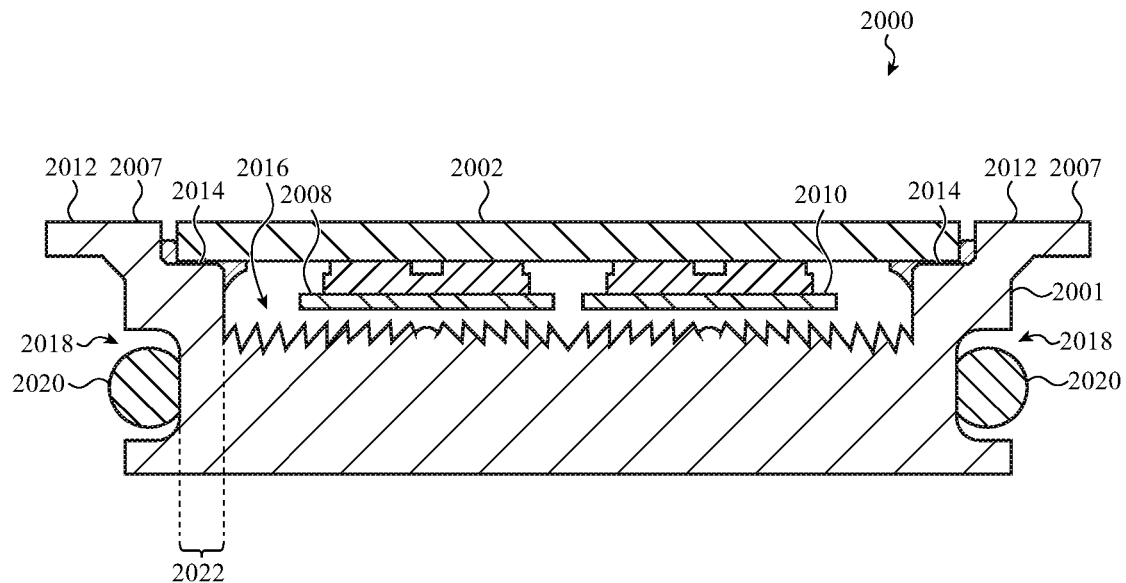
FIG. 20B depicts a partial cross-sectional view of the flash module of FIG. 20A.

FIG. 20B is a partial cross-sectional view of the flash module 2000, viewed along line 20B-20B in FIG. 20A, showing an example integration of the circuit board 2002 with the carrier 2001. The carrier 2001 may be a single unitary piece of light transmissive material, such as glass, a light-transmissive polymer, sapphire, or the like.

The carrier 2001 may define a ledge 2014, which may define a recess in which the circuit board 2002 is positioned. For example, the ledge 2014 may be recessed relative to a back surface 2012 of the carrier 2001. The ledge 2014 may be recessed from the back surface 2012 a distance that is substantially equal to the thickness of the circuit board 2002 or is otherwise configured based on a dimension of the circuit board 2002 such that the back of the circuit board 2002 is flush with or recessed relative to the back surface 2012 of the carrier 2001. The circuit board 2002 may be attached to the carrier 2001 via an adhesive (e.g., between the ledge 2014 and the circuit board 2002).

In some cases, a coating 2007, such as an ink, mask, dye, paint, film, a vapor deposition coating (e.g., chemical or plasma vapor deposition), or the like, may be applied to the back surface 2012. In some cases, the coating 2007 is an opaque white coating. In other cases, the coating 2007 is a mirror-like reflective coating (e.g., a silver PVD or CVD coating). The coating 2007 may prevent or limit the visibility of internal components of a device through the material of the carrier 2001, and may help avoid the presence of a black or dark ring-like appearance around the perimeter of the flash module 2000 (e.g., when the external-facing surface of the flash module 2000 is viewed when the flash module 2000 is integrated with a device).

FIG. 20B also shows light emitting elements 2008 and 2010 (e.g., LEDs) attached to the circuit board 2002 and configured to emit light downward, towards a lens portion 2016 of the carrier 2001. The lens portion 2016 may be or define a Fresnel lens (or other type of lens) that focuses, diffuses, or otherwise changes the light to produce a desired spread or illumination angle. The lens portion 2016 may be integrally formed into the carrier 2001 (e.g., the material of the carrier 2001 may define the lens portion 2016). In some cases, the lens portion 2016 may be a separate element that is attached to the carrier 2001.

The carrier 2001 may also define a recess 2018 in a sidewall to receive a compliant member 2020. The compliant member 2020 may be an O-ring (or other suitable compliant member) and may be configured to form an environmental seal between the carrier 2001 and part of the housing of the device in which it is integrated (e.g., the surfaces of a hole or recess in a rear cover of a device).

Figure 20C:
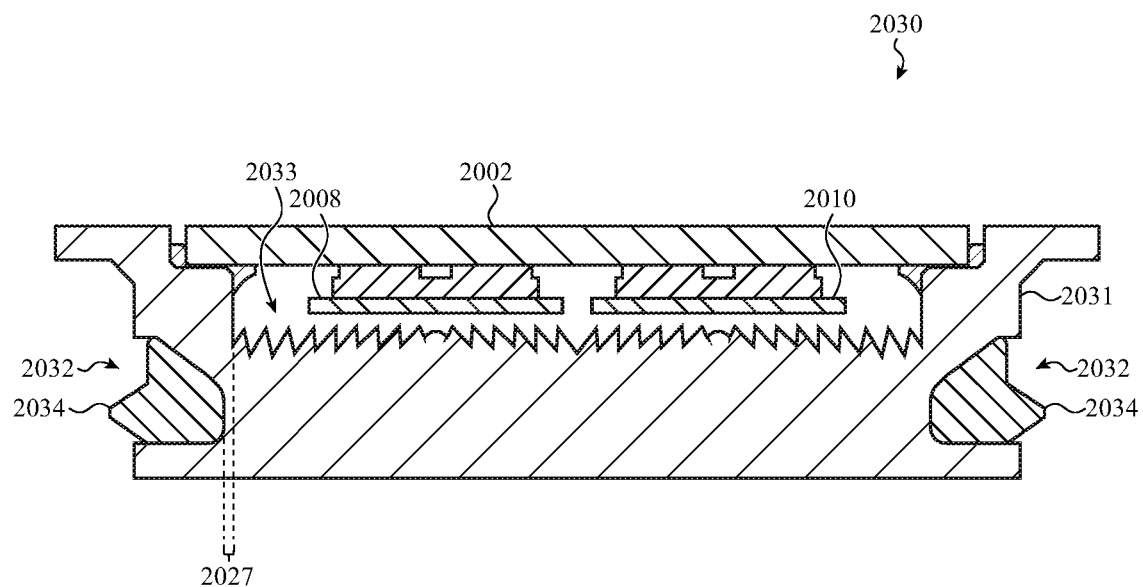
FIG. 20C depicts a partial cross-sectional view of another example flash module.

FIG. 20C is a partial cross-sectional view of a flash module 2030, showing a view similar to that of FIG. 20B. The flash module 2030 includes a differently configured carrier 2031 and compliant member 2034. In particular, the carrier 2031 may define a shaped recess 2032 in a sidewall, and the shaped recess 2032 is configured to receive a shaped compliant member 2034. The shaped compliant member 2034 may be molded in place in the recess 2032. For example, a flowable material, such as a polymer material, may be introduced into the shaped recess 2032 and allowed to at least partially cure to form the compliant member 2034. An external mold or other tool may surround the carrier 2031 during the polymer introduction and/or injection process to form the shape of the exterior surfaces of the compliant member 2034.

The shaped compliant member 2034 (and the shaped recess 2032) may extend further into the sidewall of the carrier 2031 than the compliant member 2020 and the recess 2018 in FIG. 20B. This configuration may allow the compliant member 2034, which may be opaque, to occlude or otherwise block the appearance of the internal components of the flash module 2030 and the internal components of a device more generally. For example, the shaped compliant member 2034 extends into the sidewall of the carrier 2031 such that there is a distance 2027 between the end of the shaped compliant member 2034 and the outer perimeter of the lens portion 2033 of the carrier 2031. By contrast, as shown in FIG. 20B, the compliant member 2020 may extend a shorter distance into the sidewall, resulting in a distance 2022 (which is greater than the distance 2027), thereby potentially allowing more visibility into the internals of the flash module and the device. The greater depth of the shaped recess 2032 and the increased size and the contoured shape of the compliant member 2034 may also result in a more dimensionally stable compliant member 2034 that can stay in a desired position through greater forces and deflections, as compared to an O-ring for example.

As with the carrier 2001, the carrier 2031 may be a single unitary piece of light transmissive material, such as glass, a light-transmissive polymer, sapphire, or the like. The flash module 2030 may also include the circuit board 2002 and the light emitting elements 2008 and 2010 (e.g., LEDs), and the circuit board 2002 may be attached to the carrier 2031 in the same or similar manner as the flash module 2030.

Figure 20D:
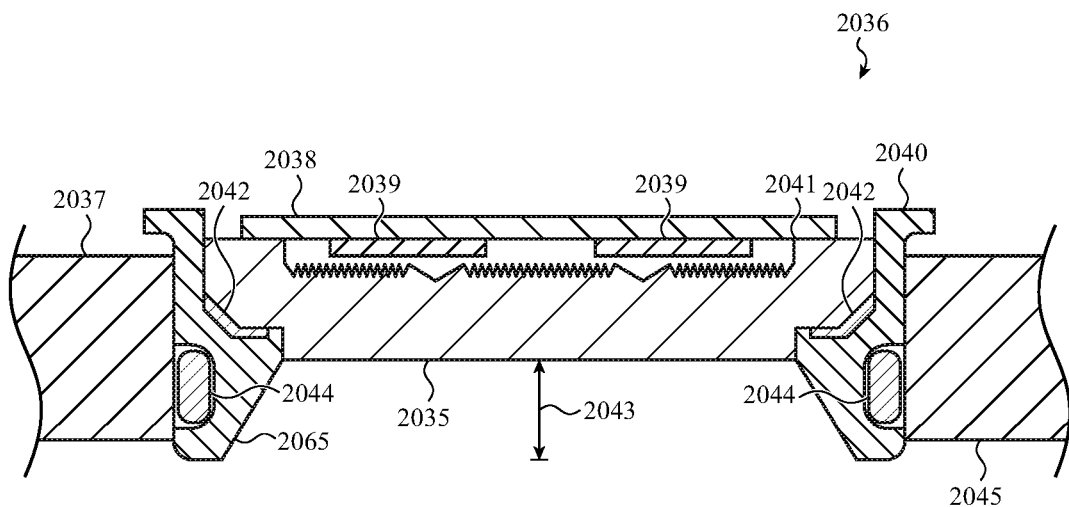
FIGS. 20D-20G depict partial cross-sectional views of example flash modules for electronic devices.

FIG. 20D is a partial cross-sectional view of a flash module 2036, showing an example integration of the flash module 2036 into a rear cover 2037 of an electronic device. The flash module 2036 may be positioned in a hole formed in a rear-facing sensor array defined by the rear cover 2037. The flash module 2036 includes a circuit board 2038 and light emitting elements 2039 (e.g., LEDs) attached to the circuit board 2038 and configured to emit light downward, towards a carrier 2041. The carrier 2041 may define a lens portion, such as a Fresnel lens (or other type of lens) that focuses, diffuses, or otherwise changes the light to produce a desired spread or illumination angle. The carrier 2041 (and the lens portion it defines) may be formed from a transparent material such as glass, polymer, polycarbonate, acrylic, or the like.

The flash module 2036 may also include a trim piece 2040 that surrounds the carrier 2041, and to which the carrier 2041 may be attached. For example, the carrier 2041 may be attached to the trim piece 2040 via an adhesive 2042. A sealing member 2044, such as an O-ring or other compliant member, may be positioned at least partially in a recess in the trim piece 2040, and may contact the trim piece 2040 and a surface of the rear cover 2037 that defines the hole in which the flash module 2036 is positioned. The sealing member 2044 may form an environmental seal between the trim piece 2040 and the rear cover 2037.

The trim piece 2040 may be opaque (e.g., it may be formed from an opaque material, or coated, painted, or otherwise treated to be opaque). The opaque trim piece 2040 may inhibit or prevent light emitted by the light emitting elements 2039 from entering the rear cover 2037, such as through the surfaces of the rear cover 2037 that define the hole in which the flash module 2036 is positioned. For example, light leakage into the rear cover 2037 through the hole surfaces may leak out of the rear cover 2037 near cameras or other light-sensitive components of the rear-facing sensor array, which may interfere with the operation of those components. As one specific example, light leakage may cause pictures captured by a rear-facing camera to have a hazy appearance that reduces the quality of the pictures. As another example, rear-facing depth sensors may not be able to properly make depth measurements due to the interference from such light leaks. Accordingly, the opaque trim piece 2040 may reduce or eliminate such light leakage. The trim piece 2040 may be a metal, polymer, or any other suitable material.

As shown in FIG. 20D, an exterior surface 2035 of the carrier 2041 may be recessed a distance 2043 relative to an exterior surface 2045 of the rear cover 2037. The exterior surface 2065 of the trim piece 2040, which is opaque, prevents light that is emitted from the recessed surface 2035 from entering the rear cover 2037. Further, the angle of the exterior surface 2065 of the trim piece 2040 (which may have a conical shape) may define the pattern of illumination produced by the flash module 2036. The pattern of illumination may be configured to illuminate a particular field of view that coincides with a target field of view of a camera of the rear-facing sensor array. The target field of view may be a particular distance from a camera of the rear-facing sensor array, at a particular magnification level for that camera.

Figure 20E:
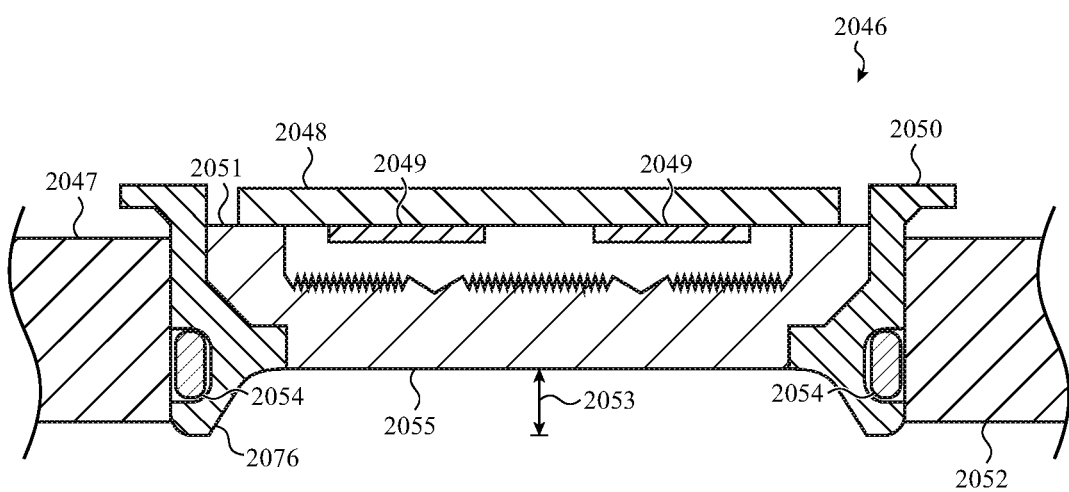

FIG. 20E is a partial cross-sectional view of another example flash module 2046, showing an example integration of the flash module 2046 into a rear cover 2047 of an electronic device. The flash module 2046 may be positioned in a hole formed in a rear-facing sensor array defined by the rear cover 2047. The flash module 2046 includes a circuit board 2048 and light emitting elements 2049 (e.g., LEDs) attached to the circuit board 2048 and configured to emit light downward, towards a carrier portion 2051. The carrier portion 2051 may define a lens, such as a Fresnel lens (or other type of lens) that focuses, diffuses, or otherwise changes the light to produce a desired spread or illumination angle. The carrier portion 2051 (and the lens portion it defines) may be formed from a transparent material such as glass, polymer, polycarbonate, acrylic, or the like.

The flash module 2046 may also include a trim portion 2050 that surrounds the carrier portion 2051. While the trim piece 2040 and carrier 2041 in FIG. 20D were two separately manufactured components that were attached together, the trim portion 2050 and the carrier portion 2051 in FIG. 20E may be manufactured using a two-shot molding process. In particular, a first material (e.g., a transparent polymer material) may be introduced into a mold to form the carrier portion 2051, and subsequently a second material (e.g., an opaque polymer material) may be introduced into the mold and against the first material to form the trim portion 2050. The combination carrier portion and trim portion may then be removed from the mold as a single component. In some cases, the order in which the first and second materials are introduced into the mold may be reversed. The first and second materials may be different materials (e.g., different polymers), or they may be transparent and opaque versions of the same material. By forming the carrier portion 2051 and trim portion 2050 as a single component, assembly time and complexity may be reduced relative to a multi-part assembly.

A sealing member 2054, such as an O-ring or other compliant member, may be positioned at least partially in a recess in the trim portion 2050, and may contact the trim portion 2050 and a surface of the rear cover 2047 that defines the hole in which the flash module 2046 is positioned. The sealing member 2054 may form an environmental seal between the trim portion 2050 and the rear cover 2047.

As noted above, the trim portion 2050 may be opaque. The opaque trim portion 2050 may inhibit or prevent light emitted by the light emitting elements 2049 from entering the rear cover 2047, such as through the surfaces of the rear cover 2047 that define the hole in which the flash module 2046 is positioned. Accordingly, the opaque trim portion 2050 may reduce or eliminate such light leakage.

As shown in FIG. 20E, an exterior surface 2055 of the carrier portion 2051 may be recessed a distance 2053 relative to an exterior surface 2052 of the rear cover 2047. The exterior surface 2076 of the trim portion 2050, which is opaque, prevents light that is emitted from the recessed surface 2055 from entering the rear cover 2037. Further, the angle of the exterior surface 2076 of the trim portion 2050 (which may have a conical shape) may define the pattern of illumination produced by the flash module 2046. The pattern of illumination may be configured to illuminate a particular field of view that coincides with a target field of view of a camera of the rear-facing sensor array. The target field of view may be a particular distance from a camera of the rear-facing sensor array, at a particular magnification level for that camera.

Figure 20F:
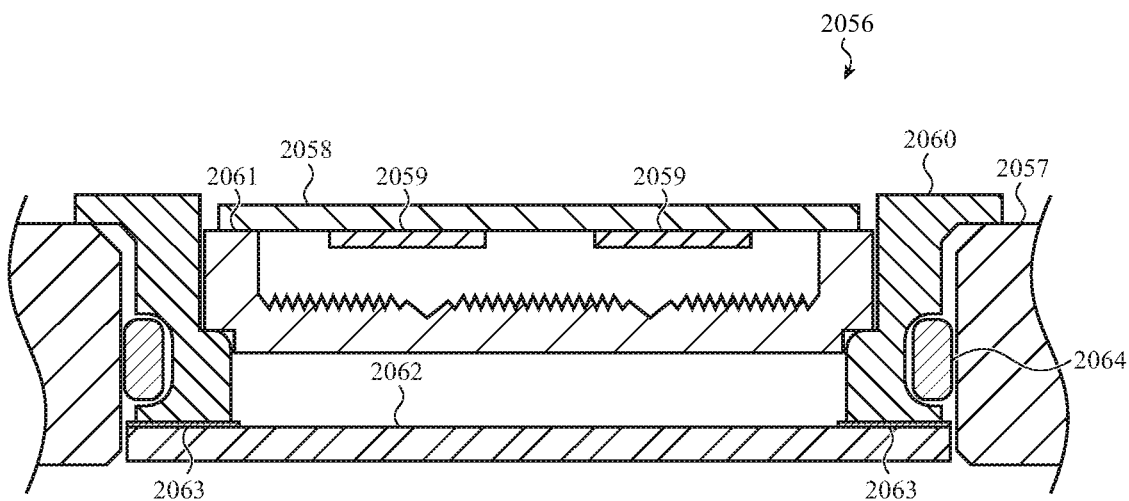

FIG. 20F is a partial cross-sectional view of another flash module 2056, showing an example integration of the flash module 2056 into a rear cover 2057 of an electronic device. The flash module 2056 may be positioned in a hole formed in a rear-facing sensor array defined by the rear cover 2057. The flash module 2056 includes a circuit board 2058 and light emitting elements 2059 (e.g., LEDs) attached to the circuit board 2058 and configured to emit light downward, towards a carrier 2061. The carrier 2061 may define a lens portion, such as a Fresnel lens (or other type of lens) that focuses, diffuses, or otherwise changes the light to produce a desired spread or illumination angle. The carrier 2061 (and the lens portion it defines) may be formed from a transparent material such as glass, polymer, polycarbonate, acrylic, or the like.

The flash module 2056 may also include a trim piece 2060 that surrounds the carrier 2061, and to which the carrier 2061 may be attached. For example, the carrier 2061 may be attached to the trim piece 2060 via an adhesive. A sealing member 2064, such as an O-ring or other compliant member, may be positioned at least partially in a recess in the trim piece 2060, and may contact the trim piece 2060 and a surface of the rear cover 2057 that defines the hole in which the flash module 2056 is positioned. The sealing member 2064 may form an environmental seal between the trim piece 2060 and the rear cover 2057.

The trim piece 2060 may be opaque (e.g., it may be formed from an opaque material, or coated, painted, or otherwise treated to be opaque). The opaque trim piece 2060 may inhibit or prevent light emitted by the light emitting elements 2059 from entering the rear cover 2057, such as through the surfaces of the rear cover 2057 that define the hole in which the flash module 2056 is positioned. For example, light leakage into the rear cover 2057 through the hole surfaces may leak out of the rear cover 2057 near cameras or other light-sensitive components of the rear-facing sensor array, which may interfere with the operation of those components. Accordingly, the opaque trim piece 2060 may reduce or eliminate such light leakage. The trim piece 2060 may be a metal, polymer, or any other suitable material.

The flash module 2056 also includes a cover 2062 positioned over the exterior surface of the carrier 2061 and defining an exterior surface of the device. The cover 2062 may be formed from glass, sapphire, a polymer (e.g., polycarbonate, acrylic), or the like. The cover 2062 may be attached to the trim piece 2060 via an adhesive 2063. The cover may help prevent liquid, debris, or other materials from becoming caught in the recess defined by the exterior surface of the carrier 2061 and the walls of the trim piece 2060. In some cases, the adhesive 2063 is an opaque adhesive that hides the trim piece 2060 from view through the cover 2062. In other cases, an opaque material (e.g., an ink, dye, paint, film, layer, etc.) is applied to the adhesive 2063, the trim piece 2060, and/or the cover 2062 to block the trim piece 2060.

Figure 20G:
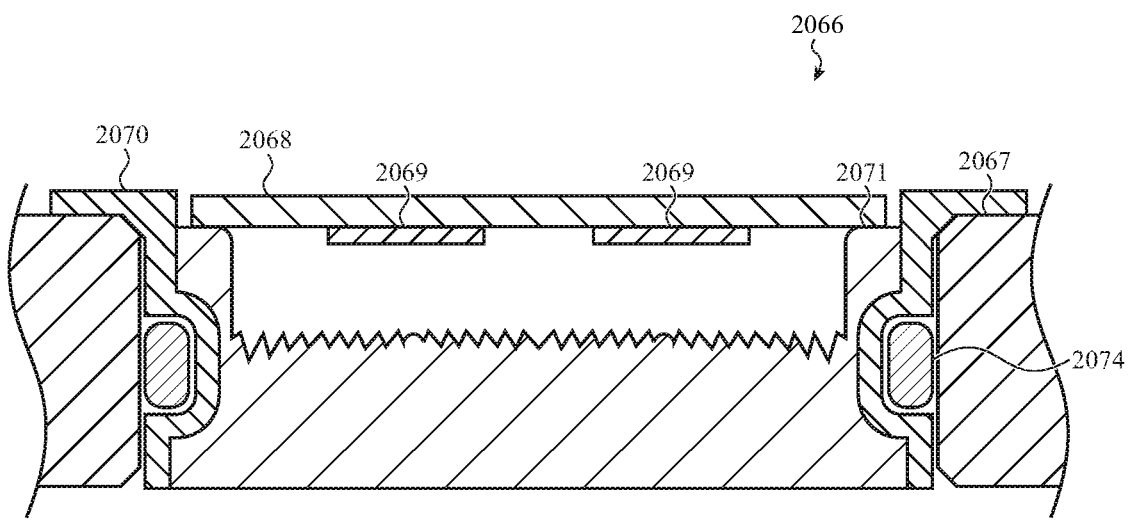

FIG. 20G is a partial cross-sectional view of another example flash module 2066, showing an example integration of the flash module 2066 into a rear cover 2067 of an electronic device. The flash module 2066 may be positioned in a hole formed in a rear-facing sensor array defined by the rear cover 2067. The flash module 2066 includes a circuit board 2068 and light emitting elements 2069 (e.g., LEDs) attached to the circuit board 2068 and configured to emit light downward, towards a carrier portion 2071. The carrier portion 2071 may define a lens, such as a Fresnel lens (or other type of lens) that focuses, diffuses, or otherwise changes the light to produce a desired spread or illumination angle. The carrier portion 2071 (and the lens portion it defines) may be formed from a transparent material such as glass, polymer, polycarbonate, acrylic, or the like.

The flash module 2066 may also include a trim portion 2070 that surrounds the carrier portion 2071. Similar to the trim portion 2050 and the carrier portion 2051 in FIG. 20E, the trim portion 2070 and the carrier portion 2071 may be manufactured using a two-shot molding process. In particular, a first material (e.g., a transparent polymer material) may be introduced into a mold to form the carrier portion 2071, and subsequently a second material (e.g., an opaque polymer material) may be introduced into the mold and against the first material to form the trim portion 2070. The combination carrier portion and trim portion may then be removed from the mold as a single component. In some cases, the order in which the first and second materials are introduced into the mold may be reversed. The first and second materials may be different materials (e.g., different polymers), or they may be transparent and opaque versions of the same material. By forming the carrier portion 2071 and trim portion 2070 as a single component, assembly time and complexity may be reduced relative to a multi-part assembly.

A sealing member 2074, such as an O-ring or other compliant member, may be positioned at least partially in a recess in the trim portion 2070, and may contact the trim portion 2070 and a surface of the rear cover 2067 that defines the hole in which the flash module 2066 is positioned. The sealing member 2074 may form an environmental seal between the trim portion 2070 and the rear cover 2067.

As noted above, the trim portion 2070 may be opaque. The opaque trim portion 2070 may inhibit or prevent light emitted by the light emitting elements 2069 from entering the rear cover 2067, such as through the surfaces of the rear cover 2067 that define the hole in which the flash module 2066 is positioned. Accordingly, the opaque trim portion 2070 may reduce or eliminate such light leakage.

Figure 21A:
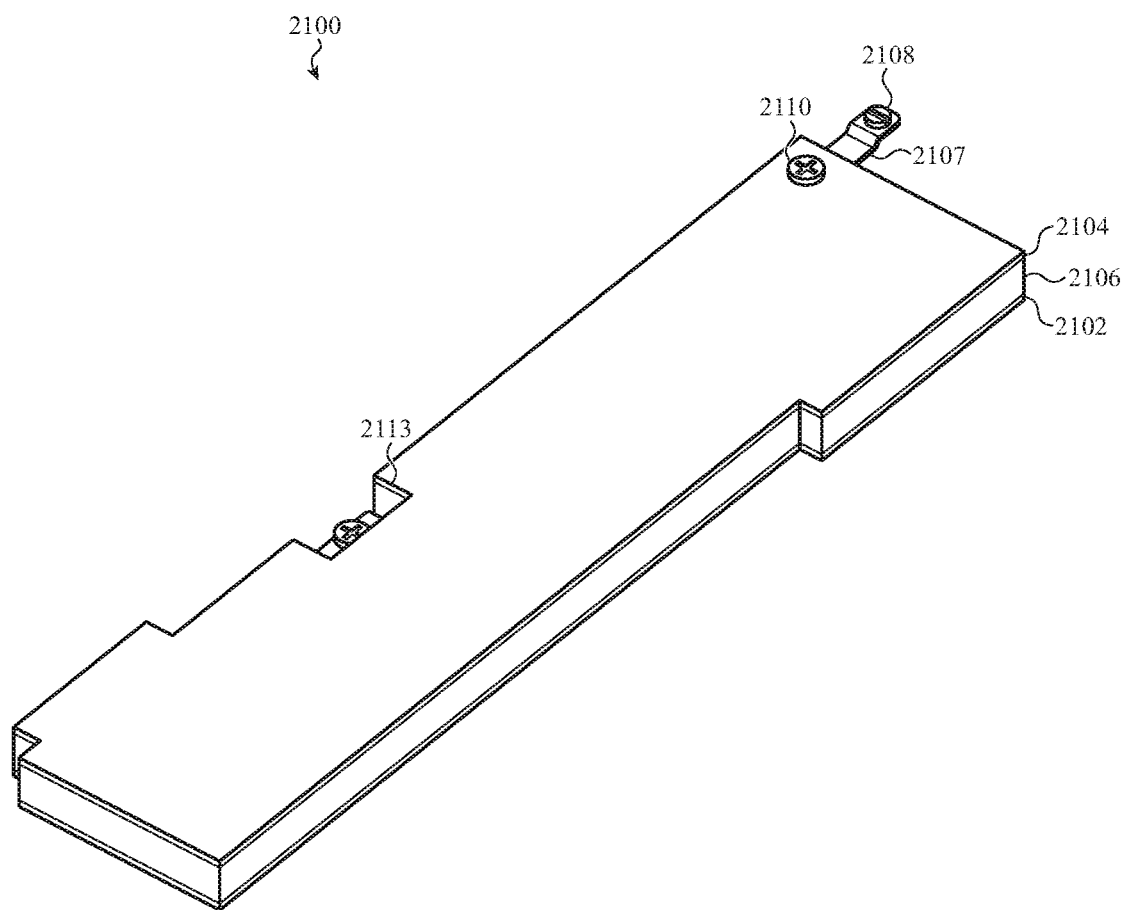
FIG. 21A depicts an example logic board for an electronic device.

As described herein, devices such as mobile phones may include logic boards, which may include processors, memory, and other electrical circuitry that control the device and/or portions of the device. FIG. 21A depicts an example logic board 2100 for a device. The logic board 2100 may correspond to or be an embodiment of the logic board 220, 320, or any other logic board described herein.

The logic board 2100 includes a first substrate 2102 and a second substrate 2104 supported above the first substrate 2102. The first and second substrates 2102, 2104 may also be referred to as circuit boards. Electrical components and/or circuit elements such as processors, memory, antenna circuitry, and the like, may be coupled to the first and/or the second substrates 2102, 2104.

The first and second substrates 2102, 2104 may be connected to one another via a wall structure 2106 (which supports the second substrate 2104 above the first substrate 2102). As described herein the first and second substrates 2102, 2104 may be soldered to conductive members (e.g., vias) in the wall structure 2106, thereby allowing components on the first and second substrates 2102, 2104 to be conductively coupled to one another via the wall structure 2106. The wall structure 2106 may also surround electrical components (e.g., a processor) and, along with the first and second substrates 2102, 2104, define a substantially enclosed and optionally sealed internal volume in which the processor (and/or other components) may be protected.

The logic board 2100 may be structurally mounted to a housing member or other structure of a device to secure the logic board 2100. To facilitate the structural mounting, the logic board 2100 may include a tab portion 2108 of an attachment member 2107, which may be attached to a post (e.g., the post 2114, FIG. 21B) or other structural component (e.g., via a fastener extending through a hole in the tab portion). The logic board 2100 may also include a notch region 2113 that exposes the first substrate 2102 so that a fastener may secure the logic board to a post or other structural component via the first substrate 2102.

The logic board 2100 may also act as a structural mounting point for other components of the device. Accordingly, mounting features may be provided on the logic board 2100 for both mounting the logic board 2100 to other components and for mounting other components to the logic board. For example, FIG. 21A shows a mounting stud 2110 attached to the second substrate 2104, and a tab portion 2108 extending from a side of the logic board 2100. As described herein, the mounting stud 2110 may be used to secure another component to the logic board 2100, while the tab portion 2108 is used to secure the logic board 2100 to a housing structure or other component of a device.

Figure 21B:
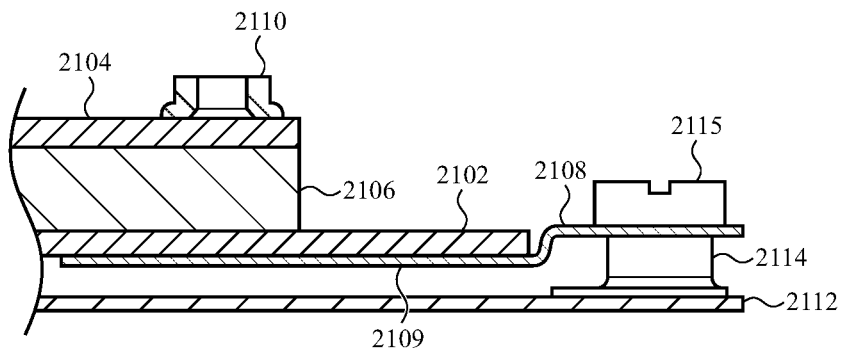
FIG. 21B depicts a partial cross-sectional view of the logic board of FIG. 21A.

FIG. 21B illustrates a side (and partially cut-away) view of a portion of the logic board 2100, showing example configurations for the mounting stud 2110 and the tab portion 2108. The mounting stud 2110 may be attached to a top surface of the second substrate 2104. The mounting stud 2110 may be attached to the second substrate 2104 via a soldering, welding, adhesive, or the like. Notably, the mounting stud 2110 does not extend into or through the second substrate 2104. In this way, the mounting stud 2110 does not impart any clamping, compression, or other such forces to the logic board. For example, in other implementations, a mounting point was provided by a fastener that extended through both the first and second substrates and was secured to the logic board with a clamping force. The mounting stud 2110 shown in FIGS. 21A and 21B, by contrast, provides a mounting point without imparting a compressive stress on the substrates, thereby reducing the risk of potential damage to the logic board due to over-tightening or otherwise generally constricting the logic board.

FIG. 21B also illustrates an example configuration of an attachment member 2107 that may be used to attach the logic board 2100 to the device. For example, FIG. 21B shows the tab portion 2108 secured to a post 2114 with a fastener (e.g., a screw) 2115 extending through a hole in the tab portion 2108. The post may be secured to or part of a substrate 2112, which may be a chassis (e.g., the chassis 219, 319) or any other suitable structure of a device. The tab portion 2108 may be attached to the logic board (e.g., to the first substrate 2102) via a mounting portion 2109. The mounting portion 2109 may be attached to the first substrate 2102 in any suitable way, including soldering, welding, adhesives, or the like. The tab portion 2108 may provide a degree of compliance to the physical coupling of the logic board 2100 to the device. For example, the material of the tab portion 2108 (and mounting portion 2109 where those components are unitary) may be more resilient or flexible than the substrates themselves. Further, the shapes, dimensions, curvatures, thicknesses, and material properties of the tab portion 2108 may be selected to provide a target degree of compliance and/or flexibility. Accordingly, the tab portion 2108 may flex to reduce the effects of forces (e.g., shock loading) on the logic board 2100 due to drop events, impacts, or other forceful events to which the device may be subjected.

Figure 21C:
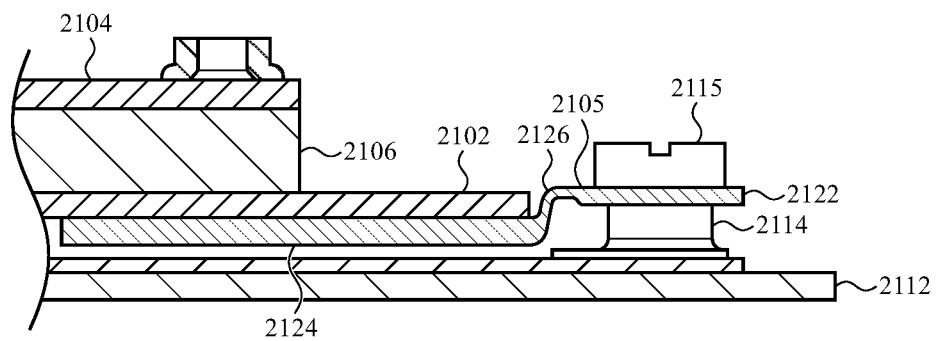
FIG. 21C depicts a partial cross-sectional view of another example logic board.

FIG. 21C illustrates another example configuration of an attachment member 2105 with a mounting portion 2124 and a tab portion 2122 that may be used to secure the logic board 2100 to the device. While the tab portion 2108 and the mounting portion 2109 in FIG. 21B are different portions of a unitary structure with a substantially uniform thickness (e.g., a stamped metal attachment member), the unitary structure defining the tab portion 2122 and mounting portion 2124 of the attachment member 2105 may have a variable thickness. For example, the mounting portion 2124 may have a first thickness, the tab portion 2122 may have a second thickness different from the first thickness, and a joining portion 2126 may have a third thickness that is different from the first and second thicknesses. The particular thicknesses of the mounting portion 2124, tab portion 2122, and joining portion 2126 may be configured to provide target strength and flexibility parameters. For example, the joining portion 2126 may be thinner than the mounting portion 2124 and tab portion 2122 to provide increased flexibility and/or compliance, while the mounting portion 2124 and tab portion 2122 may be thicker to provider greater rigidity and strength. The greater flexibility of the joining portion 2126 may help reduce the effects of forces (e.g., shock loading) on the logic board 2100 due to drop events, impacts, or other forceful events to which a device may be subjected, while the thicker mounting portion 2124 provides greater strength and stiffness to the first substrate 2102. The thicker (and stiffer) mounting portion 2124 also may improve the reliability of the bond between the mounting portion 2124 and the first substrate 2102 by ensuring that loads are evenly distributed throughout the bonding region between the mounting portion 2124 and the first substrate 2102. The thicker (and stronger) tab portion 2122 may provide greater strength to help resist breaking or other damage. The variable-thickness attachment member 2105 may be formed by forging, molding, welding multiple layers together, or the like.

Figure 21D:
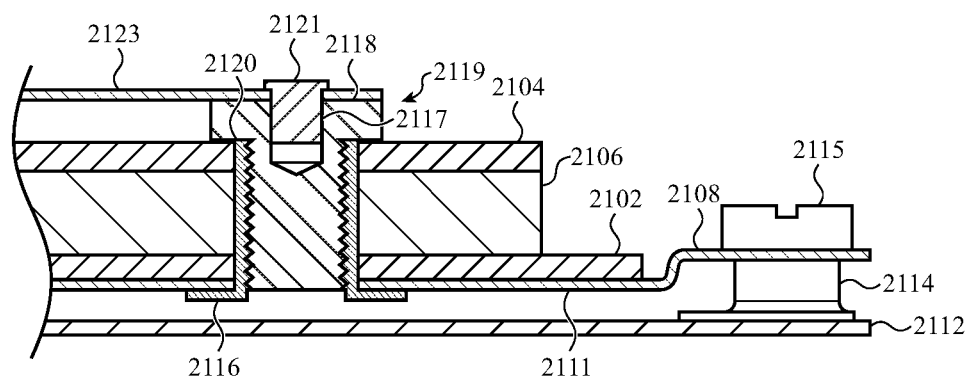
FIG. 21D depicts a partial cross-sectional view of another example logic board.

FIG. 21D illustrates another example technique for providing a mounting point on the logic board 2100 without imparting unwanted compressive forces onto the substrates 2102, 2104 and/or the wall structure 2106. In particular, a fastener assembly 2119 may be configured to retain the first substrate to the second substrate and may include a first fastener element, such as a flanged nut 2116, and a second fastener element, such as a fastener 2118. A barrel portion of the flanged nut 2116 may be positioned in holes formed through the first and second substrates 2102, 2104 and the wall structure 2106, while a flange portion of the flanged nut 2116 contacts an outer (e.g., bottom) surface of the second substrate 2104. The holes through the first and second substrates 2102, 2104 and the wall structure 2106 may be aligned (e.g., having collinear cylindrical axes) and may have a same inner diameter. Because the barrel portion of the flanged nut 2116 extends through the holes in the first and second substrates 2102, 2104 and the wall structure 2106, lateral motion (e.g., parallel to the outer surfaces of the substrates 2102, 2104) may be inhibited.

The flanged nut 2116 may have a height that is greater than the thickness of the combined first and second substrates 2102, 2104 and the wall structure 2106. That is, a top portion of the barrel of the flanged nut 2116 may extend above the top surface of the second substrate 2104, such that a flange portion of the fastener 2118, when secured to the flanged nut 2116, does not compress (or in some cases contact) the second substrate 2104. In some cases, the flanged nut 2116 may have a height that is equal to the thickness of the combined first and second substrates 2102, 2104 and the wall structure 2106.

The flange portion of the fastener 2118 may be seated against the end surface of the barrel of the flanged nut 2116. In cases where the end surface of the barrel portion extends past the outer surface of the first substrate 2102, the flange of the fastener 2118 does not contact the outer surface of the first substrate 2102, and does not compress the logic board.

In cases where the end surface of the barrel portion is flush with the outer surface of the first substrate, the flange portion of the fastener 2118 may contact the surface of the first substrate 2102 but not compress it (e.g., not apply a force to the logic board beyond a threshold (e.g., an incidental or nominal) amount). Stated another way, the distance between a contact surface of the flange portion of the flanged nut 2116 and a contact surface of the flange portion of the fastener 2118, when the fastener 2118 is secured to the flanged nut 2116, is equal to a distance from the outer surface of the first substrate 2102 to the outer surface of the second substrate 2104.

The fastener 2118 may define a receptacle 2117, which may be threaded, for receiving another fastener 2121 to secure a component (e.g., a metal shroud 2123, or another component) to the logic board 2100. Accordingly, a mounting point may be provided on the logic board 2100 without introducing a compressive stress on the logic board. In the implementation shown in FIG. 21D, a mounting portion 2111 may be configured so that it is not captured between the flanged nut 2116 and the first substrate 2102. In some cases, the fastener 2118 does not have the receptacle 2117.

Figure 21E:
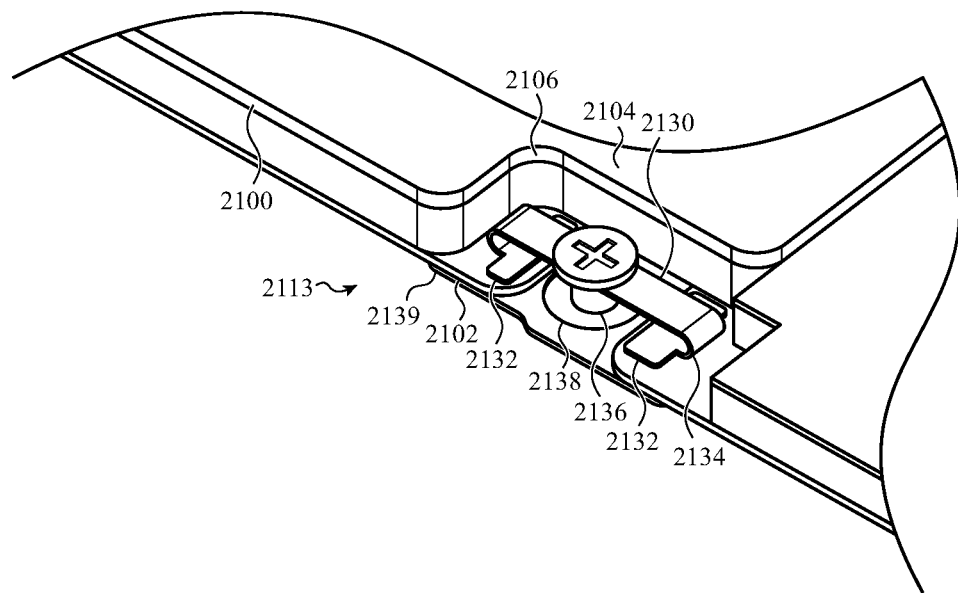
FIG. 21E depicts a partial view of an example fastening configuration for a logic board.

FIG. 21E depicts the notch region 2113 of the logic board 2100, illustrating how a compliant fastening system may be used to secure the logic board 2100 to a device. The notch region 2113 may be defined by a recess in the wall structure 2106 and the second substrate 2104. The notch region exposes a portion of the first substrate 2102, and a compliant brace 2130 may be mounted to an upper surface of the first substrate 2102. More particularly, base plates 2132 of the compliant brace 2130 may be mounted to the upper surface of the first substrate 2102, such as via soldering, welding, adhesives, fasteners, or the like (as shown by attachment element 2142, which may be solder, an adhesive, a weldment, etc.). A reinforcement plate 2139 may be attached to a bottom surface of the first substrate 2102. The compliant brace 2130 may be a unitary structure formed of metal or any other suitable material.

Figure 21F:
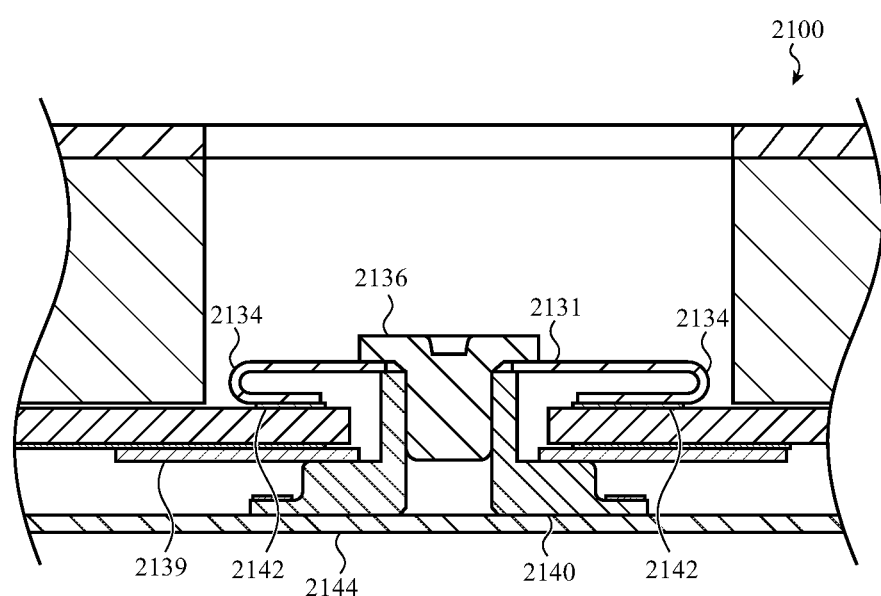
FIG. 21F depicts a partial cross-sectional view of the logic board of FIG. 21A, illustrating the fastening configuration shown in FIG. 21E.

A fastener 2136, such as a threaded screw or bolt, may extend through a hole in the compliant brace 2130, through a hole or cutaway in the first substrate 2102, and through a hole in the reinforcement plate 2139, and may be coupled to a mounting feature such as a mounting boss 2140 (FIG. 21F) to secure the logic board 2100 to the device. FIG. 21F is a partial cross-sectional view of the notch region 2113, and shows the fastener 2136 secured to the mounting boss 2140, which is in turn attached to a component 2144 (which may be a housing component, rear cover, frame member, or any other structural component of a device). With reference to both FIGS. 21E and 21F, the compliant brace 2130 is configured to allow the logic board 2100 to deflect upwards (as shown in FIG. 21F) during drop events, impacts, or other forceful events to which the device may be subjected. For example, the loop portions 2134 and the top beam portion 2131 of the compliant brace 2130 may be configured to deflect, bend, or otherwise deform such that the first substrate 2102 (and thus the whole logic board 2100) can move in at least one direction. For example, in response to a first force (e.g., a force perpendicular to the main plane of the logic board 2100), the compliant brace may deflect to allow upwards movement of the logic board 2100 such that the reinforcing plate 2139 temporarily lifts off of the mounting boss 2140. In this way, a degree of compliance and suspension may be provided to the logic board 2100, which may reduce the magnitude and/or effect of shock loading or other potentially detrimental forces on the logic board 2100. In some cases, the compliant brace also deflects, bends, or otherwise deforms to allow the logic board 2100 to move in a second direction, such as a lateral direction (e.g., left-to-right in FIG. 21F) in response to a second force (e.g., a force that is parallel to the main plane of the logic board 2100). In some cases, the mounting boss 2140 inhibits downward movement of the logic board 2100.

In some cases, the compliant brace 2130 is configured to be in a stressed condition when in a static condition, such as that shown in FIG. 21F. For example, when the fastener 2136 is threaded into the mounting boss 2140, the fastener 2136 may slightly deform (e.g., compress) the compliant brace 2130. In this way, the compliant brace 2130 may decouple the attachment force between the fastener 2136 and the mounting boss 2140 from the amount of force applied to the logic board 2100. For example, the compliant brace 2130 may be clamped rigidly between the fastener 2136 and the mounting boss 2140 with a relatively high degree of clamping force to ensure that the logic board 2100 remains securely attached to the device. However, that amount of clamping force, if applied directly to the first substrate 2102 for example, may crush or unduly stress the first substrate 2102. Accordingly, the compliant brace 2130 does not transfer all of the clamping load directly to the first substrate 2102. Rather, the only force applied directly to the first substrate 2102 is that which results from any bending or compression of the compliant brace 2130 (as defined by the shape of the compliant brace 2130, the mounting boss 2140, and the thickness of the first substrate 2102 and the reinforcing plate 2139, for example). In this way, the logic board 2100 may be secured to the housing with a high degree of security (e.g., due to the clamping force on the compliant brace 2130, while still providing a high degree of compliance and a relatively low force applied directly to the first substrate 2102.

In some cases, the compliant brace 2130 provides an electrical ground path between the logic board 2100 and a ground plane of the device. For example, the base plates 2132 of the compliant brace 2130 may be soldered to grounding solder pads on the first substrate 2102, and the compliant brace 2130, fastener 2136, and mounting boss 2140 may define a conductive path to an electrical ground plane of the device. In some cases, the downwards bias produced by the compliant brace 2130 on the logic board 2100 helps force the logic board 2100 against an electrical ground plane (e.g., by biasing conductive grounding contacts against one another).

Figure 21G:
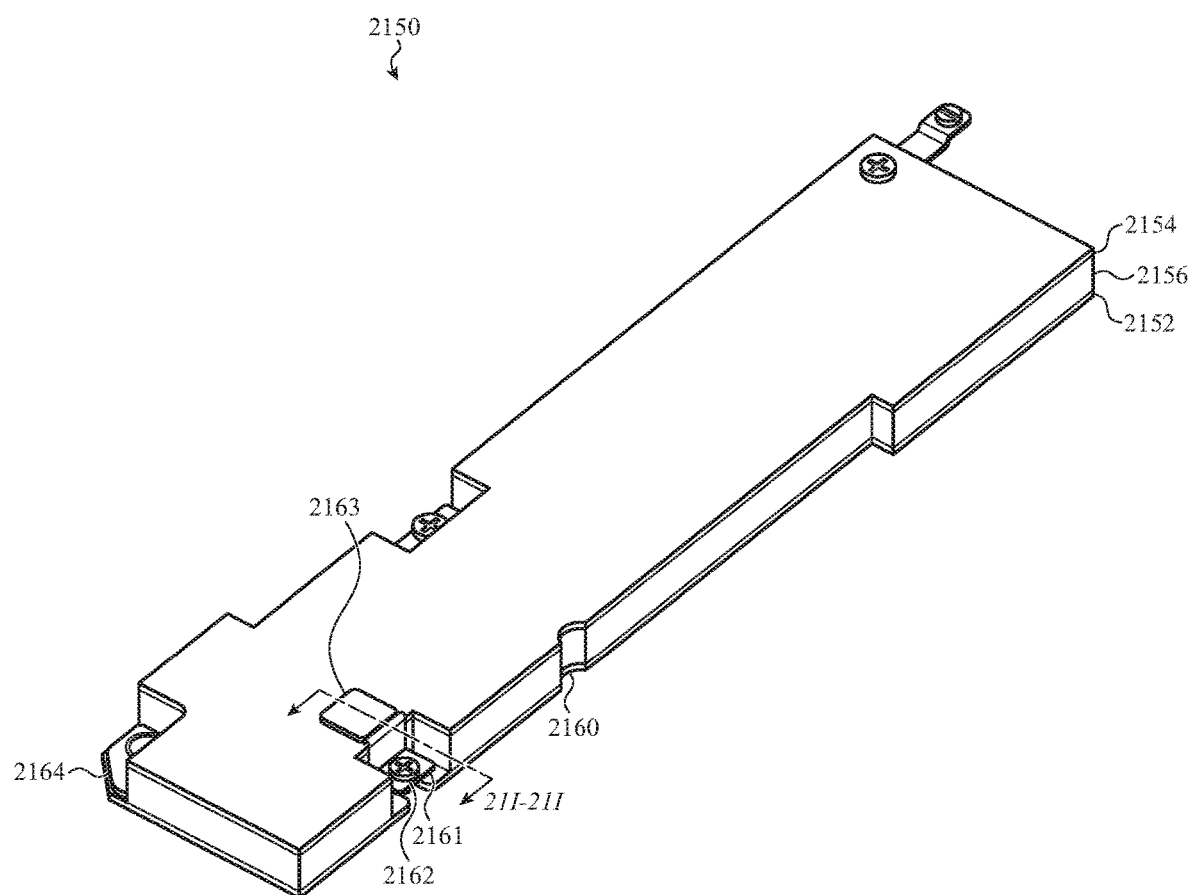
FIGS. 21G-21I depict another example logic board.

FIG. 21G illustrates another example logic board 2150. The features described with respect to the logic board 2150 may be included in any other logic board described herein.

The logic board 2150 includes a first substrate 2152 and a second substrate 2154 supported above the first substrate 2152. The first and second substrates 2152, 2154 may also be referred to as circuit boards. Electrical components and/or circuit elements such as processors, memory, antenna circuitry, and the like, may be coupled to the first and/or the second substrates 2152, 2154.

The first and second substrates 2152, 2154 may be connected to one another via a wall structure 2156 (which supports the second substrate 2154 above the first substrate 2152). As described herein the first and second substrates 2152, 2154 may be soldered to conductive members (e.g., vias) in the wall structure 2156, thereby allowing components on the first and second substrates 2152, 2154 to be conductively coupled to one another via the wall structure 2156. The wall structure 2156 may also surround electrical components (e.g., a processor) and, along with the first and second substrates 2152, 2154, define a substantially enclosed and optionally sealed internal volume in which the processor (and/or other components) may be protected.

The logic board 2150 may be structurally mounted to a housing member or other structure of a device to secure the logic board 2150. In some cases, the logic board 2150 uses the same or similar mounting techniques as those described above with respect to the logic board 2100.

The logic board 2150 may include an alignment feature 2160. The alignment feature may be defined by recesses formed along an exterior side of each of the first and second substrates 2152, 2154 and the wall structure 2156. The recesses may have the same size and shape, such that a single recess is defined along the side of the logic board 2150. The alignment feature 2160 may be used when assembling the logic board 2150. For example, a pin, rod, or other alignment tool may be positioned in the alignment feature 2160 and the alignment tool and the first and second substrates 2152, 2154 and the wall structure 2156 may be forced against each other with an alignment force. The alignment force may force the first and second substrates 2152, 2154 and the wall structure 2156 into contact with the alignment tool, thereby causing the recesses in the first and second substrates 2152, 2154 and the wall structure 2156 to become aligned, which, in turn, causes the first and second substrates 2152, 2154 and the wall structure 2156 to be aligned. Once aligned and retained in position by the alignment tool, the first and second substrates 2152, 2154 and the wall structure 2156 may be attached together, such as via soldering. In some cases, the alignment tool has a complementary shape and size as the recesses of the alignment feature 2160.

In some cases, additional alignment features are also provided on the logic board 2150, such as through-holes extending through the first and second substrates 2152, 2154 and the wall structure 2156 and configured to receive a rod or pin therein for alignment purposes. By forming the alignment feature 2160 along an outer or exterior edge of the logic board 2150, the space requirement for the alignment feature 2160 may be less than the space requirement for through-holes, thereby allowing for more compact construction of the logic board 2150 and/or allowing more space on the logic board 2150 for other components.

The logic board 2150 also includes a clamp 2161 that may be used to help secure the logic board 2150 to a device. FIG. 21I is a partial cross-sectional view of the logic board 2150, showing details of the clamp 2161. The clamp 2161 may include a base portion 2173 and a hook portion 2172 extending from the base portion 2173. The hook portion 2172 hooks over the top of the second substrate 2154 and applies a clamping force to the second substrate 2154. A fastener 2162, such as a screw, may extend through a hole in the base portion 2173 and be anchored to a boss 2171 or other feature below the logic board 2150. The boss 2171 may be attached to a structure of the electronic device, such as a chassis as described herein. The fastener 2162 may apply a downward force on the base portion 2173, which in turn results in the hook portion 2172 applying the clamping force. The clamping force thus helps retain the logic board 2150 to the device.

In some cases, the logic board 2150 includes a shroud component 2163 on the top of the second substrate 2154. The shroud component 2163 may be an EMF shield or other protective structure over a component (e.g., a processor) that is coupled to the second substrate 2154. The shroud component may be formed of metal, plastic, or any other suitable material, and may define a lip structure 2170 that engages or otherwise overlaps the hook portion 2172 of the clamp 2161. The lip structure 2170 may prevent or inhibit movement of the hook portion 2172 to maintain the hook portion 2172 in place (e.g., and prevent or inhibit the hook portion 2172 from slipping off of the top surface of the second substrate 2154). In some cases, the shroud component 2163 may be omitted, and a lip or other retention feature (e.g., channel, groove, bump, etc.) may be defined by another component, such as a solder pad on the second substrate 2154, the second substrate itself, a screw or other fastener, or the like.

Figure 21H:
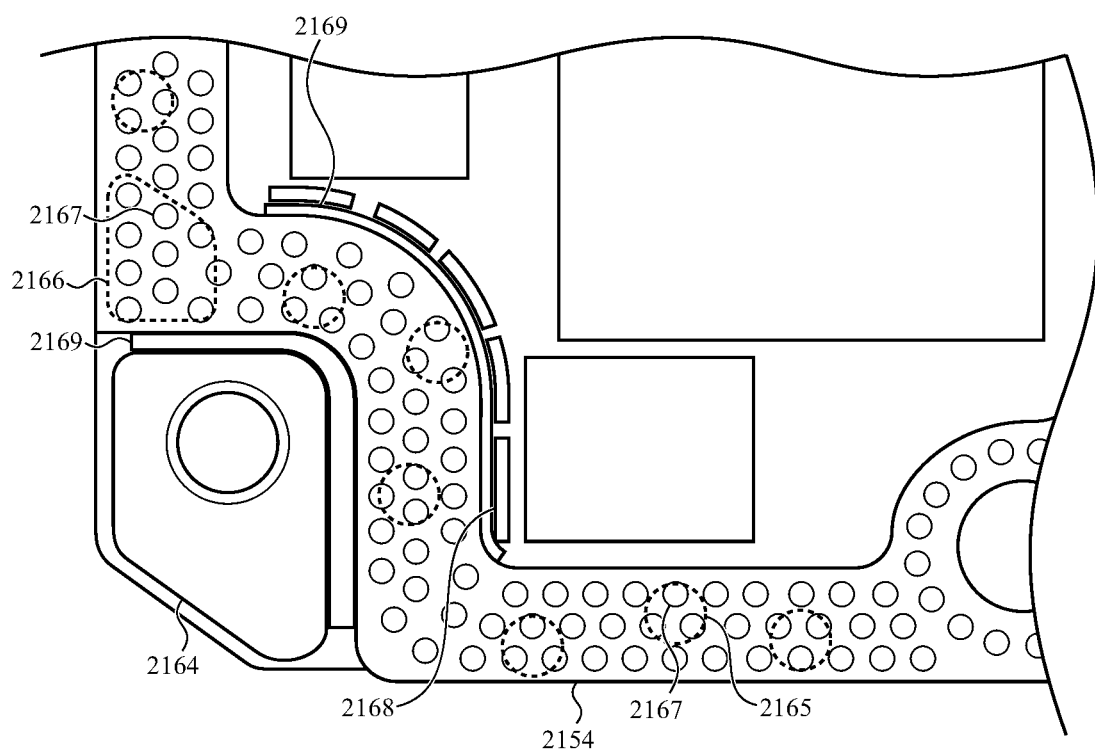
Figure 21I:
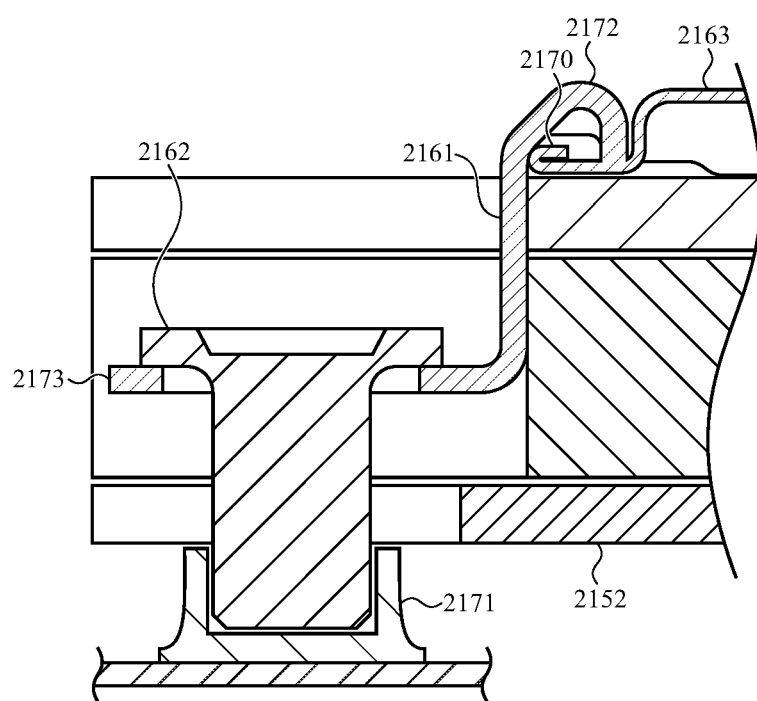

FIG. 21H illustrates a detail view of a portion of the logic board 2150, illustrating example techniques for securing the first and second substrates 2152, 2154 and the wall structure 2156 together. For example, the wall structure 2156 may include vias 2167 and the first and second substrates 2152, 2154 may include solder pads (represented by circles 2165) that are soldered to the vias 2167 to secure the first and second substrates 2152, 2154 and the wall structure 2156 together. The solder pads may include a first set of uniformly shaped solder pads 2165, each having the same shape (e.g., circles as shown in FIG. 21H, though other shapes are also contemplated). In some cases, each solder pad 2165 may have a size, shape, and location such that it encompasses (and is ultimately soldered to) a certain number of vias 2167 (e.g., 3 vias, 4 vias, or any other suitable amount). The solder pads may also include one or more solder pads having a different shape than the first set of uniformly shaped solder pads 2165. For example, the solder pad 2166 may have an irregular shape that encompasses (and is ultimately soldered to) a greater number of vias 2167 than the solder pads 2165 of the first set of solder pads (e.g., if the solder pads 2165 encompass three vias, the solder pad 2166 may encompass 4 or more vias).

In some cases, the first and second substrates 2152, 2154 each include a complementary set of matching solder pads (e.g., the solder pads shown in FIG. 21H may be present on both the first and second substrates 2152, 2154).

In some cases, an underfill material 2169 may be introduced between the substrates and the wall structure and allowed to harden or cure to bond the substrates to the wall structure and/or reinforce the solder joints between the sub states and the wall structure. The underfill material 2169 may be an adhesive, epoxy, or any other suitable material. The underfill material 2169 may be introduced between a substrate and the wall structure 2156 after the substrate is soldered to the wall structure. The underfill material 2169 may flow or wick into the space between the substrate and the wall structure, and thereafter harden in place. In some cases, the logic board 2150 includes one or more features that help contain and/or guide the underfill material 2169 into the target areas between a substrate and the wall structure. For example, a pad 2164, which may be a solder pad or a reinforcement plate on the first substrate 2152, may act as a barrier wall to retain the underfill material 2169 during and after it is flowed below the wall structure 2156 and while it hardens. In some cases, the pad 2164 may cause the underfill material 2169 to build up along an outer side of the wall structure 2156, forming a fillet of underfill material 2169 at the corner interface between the wall structure 2156 and the first substrate 2152. Stated another way, the underfill material 2169 may extend part way up the outer surface of the wall structure to a height that is higher than the gap between the first substrate 2152 and the wall structure 2156. By contrast, without the pad 2164, the underfill material 2169 might have a maximum height that is equal to the gap between the first substrate 2152 and the wall structure 2156, thereby providing less reinforcement to the interface between the first substrate 2152 and the wall structure 2156. In some cases, other flow control features 2168 may provide a similar functionality along another side of the wall structure (e.g., inside the internal volume defined by the logic board 2150). The flow control features 2168 may be formed from any suitable material, such as solder, plastic, adhesive, or the like, and may serve the same or similar function as the pad 2164. Flow control features such as the features 2168 and the pad 2164 may be used in various locations on the logic board 2150 to help guide and/or control the location of the underfill material. Further, such flow control features may be used between the first substrate 2152 and the wall structure 2156, and between the second substrate 2154 and the wall structure 2156

Figure 22A:
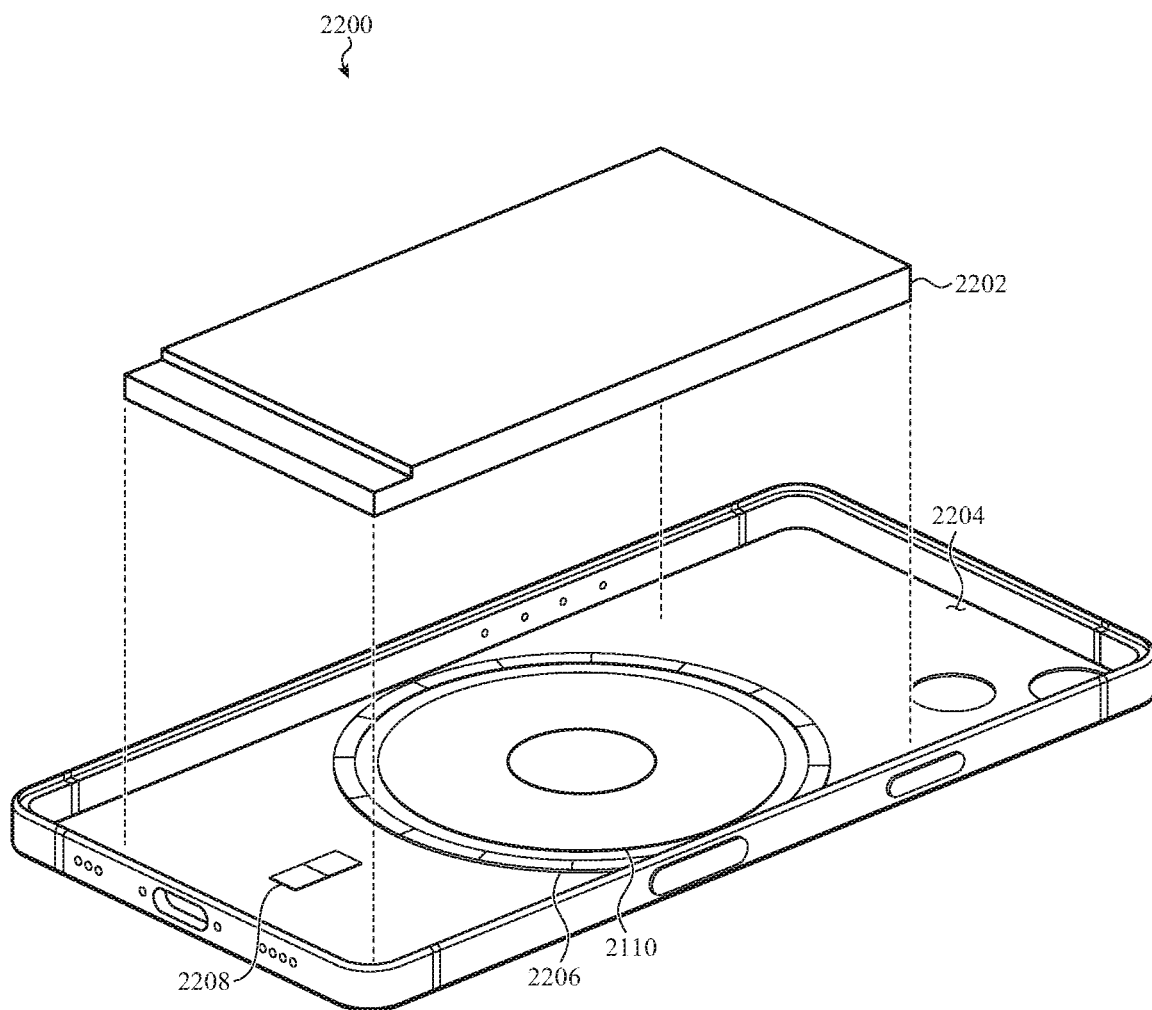
FIG. 22A depicts a portion of an electronic device with a battery shown detached from a housing.

FIG. 22A depicts a partial exploded view of a device 2200, illustrating a battery 2202 separated from a rear cover 2204 (or other housing structure to which the battery may otherwise be coupled. The device 2200 may include an array of magnetic elements 2206 that are arranged in a circular or radial pattern. The magnetic elements 2206 may help to locate the device 2200 with respect to a separate wireless charging device or other accessory. In some implementations, the array of magnets also help to radially locate, orient, or "clock" the device 2200 with respect to the separate wireless charging device or other accessory. This functionality may be described as self-aligning or self-locating wireless charging. As shown in FIG. 22A, the device 2200 may also include a magnetic fiducial 2208 for helping to locate the separate wireless charging device or accessory. The device may also include a coil 2210 that inductively couples to an output or transmitting coil of a wireless charger. The coil 2210 may provide current to the device 2200 to charge the battery 2202 and/or power the device. The coil 2210 may include multiple wraps of a conductive wire or other conduit that is configured to produce a (charging) current in response to being placed in an inductive charging electromagnetic field produced by a separate wireless charging device or accessory. The battery 2202 may be positioned over the charging coil 2210 and attached to the housing. The areas where the battery 2202 and the charging coil 2210 overlap may be referred to as an overlap region.

The battery 2202 may be attached to the rear cover 2204 in various ways, including using adhesives, fasteners, mechanical interlocks, etc. The attachment of the battery 2202 to the rear cover 2204 needs to be sufficiently secure so that the battery does not become detached from the rear cover 2204 during use of the device. However, it may also be advantageous to allow the battery 2202 to be removed from the device for repairs, replacement, or the like. Further, due to components that are positioned under the battery 2202, such as the array of magnetic elements 2206 (also referred to as magnets 2206) and the coil 2210, the locations and areas that can be used to fasten the battery 2202 to the rear cover 2204 may be limited. For example, in some cases, adhesives may not be used on the magnets 2206 or the coil 2210, as the surfaces of those components may not be suited for bonding to adhesives, and/or it may risk damaging those components.

Figure 22B:
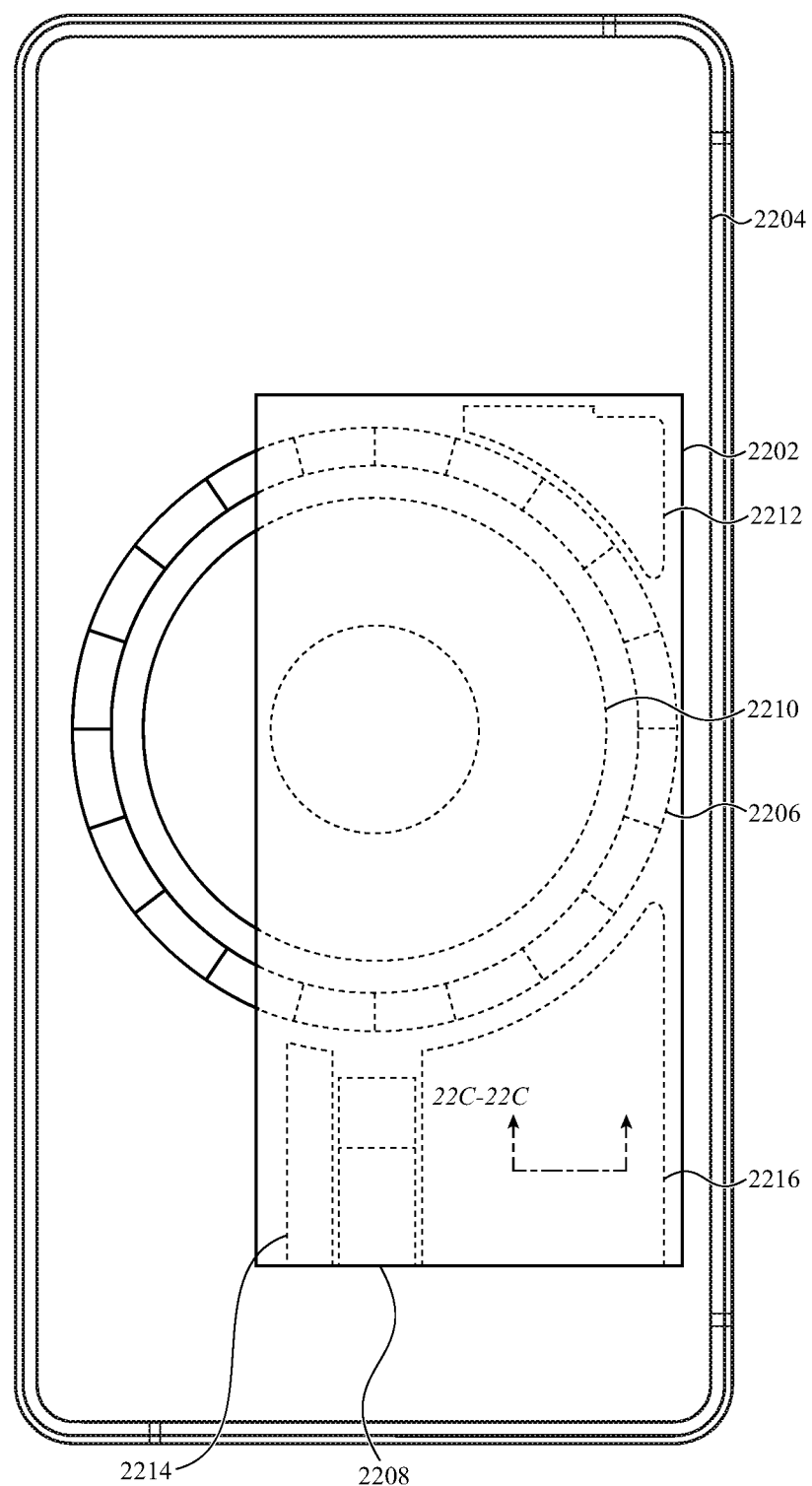
FIG. 22B depicts an example adhesive configuration for attaching a battery to a housing of an electronic device.

FIG. 22B depicts an example arrangement of adhesives that may be used to attach the battery 2202 to the rear cover 2204. In particular, first, second, and third adhesive structures 2212, 2214, and 2216 may be positioned between the battery 2202 and the rear cover 2204 to adhere the battery 2202 to the rear cover 2204. The adhesive structures 2212, 2214, and 2216 may be positioned between the battery 2202 and the rear cover 2204 in coupling regions outside of the outer periphery of the coil 2210 (e.g., outside of the overlap region and between the battery 2202 and the rear cover 2204), the magnets 2206, and the magnetic fiducial 2208, such that the adhesive structures can bond to the rear cover 2204 without contacting the coil 2210, the magnets 2206, and the magnetic fiducial 2208. As shown, the adhesive structures 2212, 2214, and 2216 may conform to a shape of the array of magnets 2206 (e.g., they may have a curved edge that conforms to or follows the curved outer periphery of the array of magnets 2206) to increase the surface area covered by the adhesive structures 2212, 2214, and 2216, without contacting the magnets 2206.

Figure 22C:
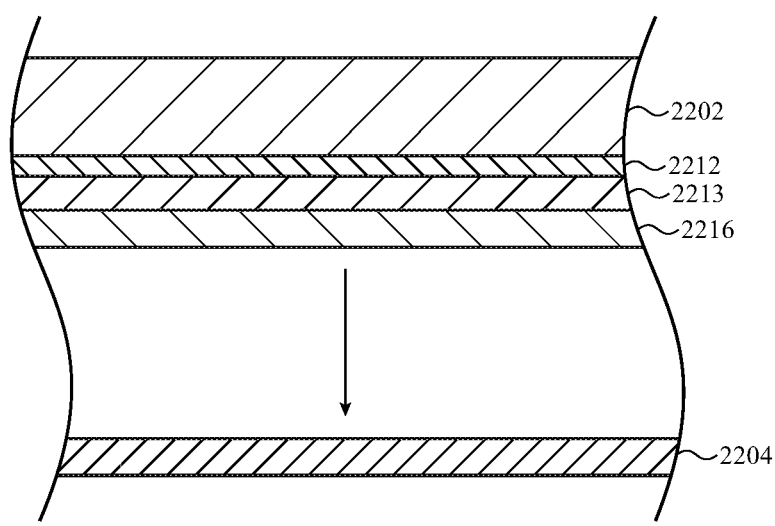
FIG. 22C depicts a partial cross-sectional view of an adhesive stack for attaching a battery to a housing of an electronic device.

FIG. 22C is a partial cross-sectional view of the device 2200, viewed along line 22C-22C in FIG. 22B, illustrating an example configuration of an adhesive structure (e.g., the adhesive structure 2216) for use in adhering a battery to a rear cover. As noted above, it may be advantageous to adhere a battery to a rear cover (or other housing structure) such that the battery can be removed for replacement, repair, or the like, without permanently damaging the battery or the rear cover. Accordingly, a releasable adhesive, such as a stretch-release adhesive, may be used to adhere the battery to the rear cover. In some cases, however, a releasable adhesive may not bond equally well to the rear cover and the battery. In particular, the material used to form the outer surface of a battery 2202 may form a weaker bond with the releasable adhesive than the rear cover 2204. Accordingly, a multi-layer structure may be used to produce a greater attachment force between the battery and the housing, while still facilitating the use of a releasable adhesive. For example, the multi-layer structure shown in FIG. 22C includes a first adhesive 2212, which may be a permanent or non-releasable adhesive, that adheres a polymer layer 2213 to the battery 2202. The first adhesive 2212 may be an adhesive that forms a strong bond with both the battery 2202 (e.g., the material that forms the pouch of the battery 2202) and the polymer layer 2213. The polymer layer 2213 may be any suitable material, such as a polyimide sheet.

The multi-layer structure may also include a releasable adhesive 2216 that is adhered to both the polymer layer 2213 and the rear cover 2204. The releasable adhesive 2216 may form a strong bond with both the polymer layer 2213 and the rear cover 2204. In some cases, the strength of each adhesive bond in the multi-layer structure is greater than an adhesive bond between the releasable adhesive 2216 and the battery 2202. In this way, the benefits of the releasable adhesive are provided (e.g., the ability to non-destructively remove the battery 2202 from the rear cover 2204) without compromising on the ultimate bond strength between the battery 2202 and the rear cover 2204. The adhesives 2212, 2216 may be films, sheets, liquids, or the like. Further, while FIG. 22C illustrates an example multi-layer structure, in some cases a single adhesive layer is used to adhere the battery 2202 to the rear cover 2204.

Figure 22D:
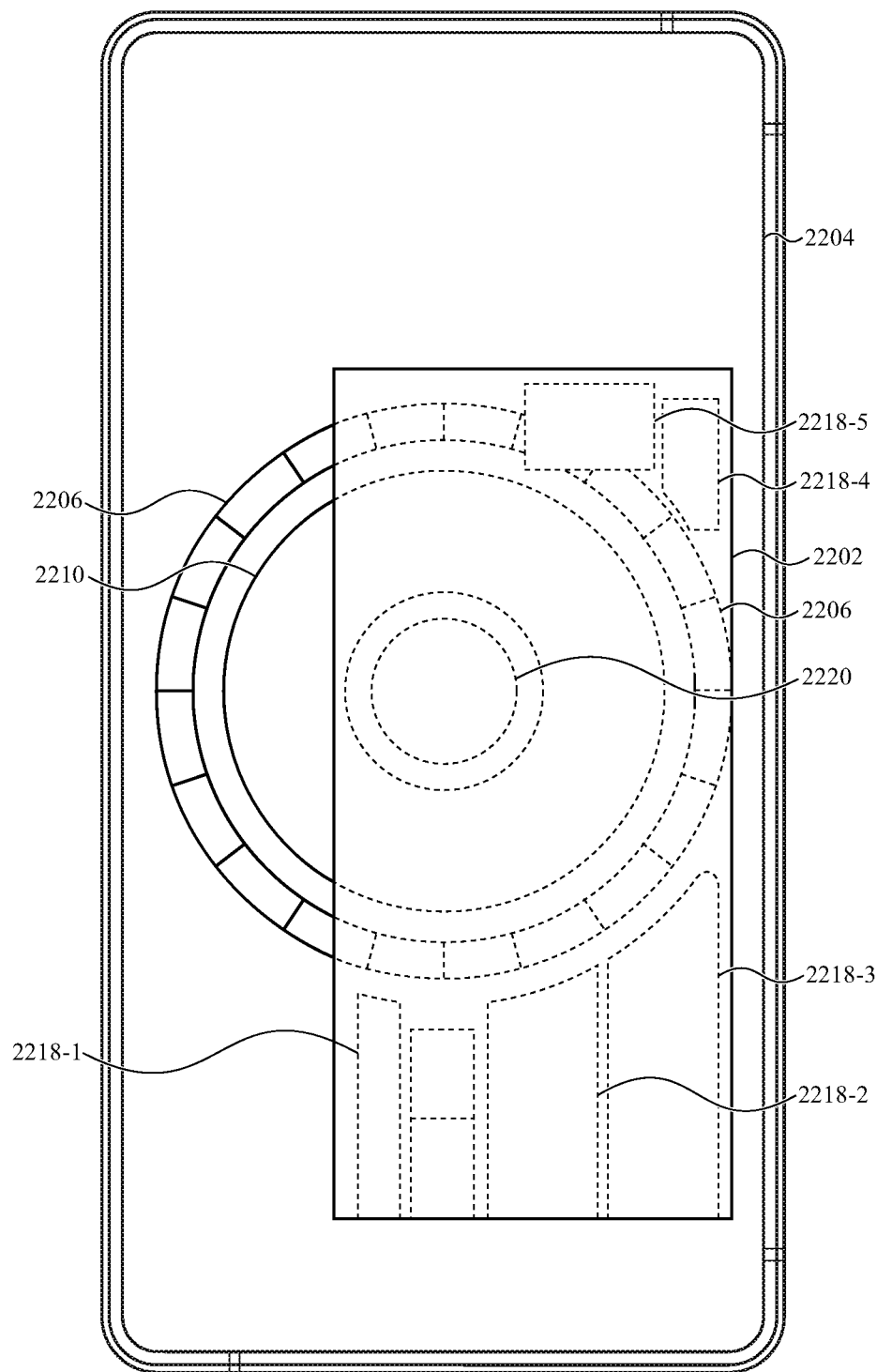
FIGS. 22D-22F depict example adhesive configurations for attaching a battery to a housing of an electronic device.

FIG. 22D depicts another example arrangement of adhesives that may be used to attach the battery 2202 to the rear cover 2204. More particularly, FIG. 22D depicts an example in which multiple different types of adhesives with different bonding strengths and releasability are used together. For example, first adhesive structures 2218-1 through 2218-5 are a first adhesive (e.g., stretch-release adhesives) with a first bond strength, and a second adhesive structure 2220 is a second adhesive with a second bond strength higher than the first bond strength. The first and second adhesive structures 2218, 2220 may be positioned between the battery 2202 and the rear cover 2204 to adhere the battery 2202 to the rear cover 2204. While most of the first adhesives structures are positioned in areas outside of the outer periphery of the coil 2210, the magnets 2206, and the magnetic fiducial 2208, at least one adhesive structure (e.g., adhesives structure 2218-5) may contact one or more magnets 2206. As shown, adhesive structures 2218-1-2218-4 may conform to a shape of the array of magnets 2206 (e.g., they may have a curved edge that conforms to or follows the curved outer periphery of the array of magnets 2206) to increase the surface area covered by the adhesive structures. The combination of different adhesives with different adhesive strengths (and different abilities to be removed or released) provides a balance of bond strength and ease of releasability. It should be noted that while an adhesive with a higher bond strength may be more difficult to remove or release than an adhesive with a lower bond strength, a higher bond strength adhesive may still ultimately be removable, though complete removal may be more difficult (and may in some cases be aided by the use of solvents, heat, or the like).

Figure 22E:
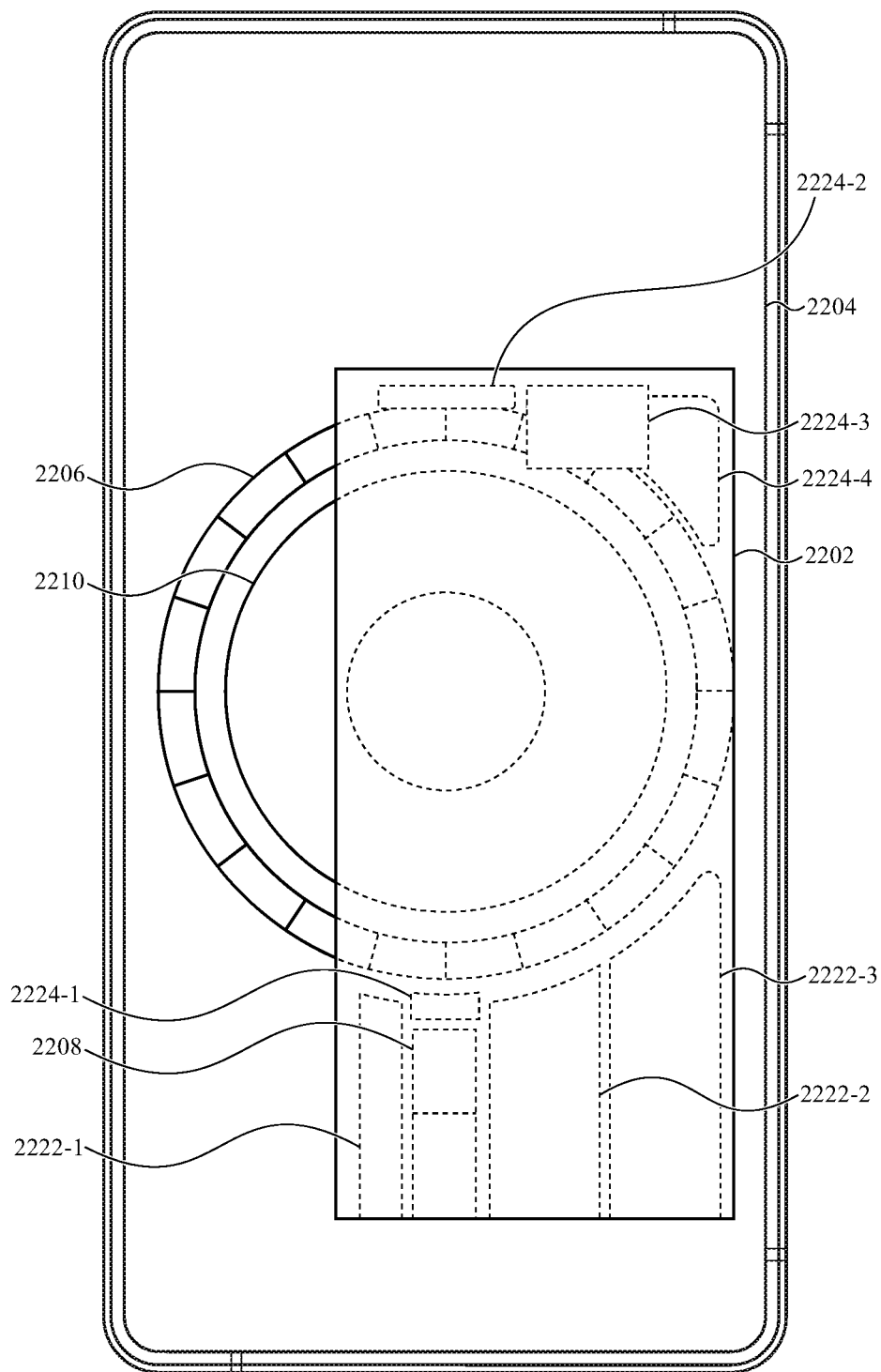

FIG. 22E depicts another example arrangement of adhesives that may be used to attach the battery 2202 to the rear cover 2204. More particularly, FIG. 22E depicts an example in which multiple different types of adhesives with different bonding strengths and releasability are used together. For example, first adhesive structures 2222-1 through 2222-3 are a first adhesive (e.g., stretch-release adhesives) with a first bond strength, and second adhesive structures 2224-1 through 2224-4 are a second adhesive with a second bond strength higher than the first bond strength. The first and second adhesive structures 2222, 2224 may be positioned between the battery 2202 and the rear cover 2204 to adhere the battery 2202 to the rear cover 2204. The arrangement of adhesives shown in FIG. 22E includes an adhesive structure 2224-1 positioned between the magnetic fiducial 2208, as well as an additional adhesive structure 2224-2 positioned in a corner region of the battery 2202, between a top of the array of magnets 2206 and a top edge of the battery 2202. As described above, the combination of different adhesives with different adhesive strengths (and different abilities to be removed or released) provides a balance of bond strength and ease of releasability.

Figure 22F:
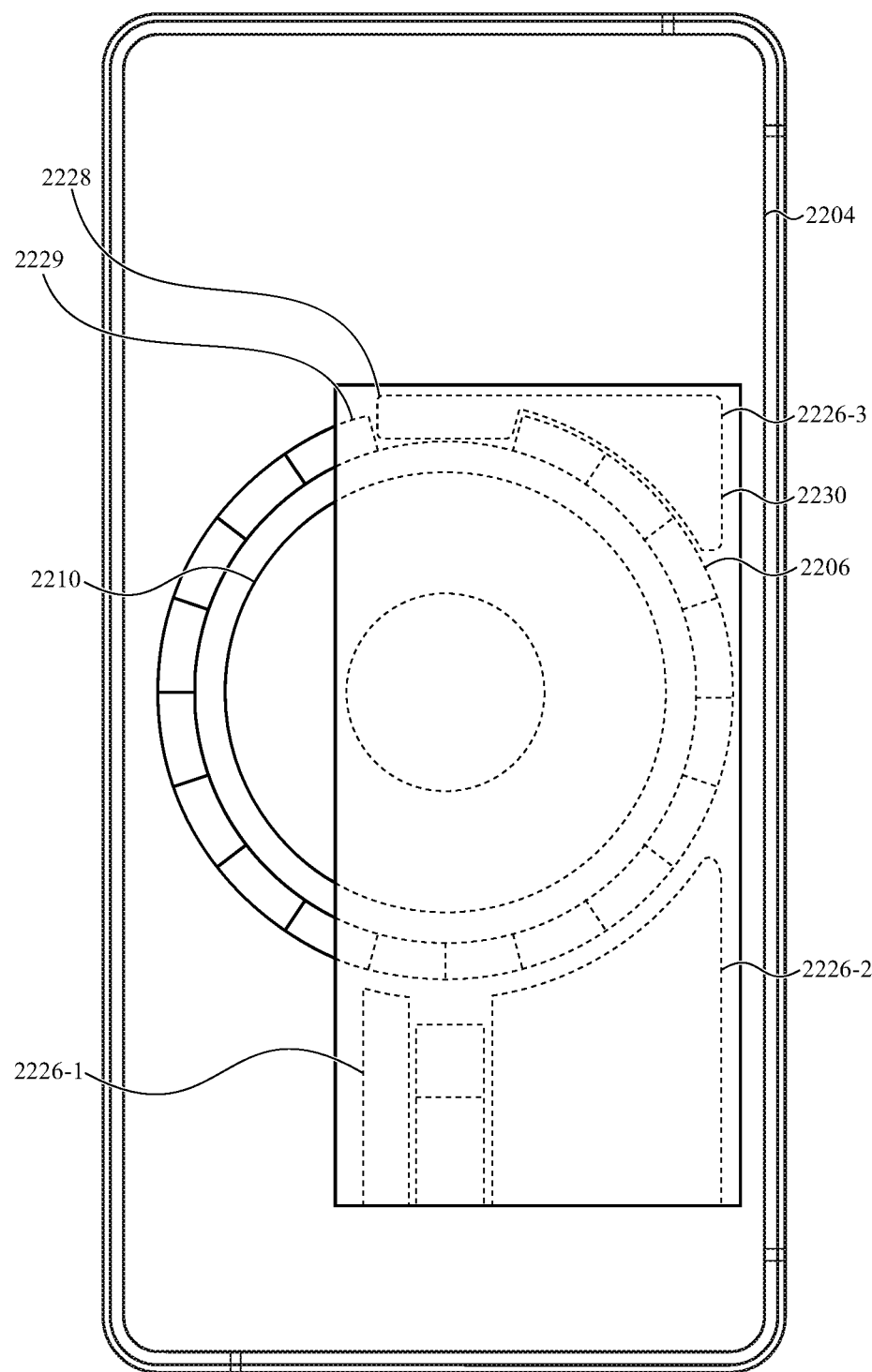

FIG. 22F depicts another example arrangement of adhesives that may be used to attach the battery 2202 to the rear cover 2204. More particularly, FIG. 22F depicts an example in which a gap 2229 is defined in the array of magnets 2206 to provide an additional area for an adhesive. For example, the magnets 2206 in FIG. 22F are positioned in a circular array, with a gap 2229 defined between two of the magnets 2206 at an area along a top of the array. The gap 2229 may be proximate a top edge of the battery 2202, such that the gap provides additional area for locating an adhesive structure. This location for the gap 2229 may be particularly advantageous because it allows adhesive to be positioned in the upper left corner of the battery 2202 where there would be little or no space for adhesives if the array of magnets were continuous in that area. The adhesive structure 2226-3 is a unitary or single adhesive structure that defines a first lobe 2228 and a second lobe 2230. The second lobe 2230 follows a contour or shape of the outer perimeter of the array of magnets 2206, and is positioned at a top right region of the battery 2202. The first lobe 2228 extends into the gap 2229 in the array of magnets 2206. For example, a first side of the first lobe 2228 may be adjacent one of the magnets 2206, and a second side of the first lobe 2228 may be adjacent another one of the magnets 2206. The combination of the gap 2229 in the array and the multi-lobe adhesive structure 2226-3 results in adhesive being positioned along substantially an entire top edge of the battery 2202.

In addition to the adhesive structure 2226-3, the example in FIG. 22F includes adhesive structures 2226-1 and 2226-2, which conform to a shape of the array of magnets 2206 (e.g., they have a curved edge that conforms to or follows the curved outer periphery of the array of magnets 2206) to increase the surface area covered by the adhesive structures 2226 without contacting the magnets 2206. The adhesive structures 2226-1 through 2226-3 may be any type of adhesive(s), including a releasable adhesive, a non-releasable adhesive, or the like.

Figure 22G:
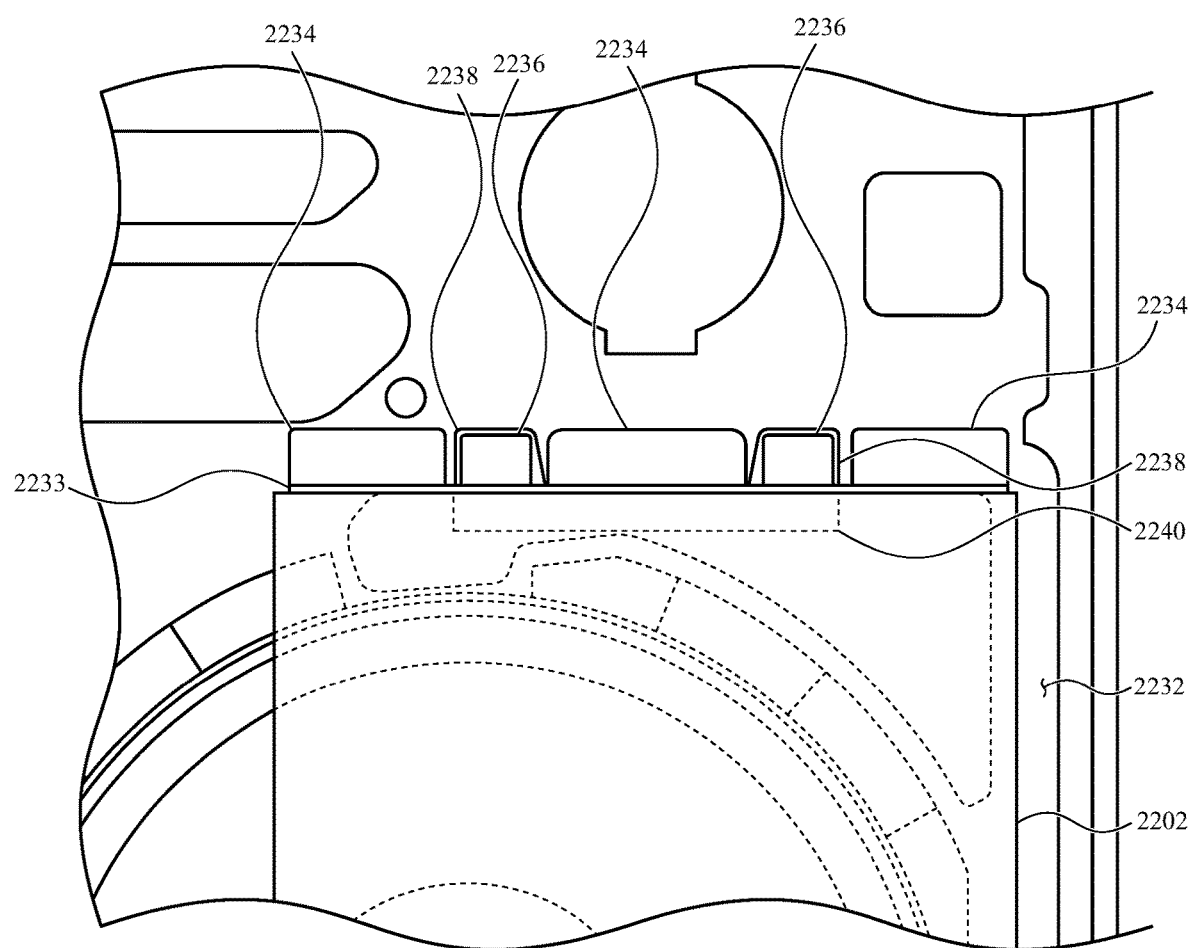
FIGS. 22G-22H depict example battery mounting structures for attaching a battery to an electronic device.
Figure 22H:
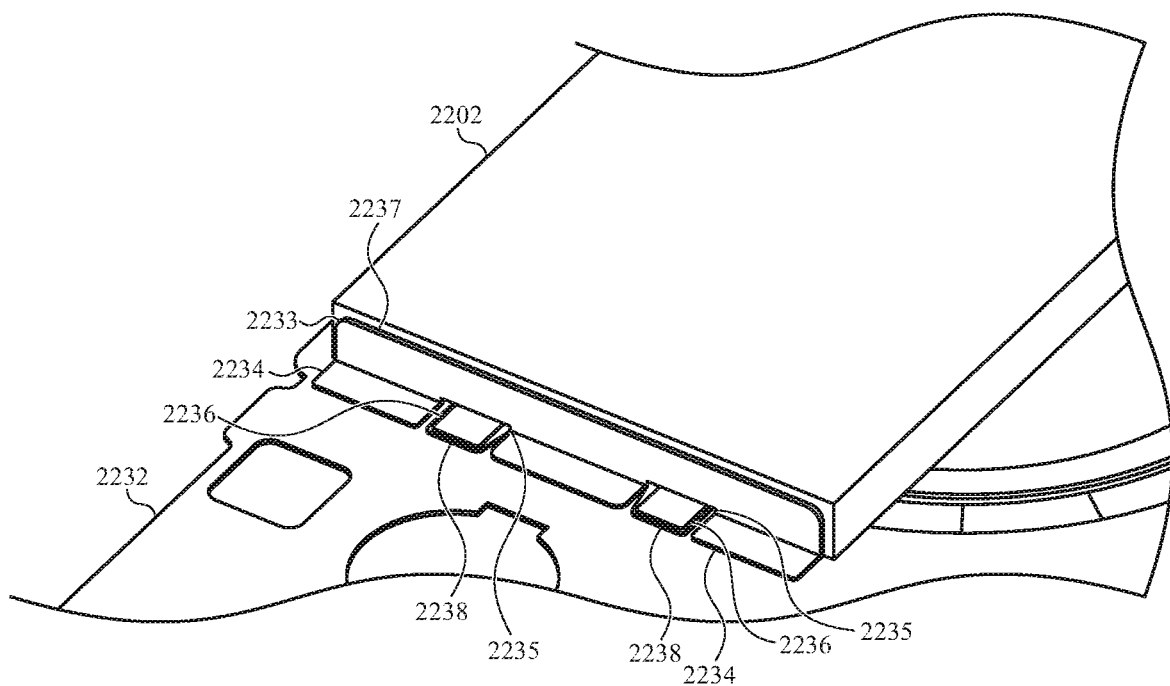

FIGS. 22G and 22H depict a portion of an electronic device, illustrating a battery retention structure that may be used to retain a battery (e.g., the battery 2202) in place in a device. In particular, the device includes a base plate 2232, which may be a housing component, rear cover, frame member, or any other structural component of a device. In some cases, the base plate 2232 is attached to a rear cover of a device. The base plate 2232 may be metal, glass, polymer, or any other suitable material(s). A retention bracket 2233 (which may be or be an embodiment of the barrier wall 1740, FIG. 17A) may be attached to the base plate 2232. For example, mounting pads 2234 of the retention bracket 2233 may be attached to the base plate 2232 via welding, adhesives, fasteners, or the like. The retention bracket 2233 defines underpasses 2235, also referred to as a retention slot, and retention tabs 2238 of a retention plate 2240 that is coupled to the battery 2202 (e.g., to a bottom surface of the battery 2202) may extend into the underpasses 2235. As described herein, the engagement between the retention bracket 2233 and the retention tabs 2238 (and the battery 2202 more broadly) helps retain the battery 2202 in a fixed position in the device, and can help prevent or inhibit battery movement during drops or other forceful events to which a device may be subjected.

Each underpass 2235 may be defined between two mounting pads 2234, and below a biasing tab 2236. The mounting pads 2234, biasing tabs 2236, and the bracket wall 2237 may be portions of a unitary component, such as a single piece of metal, polymer, or the like.

When the retention tabs 2238 are positioned in the underpasses 2235 as shown in FIGS. 22G and 22H, the retention tabs 2238 may be held captive in multiple directions, thereby retaining the battery 2202 in a target position and/or location. More particularly, the biasing tabs 2236 may prevent the retention tabs 2238, and thus the battery 2202, from moving in a z direction (e.g., into or out of the page, as shown in FIG. 22G). Similarly, the mounting pads 2234 may prevent the retention tabs 2238, and thus the battery 2202, from moving in an x direction (e.g., left or right, as shown in FIG. 22G). Further, the bracket wall 2237 may prevent the battery 2202 from moving in a positive y direction (e.g., upwards, as shown in FIG. 22G). Accordingly, the retention bracket 2233, along with the retention tabs 2238, may securely retain the battery 2202 in multiple directions (and in some cases, all but one direction).

The particular shapes and overall configuration of the retention bracket 2233 and the retention tabs 2238 may help maintain the battery 2202 in a given position, and help reduce the likelihood of the battery 2202 shifting or otherwise changing position. For example, the biasing tabs 2236 may be biased downward against the retention tabs 2238, thereby increasing the frictional force of the biasing tabs 2236 on the retention tabs 2238 and helping prevent unwanted movement of the battery 2202, especially in the z and y directions of the device. Further, the retention tabs 2238 may be tapered (e.g., tapering from a first width proximate the battery 2202 to a narrower width at a distal end of the tabs). The wider portion of the tabs may contact or be close to (e.g., about 0.25 mm or less away from) the sides of the underpasses 2235. In this way, the amount that the battery 2202 may move in the x direction (e.g., left and right, as shown in FIG. 22G) is limited to the smallest distance between the retention tabs 2238 and the side of the underpasses 2235. In the case where the sides of the retention tabs 2238 contact the sides of the underpasses 2235, the battery 2202 may be generally fixed in the x direction.

The tapered shape of the retention tabs 2238 may help ensure that the retention tabs 2238 contact the sides of the underpasses 2235. For example, the size of the underpasses 2235 may be smaller than a maximum width of the retention tabs 2238. Thus, during assembly of the device in which the battery is translated in the positive y direction (e.g. upwards, as shown in FIG. 22G), the retention tabs 2238 may be pushed into the underpasses 2235 until the sides of the retention tabs 2238 contact the sides of the underpasses 2235. The physical interaction between the sides of the retention tabs 2238 and the sides of the underpass 2235 may therefore fix the position of the battery in both the positive y direction and in the x direction. Once the retention tabs 2238 are contacting the sides of the underpass 2235, the battery 2202 may be secured to the housing (e.g., using adhesives as described with respect to FIGS. 22A-22F, and/or with other fasteners, brackets, or the like), thus fixing the battery in all directions.

In some cases, the battery 2202 itself or a portion of the retention plate 2240 limits the travel of the battery 2202 in the y direction prior to the retention tabs 2238 contacting the underpass 2235. This may help limit the variability in the position of the batteries across devices, as different manufacturing tolerances for the retention tabs 2238 and the underpasses 2235 may result in different products having different battery positioning.

In electronic devices as described herein (e.g., mobile phones), various types of components or systems that are housed within the device need access to the external environment. For example, speakers, microphones, pressure sensors, cameras, etc., all need some type of access to the external environment (e.g., optical access, fluid/air access, etc.). Furthermore, in order to help prevent or limit air pressure differences between an external environment and an internal volume of a device, a venting system may be provided so that the internal volume can pressure equalize with the external environment.

Figure 23A:
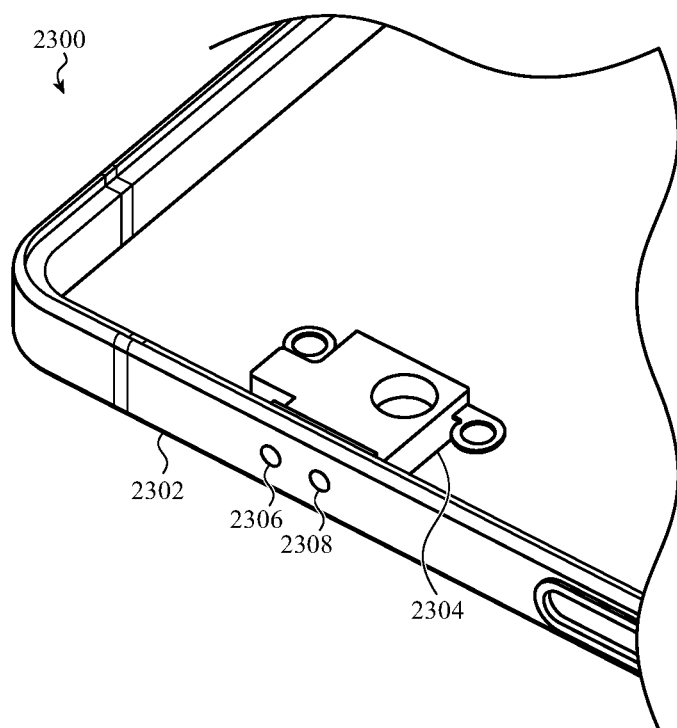
FIG. 23A depicts a partial view of an electronic device, illustrating an example arrangement of a sensor module relative to a housing member.

FIGS. 23A-23G depict various examples of a module 2304 (e.g., an acoustic module) that includes at least a pressure sensor and a microphone, and optionally a venting system (also referred to as a barometric vent) all at least partially housed in an audio enclosure. The pressure sensor may be configured to detect a barometric pressure of the ambient environment, while the microphone may receive audio input, such as during a telephone call or a video recording. These components all rely on fluidic communication with the external environment in order to operate effectively. Accordingly, as shown in FIG. 23A, the module 2304 may be positioned within a housing 2302 of a device 2300 proximate holes 2306 (e.g., an audio port or microphone port) and 2308 (e.g., a venting port). The holes 2306, 2308 extend through the housing 2302 from an exterior surface of the housing 2302 to an interior surface of the housing 2302.

Figure 23B:
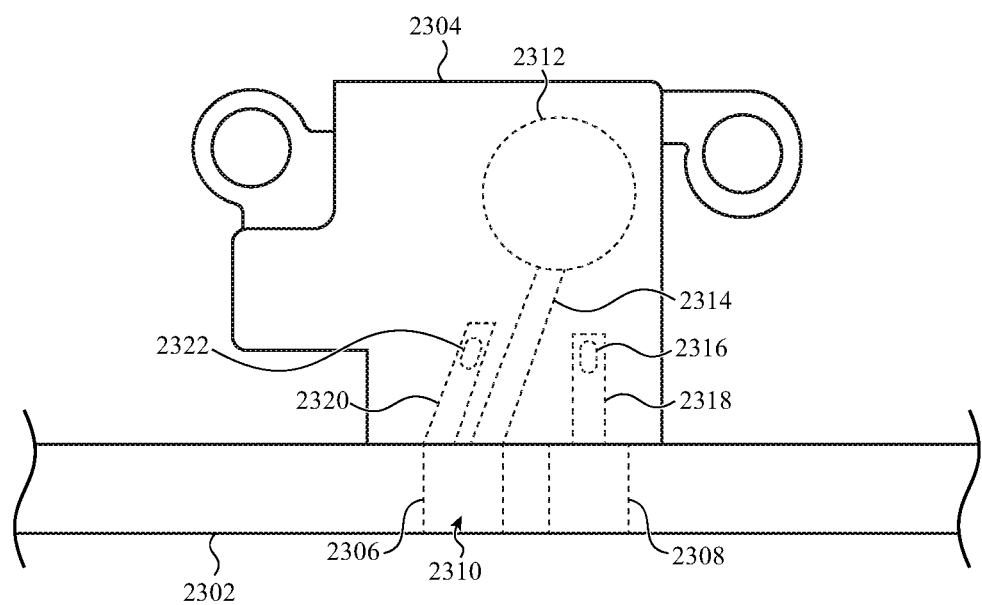
FIGS. 23B-23G depict example configurations of sensor modules having multiple sensing components sharing common volumes.

In some cases, multiple systems of the module 2304 are fluidically coupled to the external environment via a same hole. For example, as shown in FIG. 23B, a microphone 2322 may be operably coupled (e.g., fluidically coupled) to a first hole 2306 (e.g., the audio port or a microphone port) via a first passage 2320 in the audio enclosure, and a pressure sensor 2312 may be operably coupled (e.g., fluidically coupled) to the first hole 2306 via a second passage 2314 in the audio enclosure. Notably, the fluid path to both the microphone 2322 and the pressure sensor 2312 share a common volume 2310 in the first hole 2306. Separately, a barometric venting system 2316 may be fluidically coupled with the second hole 2308 (e.g., a venting port) via a third passage 2318 and configured to equalize an internal pressure within the housing with an external pressure external to the housing.

Because the fluid paths to both the microphone 2322 and the pressure sensor 2312 share a common partially enclosed volume 2310 (and partially due to the different lengths of the first and second passages), sound waves (e.g., air pressure waves) in the volume 2310, first passage 2320, and second passage 2314 may all be impacted by one another. Thus, for example, sound waves travelling to the microphone 2322 through the first passage 2320 may be affected by the presence of (and/or properties of) the second passage 2314. In some cases, the fluidic coupling between the first and second passages 2320, 2314 may negatively affect the operation of the microphone 2322, such as by attenuating certain frequencies of sound that would otherwise reach the microphone 2322. Such attenuation or other effects may be due, for example, to a resonance or other phenomena caused by the first and second passages 2320, 2314 being fluidically coupled at the common volume 2310. Accordingly, it may be advantageous to reduce the extent and/or effect of the fluidic coupling between the first and second passages 2320, 2314, thereby improving the overall function of the microphone 2322 and/or the pressure sensor 2312.

Figure 23C:
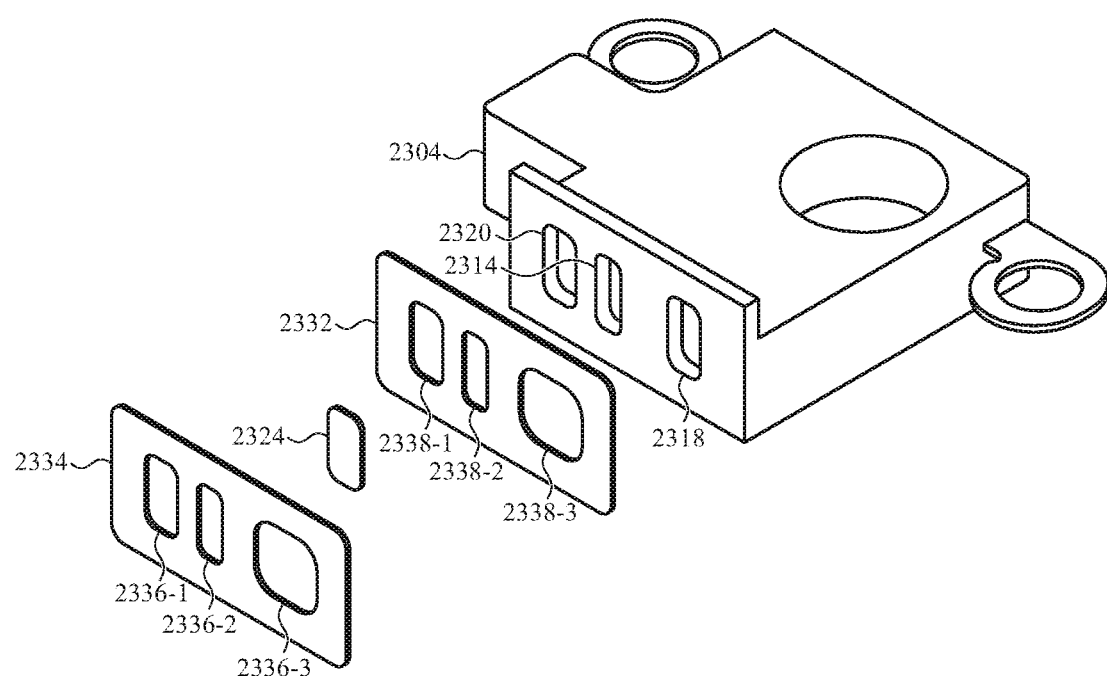

One technique for reducing the extent and/or effect of the fluidic coupling between the first and second passages 2320, 2314 includes providing a baffle somewhere between the first and second passages 2320, 2314. FIG. 23C depicts an example in which a baffle 2324 (which may be an acoustic mesh) is positioned between two compliant gasket layers 2332, 2334 and covers an opening to the second passage 2314 (e.g., it is between the end of the second passage 2314 and the audio port). The baffle 2324, or acoustic mesh, allows air to pass through it so that the pressure sensor 2312 (or other sensor or component) is still in fluidic communication with the external environment via the second passage 2314, while also providing an acoustic or fluidic dampening between the first passage 2320 and the second passage 2314. In this way, the negative effect of the second passage 2314 on sound waves passing through the first passage 2320 may be reduced or eliminated. In some cases, no baffle or acoustic mesh is positioned over the opening to the first passage 2320.

The baffle 2324 may be formed from any suitable material or structure, such as an open-cell foam, metal mesh, air-permeable polymer mesh (e.g., a polyethylene terephthalate mesh), fabric, perforated or semi-permeable polymer film, or the like. The baffle 2324 may be captured between two gaskets 2332, 2334. The baffle 2324 may have an acoustic impedance property or characteristic that reduces the impact of the second passage 2314 on pressure waves in the first passage 2320, while also allowing air to pass into the second passage 2314 without significantly impacting the operation of the pressure sensor 2312. For example, the baffle 2324 may have an acoustic impedance of between about 100 and about 700 Rayl. In some cases, the baffle 2324 has an acoustic impedance of between about 150 Rayl and about 300 Rayl. The baffle 2324 may have a thickness between about 40 microns and about 100 microns.

The gaskets 2332, 2334 may hold the baffle 2324 in place over the opening of the second passage 2314, and also provide a seal between the module 2304 and the housing 2302. The gaskets 2332, 2334 may each define a distinct hole 2336, 2338, respectively, corresponding to each of the first, second, and third passages 2320, 2314, 2318 of the module 2304. The holes 2336-1 and 2338-1 communicate with the microphone, and may be referred to as acoustic holes, and the holes 2336-2 and 2338-2 communicate with the pressure sensor and may be referred to as pressure holes Both the hole 2336-1 and the hole 2336-2 may open to the same partially enclosed volume of the audio port 2306 in the housing 2302, and thus serve as the openings where the passages 2320, 2314 ultimately open into the common volume 2310.

The gaskets 2332, 2334 may be or may be formed from adhesive films, such as a PSA film, and may adhesively bond to the housing 2302, the module 2304, the baffle 2324, and/or each other. In some cases, the gaskets 2332, 2334 are formed from or include compliant materials, such as a foam, elastomer, polymer, or the like. The gaskets 2332, 2334 may be compressed between (and optionally deformed by) the module 2304 and the housing 2302.

Figure 23D:
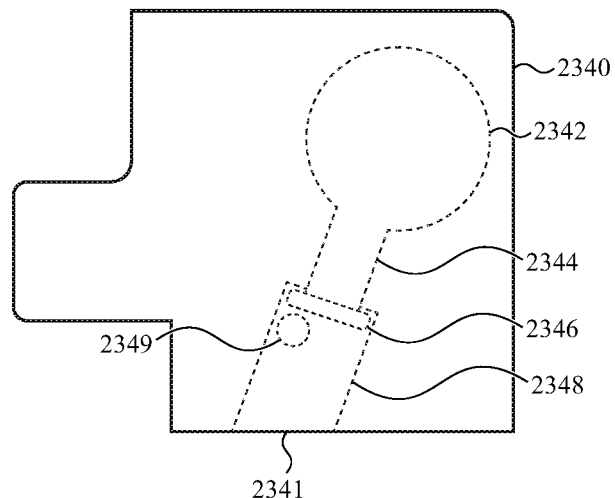

FIG. 23D depicts another example module 2340 (e.g., acoustic module) that includes at least a pressure sensor 2342 and a microphone 2349, and optionally a barometric vent (similar to or the same as the barometric vent shown in FIG. 23B). The microphone 2349 and pressure sensor 2342 are both fluidically coupled to a common volume within the module 2340, as well as the common volume 2310 defined by the housing 2302 (when integrated into a device as shown in FIGS. 23A-23B). In particular, the module 2340 defines a first passage 2348 that extends from the opening 2341 in the module 2340 to a second passage 2344. The microphone 2349 (or an opening that fluidically couples to a microphone) is positioned in the first passage 2348, and the second passage 2344 fluidically couples the first passage 2348 to the pressure sensor 2342. A baffle 2346 is positioned between the first passage 2348 and the second passage 2344.

The baffle 2346 may be formed from any suitable material or structure, such as an open-cell foam, metal mesh, polymer mesh (e.g., a polyethylene terephthalate mesh), fabric, perforated or semi-permeable polymer film, or the like. The baffle 2346 may include or be incorporated with adhesives (e.g., an adhesive gasket) to secure the baffle 2346 in place between the first and second passages 2348, 2344. The baffle 2346 may have an acoustic impedance property or characteristic that reduces the impact of the second passage 2344 on pressure waves in the first passage 2348, while also allowing air to pass into the second passage 2344 without significantly impacting the operation of the pressure sensor 2342. For example, the baffle 2346 may have an acoustic impedance of between about 100 and about 700 Rayl. In some cases, the baffle 2346 has an acoustic impedance of between about 150 Rayl and about 300 Rayl. The baffle 2346 may have a thickness between about 40 microns and about 100 microns.

Figure 23E:
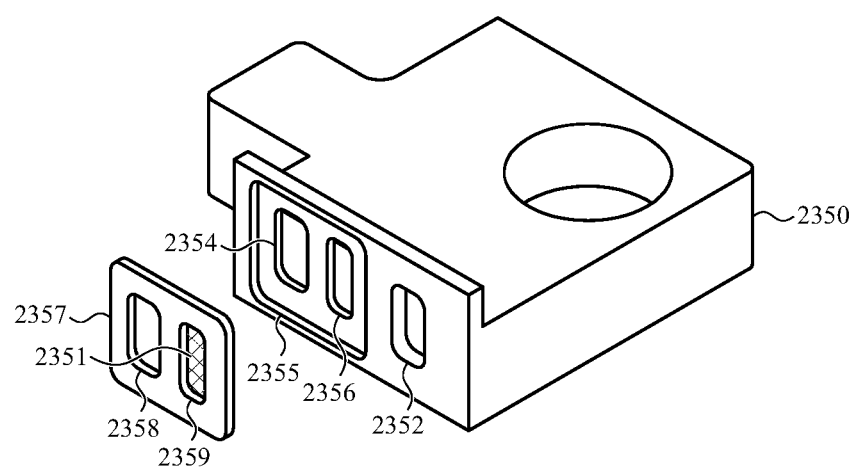

FIG. 23E depicts another example module 2350 (e.g., acoustic module) that includes at least a pressure sensor and a microphone, and optionally a barometric vent (similar to or the same as the barometric vent shown in FIG. 23B). The microphone and pressure sensor are both fluidically coupled to the common volume 2310 defined by the housing 2302 when integrated into a device as shown in FIGS. 23A-23B. The module 2350 defines a first passage 2354 that communicates with the common volume 2310 and is fluidically coupled to a microphone, and a second passage 2356 that communicates with the common volume 2310 and is fluidically coupled to a pressure sensor. The module 2350 also defines a third passage 2352 that is fluidically coupled to a barometric vent.

The module 2350 also defines a recess 2355 in a mounting surface of the module 2350. The openings to both of the first and second passages 2354, 2356 are within the recess. A gasket 2357 may be positioned in the recess 2355. The gasket 2357 may have a thickness that is equal to or greater than the recess 2355 such that the gasket 2357 contacts the surface of the housing 2302 when the module 2350 is assembled into a device, and optionally is compressed between the module 2350 and the housing 2302. The gasket 2357 may define a first hole 2358, which corresponds to and/or is aligned with the opening to the first passage 2354, and a second hole 2359, which corresponds to and/or is aligned with the opening to the second passage 2356.

The gasket 2357 may include a baffle 2351 (e.g., an acoustic mesh) positioned in the second hole 2359 of the gasket 2357. When the gasket 2357 is positioned in the recess 2355 and captured between the module 2350 and the housing 2302, the baffle 2351 provides an acoustic or fluidic dampening between the first passage 2354 and the second passage 2356. More particularly, because the first passage 2354 and the second passage 2356 (through the baffle 2351) both open directly into the common volume 2310, the baffle 2351 forms an air-permeable, acoustic dampening barrier between the first and second passages 2354, 2356.

The baffle 2351 may be formed from any suitable material or structure, such as an open-cell foam, metal mesh, polymer mesh (e.g., a polyethylene terephthalate mesh), fabric, perforated or semi-permeable polymer film, or the like. The baffle 2351 may be attached (e.g., adhered) to a surface of the gasket 2357, or it may be positioned between layers of the gasket 2357 (e.g., where the gasket 2357 is formed of multiple layers, such as two layers of PSA film).

The baffle 2351 may have an acoustic impedance property or characteristic that reduces the impact of the second passage 2356 on pressure waves in the first passage 2354, while also allowing air to pass into the second passage 2356 without significantly impacting the operation of the pressure sensor. For example, the baffle 2351 may have an acoustic impedance of between about 100 and about 700 Rayl. In some cases, the baffle 2351 has an acoustic impedance of between about 150 Rayl and about 300 Rayl. The baffle 2351 may have a thickness between about 40 microns and about 100 microns.

Figure 23F:
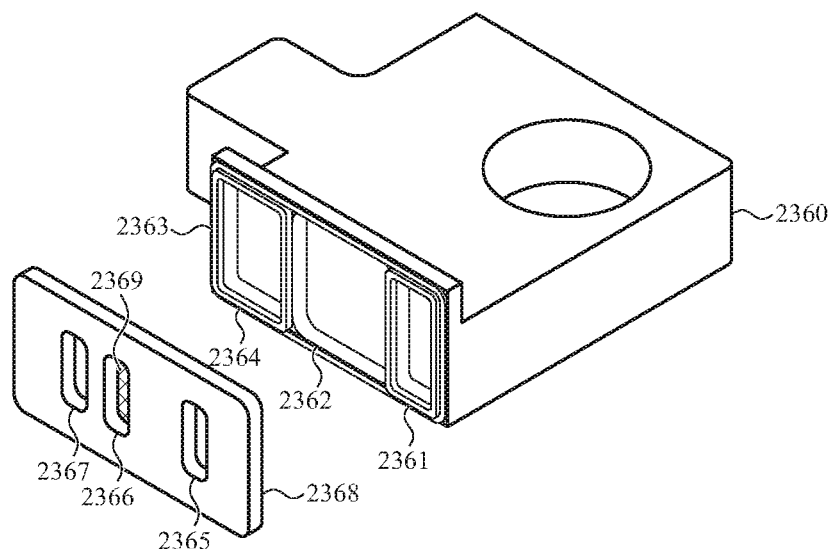

FIG. 23F depicts another example module 2360 that includes at least a pressure sensor and a microphone, and optionally a barometric vent (similar to or the same as the barometric vent shown in FIG. 23B). The microphone and pressure sensor are both fluidically coupled to the common volume 2310 defined by the housing 2302 when integrated into a device as shown in FIGS. 23A-23B. The module 2360 defines a first passage 2364 that communicates with the common volume 2310 and is fluidically coupled to a microphone, and a second passage 2362 that communicates with the common volume 2310 and is fluidically coupled to a pressure sensor. The module 2360 also defines a third passage 2361 that is fluidically coupled to a barometric vent.

In the example of FIG. 23F, a baffle 2369 (e.g., an acoustic mesh) is integrated with a first gasket 2368. More particularly, the first gasket 2368 may define a first hole 2367, which corresponds to and/or is aligned with the opening to the first passage 2364, a second hole 2366, which corresponds to and/or is aligned with the opening to the second passage 2362, and a third hole 2365, which corresponds to and/or is aligned with the opening to the third passage 2361. The baffle 2369 may be positioned in the second hole 2366 of the first gasket 2368. When the first gasket 2368 is captured between the module 2360 and the housing 2302, the baffle 2369 provides an acoustic or fluidic dampening between the first passage 2364 and the second passage 2362. More particularly, because the first passage 2364 and the second passage 2362 (through the baffle 2369) both open directly into the common volume 2310, the baffle 2369 forms an air-permeable, acoustic dampening barrier between the first and second passages 2364, 2362.

The baffle 2369 may be formed from any suitable material or structure, such as an open-cell foam, metal mesh, polymer mesh (e.g., a polyethylene terephthalate mesh), fabric, perforated or semi-permeable polymer film, or the like. The baffle 2369 may be attached (e.g., adhered) to a surface of the first gasket 2368, or it may be positioned between layers of the first gasket 2368 (e.g., where the first gasket 2368 is formed of multiple layers, such as two layers of PSA film).

The baffle 2369 may have an acoustic impedance property or characteristic that reduces the impact of the second passage 2362 on pressure waves in the first passage 2364, while also allowing air to pass into the second passage 2362 without significantly impacting the operation of the pressure sensor. For example, the baffle 2369 may have an acoustic impedance of between about 100 and about 700 Rayl. In some cases, the baffle 2369 has an acoustic impedance of between about 150 Rayl and about 300 Rayl. The baffle 2369 may have a thickness between about 40 microns and about 100 microns.

In some cases, a second gasket 2363 may be provided around the openings to the first, second, and third passages 2364, 2362, 2361 of the module 2360. The second gasket 2363 may be a compliant material, such as rubber, elastomer, foam, or the like, and may be compressed between or otherwise make contact with the module 2360 and the first gasket 2368. In some cases, the first and second gaskets are formed of different materials and/or have different hardnesses. The second gasket 2363 and the housing of the module 2360 may be formed together, such as via a multi-shot molding process in which the housing and the second gasket 2363 are formed in the same mold to produce a unitary component with different materials.

Figure 23G:
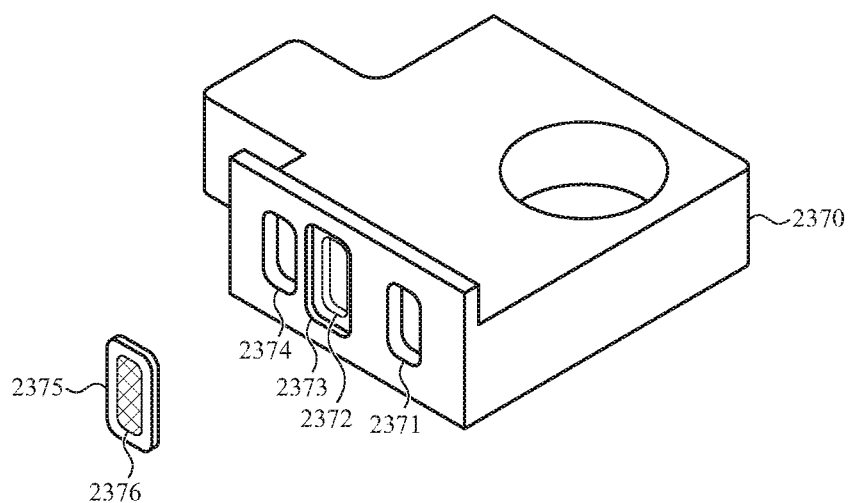

FIG. 23G depicts another example module 2370 (e.g., acoustic module) that includes at least a pressure sensor and a microphone, and optionally a barometric vent (similar to or the same as the barometric vent shown in FIG. 23B). The microphone and pressure sensor are both fluidically coupled to the common volume 2310 defined by the housing 2302 when integrated into a device as shown in FIGS. 23A-23B. The module 2370 defines a first passage 2374 that communicates with the common volume 2310 and is fluidically coupled to a microphone, and a second passage 2372 that communicates with the common volume 2310 and is fluidically coupled to a pressure sensor. The module 2370 also defines a third passage 2371 that is fluidically coupled to a barometric vent.

The module 2370 also defines a recess 2373 in a mounting surface of the module 2370. The openings to the second passage 2372 is within the recess 2373, while the opening to the first passage 2374 is not within the recess. A gasket 2375 may be positioned in the recess 2373. The gasket 2375 may have a thickness that is equal to or greater than the recess 2373 such that the gasket 2375 contacts the surface of the housing 2302 when the module 2370 is assembled into a device, and optionally is compressed between the module 2370 and the housing 2302.

The gasket 2375 may include a baffle 2376 (e.g., an acoustic mesh) positioned in a hole defined in the gasket 2375. When the gasket 2375 is positioned in the recess 2373 and captured between the module 2370 and the housing 2302, the baffle 2376 provides an acoustic or fluidic dampening between the first passage 2374 and the second passage 2372. More particularly, because the first passage 2374 and the second passage 2372 (through the baffle 2376) both open directly into the common volume 2310, the baffle 2376 forms an air-permeable, acoustic dampening barrier between the first and second passages 2374, 2372.

The baffle 2376 may be formed from any suitable material or structure, such as an open-cell foam, metal mesh, polymer mesh (e.g., a polyethylene terephthalate mesh), fabric, perforated or semi-permeable polymer film, or the like. The baffle 2376 may be attached (e.g., adhered) to a surface of the gasket 2375, or it may be positioned between layers of the gasket 2375 (e.g., where the gasket 2375 is formed of multiple layers, such as two layers of PSA film).

The baffle 2376 may have an acoustic impedance property or characteristic that reduces the impact of the second passage 2372 on pressure waves in the first passage 2374, while also allowing air to pass into the second passage 2372 without significantly impacting the operation of the pressure sensor. For example, the baffle 2376 may have an acoustic impedance of between about 100 and about 700 Rayl. In some cases, the baffle 2376 has an acoustic impedance of between about 150 Rayl and about 300 Rayl. The baffle 2376 may have a thickness between about 40 microns and about 100 microns.

As noted above, modules for use in electronic devices may include barometric vents. The barometric vents may define a passage between the internal volume of the device and the exterior environment to allow pressure equalization between the internal volume and the exterior environment. In some cases, the barometric vents include an air-permeable, waterproof component (e.g., an air-permeable, waterproof polymer membrane) to allow air to pass between the internal volume and the exterior environment (to allow for pressure equalization), while inhibiting or limiting passage of water or other liquids or contaminants.

Figure 24:
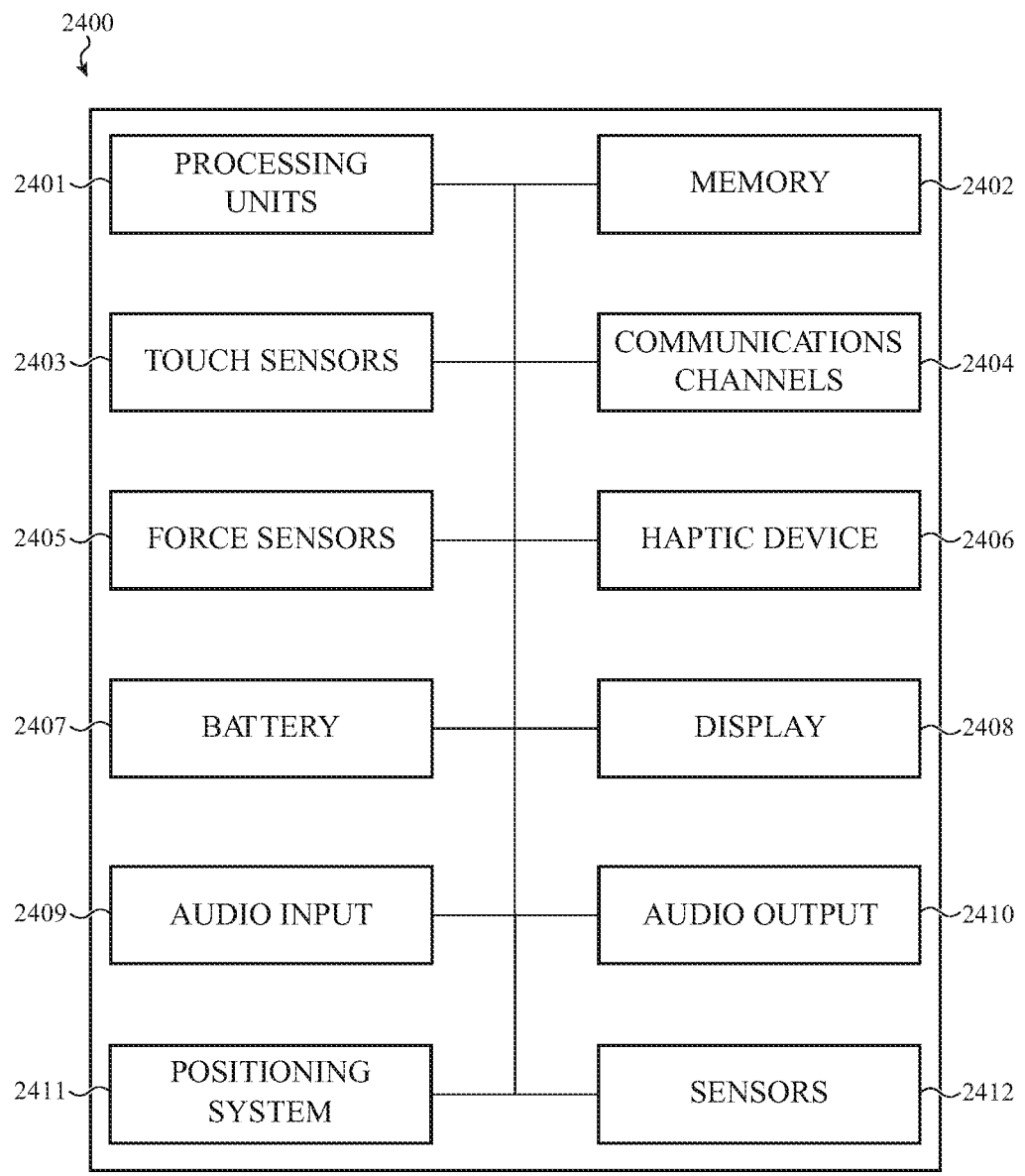
FIG. 24 depicts a schematic diagram of an example electronic device.

FIG. 24 depicts an example schematic diagram of an electronic device 2400. The electronic device 2400 may be an embodiment of or otherwise represent the device 100 (or other devices described herein, such as the devices 100, 140, 200, 300, 400, 900, 1300, 1400, 1700, 2200, or the like). The device 2400 includes one or more processing units 2401 that are configured to access a memory 2402 having instructions stored thereon. The instructions or computer programs may be configured to perform one or more of the operations or functions described with respect to the electronic devices described herein. For example, the instructions may be configured to control or coordinate the operation of one or more displays 2408, one or more touch sensors 2403, one or more force sensors 2405, one or more communication channels 2404, one or more audio input systems 2409, one or more audio output systems 2410, one or more positioning systems 2411, one or more sensors 2412, and/or one or more haptic feedback devices 2406.

The processing units 2401 of FIG. 24 may be implemented as any electronic device capable of processing, receiving, or transmitting data or instructions. For example, the processing units 2401 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements. The processing units 2401 may be coupled to a logic board, such as the logic board 2100 of FIG. 21A.

The memory 2402 can store electronic data that can be used by the device 2400. For example, a memory can store electrical data or content such as, for example, audio and video files, images, documents and applications, device settings and user preferences, programs, instructions, timing and control signals or data for the various modules, data structures or databases, and so on. The memory 2402 can be configured as any type of memory. By way of example only, the memory can be implemented as random access memory, read-only memory, Flash memory, removable memory, or other types of storage elements, or combinations of such devices. The memory 2402 may be coupled to a logic board, such as the logic board 2100 of FIG. 21A.

The touch sensors 2403 may detect various types of touch-based inputs and generate signals or data that are able to be accessed using processor instructions. The touch sensors 2403 may use any suitable components and may rely on any suitable phenomena to detect physical inputs. For example, the touch sensors 2403 may be capacitive touch sensors, resistive touch sensors, acoustic wave sensors, or the like. The touch sensors 2403 may include any suitable components for detecting touch-based inputs and generating signals or data that are able to be accessed using processor instructions, including electrodes (e.g., electrode layers), physical components (e.g., substrates, spacing layers, structural supports, compressible elements, etc.), processors, circuitry, firmware, and the like. The touch sensors 2403 may be integrated with or otherwise configured to detect touch inputs applied to any portion of the device 2400. For example, the touch sensors 2403 may be configured to detect touch inputs applied to any portion of the device 2400 that includes a display (and may be integrated with a display). The touch sensors 2403 may operate in conjunction with the force sensors 2405 to generate signals or data in response to touch inputs. A touch sensor or force sensor that is positioned over a display surface or otherwise integrated with a display may be referred to herein as a touch-sensitive display, force-sensitive display, or touchscreen.

The force sensors 2405 may detect various types of force-based inputs and generate signals or data that are able to be accessed using processor instructions. The force sensors 2405 may use any suitable components and may rely on any suitable phenomena to detect physical inputs. For example, the force sensors 2405 may be strain-based sensors, piezoelectric-based sensors, piezoresistive-based sensors, capacitive sensors, resistive sensors, or the like. The force sensors 2405 may include any suitable components for detecting force-based inputs and generating signals or data that are able to be accessed using processor instructions, including electrodes (e.g., electrode layers), physical components (e.g., substrates, spacing layers, structural supports, compressible elements, etc.), processors, circuitry, firmware, and the like. The force sensors 2405 may be used in conjunction with various input mechanisms to detect various types of inputs. For example, the force sensors 2405 may be used to detect presses or other force inputs that satisfy a force threshold (which may represent a more forceful input than is typical for a standard "touch" input). Like the touch sensors 2403, the force sensors 2405 may be integrated with or otherwise configured to detect force inputs applied to any portion of the device 2400. For example, the force sensors 2405 may be configured to detect force inputs applied to any portion of the device 2400 that includes a display (and may be integrated with a display). The force sensors 2405 may operate in conjunction with the touch sensors 2403 to generate signals or data in response to touch- and/or force-based inputs.

The device 2400 may also include one or more haptic devices 2406 (e.g., the haptic actuator 222, 322 of FIGS. 2-3). The haptic device 2406 may include one or more of a variety of haptic technologies such as, but not necessarily limited to, rotational haptic devices, linear actuators, piezoelectric devices, vibration elements, and so on. In general, the haptic device 2406 may be configured to provide punctuated and distinct feedback to a user of the device. More particularly, the haptic device 2406 may be adapted to produce a knock or tap sensation and/or a vibration sensation. Such haptic outputs may be provided in response to detection of touch and/or force inputs, and may be imparted to a user through the exterior surface of the device 2400 (e.g., via a glass or other surface that acts as a touch- and/or force-sensitive display or surface).

The one or more communication channels 2404 may include one or more wireless interface(s) that are adapted to provide communication between the processing unit(s) 2401 and an external device. The one or more communication channels 2404 may include antennas (e.g., antennas that include or use the housing members of the housing 104 as radiating members), communications circuitry, firmware, software, or any other components or systems that facilitate wireless communications with other devices. In general, the one or more communication channels 2404 may be configured to transmit and receive data and/or signals that may be interpreted by instructions executed on the processing units 2401. In some cases, the external device is part of an external communication network that is configured to exchange data with wireless devices. Generally, the wireless interface may communicate via, without limitation, radio frequency, optical, acoustic, and/or magnetic signals and may be configured to operate over a wireless interface or protocol. Example wireless interfaces include radio frequency cellular interfaces (e.g., 2G, 3G, 4G, 4G long-term evolution (LTE), 5G, GSM, CDMA, or the like), fiber optic interfaces, acoustic interfaces, Bluetooth interfaces, infrared interfaces, USB interfaces, Wi-Fi interfaces, TCP/IP interfaces, network communications interfaces, or any conventional communication interfaces. The one or more communications channels 2404 may also include ultra-wideband interfaces, which may include any appropriate communications circuitry, instructions, and number and position of suitable UWB antennas.

As shown in FIG. 24, the device 2400 may include a battery 2407 that is used to store and provide power to the other components of the device 2400. The battery 2407 may be a rechargeable power supply that is configured to provide power to the device 2400. The battery 2407 may be coupled to charging systems (e.g., wired and/or wireless charging systems) and/or other circuitry to control the electrical power provided to the battery 2407 and to control the electrical power provided from the battery 2407 to the device 2400.

The device 2400 may also include one or more displays 2408 configured to display graphical outputs. The displays 2408 may use any suitable display technology, including liquid crystal displays (LCD), organic light emitting diodes (OLED), active-matrix organic light-emitting diode displays (AMOLED), or the like. The displays 2408 may display graphical user interfaces, images, icons, or any other suitable graphical outputs. The display 2408 may correspond to a display 103, 203, 303, 610.

The device 2400 may also provide audio input functionality via one or more audio input systems 2409. The audio input systems 2409 may include microphones, transducers, or other devices that capture sound for voice calls, video calls, audio recordings, video recordings, voice commands, and the like.

The device 2400 may also provide audio output functionality via one or more audio output systems (e.g., speakers) 2410, such as the speaker systems and/or modules 224, 250, 324, 350, 620. The audio output systems 2410 may produce sound from voice calls, video calls, streaming or local audio content, streaming or local video content, or the like.

The device 2400 may also include a positioning system 2411. The positioning system 2411 may be configured to determine the location of the device 2400. For example, the positioning system 2411 may include magnetometers, gyroscopes, accelerometers, optical sensors, cameras, global positioning system (GPS) receivers, inertial positioning systems, or the like. The positioning system 2411 may be used to determine spatial parameters of the device 2400, such as the location of the device 2400 (e.g., geographical coordinates of the device), measurements or estimates of physical movement of the device 2400, an orientation of the device 2400, or the like.

The device 2400 may also include one or more additional sensors 2412 to receive inputs (e.g., from a user or another computer, device, system, network, etc.) or to detect any suitable property or parameter of the device, the environment surrounding the device, people, or things interacting with the device (or nearby the device), or the like. For example, a device may include temperature sensors, biometric sensors (e.g., fingerprint sensors, photoplethysmographs, blood-oxygen sensors, blood sugar sensors, or the like), eye-tracking sensors, retinal scanners, humidity sensors, buttons, switches, lid-closure sensors, or the like.

To the extent that multiple functionalities, operations, and structures described with reference to FIG. 24 are disclosed as being part of, incorporated into, or performed by the device 2400, it should be understood that various embodiments may omit any or all such described functionalities, operations, and structures. Thus, different embodiments of the device 2400 may have some, none, or all of the various capabilities, apparatuses, physical features, modes, and operating parameters discussed herein. Further, the systems included in the device 2400 are not exclusive, and the device 2400 may include alternative or additional systems, components, modules, programs, instructions, or the like, that may be necessary or useful to perform the functions described herein.

As described above, one aspect of the present technology is the gathering and use of data available from various sources to improve the usefulness and functionality of devices such as mobile phones. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to locate devices, deliver targeted content that is of greater interest to the user, or the like. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings. Also, when used herein to refer to positions of components, the terms above, below, over, under, left, or right (or other similar relative position terms), do not necessarily refer to an absolute position relative to an external reference, but instead refer to the relative position of components within the figure being referred to. Similarly, horizontal and vertical orientations may be understood as relative to the orientation of the components within the figure being referred to, unless an absolute horizontal or vertical orientation is indicated.

Features, structures, configurations, components, techniques, etc. shown or described with respect to any given figure (or otherwise described in the application) may be used with features, structures, configurations, components, techniques, etc. described with respect to other figures. For example, any given figure of the instant application should not be understood to be limited to only those features, structures, configurations, components, techniques, etc. shown in that particular figure. Similarly, features, structures, configurations, components, techniques, etc. shown only in different figures may be used or implemented together. Further, features, structures, configurations, components, techniques, etc. that are shown or described together may be implemented separately and/or combined with other features, structures, configurations, components, techniques, etc. from other figures or portions of the instant specification. Further, for ease of illustration and explanation, figures of the instant application may depict certain components and/or sub-assemblies in isolation from other components and/or sub-assemblies of an electronic device, though it will be understood that components and sub-assemblies that are illustrated in isolation may in some cases be considered different portions of a single electronic device (e.g., a single embodiment that includes multiple of the illustrated components and/or sub-assemblies).

What is claimed is:

1. A portable electronic device comprising:
a housing;
a display at least partially within the housing;
a front cover coupled to the housing and positioned over the display; and
a biometric sensor module configured to illuminate an object and capture an image of the object through the front cover, the biometric sensor module comprising:
a first lens positioned below the front cover;
a first light source positioned below a central region of the first lens and configured to project, through the first lens, a dot pattern on the object;
a second light source positioned below a peripheral region of the first lens and configured to illuminate, through the first lens, the object with a flood of light;
a second lens positioned below the front cover; and
a light sensor positioned below the second lens and configured to capture an image of the object.

2. The portable electronic device of claim 1, wherein:
the object is a user's face; and
the portable electronic device is configured to:
determine a depth map of the user's face using the dot pattern projected onto the user's face; and
authenticate the user based at least in part on the depth map of the user's face.

3. The portable electronic device of claim 1, wherein:
the first light source projects infrared light;
the flood of light is infrared light; and
the light sensor is an infrared light sensor.

4. The portable electronic device of claim 1, wherein:
light from the first light source passing through the central region of the first lens is rendered in focus on the object; and
light from the second light source passing through the peripheral region of the first lens is rendered out of focus on the object.

5. The portable electronic device of claim 1, wherein:
the biometric sensor module comprises a housing structure; and
the first lens, the first light source, the second lens, the second light source, and the light sensor are positioned at least partially within the housing structure.

6. The portable electronic device of claim 1, wherein the second light source comprises a radial array of light-emitting elements.

7. The portable electronic device of claim 1, wherein the peripheral region of the first lens is configured to blur light emitted by the second light source.

8. The portable electronic device of claim 7, wherein the central region of the first lens is configured to focus light emitted by the first light source.

9. A mobile phone comprising:
a housing;
a display at least partially within the housing;
a front cover coupled to the housing and positioned over the display;
a light emitter below the front cover and configured to emit light through the front cover, the light emitter comprising:
 a first lens positioned below the front cover;
 a first light source positioned below a central region of the first lens, the central region configured focus a pattern of light emitted by the first light source; and
 a second light source positioned below a peripheral region of the first lens, the peripheral region configured to blur light emitted by the second light source; and
a light receiver below the front cover and comprising:
 a second lens positioned below the front cover and configured to receive light through the front cover; and
 a light sensor positioned below the second lens.

10. The mobile phone of claim 9, wherein:
the first light source is aligned with an optical axis of the first lens; and
the second light source is offset from the optical axis of the first lens.

11. The mobile phone of claim 9, wherein the pattern of light is a grid of discrete points of infrared light.

12. The mobile phone of claim 11, wherein the light emitted by the second light source is configured to illuminate the object with a flood of infrared light.

13. The mobile phone of claim 11, wherein the light receiver is configured to capture an infrared image of the object while the pattern of light is focused on the object.

14. The mobile phone of claim 9, wherein the light emitter and the light receiver are positioned at least partially within a housing structure of a biometric sensor module.

15. A portable electronic device comprising:
a housing;
a display at least partially within the housing;
a front cover coupled to the housing and positioned over the display; and
a biometric sensor module configured to illuminate a face of a user and to capture an image of the face of the user through the front cover, the biometric sensor module comprising:
 a housing structure;
 a first lens at least partially within the housing structure;
 a light sensor positioned below the first lens;
 a second lens at least partially within the housing structure;
 a first light source positioned below a central region of the second lens and configured to project a first illumination pattern on the face of the user; and
 a second light source positioned below a peripheral region of the second lens and configured to project a second illumination pattern of light that, when reflected off of the face of the user and captured by the light sensor, produces an image of the face of the user.

16. The portable electronic device of claim 15, wherein the first illumination pattern is a set of discrete points of light.

17. The portable electronic device of claim 15, wherein the first light source is an infrared laser light source.

18. The portable electronic device of claim 17, wherein:
the infrared laser light source is a first infrared laser light source; and
the second light source is a second infrared laser light source.

19. The portable electronic device of claim 18, wherein:
the first infrared laser light source is a first vertical-cavity surface-emitting laser; and
the second infrared laser light source is a second vertical-cavity surface-emitting laser.

20. The portable electronic device of claim 15, wherein:
the peripheral region of the second lens is configured to blur light emitted by the second light source.

* * * * *